US011732026B2

(12) United States Patent
Rees Smith et al.

(10) Patent No.: US 11,732,026 B2
(45) Date of Patent: Aug. 22, 2023

(54) GLYCOPROTEIN HORMONE RECEPTOR MUTATIONS

(71) Applicant: RSR Limited, Cardiff (GB)

(72) Inventors: Bernard Rees Smith, Cardiff (GB);
Jadwiga Furmaniak, Cardiff (GB);
Jane Sanders, Barry (GB); Jennifer Miller-Gallacher, Cardiff (GB)

(73) Assignee: RSR Limited, Cardiff (GB)

( * ) Notice: Subject to any disclaimer, the term of this patent is extended or adjusted under 35 U.S.C. 154(b) by 107 days.

(21) Appl. No.: 15/317,687

(22) PCT Filed: Jun. 11, 2015

(86) PCT No.: PCT/GB2015/000171
§ 371 (c)(1),
(2) Date: Dec. 9, 2016

(87) PCT Pub. No.: WO2015/189543
PCT Pub. Date: Dec. 17, 2015

(65) Prior Publication Data
US 2017/0204159 A1 Jul. 20, 2017

(30) Foreign Application Priority Data

Jun. 11, 2014 (GB) .................................... 1410409

(51) Int. Cl.
*C07K 14/705* (2006.01)
*C07K 14/72* (2006.01)
*G01N 33/68* (2006.01)

(52) U.S. Cl.
CPC ....... *C07K 14/723* (2013.01); *G01N 33/6854* (2013.01)

(58) Field of Classification Search
None
See application file for complete search history.

(56) References Cited

FOREIGN PATENT DOCUMENTS

| CN | 101006099 A | 7/2007 | |
|---|---|---|---|
| CN | 101595129 A | 12/2009 | |
| CN | 102264764 A | 11/2011 | |
| CN | 103458915 A | 12/2013 | |
| EP | 1021721 A1 | 7/2000 | |
| EP | 1565493 B1 | 8/2005 | |
| EP | 2121919 B1 | 3/2008 | |
| EP | 2367850 A2 | 9/2011 | |
| GB | 2527286 A | 12/2015 | |
| WO | 2004050708 A2 | 6/2004 | |
| WO | 2006016121 A1 | 2/2006 | |
| WO | WO-2006016121 A1 * | 2/2006 | ........... C07K 14/723 |
| WO | 2008025991 A1 | 3/2008 | |
| WO | 2008099185 A1 | 8/2008 | |
| WO | 2010073012 A1 | 7/2010 | |
| WO | WO-2010073012 A2 * | 7/2010 | ........... C07K 16/28 |
| WO | 2012098413 A1 | 7/2012 | |
| WO | WO-2012098413 A1 * | 7/2012 | ........... C07K 14/723 |
| WO | WO2012116203 A1 | 8/2012 | |
| WO | 2015189543 A2 | 12/2015 | |

OTHER PUBLICATIONS

Smit et al. (2003) EMBO 22: 2692-2703).*
Foreign Communication from a related application—Examination Report of European Application No. 15738404.1, dated May 2, 2018, 5 pages.
Shibata, Y., et al., "Thermostabilization of the Neurotensin Receptor NTS1," Journal of Molecular Biology, 2009, pp. 262-277, vol. 390, Elsevier Ltd.
Smith, C.K., et al., "A Thermodynamic Scale for the β-Sheet Forming Tendencies of the Amino Acids," Biochemistry, 1994, pp. 5510-5517, vol. 33, American Chemical Society.
De St. Groth, F., et al., "Production of monoclonal antibodies: Strategy and tactics," Journal of Immunological Methods, Jul. 15, 1980, pp. 1-21, vol. 35, Elsevier.
Szilágyi, A., et al., "Structural differences between mesophilic, moderately thermophilic and extremely thermophilic protein subunits: results of a comprehensive survey," Structure, 2000, pp. 493-504, vol. 8, No. 5, Elsevier Science Ltd.
Vetriani, C., et al., "Protein thermostability above 100° C.: A key role for ionic interactions," Proceedings of the National Academy of Sciences of the USA, Oct. 1998, pp. 12300-12305, vol. 95, No. 21, The National Academy of Sciences of the USA.
Vieille, C., et al., "Hyperthermophilic Enzymes: Sources, Uses, and Molecular Mechanisms for Thermostability," Micribiology and Molecular Biology Reviews, Mar. 2001, pp. 1-43, vol. 65, No. 1, American Society for Microbiology.
Vogt, G., et al., "Protein Thermal Stability, Hydrogen Bonds, and Ion Pairs," Journal of Molecular Biology, Jun. 1997, pp. 631-643, vol. 269, No. 4, Academic Press Ltd.

(Continued)

Primary Examiner — Michael D Pak
(74) Attorney, Agent, or Firm — Conley Rose, P.C.; Rodney B. Carroll

(57) ABSTRACT

A mutant thyroid stimulating hormone receptor (TSHR) or fragment thereof comprises one or more mutations, wherein the mutant TSHR has increased thermostability with respect to the equivalent wild type TSHR or fragment. The one or more mutation is preferably within the extracellular leucine-rich repeat domain (LRD) of the TSHR, or within residues 22 to 260 (TSHR260) of the TSHR, or may be in the transmembrane domain (TMD), A mutant TSHR or fragment thereof of the invention preferably consists of, or consists essentially of, the subdomain TSHR260 of the TSHR receptor. A mutant TSHR or fragment thereof according to the invention has a greater thermostability than the equivalent wild type TSHR or fragment as determined by its half-life at a given temperature, and can be purified whilst retaining activity. A mutant TSHR or fragment thereof according to the invention may also be deglycosylated whilst retaining activity. Methods, kits and uses employing the mutant TSHR or fragment thereof according to the invention are also provided.

8 Claims, 45 Drawing Sheets

Specification includes a Sequence Listing.

(56) References Cited

OTHER PUBLICATIONS

Xiong, H., et al., "Periodicity of polar and nonpolar amino acids is the major determinant of secondary structure in self-assembling oligomeric peptides," Proceedings of the National Academy of Sciences of the USA, 1995, pp. 6349-6353, vol. 92, No. 14, The National Academy of Sciences of the USA.
Yokota, K., et al., "Comparative analysis of protein thermostability: Differences in amino acid content and substitution at the surfaces and in the core regions of thermophilic and mesophilic proteins," Science and Technology of Advanced Materials, May 2006, pp. 255-262, vol. 7, No. 3, NIMS and Elsevier Ltd.
Foreign Communication from the Priority Application—International Search Report and Written Opinion of the International Searching Authority of International Application No. PCT/GB2015/000171 dated Jan. 5, 2016, 16 pages.
Foreign Communication from the Priority Application—International Preliminary Report on Patentability of International Application No. PCT/GB2015/000171 dated Dec. 15, 2016, 9 pages.
Bhattacharya, S., et al., "Rapid Computational Prediction of Thermostabilizing Mutations for G Protein-Coupled Receptors," Journal of Chemical Theory and Computation, Oct. 14, 2014, pp. 5149-5160, vol. 10, No. 11, American Chemical Society.
Bolton, J., et al., Measurement of Thyroid-stimulating Hormone Receptor Autoantibodies by Elisa,Clinical Chemistry, 1999, pp. 2285-2287, vol. 45, No. 12.
Burns, C., et al., "WHO International Collaborative Study of the proposed 2nd International Standard for Thyroid Stimulating Antibody," Oct. 2010, World Health Organization, WHO/BS/10.2142, 27 pages.
Cambillau, C., et al., "Structural and Genomic Correlates of Hyperthermostability," The Journal of Biological Chemistry, Oct. 20, 2000, pp. 32383-32386, vol. 275, No. 42, The American Society for Biochemistry and Molecular Biology, Inc.
Chomczynski, P., et al., "Single-Step Method of RNA Isolation by Acid Guanidinium Thiocyanate-Phenol-Chloroform Extraction," Analytical Biochemistry, 1987, pp. 156-159, vol. 162, No. 1, Academic Press, Inc.
Cooper, G.S., et al., "Recent insights in the epidemiology of autoimmune diseases: Improved prevalence estimates and understanding of clustering of diseases," Journal of Autoimmunity, 2009, pp. 197-207, vol. 33, No. 3, Elsevier Ltd.
Dodevski, I., et al., "Evolution of Three Human GPCRs for Higher Expression and Stability," Journal of Molecular Biology, 2011, pp. 599-615, vol. 408, Elsevier Ltd.
Doré A.S., et al., "Structure of the Adenosine A2A Receptor in Complex with ZM241385 and the Xanthines XAC and Caffeine," Structure, Sep. 7, 2011, pp. 1283-1293, vol. 19, Elsevier Ltd.
Egloff, P., et al., "Structure of signaling-competent neurotensin receptor 1 obtained by directed evolution in *Escherichia coli*," Proceedings of the National Academy of Sciences of the USA, Jan. 22, 2014, pp. E655-E662, vol. 111, The National Academy of Sciences of the USA.
Evans, M., et al., "Monoclonal autoantibodies to the TSH receptor, one with stimulating activity and one with blocking activity, obtained from the same blood sample," Clinical Endocrinology, 2010, pp. 404-412, vol. 73, No. 3.
Hasan, U.A., et al., "Nucleic acid immunization: concepts and techniques associated with third generation vaccines," Journal of immunological Methods, Oct. 29, 1999, pp. 1-22, vol. 229, No. 1-22, Elsevier Science B. V.
Hayakawa, N., et al., "Isolation and Characterization of Human Monoclonal Autoantibodies to Glutamic Acid Decarboxylase," Autoimmunity, 2002, pp. 343-355, vol. 35, No. 5, Taylor & Francis Ltd.
Hollenstein, K., et al., "Structure of class B GPCR corticotropin-releasing factor receptor 1," Nature, Jul. 25, 2013, pp. 438-443, vol. 499.

Jacobson, D., et al., "Epidemiology and Estimated Population Burden of Selected Autoimmune Diseases in the United States," Clinical Immunology and Immunopathology, Sep. 1997, pp. 223-243, vol. 84, No. 3, Academic Press.
Jeffreys, J., et al., "Characterization of the Thyrotropin Binding Pocket," Thyroid, 2002, pp. 1051-1061, vol. 12, No. 12, Mary Ann Liebert, Inc.
Kim, C.A., et al., "Thermodynamic β-sheet propensities measured using a zinc-finger host peptide," Nature, Mar. 18, 1993, pp. 267-270, vol. 362.
Kreuchwig, A., et al., "Research Resource: Novel Structural Insights Bridge Gaps in Glycoprotein Hormone Receptor Analyses," Journal of the Endocrine Society, 2013, pp. 1357-1363, vol. 27 No. 8, Molecular Endocrinology.
Kumar, S., et al., "Contribution of Salt Bridges Toward Protein Thermostability," Journal of Biomolecular Structure and Dynamics, 2000, pp. 79-85, vol. 17, Supplement 1, Adenine Press.
Latif, R., et al., "The Thyroid-Stimulating Hormone Receptor: Impact of Thyroid-Stimulating Hormone and Thyroid-Stimulating Hormone Receptor Antibodies on Multimerization, Cleavage, and Signaling," Endocrinology and Metabolism Clinics of North America, 2009, pp. 319-341, vol. 38, No. 2, Elsevier Inc.
Lehmann, M., et al., "Engineering proteins for thermostability: the use of sequence alignments versus rational design and directed evolution," Current Opinion in Biotechnology, 2001, pp. 371-375, vol. 12, Elsevier Science Ltd.
Magnani, F., et al., "Co-evolving stability and conformational homogeneity of the human adenosine A2a receptor," Proceedings of the National Academy of Sciences of the USA, Aug. 5, 2008, pp. 10744-10749, vol. 105, No. 31, The National Academy of Sciences of the USA.
Matsushima, N., et al., "A nested leucine rich repeat (LRR) domain: The precursor of LRRs is a ten or eleven residue motif," BMC Microbiology, 2010, pp. 235-245, vol. 10, BioMed Central.
Miller, J.L., et al., "Engineering an Ultra-Thermostable β1-Adrenoceptor," Journal of Molecular Biology, Jul. 4, 2011, pp. 628-638, vol. 413, Elsevier Ltd.
Minor, D.L., Jr et al., "Measurement of the β-sheet-forming propensities of amino acids," Nature, Feb. 17, 1994, pp. 660-663, vol. 367.
Minor, D.L., Jr., et al., "Context is a major determinant of β-sheet propensity," Nature, Sep. 15, 1994, pp. 264-267, vol. 371.
Montanucci, L., et al., "Predicting protein thermostability changes from sequence upon multiple mutations," Bioinfomatics, 2008, pp. i190-i195, vol. 24.
Nakatake, N., et al., "Estimation of Serum TSH Receptor Autoantibody Concentration and Affinity," Thyroid, 2006, pp. 1077-1084, vol. 11, Mary Ann Liebert, Inc.
Núñez Miguel, R., et al., "Analysis of the Thyrotropin Receptor-Thyrotropin Interaction by Comparative Modeling," Thyroid, 2004, pp. 991-1011, vol. 14, No. 12, Mary Ann Liebert, Inc.
Núñez, Miguel, R., et al., "Similarities and differences in interactions of thyroid stimulating and blocking autoantibodies with the TSH receptor," Journal of Molecular Endocrinology, 2012, pp. 137-151, vol. 49, Society for Endocrinology.
O'Gorman, S., et al., "Recombinase-Mediated Gene Activation and Site-Specific Integration in Mammalian Cells," Science, Mar. 15, 1991, pp. 1351-1355, vol. 251, No. 4999.
Oda, Y., et al., "Binding characteristics of antibodies to the TSH receptor," Journal of Molecular Endocrinology, 1998, pp. 233-244, vol. 20, Journal of Endocrinology.
Pack, S.P., et al., "Protein thermostability: structure-based difference of amino acid between thermophilic and mesophilic proteins," Journal of Biotechnology, 2004, pp. 269-277, vol. 111, Elsevier Ltd.
Prentice, L., et al., "Thyrotropin (TSH) Receptor Autoantibodies Do Not Appear to Bind to the TSH Receptor Produced in an in Vitro Transcription/Translation System," Journal of Clinical Endocrinology and Metabolism, 1997, pp. 1288-1292, vol. 82, No. 4, The Endocrine Society.
Rees-Smith, B., et al., "A New Assay for Thyrotropin Receptor Autoantibodies," Thyroid, 2004, pp. 830-835, vol. 14, No. 10, Mary Ann Liebert, Inc.

(56) References Cited

OTHER PUBLICATIONS

Rees-Smith, B., et al., "Autoantibodies to the Thyrotropin Receptor," Endocrine Reviews, 1988, pp. 106-121, vol. 9, No. 1, The Endocrine Society.

Rees-Smith, B., et al., "Implications of new monoclonal antibodies and the crystal structure of the TSH receptor for the treatment and management of thyroid diseases," Biomarkers Medicine, 2008, pp. 567-576, vol. 2, No. 6, Future Medicine Ltd.

Seethalakshmi, I. et al., "Immunopathogenesis of Graves' ophthalmopathy: The role of the TSH receptor," Best Practice & Research Clinical Endocrinology & Metabolism, Jun. 2012, pp. 281-289, vol. 26, No. 3, Elsevier Ltd.

Serrano-Vega, M.J., et al., "Conformational thermostabilization of the β1-adrenergic receptor in a detergent-resistant form," Proceedings of the National Academy of Sciences of the USA, 2008, pp. 877-882, vol. 105, No. 3, The National Academy of Sciences of the USA.

Rees-Smith, B., et al., "TSH Receptor—Autoantibody Interactions," 2009, pp. 448-455, vol. 6, Georg Thieme Verlag KG.

Rees-Smith, B., et al., "TSH Receptor Antibodies," Thyroid, 2007, pp. 923-938, vol. 17, No. 10, Mary Ann Liebert, Inc.

Sanders J., et al., "The Interaction of TSH Receptor Autoantibodies with 125I-Labelled TSH Receptor," The Journal of Clinical Endocrinology & Metabolism, 1999, pp. 3797-3802, vol. 84, No. 10, The Endocrine Society.

Sanders, J., et al., "Crystal Structure of the TSH Receptor in Complex with a Thyroid-Stimulating Autoantibody," Thyroid, 2007, pp. 395-410, vol. 17, No. 5, Mary Ann Liebert, Inc.

Sanders, J., et al., "Effects of TSH receptor mutations on binding and biological activity of monoclonal antibodies and TSH," Thyroid, 2006, pp. 1195-1206, vol. 16, No. 12, Mary Ann Liebert, Inc.

Sanders, J., et al., "Human monoclonal thyroid stimulating autoantibody," The Lancet, Jul. 12, 2003, pp. 126-128, vol. 362, No. 9378.

Sanders, J., et al., "Understanding the thyrotropin receptor function-structure relationship," Ballière's Clinical Endocrinology and Metabolism, 1997, pp. 451-479, vol. 11, No. 3, Ballière Tindall.

Sanders, P., et al., "Crystal structure of the TSH receptor (TSHR) bound to a blocking-type TSHR autoantibody," Journal of Molecular Endocrinology, 2011, pp. 81-99, vol. 46, Society for Endocrinology.

Sanger, F., et al., "DNA sequencing with chain-terminating inhibitors," Proceedings of the National Academy of Sciences of the USA, Dec. 1977, pp. 5463-5467, vol. 74, No. 12, The National Academy of Sciences of the USA.

Scatchard, G., et al., "The Attractions of Proteins for Small Molecules and Ions," Annals of the New York Academy of Sciences, 1949, pp. 660-672, vol. 51, No. 4.

Foreign communication from related application—Chinese Office Action and English Translation for Chinese Patent Application No. 2015800443074.6, dated Jan. 3, 2020, 27 pages.

Ma, Shaogang, "The Study on Mutation in Congenital Hypothyrodism", Medicine, Hygiene & Science, 2002, vol. Chinese Doctoral Dissertations Full Text Database, 85 pages, Eng abstract.

Foreign communication from related application—Chinese Office Action and English Translation for Chinese Patent Application No. 201580043074.6, dated Jan. 3, 2020, 27 pages.

Ma, Shaogang, "The Study on Mutation in Congenital Hypothyrodism", Medicine, Hygiene & Science, 2002, vol. Chinese Doctoral Dissertations Full Text Database, 85 pages.

Foreign Communication from Related Application—Japanese Office Action and English Translation, regarding Japanese Application No. 2022-019621, dated Feb. 6, 2023, 5 pages.

\* cited by examiner

FIG. 1  HUMAN (wild type) TSHR DNA (SEQ ID No 1)

```
1      atgaggccgg cggacttgct gcagctggtg ctgctgctcg acctgcccag 50
51     ggacctgggc ggaatggggt gttcgtctcc accctgcgag tgccatcagg 100
101    aggaggactt cagagtcacc tgcaaggata ttcaacgcat ccccagctta 150
151    ccgcccagta cgcagactct gaagcttatt gagactcacc tgagaactat 200
201    tccaagtcat gcattttcta atctgcccaa tatttccaga atctacgtat 250
251    ctatagatgt gactctgcag cagctggaat cacactcctt ctacaatttg 300
301    agtaaagtga ctcacataga aattcggaat accaggaact taacttacat 350
351    agaccctgat gccctcaaag agctccccct cctaaagttc cttggcattt 400
401    tcaacactgg acttaaaatg ttccctgacc tgaccaaagt ttattccact 450
451    gatatattct ttatacttga aattacagac aaccttacat gacgtcaat 500
501    ccctgtgaat gcttttcagg gactatgcaa tgaaaccttg cactgaagc 550
551    tgtacaacaa cggctttact tcagtccaag gatatgcttt caatgggaca 600
601    aagctggatg ctgtttacct aaacaagaat aaatacctga cagttattga 650
651    caaagatgca tttggaggag tatacagtgg accaagcttg ctggacgtgt 700
701    ctcaaaccag tgtcactgcc cttccatcca aaggcctgga gcacctgaag 750
751    gaactgatag caagaaacac ctggactctt aagaaacttc cactttcctt 800
801    gagtttcctt cacctcacac gggctgacct ttcttaccca gccactgct 850
851    gtgcctttaa gaatcagaag aaaatcagag gaatccttga gtccttgatg 900
901    tgtaatgaga gcagtatgca gagcttgcgc cagagaaaat ctgtgaatgc 950
951    cttgaatagc ccctccacc aggaatatga agagaatctg ggtgacagca 1000
1001   ttgttgggta caaggaaaag tccaagttcc aggatactca taacaacgct 1050
1051   cattattacg tcttctttga gaacaagag gatgagatca ttggtttggg 1100
1150   ccaggagctc aaaaaccccc aggaagagac tctacaagct tttgacagcc 1150
1151   attatgacta caccatatgt ggggacagtg aagacatggt gtgtaccccc 1200
1201   aagtccgatg agttcaaccc gtgtgaagac ataatggct acaagttcct 1250
1251   gagaattgtg gtgtggttcg ttagtctgct ggctcctg gcaatgtct 1300
1301   ttgtcctgct tattctcctc accagccact acaaactgaa cgtccccgc 1350
1351   tttctcatgt gcaacctggc ctttgcggat ttctgcatgg ggatgtacct 1400
1401   gctcctcatc gcctctgtag acctctacac tcactctgag tactacaacc 1450
1451   atgccatcga ctggcagaca ggccctgggt gcaacacggc tggtttcttc 1500
1501   actgtctttg caagcgagtt atcggtgtat acgctgacgg tcatcaccct 1550
1551   ggagcgctgg tatgccatca ccttcgccat cgcctggac cggaagatcc 1600
1601   gcctcaggca cgcatgtgcc atcatggttg ggggctgggt ttgctgcttc 1650
1651   cttctcgccc tgcttccttt ggtgggaata agtagctatg ccaaagtcag 1700
1701   tatctgcctg cccatggaca ccgagacccc tcttgctctg catatattg 1750
1751   ttttgttct gacgctcaac atagttgcct tcgtcatcgt ctgctgctgt 1800
1801   tatgtgaaga ctacatcac agtccgaaat ccgcagtaca accagggga 1850
1851   caaagatacc aaaattgcca gaggatggc tgtgttgatc ttcaccgact 1900
1901   tcatatgcat ggccccaatc tcattctatg ctctgtcagc aattctgaac 1950
1951   aagcctctca tcactgttag caactccaaa atcttgctgg tactcttcta 2000
2001   tccacttaac tcctgtgcca atccattcct ctatgctatt ttcaccaagg 2050
2051   ccttccagag ggatgtgttc atcctactca gcaagtttgg catctgtaaa 2100
2101   cgccaggctc aggcataccg ggggcagagg gttcctccaa agaacagcac 2150
2151   tgatattcag gttcaaaagg ttacccacga gatgaggcag gtctccaca 2200
2201   acatggaaga tgtctatgaa ctgattgaaa agtccatct aaccccaaag 2250
2251   aagcaaggcc aaatctcaga agagtatatg caaacggttt tgtaa       2295
```

FIG. 2 HUMAN (wild type) TSHR PROTEIN (SEQ ID No 2)

```
  1    MRPADLLQLV  LLLDLPRDLG  GMGCSSPPCE  CHQEEDFRVT  CKDIQRIPSL  PPSTQTLKLI   60
 61    ETHLRTIPSH  AFSNLPNISR  IYVSIDLTLQ  QLESHSFYNL  SKVTHIEIRN  TRNLTYIDPD  120
121    ALKELPLLKF  LGIFNTGLKM  FPDLTKVYST  DIFFILEITD  NPYMTSIPVN  AFQGLCNETL  180
181    TLKLYNNGFT  SVQGYAFNGT  KLDAVYLNKN  KYLTVIDKDA  FGGVYSGPSL  LDVSQTSVTA  240
241    LPSKGLEHLK  ELIARNTWTL  KKLPLSLSFL  HLTRADLSYP  SHCCAFKNQK  KIRGILESLM  300
301    CNESSMQSLR  QRKSVNALNS  PLHQEYEENL  GDSIVGYKEK  SKFQDTHNNA  HYYVFFEEQE  360
361    DEIIGFGQEL  KNPQEETLQA  FDSHYDYTIC  GDSEDMVCTP  KSDEFNPCED  IMGYKFLRIV  420
421    VWFVSLLALL  GNVFVLLILL  TSHYKLNVPR  FLMCNLAFAD  FCMGMYLLLI  ASVDLYTHSE  480
481    YYNHAIDWQT  GPGCNTAGFF  TVFASELSVY  TLTVITLERW  YAITFAMRLD  RKIRLRHACA  540
541    IMVGGWVCCF  LLALLPLVGI  SSYAKVSICL  PMDTETPLAL  AYIVFVLTLN  IVAFVIVCCC  600
601    YVKIYITVRN  PQYNPGDKDT  KIAKRMAVLI  FTDFICMAPI  SFYALSAILN  KPLITVSNSK  660
661    ILLVLFYPLN  SCANPFLYAI  FTKAFQRDVF  ILLSKFGICK  RQAQAYRGQR  VPPKNSTDIQ  720
721    VQKVTHDMRQ  GLHNMEDVYE  LIENSHLTPK  KQGQISEEYM  QTVL                    764
```

FIG. 3 HUMAN (wild type) TSHR260 DNA (SEQ ID No 3)

```
  1   atgaggccgg cggacttgct gcagctggtg ctgctgctcg acctgcccag   50
 51   ggacctgggc ggaatggggt gttcgtctcc accctgcgag tgccatcagg  100
101   aggaggactt cagagtcacc tgcaaggata ttcaacgcat ccccagctta  150
151   ccgcccagta cgcagactct gaagcttatt gagactcacc tgagaactat  200
201   tccaagtcat gcatttctca atctgcccaa tatttccaga atctacgtat  250
251   ctatagatgt gactctgcag cagctggaat cacactcctt ctacaatttg  300
301   agtaaagtga ctcacataga aattcggaat accaggaact taacttacat  350
351   agaccctgat gcctcaaag agctcccct cctaaagttc cttggcattt  400
401   tcaacactgg acttaaaatg ttccctgacc tgaccaaagt ttattccact  450
451   gatatattct ttatacttga aattacagac aaccttacat gacgtcaat  500
501   ccctgtgaat gcttttcagg gactatgcaa tgaaaccttg acactgaagc  550
551   tgtacaacaa cggctttact tcagtccaag gatatgcttt caatgggaca  600
601   aagctggatg ctgtttacct aaacaagaat aaatacctga cagttattga  650
651   caaagatgca tttggaggag tatacagtgg accaagcttg ctggacgtgt  700
701   ctcaaaccag tgtcactgcc cttccatcca aaggcctgga gcacctgaag  750
751   gaactgatag caagaaacac ctggactctt                        780
```

FIG. 4 HUMAN (wild type) TSHR260 PROTEIN (SEQ ID No 4)

```
  1   MRPADLLQLV LLLDLPRDLG GMGCSSPPCE CHQEEDFRVT CKDIQRIPSL PPSTQTLKLI   60
 61   ETHLRTIPSH AFSNLPNISR IYVSIDLTLQ QLESHSFYNL SKVTHIEIRN TRNLTYIDPD  120
121   ALKELPLLKF LGIFNTGLKM FPDLTKVYST DIFFILEITD NPYMTSIPVN AFQGLCNETL  180
181   TLKLYNNGFT SVQGYAFNGT KLDAVYLNKN KYLTVIDKDA FGGVYSGPSL LDVSQTSVTA  240
241   LPSKGLEHLK ELIARNTWTL                                              260
```

FIG. 5 DNA sequences of thermostabilising single point mutations of TSHR.

| Mutation | DNA sequence (3'-5') | Seq ID No |
|---|---|---|
| P28E | $G_{61}$GAATGGGGTGTTCGTCTCCA$G_{82}$ $A_{83}$ $G_{84}$ TGCGAGTGCCATCAGGAGGAG$_{105}$ | 11 |
| L59F | $C_{154}$CCAGTACGCAGACTCTGAAG$T_{175}T_{176}C_{177}$ATTGAGACTCACCTGAGAACT$_{198}$ | 12 |
| T62V | $C_{163}$AGACTCTGAAGCTTATTGAG$G_{184}T_{185}G_{186}$CACCTGAGAACTATTCCAAGT$_{207}$ | 13 |
| H63C | $A_{166}$CTCTGAAGCTTATTGAGAC$TT_{187}G_{188}C_{189}$CTGAGAACTATTCCAAGTCAT$_{210}$ | 14 |
| L64Y | $C_{169}$TGAAGCTTATTGAGACTCAC$T_{190}A_{191}C_{192}$AGAACTATTCCAAGTCATGCA$_{213}$ | 15 |
| R112P | $C_{313}$ACATAGAAATTCGGAATACC$C_{334}C_{335}C_{336}$AACTTAACTTACATAGACCCT$_{357}$ | 16 |
| P142I | $A_{403}$ACACTGGACTTAAAATGTTC$A_{424}T_{425}C_{426}$GACCTGACCAAAGTTTATTCC$_{447}$ | 17 |
| D143P | $A_{406}$CTGGACTTAAAATGTTCCCT$C_{427}C_{428}C_{429}$CTGACCAAAGTTTATTCCACT$_{450}$ | 18 |
| D151E | $C_{430}$TGACCAAAGTTTATTCCACT$G_{451}A_{452}G_{453}$ATATTCTTTATACTTGAAATT$_{474}$ | 19 |
| S166T | $A_{475}$CAGACAACCCTTACATGACG$A_{496}C_{497}C_{498}$ATCCCTGTGAATGCTTTTCAG$_{519}$ | 20 |
| I167F | $G_{478}$ACAACCCTTACATGACGTCA$T_{499}T_{500}C_{501}$CCTGTGAATGCTTTTCAGGGA$_{522}$ | 21 |
| P168Y | $A_{481}$ACCCTTACATGACGTCAATC$T_{502}A_{503}C_{504}$GTGAATGCTTTTCAGGGACTA$_{525}$ | 22 |
| V169R | $C_{484}$CTTACATGACGTCAATCCCT$A_{505}G_{506}G_{507}$AATGCTTTTCAGGGACTATGC$_{528}$ | 23 |
| N170W | $T_{487}$ACATGACGTCAATCCCTGTG$T_{508}G_{509}G_{510}$GCTTTTCAGGGACTATGCAAT$_{531}$ | 24 |
| T179C | $T_{514}$TTCAGGGACTATGCAATGAA$T_{535}G_{536}C_{537}$TTGACACTGAAGCTGTACAAC$_{558}$ | 25 |
| S191E | $C_{550}$TGTACAACAACGGCTTTACT$G_{571}A_{572}G_{573}$GTCCAAGGATATGCTTTCAAT$_{594}$ | 26 |
| I253R | $C_{736}$TGGAGCACCTGAAGGAACTGA$_{757}G_{758}A_{759}$GCAAGAAACACCTGGACTCTT$_{780}$ | 27 |
| R255Y | $C_{742}$ACCTGAAGGAACTGATAGCA$T_{763}A_{764}C_{765}$AACACCTGGACTCTT$_{780}$ | 28 |

Eighteen single TSHR mutations increased the thermostability by 1.5 times greater or more than the wild type TSHR260 fragment. The thermostability of the mutant was determined by its half-life at 42°C compared to the half-life of the wild type TSHR260. Seventeen of the single mutations were used in combination to further improve the thermostability of the TSHR260 fragment. S191E was not used for further mutant combination.

The mutated nucleotides are in bold. The subscript numbers are the positions of the nucleotides in the TSHR nucleotide sequence.

FIG. 6 Protein sequences of the thermostabilising single point mutations of TSHR.

| Mutation | Protein sequence | SEQ ID No |
|---|---|---|
| P28E | $G_{21}MGCSSP\mathbf{E_{28}}CECHQEE_{35}$ | 29 |
| L59F | $P_{52}STQTLK\mathbf{F_{59}}IETHLRT_{66}$ | 30 |
| T62V | $Q_{55}TLKLIE\mathbf{V_{62}}HLRTIPS_{69}$ | 31 |
| H63C | $T_{56}LKLIET\mathbf{C_{63}}LRTIPSH_{70}$ | 32 |
| L64Y | $L_{57}KLIETH\mathbf{Y_{64}}RTIPSHA_{71}$ | 33 |
| R112P | $H_{105}IEIRNT\mathbf{P_{112}}NLTYIDP_{119}$ | 34 |
| P142I | $N_{135}TGLKMF\mathbf{I_{142}}DLTKVYS_{149}$ | 35 |
| D143P | $T_{136}GLKMFP\mathbf{P_{143}}LTKVYST_{150}$ | 36 |
| D151E | $L_{144}TKVYST\mathbf{E_{151}}IFFILEI_{158}$ | 37 |
| S166T | $T_{159}DNPYMT\mathbf{T_{166}}IPVNAFQ_{173}$ | 38 |
| I167F | $D_{160}NPYMTS\mathbf{F_{167}}PVNAFQG_{174}$ | 39 |
| P168Y | $N_{161}PYMTSI\mathbf{Y_{168}}VNAFQGL_{175}$ | 40 |
| V169R | $P_{162}YMTSIP\mathbf{R_{169}}NAFQGLC_{176}$ | 41 |
| N170W | $Y_{163}MTSIPV\mathbf{W_{170}}AFQGLCN_{177}$ | 42 |
| T179C | $F_{172}QGLCNE\mathbf{C_{179}}LTLKLYN_{186}$ | 43 |
| S191E | $L_{184}YNNGFT\mathbf{E_{191}}VQGYAFN_{198}$ | 44 |
| I253R | $L_{246}EHLKEL\mathbf{R_{253}}ARNTWTL_{260}$ | 45 |
| R255Y | $H_{248}LKELIA\mathbf{Y_{255}}NTWTL_{260}$ | 46 |

Eighteen single TSHR mutations increased the thermostability by 1.5 times greater or more than the wild type TSHR260 fragment. The thermostability of the mutant was determined by its half-life at 42°C compared to the half-life of the wild type TSHR260. Seventeen of the single mutations were used in combination to further improve the thermostability of the TSHR260 fragment. S191E was not used for further mutant combination.

The mutated amino acid residues are in bold. The subscript numbers are the positions of the amino acids in the TSHR amino acid sequence.

FIG. 7A Thermostability of TSHR260-WT, TSHR260-I253R and TSHR260-JMG22 at 42°C

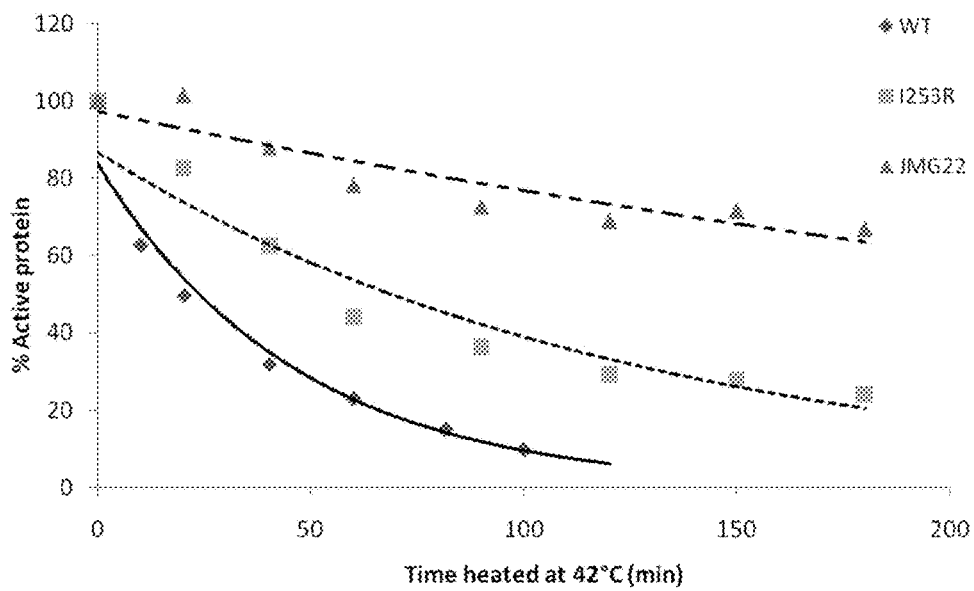

A representative thermostability assay at 42°C (Figure 12b). In this assay $t_{1/2}$(TSHR260-WT) = 31.5 ± 1.7 minutes; $t_{1/2}$(TSHR260-I253R) = 86 ± 7 minutes and $t_{1/2}$(TSHR260-JMG22) = 307 ± 49 minutes (TSHR260-JMG22 is too thermostable to accurately determine its half-life at 42°C.)

FIG. 7B Thermostability of TSHR260-I253R, TSHR260-JMG22 and TSHR260-JMG37 at 50°C

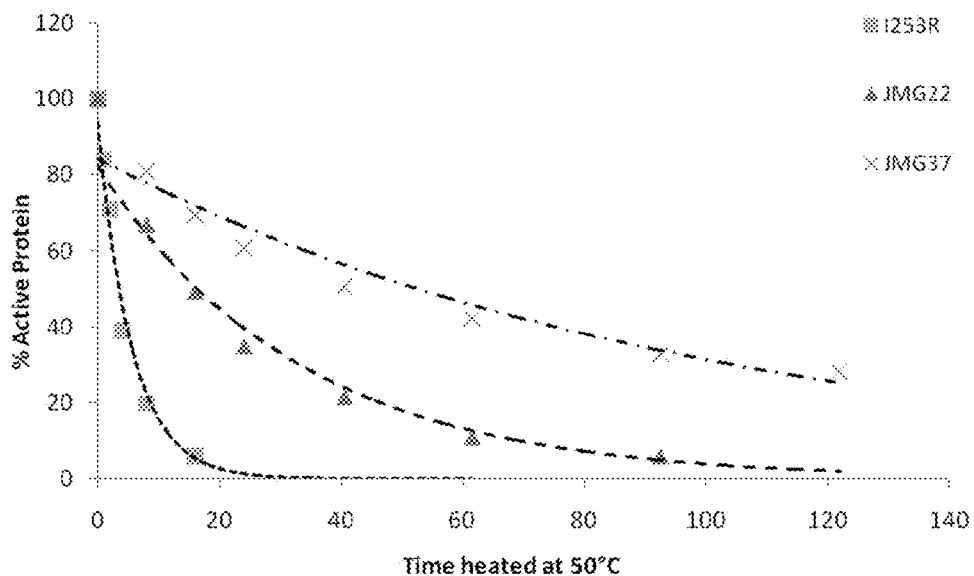

A representative thermostability assay at 50°C (Figure 12b). In this assay $t_{1/2}$(TSHR260-I253R) = 3.87 ± 0.14 minutes; $t_{1/2}$(TSHR260-JMG22) = 22.8 ± 1.0 minutes and $t_{1/2}$(TSHR260-JMG37) = 70 ± 5 minutes.

FIG. 7C Thermostability of TSHR260-I253R, TSHR260-JMG37 and TSHR260-JMG45 at 50°C

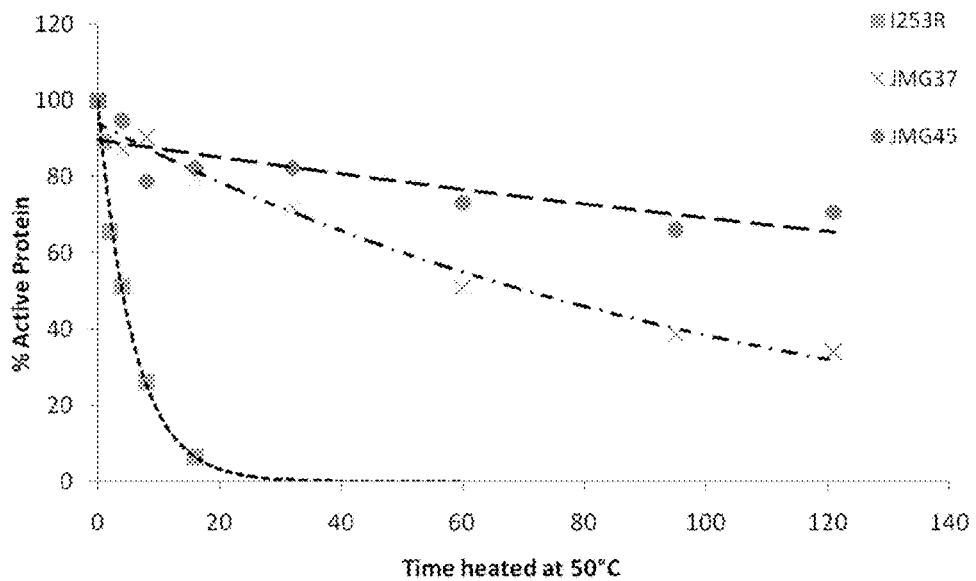

A representative thermostability assay at 50°C (Figure 12b). In this assay $t_{1/2}$(TSHR260-I253R) = 4.12 ± 0.16 minutes; $t_{1/2}$(TSHR260-JMG37) = 77 ± 3 minutes and $t_{1/2}$(TSHR260-JMG45) = 194 ± 32 minutes. (TSHR260-JMG45 is too thermostable to accurately determine its half-life at 50°C.)

FIG. 7D Thermostability of TSHR260-I253R, TSHR260-JMG45, TSHR260-JMG52 and TSHR260-JMG55 at 55°C

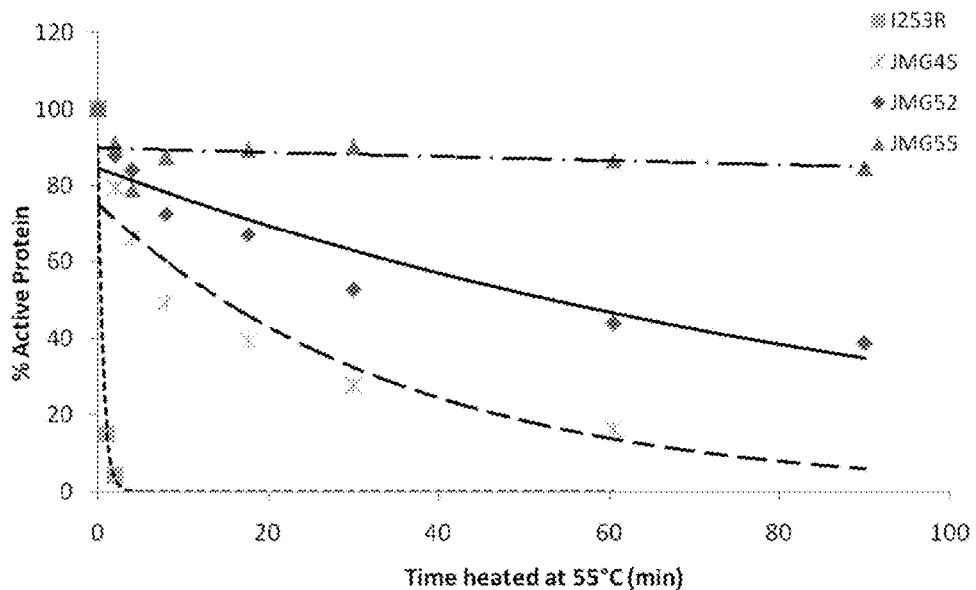

A representative thermostability assay at 55°C (Figure 12b). In this assay $t_{1/2}$(TSHR260-I253R) = 0.43 ± 0.03 minutes; $t_{1/2}$(TSHR260-JMG45) = 27.8 ± 1.8 minutes and $t_{1/2}$(TSHR260-JMG52) = 54 ± 6 minutes. (TSHR260-JMG55 is too thermostable to accurately determine its half-life at 50°C.)

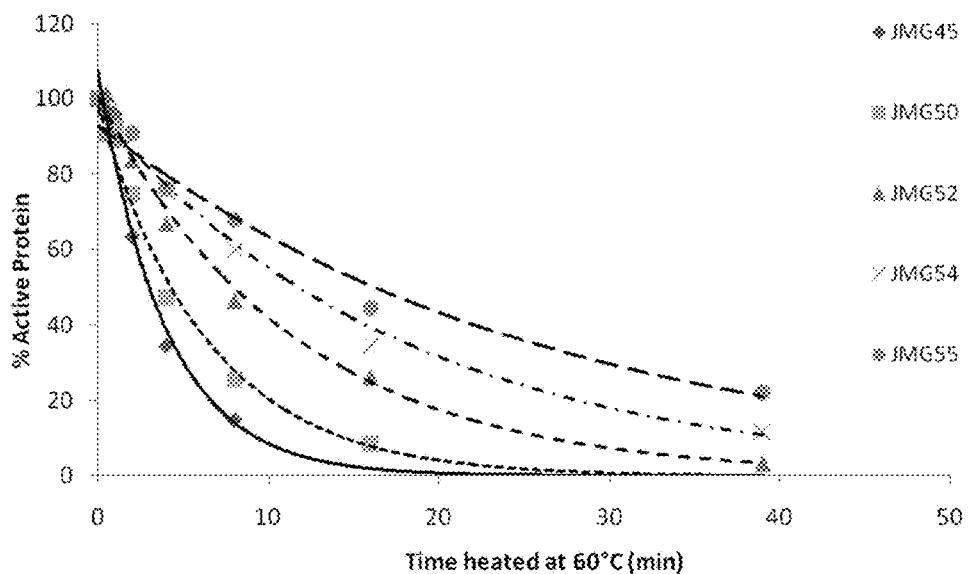
FIG. 7E Thermostability of TSHR260-JMG45, TSHR260-JMG50, TSHR260-JMG52, TSHR260-JMG54 and TSHR260-JMG55 at 60°C
A representative thermostability assay at 60°C (Figure 12b). In this assay $t_{1/2}$(TSHR260-JMG45) = 2.72 ± 0.11 minutes; $t_{1/2}$(TSHR260-JMG50) = 4.41 ± 0.11 minutes, $t_{1/2}$(TSHR260-JMG52) = 7.89 ± 0.09 minutes, $t_{1/2}$(TSHR260-JMG54) = 12.4 ± 0.3 minutes and $t_{1/2}$(TSHR260-JMG55) = 18.1 ± 0.6 minutes.

FIG. 8  Thermostability of full-length TSHR-WT, TSHR-JMG37, TSHR-JMG45, TSHR-JMG52, and TSHR-JMG55 at 50°C, on 14C4 Fab$_2$ plates.
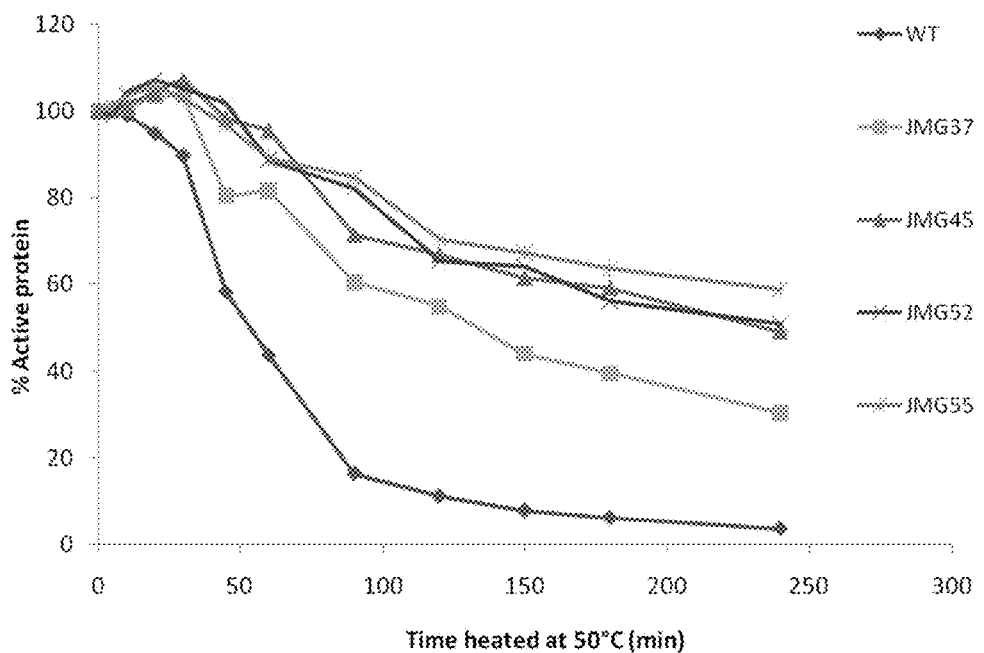
Full-length TSHR heated at 50°C, on 14C4-Fab$_2$ plates (Figure 14b): $t_{1/2}$(TSHR-WT) = 32.5 minutes; $t_{1/2}$(TSHR-JMG37) = 110 minutes, $t_{1/2}$(TSHR-JMG45) = 173 minutes, $t_{1/2}$(TSHR-JMG52) = 175.4 minutes and $t_{1/2}$(TSHR-JMG55) = 226 minutes.

FIG. 9 Positions of the native residues of most thermostabilising single mutations of TSHR260.
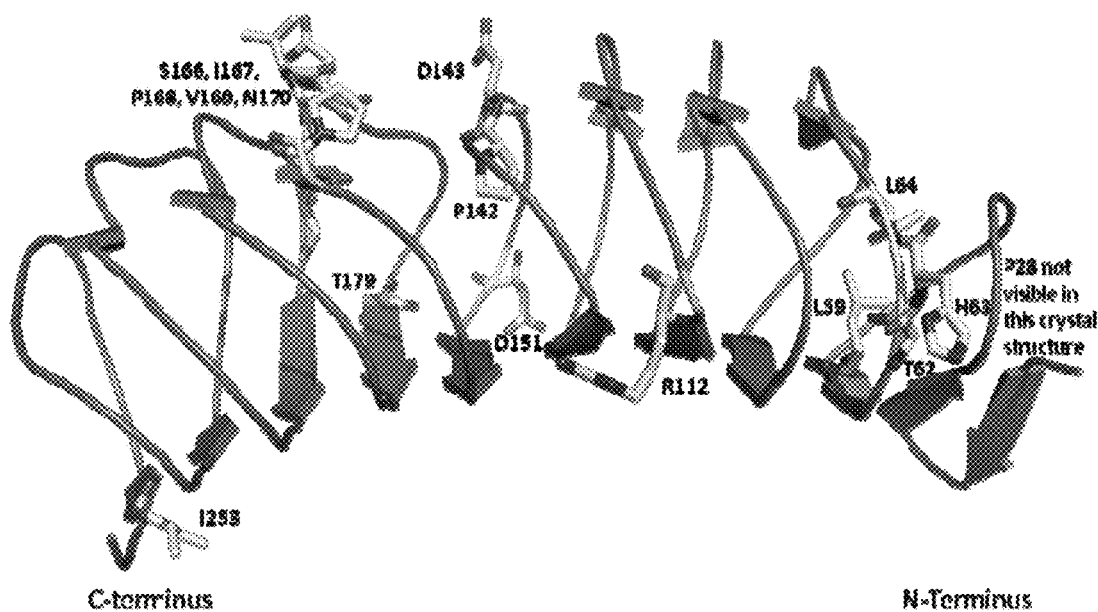
TSHR260 is in cartoon representation (PDB code 3G04). The residues which formed the most thermostabilising single mutations are in stick representation. Figure made with Pymol (Schrodinger, LLC).

FIG. 10A    Sequence alignment of TSHR260 from different species. SEQ ID Nos given in brackets following the species.

| Species | Amino acid sequence | |
|---|---|---|
| Human (2) | MRPADLLQLVLLLDLPRDLGGMGCSSPPCECHQEEDFRVTCKDIQRIPSLPPSTQTLKLIETHLR | 65 |
| Grivet monkey (47) | MRPADLLQLVLLLVLPRDLGGKGCSSPPCECQQEEDFRVTCKDIQRIPSLPPSTQTLKLIETRLR | 65 |
| Rhesus monkey (48) | MRPADLLQLVLLLVLPRDLGGKGCSSPPCECQQEEDFRVTCKDIQRIPSLPPSTQTLKLIETRLR | 65 |
| Porcine (49) | MSLTPLLQLALVLALPRSLRGKGCPSPPCECHQEDDFRVTCKDIHSIPPLPPNTQTLKFIETHLK | 65 |
| Bovine (50) | MRPTPLLRLALFLVLPSSLGGERCPSPPCECRQEDDFRVTCKDIQSIPSLPPSTQTLKFIETHLK | 65 |
| Cat (51) | MRQTPLLQLALLLSLPRSLGGKGCPSPPCECHQEDDFRVTCKDIHRIPSLPPSTQTLKFIETHLK | 65 |
| Dog (52) | MRPPPLLHLALLLALPRSLGGKGCPSPPCECHQEDDFRVTCKDIHRIPTLPPSTQTLKFIETQLK | 65 |
| Mouse (53) | MRPGSLLLLVLLLALSRSLRGKECASPPCECHQEDDFRVTCKELHRIPSLPPSTQTLKLIETHLK | 65 |
| Rat (54) | MRPGSLLQLTLLLALPRSLWGRGCTSPPCECHQEDDFRVTCKELHQIPSLPPSTQTLKLIETHLK | 65 |
| Sheep (55) | MRPTPLLRLALLLVLPSSLWGERCPSPPCECRQEDDFRVTCKDIQRIPSLPPSTQTLKFIETHLK | 65 |
| Horse (56) | MRPTPLLQLVLLLALPRSLGGKGCPSPPCECHQEDDFRVTCKDIHHIPSLPPSTQTLKFTETHLK | 65 |

| Species | Amino acid sequence | |
|---|---|---|
| Human (2) | TIPSHAFSNLPNISRIYVSIDVTLQQLESHSFYNLSKVTHIEIRNTRNLTYIDPDALKELPLLKF | 130 |
| Grivet monkey (47) | TIPSHAFSSLPNISRIYLSIDATLQQLESHSFYNLNKVTHIEIRNTRSLTYIDPDALKELPLLKF | 130 |
| Rhesus monkey (48) | TIPSHAFSSLPNISRIYLSIDATLQQLETHSFYNLNKVTHIEIRNTRSLTYIDPDALKELPLLKF | 130 |
| Porcine (49) | TIPSRAFSNLPNISRIYLSIDATLQQLESQSFYNLSKMTHIEIRNTRSLTYINPGALKDLPLLKF | 130 |
| Bovine (50) | TIPSRAFSNLPNISRIYLSIDATLQQLESHSFYNLSKVTHIEIRNTRSLTYIDSGALKELPLLKF | 130 |
| Cat (51) | TIPSRAFSNLPNISRIYLSIDATLQRLESHSFYNLSKMTHIEIRNTRSLTYIDPGALKELPLLKF | 130 |
| Dog (52) | TIPSRAFSNLPNISRIYLSIDATLQRLESHSFYNLSKMTHIEIRNTRSLTSIDPDALKELPLLKF | 130 |
| Mouse (53) | TIPSLAFSSLPNISRIYLSIDATLQRLEPHSFYNLSKMTHIEIRNTRSLTYIDPDALTELPLLKF | 130 |
| Rat (54) | TIPSLAFSSLPNISRIYLSIDATLQRLEPHSFYNLSKMTHIEIRNTRSLTYIDPDALTELPLLKF | 130 |
| Sheep (55) | TIPSRAFSNLPNISRIYLSIDATLQQLESHSFYNLSKVTHIEIRNTRSLTYIDSGALKELPLLKF | 130 |
| Horse (56) | TIPSRAFSNLPNISRIYLSIDTSLQRLESHSFYNLSKMTHIEIRNTRSLTYIEPGALKELPLLKF | 130 |

| Species | Amino acid sequence | |
|---|---|---|
| Human (2) | LGIFNTGLKMFPDLTKVYSTDIFFILEITDNPYMTSIPVNAFQGLCNETLTLKLYNNGFTSVQGY | 195 |
| Grivet monkey (47) | LGIFNTGLKMFPDLTKVYSTDIFFILEITDNPYMTSIPVNAFQGLCNETLTLKLYNNGFTSIQGY | 195 |
| Rhesus monkey (48) | LGIFNTGLKMFPDLTKVYSTDIFFILEITDNPYMTSIPVNAFQGLCNETLTLKLYNNGFTSIQGY | 195 |
| Porcine (49) | LGIFNTGLRIFPDLTKVYSTDVFFILEITDNPYMTSIPANAFQGLCNETLTLKLYNNGFTSVQGH | 195 |
| Bovine (50) | LGIFNTGLRVFPDLTKIYSTDVFFILEITDNPYMTSIPANAFQGLCNETLTLKLYNNGFTSIQGH | 195 |
| Cat (51) | LGIFNTGLGVFPDLTKVYSTDVFFILEITDNPYMTSIPANAFQGLCNETLTLKLYNNGFTSIQGH | 195 |
| Dog (52) | LGIFNTGLGVFPDVTKVYSTDVFFILEITDNPYMASIPANAFQGLCNETLTLKLYNNGFTSIQGH | 195 |
| Mouse (53) | LGIFNTGLRIFPDLTKIYSTDIFFILEITDNPYMTSVPENAFQGLCNETLTLKLYNNGFTSVQGH | 195 |
| Rat (54) | LGIFNTGLRIFPDLTKIYSTDVFFILEITDNPYMTSVPENAFQGLCNETLTLKLYNNGFTSIQGH | 195 |
| Sheep (55) | LGIFNTGLRVFPDLTKIYSTDVFFILEITDNPYMTSVPANAFQGLSNETLTLKLYNNGFTSIQGH | 195 |
| Horse (56) | LGIFNTGLRVFPDLTKVYSTDVFFILEITDNPYMTSIPANAFQGLCNETLTVKLYNNGFTSIQGH | 195 |

| Species | Amino acid sequence | |
|---|---|---|
| Human (2) | AFNGTKLDAVYLNKNKYLTVIDKDAFGGVYSGPSLLDVSQTSVTALPSKGLEHLKELIARNTWTL | 260 |
| Grivet monkey (47) | AFNGTKLDAVYLNKNKYLTVIDKDAFGGVYSGPSLLDVSHTSVTALPSKGLEHLKELIARNTWTL | 260 |
| Rhesus monkey (48) | AFNGTKLDAVYLNKNKYLTVIDKDAFGGVYSGPSLLDVSHTSVTALPSKGLEHLKELIARNTWTL | 260 |
| Porcine (49) | AFNGTKLDAVYLNKNKYLTVIDKDAFGGVFSGPTLLDVSYTSVTALPPKGLEHLKELIARNTWTL | 260 |
| Bovine (50) | AFNGTKLDAVYLNKNKYLTVIGQDAFAGVYSGPTLLDISYTSVTALPSKGLEHLKELIARNTWTL | 260 |
| Cat (51) | AFNGTKLDAVYLNKNKYLTAIDQDAFGGVYSGPTLLDVSYTSVTALPSKGLEHLKELIARNTWTL | 260 |
| Dog (52) | AFNGTKLDAVYLNKNKYLSAIDKDAFGGVYSGPTLLDVSYTSVTALPSKGLEHLKELIARNTWTL | 260 |
| Mouse (53) | AFNGTKLDAVYLNKNKYLTAIDNDAFGGVYSGPTLLDVSSTSVTALPSKGLEHLKELIAKDTWTL | 260 |
| Rat (54) | AFNGTKLDAVYLNKNKYLTAIDKDAFGGVYSGPTLLDVSSTSVTALPSKGLEHLKELIAKNTWTL | 260 |
| Sheep (55) | AFNGTKLDAVYLNKNKYLTVIDQDAFAGVYSGPTLLDISYTSVTALPSKGLEHLKELIARNTWTL | 260 |
| Horse (56) | AFNGTKLDAVYLNKNKYLTVIDKDAFGGVYSGPTLLDVSYTTLTALPSKGLEHLKELIARNTWTL | 260 |

FIG 10B    Sequence alignment of TSHR260 from different species. SEQ ID Nos given in brackets following the species.

| Species | Amino acid sequence | |
|---|---|---|
| Human (2) | KKLPLSLSFLHLTRADLSYPSHCCAFKNQKKIRGILESLMCNESSMQSLRQRKSVNALNSPLHQE | 325 |
| Grivet monkey (47) | KKLPLSLSFLHLTRADLSYPSHCCAFKNQKKIRGILESLMCNESSMQSLRQRKSVNALNSPLHQE | 325 |
| Rhesus monkey (48) | KKLPLSLSFLHLTRADLSYPSHCCAFKNQKKIRGIPESLMCNESSMQSLRQRKSVNALNSPLHQE | 325 |
| Porcine (49) | KKLPLSLSFLHLTRADLSYPSHCCAFKNQKKIRGILESLMCNESSIRSLRQRKSVNAVNGPFYQE | 325 |
| Bovine (50) | RKLPLSLSFLHLTRADLSYPSHCCAFKNQKKIRGILQSLMCNESSIRGLRQRKSASALNGPFYQE | 325 |
| Cat (51) | KKLPLTLSFLHLTRADLSYPSHCCAFKNQKKIRGILESFMCNDSSIRSLRQRKSVNALNGPFDQE | 325 |
| Dog (52) | KKLPLSLSFLHLTRADLSYPSHCCAFKNQKKIRGILESLMCNESSIRSLRQRKSVNTLNGPFDQE | 325 |
| Mouse (53) | KKLPLSLSFLHLTRADLSYPSHCCAFKNQKKIRGILESLMCNESSIRNLRQRKSVNILRGPIYQE | 325 |
| Rat (54) | KKLPLSLSFLHLTRADLSYPSHCCAFKNQKKIRGILESLMCNESSIRNLRQRKSVNVMRGPVYQE | 325 |
| Sheep (55) | KKLPLSLSFLHLTRADLSYPSHCCAFKNQKNIRGILQSLMCNESSIWGLRQRKSASALNGPFYQE | 325 |
| Horse (56) | KKLPLSLSFLHLTRADLSYPSHCCAFKNQKKIRGILESLMCNESSIRNLRQKKSVNALNGPFYQE | 325 |

| Species | Amino acid sequence | |
|---|---|---|
| Human (2) | YEENLGDSIVGYKEKSKFQDTHNNAHYYVFFEEQEDEIIGFGQELKNPQEETLQAFDSHYDYTIC | 390 |
| Grivet monkey (47) | YEENLDDGIVGYKEKSKFQDAHNNAHYYVFFEEQEDEIIGFGQELKNPQEETLQAFDSHYDYTVC | 390 |
| Rhesus monkey (48) | YEENLDDGIVGYKEKSKFQDAHNNAHYYVFFEEQEDEIIGFGQELKNPQEETLQAFDSHYDYTVC | 390 |
| Porcine (49) | YEEDLGDTSVGNKENSKFQDTHSNSHYYVFFEEQEDEIIGFGQELKNPQEETLQAFDSHYDYTVC | 390 |
| Bovine (50) | YEDXLGDGSAGYKENSKFQDTQSNSHYYVFFEEQEDEIIGFGQQLKNPQEETLQAFDSHYDYTVC | 389 |
| Cat (51) | YEEYLGDSHAGYKDNSKFQDTRSNSHYYVFFEEQXDEILGFGQELKNPQEETLQAFDSHYDYTVC | 389 |
| Dog (52) | YEEYLGDSHAGYKDNSQFQDTDSNSHYYVFFEEQEDEILGFGQELKNPQEETLQAFDSHYDYTVC | 390 |
| Mouse (53) | YEEDPGDNSVGYKQNSKFQESPSNSHYYVFFEEQEDEVVGFGQELKNPQEETLQAFESHYDYTVC | 390 |
| Rat (54) | YEEGLGDNHVGYKQNSKFQEGPSNSHYYVFFEEQEDEIIGFGQELKNPQEETLQAFDSHYDYTVC | 390 |
| Sheep (55) | YEEDLGDGSAGYKENSKFQDTHSNSHYYVFFEDQEDEIIGFGQELKNPQEETLQAFDNHYDYTVC | 390 |
| Horse (56) | YEEGLGDSSAGYKENSKFQDIHSNSHYYVFFEEQEDEIIGFGQELKNPQEETLQAFDSSYDYTVC | 390 |

| Species | Amino acid sequence | |
|---|---|---|
| Human (2) | GDSEDMVCTPKSDEFNPCEDIMGYKFLRIVVWFVSLLALLGNVFVLLILLTSHYKLNVPRFLMCN | 455 |
| Grivet monkey (47) | GDNEDMVCTPKSDEFNPCEDIMGYKFLRIVVWFVSLLALLGNVFVLLILLTSHYKLNVPRFLMCN | 455 |
| Rhesus monkey (48) | GDNEDMVCTPKSDEFNPCEDIMGYKFLRIVVWFVSLLALLGNVFVLLILLTSHYKLNVPRFLMCN | 455 |
| Porcine (49) | GGSEDMVCTPKSDEFNPCEDIMGYRFLRIVVWFVSLLALLGNVFVLVILLTSHYKLTVPRFLMCN | 455 |
| Bovine (50) | GGSEDMVCTPKSDEFNPCEDIMGYKFLRIVVWFVSLLALLGNVFVLVILLTSHYKLTVPRFLMCN | 454 |
| Cat (51) | GGNEDMVCTPKSDEFNPCEDIMGYKFLRIVVWFVSLLALLGNVFVLIILLTSHYKLTVPRFLMCN | 454 |
| Dog (52) | GGNEDMVCTPKSDEFNPCEDIMGYKFLRIVVWFVSLLALLGNVFVLIVLLTSHYKLTVPRFLMCN | 455 |
| Mouse (53) | GDNEDMVCTPKSDEFNPCEDIMGYRFLRIVVWFVSLLALLGNIFVLLILLTSHYKLTVPRFLMCN | 455 |
| Rat (54) | GDNEDMVCTPKSDEFNPCEDIMGYKFLRIVVWFVSPMALLGNVFVLFVLLTSHYKLTVPRFLMCN | 455 |
| Sheep (55) | GGSEEMVCTPKSDEFNPCEDIMGYKFLRIVVWFVSLLALLGNVFVLVILLTSHYKLTVPRFLMCN | 455 |
| Horse (56) | GGNEDMVCTPKSDEFNPCEDIMGYKFLRIVVWFVSLLALLGNVFVLVILLTSHYKLTVPRFLMCN | 455 |

| Species | Amino acid sequence | |
|---|---|---|
| Human (2) | LAFADFCMGMYLLLIASVDLYTHSEYYNHAIDWQTGPGCNTAGFFTVFASELSVYTLTVITLERW | 520 |
| Grivet monkey (47) | LAFADFCMGMYLLLIASVDLYTHSEYYNHAIDWQTGPGCNTAGFFTVFASELSVYTLTVITLERW | 520 |
| Rhesus monkey (48) | LAFADFCMGMYLLLIASVDLYTHSEYYNHAIDWQTGPGCNTAGFFTVFASELSVYTLTVITLERW | 520 |
| Porcine (49) | LAFADFCMGMYLLLIASVDLYTQSEYYNHAIDWQTGPGCNTAGFFTVFASELSVYTLTVITLERW | 520 |
| Bovine (50) | LAFADFCMGLYLLLIASVDLYTQSEYYNHAIDWQTGPGCNTAGFFTVFASELSVYTLTVITLERW | 519 |
| Cat (51) | LAFADFCMGMYLLLIASVDLYTHSEYYNHAIDWQTGPGCNAAGFFTVFASELSVYTLTVITLERW | 519 |
| Dog (52) | LAFADFCMGMYLLLIASVDLYTHSEYYNHAIDWQTGPGCNTAGFFTVFASELSVYTLTVITLERW | 520 |
| Mouse (53) | LAFADFCMGVYLLLIASVDLYTHSEYYNHAIDWQTGPGCNTAGFFTVFASELSVYTLTVITLERW | 520 |
| Rat (54) | LAFADFCMGVYLLLIASVDLYTHTEYYNHAIDWQTGPGCNTAGFFTVFASELSVYTLTVITLERW | 520 |
| Sheep (55) | LAFADFCMGLYLLLIASVDLYTQSEYYNHAIDWQTGPGCNTAGFFTVFASELSVYTLTVITLERW | 520 |
| Horse (56) | LAFADFCMGMYLLLIASVDLYTHSEYYNHAIDWQTGPGCNTAGFFTVFASELSVYTLTVITLERW | 520 |

FIG. 10C  Sequence alignment of TSHR260 from different species. SEQ ID Nos given in brackets following the species.

| Species | Amino acid sequence | |
|---|---|---|
| Human (2) | YAITFAMRLDRKIRLRHACAIMVGGWVCCFLLALLPLVGISSYAKVSICLPMDTETPLALAYIVF | 585 |
| Grivet monkey (47) | YAITFAMRLDRKIRLRHACAIMVGGWVCCFLLALLPLVGISSYAKVSICLPMDTETPLALAYIVF | 585 |
| Rhesus monkey (48) | YAITFAMRLDRKIRLRHACAIMVGGWVCCFLLALLPLVGISSYAKVSICLPMDTETPLALAYIVF | 585 |
| Porcine (49) | YAITFAMRLDRKIRLRHAYAIMAGGWVCCFLLALLPLVGISSYAKVSICLPMDTETPLALAYIIL | 585 |
| Bovine (50) | HAITFAMRLDRKIRLWHAYVIMLGGWVCCFLLALLPLVGISSYAKVSICLPMDTETPLALAYIIL | 584 |
| Cat (51) | YAITFAMRLDRKMRLRHAYAIMVGGWVCCFLLALLPLVGISSYAKVSICLPMDTETPLALAYIIL | 584 |
| Dog (52) | YAITFAMRLDRKIRLRHAYAIMVGGWVCCFLLALLPLVGISSYAKVSICLPMDTETPLALAYIIL | 585 |
| Mouse (53) | YAITFAMRLDRKIRLRHAYTIMAGGWVSCFLLALLPMVGISSYAKVSICLPMDTDTPLALAYIVL | 585 |
| Rat (54) | YAITFAMRLDRKIRLRHAYTIMAGGWVSCFLLALLPMVGISSYAKVSICLPMDTDTPLALAYIAL | 585 |
| Sheep (55) | YAITFAMHLDRKIRLWHAYVIMLGGWVCCFLLALLPLVGISSYAKVSICLPMDTETPLALAYIIL | 585 |
| Horse (56) | YAITFAMRLDRKIRLRHAYIIMVGGWVCCFLLALLPLVGISSYAKVSICLPMDTETPLALAYIIL | 585 |

| Species | Amino acid sequence | |
|---|---|---|
| Human (2) | VLTLNIVAFVIVCCCYVKIYITVRNPQYNPGDKDTKIAKRMAVLIFTDFICMAPISFYALSAILN | 650 |
| Grivet monkey (47) | VLTLNIVAFVIVCCCYVKIYITVRNPQYNPGDKDTKIAKRMAVLIFTDFMCMAPISFYALSAILN | 650 |
| Rhesus monkey (48) | VLTLNIVAFVIVCCCYVKIYITVRNPQYNPGDKDTKIAKRMAVLIFTDFICMAPISFYALSAILN | 650 |
| Porcine (49) | VLLLNIVAFTIVCSCYVKIYITVRNPQYNPGDKDTKIAKRMAVLIFTDFMCMAPISFYALSALMN | 650 |
| Bovine (50) | VLLLNIIAFIIVCACYVKIYITVRNPHYNPGDKDTRIAKRMAVLIFTDFMCMAPISFYALSALMN | 649 |
| Cat (51) | VLLLNIVAFIIVCSCYVKIYITVRNPQYNTGDKDTKIAKRMAVLIFTDFMCMAPISFYALSALMN | 649 |
| Dog (52) | VLLLNIVAFIIVCSCYVKIYITVRNPQYNPGDKDTKIAKRMAVLIFTDFMCMAPISFYALSALMN | 650 |
| Mouse (53) | VLLLNVVAFVVVCSCYVKIYITVRNPQYNPRDKDTKIAKRMAVLIFTDFMCMAPISFYALSALMN | 650 |
| Rat (54) | VLLLNVVAFVIVCSCYVKIYITVRNPQYNPRDKDTKIAKRMAVLIFTDFMCMAPISFYALSALMN | 650 |
| Sheep (55) | VLLLNIIAFIIVCACYVKIYITVRNPHYNPGDKDTRIAKRMAVLIFTDFMCMAPISFYALSALMN | 650 |
| Horse (56) | VLLLNIVAFIIVCSCYVKIYITVRNPQYNPGDKDTKIAKRMAVLIFTDFMCMAPISFYALSALMN | 650 |

| Species | Amino acid sequence | |
|---|---|---|
| Human (2) | KPLITVSNSKILLVLFYPLNSCANPFLYAIFTKAFQRDVFILLSKFGICKRQAQAYRGQRVPPKN | 715 |
| Grivet monkey (47) | KPLITVSNSKILLVLFYPLNSCANPFLYAIFTKAFQRDVFILLSKFGICKRQAQAYRGQRVPPKN | 715 |
| Rhesus monkey (48) | KPLITVSNSKILLVLFYPLNSCANPFLYAIFTKAFQRDVFILLSKFGICKRQAQAYRGQRVPPKN | 715 |
| Porcine (49) | KPLITVTNSKILLVLFYPLNSCANPFLYAIFTKAFQRDVFILLSKFGFCKRQAQAYRGQRVSPKN | 715 |
| Bovine (50) | KPLITVTNSKILLVLFYPLNSCANPFLYAIFTKAFQRDVFMLLSKFGICKRQAQAYRGQRVSPKN | 714 |
| Cat (51) | KPLITVTNSKILLVLFYPLNSCANPFLYAIFTKFQRDVFILLSKFGICKRQAQAYRGQRVSPKN | 714 |
| Dog (52) | KPLITVTNSKILLVLFYPLNSCANPFLYAIFTKAFQRDVFILLSKFGICKRQAQAYRGQRVSPKN | 715 |
| Mouse (53) | KPLITVTNSKILLVLFYPLNSCANPFLYAIFTKAFQRDVFILLSKFGICKRQAQAYQGQRVCPNN | 715 |
| Rat (54) | KPLITVTNSGVLLVLFYPLNSCANPFLYAIFTKAFQRDVFILLSKFGLCKHQAQAYQAQRVCPNN | 715 |
| Sheep (55) | KPLITVTNSKILLVLFYPLNSCANPFLYAIFTKAFQRDVFMLLSKFGICKRQAQAYRGQRVSSKN | 715 |
| Horse (56) | KPLITVTNSKILLVLFYPLNSCANPFLYAIFTKAFQRDVFILLSKFGICKRQAQAYRGQRVSQKN | 715 |

| Species | Amino acid sequence | |
|---|---|---|
| Human (2) | STDIQVQKVTHEMRQGLHNMEDVYELIEKSHLTPKKQGQISEEYMQTVL | 764 |
| Grivet monkey (47) | STDIQVQKVTHEMRQGLHNMEDVYELIENSHLTPKKQGQISEEYTQTVL | 764 |
| Rhesus monkey (48) | STDIQVQKVTHEMRQDLHNMQDVYELLENSHLTPKKQGQISEEYTQTVL | 764 |
| Porcine (49) | STGIQVQKVTQNMRQSLPNMQDDYELLENSHLTHKKHDQISKEYKQTVL | 764 |
| Bovine (50) | STGIRVQKVPPDVRQSLPNVQDDYELLENSHLTPKQQDQTSKEYKRTVL | 763 |
| Cat (51) | STGIQVQKVTRNMRQSLPNMQDDYELLENSHLTPNKQSHISKEYNQTVL | 763 |
| Dog (52) | SAGIQIQKVTRDMRQSLPNMQDEYELLENSHLTPNKQGQISKEYNQTVL | 764 |
| Mouse (53) | STGIQIQKIPQDTRQSLPNMQDTYELLGNSQLAPKLQGQISEEYKQTAL | 764 |
| Rat (54) | NTGIQIQKIPQDTRQSLPNVQDTYEPLGSSHLTPKLQGRISEEYTQTAL | 764 |
| Sheep (55) | STGIRVQKVPPDVRQSLPNVQDDYELLGNSHLTPKQQDQTSKEYKQTVL | 764 |
| Horse (56) | STGLQVQKVTQDMRQNLPNIQDAYELLENSHLTPNKRSQISKVYKQTVL | 764 |

FIG. 11A  Sequence alignment of human TSHR, human FSHR and human LHR. SEQ ID Nos given in brackets following the receptor.

| Sequence | Amino Acid sequence | |
|---|---|---|
| TSHR (2) | MRPADLLQLVLLLDLPRDLGGMG------CSSPPCECHQEEDFRVTCKDIQ---RIPS-LPPSTQT | 56 |
| FSHR (57) | MALLLVSLLAFLSLGSG-------------CHHRICHCS---NRVFLCQESKVTEIPSDLPRNAIE | 50 |
| LHR (58) | MKQRFSALQLLKLLLLLQPPLPRALREALCP-EPCNCVP--DGALRCPGPT---------AGLTR | 53 |

| Sequence | Amino Acid sequence | |
|---|---|---|
| TSHR (2) | LKLIETHLRTIPSHAFSNLPNISRIYVSIDVTLQQLESHSFYNLSKVTHIEIRNTRNLTYIDPDA | 121 |
| FSHR (57) | LRFVLTKLRVIQKGAFSGFGDLEKIEISQNDVLEVIEADVFSNLPKLHEIRIEKANNLLYINPEA | 115 |
| LHR (58) | LSLAYLPVKVIPSQAFRGLNEVIKIEISQIDSLERIEANAFDNLLNLSEILIQNTKNLRYIEPGA | 118 |

| Sequence | Amino Acid sequence | |
|---|---|---|
| TSHR (2) | LKELPLLKFLGIFNTGLKMFPDLTKVYSTDIFFILEITDNPYMTSIPVNAFQGLCNETLTLKLYN | 186 |
| FSHR (57) | FQNLPNLQYLLISNTGIKHLPDVHKIHSLQ-KVLLDIQDNINIHTIERNSFVGLSFESVILWLNK | 179 |
| LHR (58) | FINLPRLKYLSICNTGIRKFPDVTKVFSSESNFILEICDNLHITTIPGNAFQGMNNESVTLKLYG | 183 |

| Sequence | Amino Acid sequence | |
|---|---|---|
| TSHR (2) | NGFTSVQGYAFNGTKLDAVYLNKNKYLTVIDKDAFGGVYSGPSLLDVSQTSVTALPSKGLEHLKE | 251 |
| FSHR (57) | NGIQEIHNCAFNGTQLDELNLSDNNNLEELPNDVFHGA-SGPVILDISRTRIHSLPSYGLENLKK | 243 |
| LHR (58) | NGFEEVQSHAFNGTTLTSLELKENVHLEKMHNGAFRGA-TGPKTLDISSTKLQALPSYGLESIQR | 247 |

| Sequence | Amino Acid sequence | |
|---|---|---|
| TSHR (2) | LIARNTWTLKKLPLSLSFLHLTRADLSYPSHCCAFKNQKKIRGILESLMCNESSMQSLRQRKSVN | 316 |
| FSHR (57) | LRARSTYNLKKLPTLEKLVALMEASLTYPSHCCAFAN------------------WRRQIS--- | 286 |
| LHR (58) | LIATSSYSLKKLPSRETFVNLLEATLTYPSHCCAFRN------------------LPTKE--- | 289 |

| Sequence | Amino Acid sequence | |
|---|---|---|
| TSHR (2) | ALNSPLHQEYEENLGDSIVGYKEKSKFQDTHNNAHYYVFFEEQEDEIIGFGQELKNPQEETLQAF | 381 |
| FSHR (57) | ----ELHPICNKSILRQEVDYMTQARGQRSSLAEDNESSYSRG----------------FDMT | 329 |
| LHR (58) | --------QNFSHSISENFS-KQCESTVRKVNNKTLYSSMLAES--------E---------LSGW | 329 |

| Sequence | Amino Acid sequence | |
|---|---|---|
| TSHR (2) | DSHYDYTICGDSEDMVCTPKSDEFNPCEDIMGYKFLRIVVWFVSLLALLGNVFVLLILLTSHYKL | 446 |
| FSHR (57) | YTEFDYDLCNEVVDVTCSPKPDAFNPCEDIMGYNILRVLIWFISILAITGNIIVLVILTTSQYKL | 394 |
| LHR (58) | DYEYGFCLPKTPR----CAPEPDAFNPCEDIMGYDFLRVLIWLINILAIMGNMTVLFVLLTSRYKL | 391 |

| Sequence | Amino Acid sequence | |
|---|---|---|
| TSHR (2) | NVPRFLMCNLAFADFCMGMYLLLIASVDLYTHSEYYNHAIDWQTGPGCNTAGFFTVFASELSVYT | 511 |
| FSHR (57) | TVPRFLMCNLAFADLCIGIYLLLIASVDIHTKSQYHNYAIDWQTGAGCDAAGFFTVFASELSVYT | 459 |
| LHR (58) | TVPRFLMCNLSFADFCMGLYLLLIASVDSQTKGQYYNHAIDWQTGSGCSTAGFFTVFASELSVYT | 456 |

| Sequence | Amino Acid sequence | |
|---|---|---|
| TSHR (2) | LTVITLERWYAITFAMRLDRKIRLRHACAIMVGGWVCCFLLALLPLVGISSYAKVSICLPMDTET | 576 |
| FSHR (57) | LTAITLERWHTITHAMQLDCKVQLRHAASVMVMGWIFAFAAALFPIFGISSYMKVSICLPMDIDS | 524 |
| LHR (58) | LTVITLERWHTITYAIHLDQKLRLRHAILIMLGGWLFSSLIAMLPLVGVSNYMKVSICFPMDVET | 521 |

| Sequence | Amino Acid sequence | |
|---|---|---|
| TSHR (2) | PLALAYIVFVLTLNIVAFVIVCCCYVKIYITVRNPQYNPGDKDTKIAKRMAVLIFTDFICMAPIS | 641 |
| FSHR (57) | PLSQLYVMSLLVLNVLAFVVICGCYIHIYLTVRNPNIVSSSSDTRIAKRMAMLIFTDFLCMAPIS | 589 |
| LHR (58) | TLSQVYILTILILNVVAFFIICACYIKIYFAVRNPELMATNKDTKIAKKMAILIFTDFTCMAPIS | 586 |

| Sequence | Amino Acid sequence | |
|---|---|---|
| TSHR (2) | FYALSAILNKPLITVSNSKILLVLFYPLNSCANPFLYAIFTKAFQRDVFILLSKFGICKRQAQAY | 706 |
| FSHR (57) | FFAISASLKVPLITVSKAKILLVLFHPINSCANPFLYAIFTKNFRRDFFILLSKCGCYEMQAQIY | 654 |
| LHR (58) | FFAISAAFKVPLITVTNSKVLLVLFYPINSCANPFLYAIFTKTFQRDFFLLLSKFGCCKRRAELY | 651 |

FIG. 11B    Sequence alignment of human TSHR, human FSHR and human LHR. SEQ ID Nos given in brackets following the receptor.

| Sequence | Amino Acid sequence | |
|---|---|---|
| TSHR (2) | RGQRVPPKNSTDIQVQKVTHDMRQGLHN-MEDVYELIENSHLTPKKQGQISEEYMQTVL | 764 |
| FSHR (57) | R---------TETSSTVHNTHPRNGHCS---SAPRVTNGSTYILVPLSHLAQN | 695 |
| LHR (58) | R------RK--DFSAY--TSNCKNGFTGSNKPSQSTLKLSTLHCQGTALLDKTRYTEC | 699 |

FIG. 12A  Diagram showing TSHR260-binding assay

14C4-coated ELISA plate well + TSHR260 mutant

↓ Capture

|–14C4–TSHR260 mutant

↓ + M22-POD (for example, or another autobody
such as K1-70-POD or K1-18-POD)

|–14C4–TSHR260 mutant–M22-POD

↓ + TMB

Colour change proportional to M22-POD bound to active TSHR260 mutant

FIG. 12B  Diagram showing TSHR260 thermostability assay

TSHR260 mutant

↓ + Heat treatment

↙ ↘

TSHR260 mutant(active)                                TSHR260 mutant(inactive)

↓ Capture onto 14C4-                                  ↓ Capture onto 14C4-
coated ELISA plate well                               coated ELISA plate well

|–14C4–TSHR260 mutant(active)                         TSHR260 mutant(inactive)

↓ + M22-POD (for e.g.)                                ↓ + M22-POD (for e.g.)

|–14C4–TSHR260 mutant(active)–M22-POD                 TSHR260 mutant(inactive)

↓ + TMB                                               ↓ + TMB
Colour change proportional to M22-POD bound to        No colour change
active TSHR260 mutant present FIG. 12C    Diagram showing assay for inhibition of M22-POD binding to TSHR260

14C4 coated ELISA plate well + TSHR260 mutant

↓ Capture

⊢14C4—TSHR260 mutant

↓ + TSHR autoantibody (K1-70, K1-18 or patient sera)

↙ ↘

⊢14C4—TSHR260 mutant—TSHR autoantibody    ⊢14C4—TSHR260 mutant (showing no reactivity with TSHR autoantibodies)

↓ + M22-POD            ↓ + M22-POD

⊢14C4—TSHR260 mutant—TSHR autoantibody    ⊢14C4—TSHR260 mutant—M22-POD

↓ + TMB               ↓ + TMB
Reduced or no colour change    Colour change

FIG. 12D    Diagram for assay of TSHR260-JMG55 coated ELISA plate well assay

ELISA plate well + TSHR260-JMG55

↓ Capture

⊢TSHR260-JMG55

↓ + M22-POD (or, for example, K1-70-POD or K1-18-POD)

⊢TSHR260-JMG55—M22-POD

↓ + TMB

Colour change proportional to M22-POD bound to TSHR260-JMG55

FIG. 13A      Diagram showing TSHR260-AP bridge ELISA
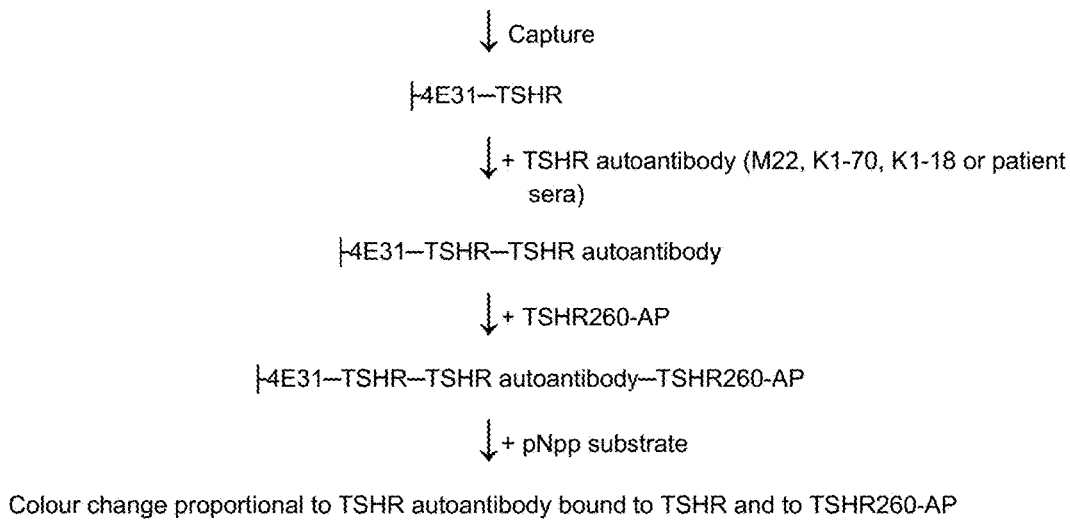
FIG. 13B      Diagram showing thermostability assay for TSHR260-AP mutants
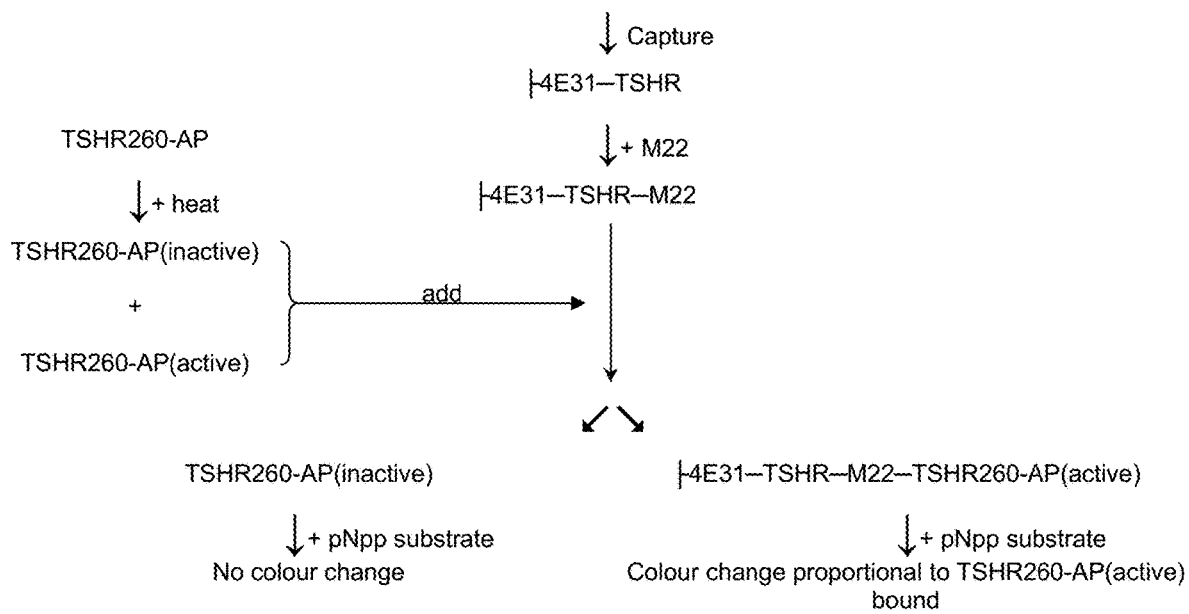

FIG. 13C    Diagram of TSHR260-AP bridge inhibition ELISA to detect activity of TSHR260 before and after purification 4E31-coated ELISA plate well + TSHR ↓ Capture

⊢4E31—TSHR

↓ + TSHR autoantibodies (for example, M22 or K1-70)

⊢4E31—TSHR—TSHR autoantibodies

↓ + TSHR260 (test sample)

(active TSHR260 (test sample) blocks TSHR260-AP binding) ↙   ↘ (inactive TSHR260 (test sample) does not block TSHR260-AP binding)

⊢4E31—TSHR—TSHR autoantibody—TSHR260                    ⊢4E31—TSHR—TSHR autoantibody

↓ + TSHR260-AP                                           ↓ + TSHR260-AP

⊢4E31—TSHR—TSHR autoantibody—TSHR260                    ⊢4E31—TSHR—TSHR autoantibody—TSHR260-AP ↓ + pNpp substrate                                       ↓ + pNpp substrate Reduced or no colour change                              Colour change TSHR260 test sample refers, for example, to TSHR260-WT, TSHR260-JMG55 or TSHR260-WT in complex with TSHR monoclonal antibodies (14C4, 2H11, 25E1, 23H4, 36F11 or 9B7), which bind to the convex surface of TSHR260.

FIG. 14A    Diagram showing TSHR-binding assay
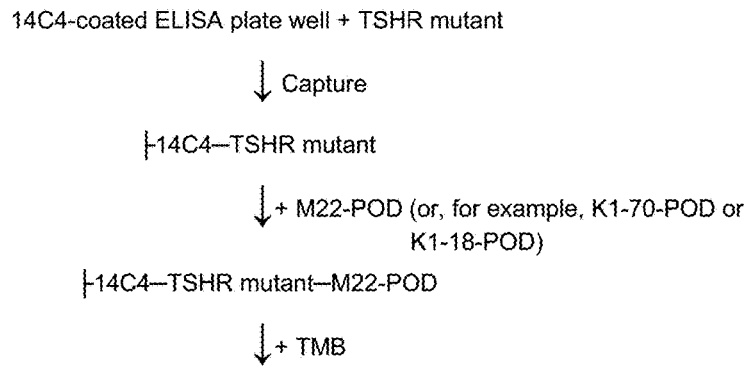
Colour change proportional to M22-POD bound to active TSHR mutant
This assay can be performed for example with either 14C4-coated ELISA plate wells or 4E31-coated ELISA plate wells.
FIG. 14B    Diagram showing TSHR stability assay A
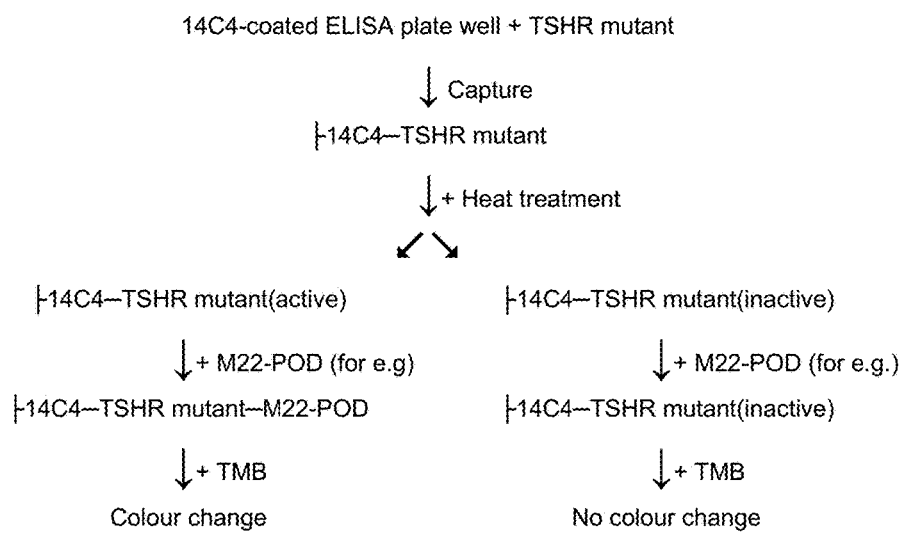

FIG. 14C     Diagram showing TSHR stability assay B

4E31-coated ELISA plate well + TSHR mutant

↓ Capture

⊢4E31—TSHR mutant

↓ + Heat treatment

↙ ↘

⊢4E31—TSHR mutant(active)            ⊢4E31—TSHR mutant(inactive)

↓ + M22-POD (for e.g.)                ↓ + M22-POD (for e.g.)

⊢4E31—TSHR mutant—M22-POD       ⊢4E31—TSHR mutant(inactive)

↓ + TMB                                       ↓ + TMB

Colour change                             No colour change

FIG. 14D     Diagram showing TSHR stability assay C

TSHR mutant

↓ + Heat treatment

↙ ↘

TSHR mutant(active)                     TSHR mutant(inactive)

↓ Capture onto 4E31-coated          ↓ Capture onto 4E31-coated
   ELISA plate well                              ELISA plate well ⊢4E31—TSHR mutant(active)           TSHR mutant(inactive)

↓ + M22-POD (for e.g.)                ↓ + M22-POD (for e.g.)

⊢4E31—TSHR mutant(active)—M22-POD     TSHR mutant(inactive)

↓ + TMB                                       ↓ + TMB

Colour change                             No colour change

FIG. 14E    Diagram showing assay based on inhibition of M22-POD binding to TSHR 14C4 coated ELISA plate well + TSHR mutant ↓ Capture ⊢14C4—TSHR mutant ↓ + TSHR autoantibody (K1-70, K1-18 or patient sera)

↙ ↘

⊢14C4—TSHR mutant—TSHR autoantibody     ⊢14C4—TSHR mutant (showing no reactivity with TSHR autoantibodies)

↓ + M22-POD (for e.g.)     ↓ + M22-POD (for e.g.)

⊢14C4—TSHR mutant—TSHR autoantibody     ⊢14C4—TSHR mutant—M22-POD

↓ + TMB     ↓ + TMB

Reduced or no colour change     Colour change

FIG. 15  TSHR260-AP DNA (SEQ ID No 59)

```
   1  atgaggccgg cggacttgct gcagctggtg ctgctgctcg acctgcccag ggacctgggc    60
  61  ggaatggggt gttcgtctcc accctgcgag tgccatcagg aggaggactt cagagtcacc   120
 121  tgcaaggata ttcaacgcat ccccagctta ccgccagta cgcagactct gaagcttatt   180
 181  gagactcacc tgagaactat tccaagtcat gcattttcta atctgcccaa tatttccaga   240
 241  atctacgtat ctatagatgt gactctgcag cagctggaat cacactcctt ctacaatttg   300
 301  agtaaagtga ctcacataga aattcggaat accaggaact taacttacat agaccctgat   360
 361  gccctcaaag agctccccct cctaaagttc cttggcattt tcaacactgg acttaaaatg   420
 421  ttccctgacc tgaccaaagt ttattccact gatatattct ttatacttga aattacagac   480
 481  aacccttaca tgacgtcaat ccctgtgaat gcttttcagg gactatgcaa tgaaaccttg   540
 541  acactgaagc tgtacaacaa cggctttact tcagtccaag gatatgcttt caatgggaca   600
 601  aagctggatg ctgtttacct aaacaagaat aaatacctga cagttattga caaagatgca   660
 661  tttggaggag tatacagtgg accaagcttg ctggacgtgt ctcaaaccag tgtcactgcc   720
 721  cttccatcca aaggcctgga gcacctgaag gaactgatag caagaaacac ctggactctt   780
 781  aacatcatcc cagttgagga ggagaacccg gacttctgga accgcgaggc agccggagca   840
 841  ctgggtgccg ccaagaagct gcagcctgca cagacagccg ccaagaacct catcatcttc   900
 901  ctgggcgatg gatgggggt gtctacggtg acagctgcca ggatcctaaa agggcagaag   960
 961  aaggacaaac tggggcctga gatacccctg gccatggacc gcttcccata tgtggctctg  1020
1021  tccaagacat acaatgtaga caaacatgtg ccagacagtg gagccacagc cacggcctac  1080
1081  ctgtgcgggg tcaaggcaa cttccagacc attggcttga gtgcagccgc ccgctttaac  1140
1141  cagtgcaaca cgacacgcgg caacgaggtc atctccgtga tgaatcgggc aagaaagca  1200
1201  gggaagtcag tgggagtggt aaccaccaca cgagtgcagc acgcctcgcc agccggcacc  1260
1261  tacgcccaca cggtgaaccg caactggtac tcggacgccg acgtgcctgc ctcggcccgc  1320
1321  caggagggt gccaggacat cgctacgcag ctcatctcca acatggacat tgacgtgatc  1380
1381  ctaggtggag gccgaaagta catgtttcgc atgggaaccc cagaccctga gtaccagat  1440
```

FIG. 16 TSHR260-AP Protein (SEQ ID No 60)

```
   1  MRPADLLQLV LLLDLPRDLG GMGCSSPPCE CHQEEDFRVT CKDIQRIPSL PPSTQTLKLI    60
  61  ETHLRTIPSH AFSNLPNISR IYVSIDVTLQ QLESHSFYNL SKVTHIEIRN TRNLTYIDPD   120
 121  ALKELPLLKF LGIFNTGLKM FPDLTKVYST DIFILEITD NPYMTSIPVN AFQGLCNETL   180
 181  TLKLYNNGFT SVQGYAFNGT KLDAVYLNKN KYLTVIDKDA FGGVYSGPSL LDVSQTSVTA   240
 241  LPSKGLEHLK ELIARNTWTL NIIPVEEENP DFWNREAAEA LGAAKKLQPA QTAAKNLIIF   300
 301  LGDGMGVSTV TAARILKGQK KDKLGPEIPL AMDRFPYVAL SKTYNVDKHV PDSGATATAY   360
 361  LCGVKGNFQT IGLSAAARFN QCNTTRGNEV ISVMNRAKKA GKSVGVVTTT RVQHASPAGT   420
 421  YAHTVNRNWY SDADVPASAR QEGCQDIATQ LISNMDIDVI LGGGRKYMFR MGTPDPEYPD   480
 481  DYSQGGTRLD GKNLVQEWLA KRQGARYVWN RTELMQASLD PSVTHLMGLF EPGDMKYEIH   540
 541  RDSTLDPSLM EMTEAALRLL SRNPRGFFLF VEGGRIDHGH HESRAYPALT ETIMFDDAIE   600
 601  RAGQLTSEED TLSLVTADHS HVFSFGGYPL RGSSIFGLAP GKARDRKAYT VLLYGNGPGY   660
 661  VLKDGARPDV TESESGSPEY RQQSAVPLDE ETHAGEDVAV FARGPQAHLV HGVQEQTFIA   720
```

FIG. 17 Porcine TSHR DNA (SEQ ID No 61)

```
1     atgagtctgacgcccctgttgcagctggcgctgcttctcgccctgccag      50
51    gagcctcaggggaaagggtgtccgtctccgccctgcgaatgccaccagg     100
101   aggacgacttcagagtcacctgcaaggatatccacagcatcccccctta     150
151   ccacccaatactcagacactaaagtttatagagactcatctgaaaccat     200
201   ccccagtcgtgcattttcaaatctgcccaatatttccaggatctacctgt    250
251   caatagatgcaactctacagcagctggaatcacagtccttctacaatttg    300
301   agcaaaatgactcacatagagattcggaataccagaagcttaacgtacat    350
351   aaaccctggtgccctaaaagatctccccttctaaagttccttggcattt     400
401   tcaacactggacttagaatattcccagacctgaccaaagtgtattccact    450
451   gatgtattcttcatacttgaaattacagacaacccttacatgacatcaat    500
501   ccctgcgaatgcttttcagggcctgtgcaacgaaaccttgacactgaaac    550
551   tatcaacaatggctttacttcagtccaaggacatgctttcaatgggaca     600
601   aagctggatgctgtttacctgaacaagaataaatacctgacagttattga    650
651   caaagatgcatttggaggagttttcagtggaccaaccttgctggatgtct    700
701   cttataccagtgttactgccctgccacccaaaggcctggaacacctgaag    750
751   gaactgatagcaagaaatacttggactctaaagaaacttccactgtcctt    800
801   gagtttccttcacctcacacgagctgacctttcttatccaagccactgct    850
851   gtgcttttaagaatcagaagaagatcagaggaatccttgagtctttaatg    900
901   tgtaatgagagcagtattcggagcctgcgtcagagaaaatctgtgaatgc    950
951   tgtaaatggtcccttttaccaagaatatgaagaggatctgggcgacagca   1000
1001  gtgttgggaataaggaaaactccaagttccaggatacccatagcaactcc   1050
1051  cattactacgtcttctttgaagaacaagaggatgagatcattggttttgg   1100
1150  ccaagagctcaaaaaccccaggaagagaccctccaggcctttgacagcc    1150
1151  attacgactacaccgtgtgtggggcagtgaagacatggtgtgcaccccc    1200
1201  aagtcagatgagttcaaccctgtgaagacataatgggctacaggttcct    1250
1251  gagaatcgtggtgtggttcgttagcctgctggctctcctgggcaatgtct   1300
1301  ttgtcctggtcatcctcctcacgagccactacaaactgacggtcccacgc   1350
1351  tttctcatgtgcaacttggcctttgcagattctgcatggggatgtatct    1400
1401  gctcctcattgcctcggtggacctctacactcagtctgagtactacaacc   1450
1451  atgccatcgactggcagacaggtcccggggtgcaacacggctggtttcttc   1500
1501  accgtctttgccagcgagctgtcagtgtacacactaacagtcatcactct   1550
1551  ggagcgctggtatgccatcaccttcgccatgcgcctggatcgcaagatcc   1600
1601  gcctcaggcacgcctacgccatcatggctggcggctgggtttgctgcttc   1650
1651  ctgctcgccctgctgcctttggtggggataagcagctatgctaaggtcag   1700
1701  catctgcctgcccatggacactgagactcctcttgccctggcgtatatta   1750
1751  tccttgttctgctgctaacatagttgcctttaccatcgtctgctcctgt    1800
1801  tacgtgaagatctacatcacagtccgaaatcccagtataacccgggaga    1850
1851  caaagacactaaaattgccaaaaggatggctgtgttgatcttcactgact   1900
1901  tcatgtgcatggccccgatctccttttacgccctctcagcacttatgaac   1950
1951  aagcctctcatcactgtcaccaactccaaaatcttgctcgttctcttcta   2000
2001  cccacttaactcctgtgccaacccgttcctctatgccattttcaccaaag   2050
2051  ccttccagagggatgtgtttatcctgctcagcaagttcggcttctgtaaa   2100
2101  cgccaggctcaggcataccggggtcagagagtgtctccaagaacagcac    2150
2151  tggtattcaggtccaaaaggttacccaaaacatgaggcaaagtctcccca   2200
2201  acatgcaggatgactatgaactgcttgaaaactcgcatctaacccacaaa   2250
2251  aagcatgaccaaatttcaaaggagtataagcaaccagttttgtaa        2295
```

FIG. 18 Porcine TSHR protein (SEQ ID No 62)

```
  1    MSLTPLLQLA LLLALPRSLR GKGCPSPPCE CHQEDDFRVT CKDIHSIPPL PPNTQTLKFI    60
 61    ETHLKTIPSR AFSNLPNISR IYLSIDATLQ QLESQSFYNL SKMTHIEIRN TRSLTYINPG   120
121    ALKDLPLLKF LGIFNTGLRI FPDLTKVYST DVFFILEITD NPYMTSIPAN AFQGLCNETL   180
181    TLKLYNNGFT SVQGHAFNGT KLDAVYLNKN KYLTVIDKDA FGGVFSGPTL LDVSYTSVTA   240
241    LPPKGLEHLK ELIARNTWTL KKLPLSLSFL HLTRADLSYP SHCCAFKNQK KIRGILESLM   300
301    CNESSIRSLR QRKSVNAVNG PFYQEYEEDL GDSSVGNKEN SKFQDTHSNS HYYVFFEEQE   360
361    DEIIGFGQEL KNPQEETLQA FDSHYDYTVC GGSEDMVCTP KSDEFNPCED IMGYRFLRIV   420
421    VWFVSLLALL GNVFVLVILL TSHYKLTVPR FLMCNLAFAD FCMGMYLLLI ASVDLYTQSE   480
481    YYNHAIDWQT GPGCNTAGFF TVFASELSVY TLTVITLERW YAITFAMRLD RKIRLRHAYA   540
541    IMAGGWVCCF LLALLPLVGI SSYAKVSICL PMDTETPLAL AYIILVLLLN IVAFTIVCSC   600
601    YVKIYITVRN PQYNPGDKDT KIAKRMAVLI FTDFMCMAPI SFYALSALMN KPLITVTNSK   660
661    ILLVLFYPLN SCANPFLYAI FTKAFQRDVF ILLSKFGFCK RQAQAYRGQR VSPKNSTGIQ   720
721    VQKVTQNMRQ SLPNMQDDYE LLENSHLTHK KHDQISKEYK QPVL                   764
```

FIG. 19 Mouse TSHR DNA (SEQ ID No 63)

```
1     atgaggccagggtccctgctgctgcttgttctgctgctcgccctgtccag     50
51    gagcctgcggggcaaagagtgtgcgtctccaccctgtgagtgtcaccagg    100
101   aggacgacttcagagtcacctgcaaggagctccaccgaatccccagcctg    150
151   ccgcccagcacccagactctgaagctcatcgagactcatctgaagaccat    200
201   acccagtcttgcattttcgagtctgcccaatatttccaggatctatttat    250
251   ctatagatgcaactctgcagcggctggaaccacattctttctacaatttg    300
301   agtaaaatgactcacatagaaatccggaacaccagaagcttaacctatat    350
351   agaccctgatgccttgacagagctccccttgctcaagtttcttggcattt    400
401   tcaatactggacttagaatattccctgacttgaccaaaatttattccacg    450
451   gacatattctttatacttgaaatcacagacaaccttacatgacttcggt     500
501   ccctgaaaacgcattccagggcctatgcaatgaaaccttgaccctgaaac    550
551   tgtacaacaatggatttacttcagtccaaggacatgctttcaatggaaca    600
601   aagctggatgctgtttacctaaacaagaataaatacctgacagctataga    650
651   caacgatgcctttggaggagtatacagtggaccaactttgctagatgtgt    700
701   cttccaccagcgtcactgcccttccttccaaaggcctggagcacctcaaa    750
751   gaactgatcgcaaaagacacctggactctcaaaaagctccgctgtcgtt     800
801   gagtttcctccacctcactcgggctgacctctcttacccgagccactgct    850
851   gcgcttttaagaaccagaagaaaatcaggggaatcctggagtctttgatg    900
901   tgtaatgagagcagtatccggaaccttcgtcaaaggaaatcagtgaacat    950
951   cttgaggggtccatctaccaggaatatgaagaagatccgggtgacaaca    1000
1001  gtgttgggtacaaacaaaactccaagttccaggagagcccaagcaactct   1050
1051  cactattacgtcttctttgaagaacaagaggatgaggtcgttggtttcgg   1100
1150  ccaagagctcaaaaatcctcaggaagagactctccaagccttcgagagcc   1150
1151  actatgactacacggtgtgtgggacaacgaggacatggtgtgtaccccc    1200
1201  aagtcggacgagtttaaccctgtgaagatatcatgggctacaggttcct    1250
1251  gagaatcgtggtgtggtttgtcagtctgctggctctcctgggcaatatct   1300
1301  tcgtcctgctcattctgctaaccagccactacaaattgaccgtgcgcgg    1350
1351  ttcctcatgtgcaacttggcctttgcagatttctgcatggggtatacct    1400
1401  gcttctcattgcctctgtagacctgtacacactctgagtactacaacc    1450
1451  acgccatcgactggcagacgggccctggtgcaacacggctggcttcttc   1500
1501  actgttttcgccagtgagttatcagtgtacacactgacggtcatcaccct   1550
1551  ggagcgatggtacgccatcaccttcgccatgcgcctggataggaagatcc   1600
1601  gcctcaggcacgcgtacaccatcatggctggggctgggtttcctgcttc    1650
1651  cttctcgccctgctccgatggtgggaatcagcagctatgccaaggtcag   1700
1701  catctgcctgccaatggacaccgacacccctcttgcactcgcatacattg   1750
1751  tcctcgttctgctgctcaatgttgttgcctttgttgtcgtctgttcctgc   1800
1801  tatgtgaagatctacatcacggtccgaaatcccagtacaaccctcgaga    1850
1851  taaagacaccaagattgccaagaggatggctgtgttgatcttcactgact   1900
1901  tcatgtgcatggcgcccatctccttctatgcgctgtcggcacttatgaac   1950
1951  aagcctctaatcactgttactaactccaaaatcttgttggttctcttcta   2000
2001  ccccctcaactcctgtgccaatccgtttctctatgctattttcaccaagg   2050
2051  ccttccagaggacgtgttcatcctgctcagcaagtttggcatctgcaaa    2100
2101  cgccaggcccaggcctatcagggtcagagagtctgtcccaacaatagcac   2150
2151  tggtattcagatccaaaagattccccaggacacgaggcagagtctcccca   2200
2201  acatgcaagataccatgaactgcttggaaactcccagctagctccaaaa    2250
2251  ctgcagggacaaatctcagaagagtataagcaaacagccttgtaa        2295
```

FIG. 20 Mouse TSHR protein (SEQ ID No 64)

```
  1    MRPGSLLLLV LLLALSRSLR GKECASPPCE CHQEDDFRVT CKELHRIPSL PPSTQTLKLI    60
 61    ETHLKTIPSL AFSSLPNISR IYLSIDATLQ RLEPHSFYNL SKMTHIEIRN TRSLTYIDPD   120
121    ALTELPLLKF LGIFNTGLRI FPDLTKIYST DIFFILEITD NPYMTSVPEN AFQGLCNETL   180
181    TLKLYNNGFT SVQGHAFNGT KLDAVYLNKN KYLTAIDNDA FGGVYSGPTL LDVSSTSVTA   240
241    LPSKGLEHLK ELIAKDTWTL KKLPLSLSFL HLTRADLSYP SHCCAFKNQK KIRGILESLM   300
301    CNESSIRNLR QRKSVNILRG PIYQEYEEDP GDNSVGYKQN SKFQESPSNS HYYVFFEEQE   360
361    DEVVGFGQEL KNPQEETLQA FESHYDYTVC GDNEDMVCTP KSDEFNPCED IMGYRFLRIV   420
421    VWFVSLLALL GNIFVLLILL TSHYKLTVPR FLMCNLAFAD FCMGVYLLLI ASVDLYTHSE   480
481    YYNHAIDWQT GPGCNTAGFF TVFASELSVY TLTVITLERW YAITFAMRLD RKIRLRHAYT   540
541    IMAGGWVSCF LLALLPMVGI SSYAKVSICL PMDTDTPLAL AYIVLVLLLN VVAFVVVCSC   600
601    YVKIYITVRN PQYNPRDKDT KIAKRMAVLI FTDFMCMAPI SFYALSALMN KPLITVTNSK   660
661    ILLVLFYPLN SCANPFLYAI FTKAFQRDVF ILLSKFGICK RQAQAYQGQR VCPNNSTGIQ   720
721    IQKIPQDTRQ SLPNMQDTYE LLGNSQLAPK LQGQISEEYK QTAL                    764
```

FIG. 21 Mutated porcine TSHR DNA (SEQ ID No 65)

```
1      atgagtctga cgccctgtt  gcagctggcg ctgcttctcg ccctgcccag gagcctcagg   60
61     gggaagggt  gtccgtctcc gccctgcgaa tgccaccagg aggacgactt cagagtcacc   120
121    tgcaaggata tccacagcat cccccctta  ccacccaata ctcagacact aaagtttata   180
181    gagacttgtc tgaaaaccat cccagtcgt  gcattttcaa atctgcccaa tatttccagg   240
241    atctacctgt caatagatgc aactctacag cagctggaat cacagtcctt ctacaatttg   300
301    agcaaaatga ctcacataga gattcggaat accccaagct taacgtacat aaaccctggt   360
361    gccctaaaag atctccccct tctaaagttc cttggcattt tcaacactgg acttagaata   420
421    ttcccacccc tgaccaaagt gtattccact gaggtattct tcatacttga aattacagac   480
451    aacccttaca tgacatcaat ccctcggaat gcttttcagg gcctgtgcaa cgaaaccttg   540
541    acactgaaac tatacaacaa tggctttact tcagtccaag acatgcttt  caatgggaca   600
601    aagctggatg ctgtttacct gaacaagaat aaatacctga cagttattga caaagatgca   660
661    tttggaggag ttttcagtgg accaaccttg ctggatgtct cttataccag tgttactgcc   720
721    ctgccaccca aaggcctgga cacctgaag  gaactgagag caagaaatac ttggactcta   780
781    aagaaacttc cactgtcctt gagtttcctt cacctcacac gagctgacct ttcttatcca   840
841    agccactgct gtgcttttaa gaatcagaag aagatcagag gaatccttga gtctttaatg   900
901    tgtaatgaga gcagtattcg gagcctgcgt cagagaaaat ctgtgaatgc tgtaaatggt   960
961    ccctttttacc aagaatatga agaggatctg ggcgacagca gtgttgggaa taaggaaaac   1020
1021   tccaagttcc aggatacca  tagcaactcc cattactacg tcttctttga agaacaagag   1080
1081   gatgagatca ttggttttgg ccaagagctc aaaaccccc  aggaagagac cctccaggcc   1140
1141   tttgacagcc attacgacta caccgtgtgt ggggcagtg  aagacatggt gtgcaccccc   1200
1201   aagtcagatg agttcaaccc ctgtgaagac ataatgggct acaggttcct gagaatcgtg   1260
1261   gtgtggttcg ttagcctgct ggctctcctg ggcaatgtct ttgtcctggt catcctcctc   1320
1321   acgagccact acaaactgac ggtcccacgc tttctcatgt gcaacttggc ctttgcagat   1380
1381   ttctgcatgg ggatgtatct gctcctcatt gcctcggtgg acctctacac tcagtctgag   1440
1441   tactacaacc atgccatcga ctggcagaca ggtcccgggt gcaacacggc tggtttcttc   1500
1501   accgtctttg ccagcgagct gtcagtgtac acactaacag tcatcactct ggagcgctgg   1560
1561   tatgccatca ccttcgccat gcgcctggat cgcaagatcc gcctcaggca cgcctacgcc   1620
1621   atcatggctg gcggctgggt ttgctgcttc ctgctcgccc tgctgccttt ggtggggata   1680
1681   agcagctatg ctaaggtcag catctgcctg cccatggaca ctgagactcc tcttgccctg   1740
1741   gcgtatatta tccttgttct gctgctcaac atagttgcct ttaccatcgt ctgctcctgt   1800
1801   tacgtgaaga tctacatcac agtccgaaat ccccagtata cccgggaga  caaagacact   1860
1861   aaaattgcca aaaggatggc tgtgttgatc ttcactgact tcatgtgcat ggcccgatc   1920
1921   tccttttacg ccctctcagc acttatgaac aagcctctca tcactgtcac caactccaaa   1980
1981   atcttgctcg ttctcttcta cccacttaac tcctgtgcca acccgttcct ctatgccatt   2040
2041   ttcaccaaag ccttccagag ggatgtgttt atcctgctca gcaagttcgg cttctgtaaa   2100
2101   cgccaggctc aggcataccg gggtcagaga gtgtctccaa agaacagcac tggtattcag   2160
2161   gtccaaaagg ttacccaaaa catgaggcaa agtctcccca acatgcagga tgactatgaa   2220
2221   ctgcttgaaa actcgcatct aacccacaaa aagcatgacc aaatttcaaa ggagtataag   2280
2281   caaccagttt tgtaa                                                    2295
```

FIG. 22 Mutated porcine TSHR protein (SEQ ID No 66)

```
1    MSLTPLLQLA LLLALPRSLR GKGCPSPPCE CHQEDDFRVT CKDIHSIPPL PPNTQTLKFI   60
61   ETCLKTIPSR AFSNLPNISR IYLSIDATLQ QLESQSFYNL SKMTHIEIRN TPSLTYINPG   120
121  ALKDLPLLKF LGIFNTGLRI FPPLTKVYST EVFFILEITD NPYMTSIPRN AFQGLCNETL   180
181  TLKLYNNGFT SVQGHAFNGT KLDAVYLNKN KYLTVIDKDA FGGVFSGPTL LDVSYTSVTA   240
241  LPPKGLEHLK ELRARNTWTL KKLPLSLSFL HLTRADLSYP SHCCAFKNQK KIRGILESLM   300
301  CNESSIRSLR QRKSVNAVNG PFYQEYEEDL GDSSVGNKEN SKFQDTHSNS HYYVFFEEQE   360
361  DEIIGFGQEL KNPQEETLQA FDSHYDYTVC GGSEDMVCTP KSDEFNPCED IMGYRFLRIV   420
421  VWFVSLLALL GNVFVLVILL TSHYKLTVPR FLMCNLAFAD FCMGMYLLLI ASVDLYTQSE   480
481  YYNHAIDWQT GPGCNTAGFF TVFASELSVY TLTVITLERW YAITFAMRLD RKIRLRHAYA   540
541  IMAGGWVCCF LLALLPLVGI SSYAKVSICL PMDTETPLAL AYIILVLLLN IVAFTIVCSC   600
601  YVKIYITVRN PQYNPGDKDT KIAKRMAVLI FTDFMCMAPI SFYALSALMN KPLITVTNSK   660
661  ILLVLFYPLN SCANPFLYAI FTKAFQRDVF ILLSKFGFCK RQAQAYRGQR VSPKNSTGIQ   720
721  VQKVTQNMRQ SLPNMQDDYE LLENSHLTHK KHDQISKEYK QPVL                    764
```

FIG. 23 Mutated mouse TSHR DNA (SEQ ID No 67)

```
   1    atgaggccag ggtccctgct gctgcttgtt ctgctgctcg ccctgtccag gagcctgcgg      60
  61    ggcaaagagt gtgcgtctcc accctgtgag tgtcaccagg aggacgactt cagagtcacc     120
 121    tgcaaggagc tccaccgaat ccccagcctg ccgcccagca cccagactct gaagctcatc     180
 181    gagacttgtc tgaagaccat acccagtctt gcatttcga gtctgcccaa tatttccagg      240
 241    atctatttat ctatagatgc aactctgcag cggctggaac cacattcttt ctacaatttg     300
 301    agtaaaatga ctcacataga aatccggaac accccaagct taacctatat agaccctgat     360
 361    gccttgacag agctcccctt gctcaagttt cttggcattt tcaatactgg acttagaata     420
 421    ttccctccct tgaccaaaat ttattccacg gagatattct ttatacttga aatcacagac     480
 481    aacccttaca tgacttcggt ccctcgaaac gcattccagg cctatgcaa tgaaaccttg      540
 541    accctgaaac tgtacaacaa tggatttact tcagtccaag acatgctttt caatggaaca      600
 601    aagctggatg ctgtttacct aaacaagaat aaatacctga cagctataga caacgatgcc      660
 661    tttggaggag tatacagtgg accaactttg ctagatgtgt cttccaccag cgtcactgcc     720
 721    cttccttcca aaggcctgga gcacctcaaa gaactgcgcg caaaagacac ctggactctc     780
 781    aaaaagctcc cgctgtcgtt gagtttcctc cacctcactc gggctgacct ctcttacccg     840
 841    agccactgct gcgcttttaa gaaccagaag aaaatcaggg gaatcctgga gtctttgatg     900
 901    tgtaatgaga gcagtatccg gaaccttcgt caaggaaat cagtgaacat cttgagggt       960
 961    cccatctacc aggaatatga agaagatccg ggtgacaaca gtgttgggta caaacaaaac    1020
1021    tccaagttcc aggagagccc aagcaactct cactattacg tcttctttga agaacaagag    1080
1081    gatgaggtcg ttggtttcgg ccaagagctc aaaaatcctc aggaagagac tctccaagcc    1140
1141    ttcgagagcc actatgacta cacggtgtgt ggggacaacg aggacatggt gtgtaccccc    1200
1201    aagtcggacg agtttaaccc ctgtgaagat atcatgggct acaggttcct gagaatcgtg    1260
1261    gtgtggtttg tcagtctgct ggctctcctg ggcaatatct tcgtcctgct cattctgcta    1320
1321    accagccact acaaattgac cgtgccgcgg ttcctcatgt gcaacttggc cttcgcagat    1380
1381    ttctgcatgg gggtatacct gcttctcatt gcctctgtag acctgtacac acactctgag    1440
1441    tactacaacc acgccatcga ctggcagacg ggccctgggt gcaacacggc tggcttcttc    1500
1501    actgttttcg ccagtgagtt atcagtgtac acactgacgg tcatcaccct ggagcgatgg    1560
1561    tacgccatca cctccgccat gcgcctggat aggaagatcc gctcaggca cgcgtacacc    1620
1621    atcatggctg ggggctgggt ttcctgcttc cttctcgccc tgctcccgat ggtgggaatc    1680
1681    agcagctatg ccaaggtcag catctgcctg ccaatggaca ccgacacccc tcttgcactc    1740
1741    gcatacattg tcctcgttct gctgctcaat gttgttgcct tgttgtcgt ctgttcctgc    1800
1801    tatgtgaaga tctacatcac ggtccgaaat ccccagtaca acccctcgaga taaagacacc    1860
1861    aagattgcca agaggatggc tgtgttgatc ttcactgact catgtgcat ggcgcccatc     1920
1921    tccttctatg cgctgtcggc acttatgaac aagcctctaa tcactgttac taactccaaa    1980
1981    atcttgttgg ttctcttcta cccctcaac tctgtgcca atccgtttct ctatgctatt      2040
2041    ttccaccagg ccttccagag ggacgtgttc atcctgctca gcaagtttgg catctgcaaa    2100
2101    cgccaggccc aggcctatca gggtcagaga gtctgtccca caatagcac tggtattcag    2160
2161    atccaaaaga ttccccagga cacgaggcag agtctcccca catgcaagaa tacctatgaa    2220
2221    ctgcttggaa actcccagct agctccaaaa ctgcagggac aaatctcaga agagtataag    2280
2281    caaacagcct tgtaa                                                     2295
```

FIG. 24 Mutated mouse TSHR protein (SEQ ID No 68)

| | | | | | | | |
|---|---|---|---|---|---|---|---|
| 1 | MRPGSLLLLV | LLLALSRSLR | GKECASPPCE | CHQEDDFRVT | CKELHRIPSL | PPSTQTLKLI | 60 |
| 61 | ETCLKTIPSL | AFSSLPNISR | IYLSIDATLQ | RLEPHSFYNL | SKMTHIEIRN | TPSLTYIDPD | 120 |
| 121 | ALTELPLLKF | LGIFNTGLRI | FPPLTKIYST | EIFFILEITD | NPYMTSVPRN | AFQGLCNETL | 180 |
| 181 | TLKLYNNGFT | SVQGHAFNGT | KLDAVYLNKN | KYLTAIDNDA | FGGVYSGPTL | LDVSSTSVTA | 240 |
| 241 | LPSKGLEHLK | ELRAKDTWTL | KKLPLSLSFL | HLTRADLSYP | SHCCAFKNQK | KIRGILESLM | 300 |
| 301 | CNESSIRNLR | QRKSVNILRG | PIYQEYEEDP | GDNSVGYKQN | SKFQESPSNS | HYYVFFEEQE | 360 |
| 361 | DEVVGFGQEL | KNPQEETLQA | FESHYDYTVC | GDNEDMVCTP | KSDEFNPCED | IMGYRFLRIV | 420 |
| 421 | VWFVSLLALL | GNIFVLLILL | TSHYKLTVPR | FLMCNLAFAD | FCMGVYLLLI | ASVDLYTHSE | 480 |
| 481 | YYNHAIDWQT | GPGCNTAGFF | TVFASELSVY | TLTVITLERW | YAITFAMRLD | RKIRLRHAYT | 540 |
| 541 | IMAGGWVSCF | LLALLPMVGI | SSYAKVSICL | PMDTDTPLAL | AYIVLVLLLN | VVAFVVVCSC | 600 |
| 601 | YVKIYITVRN | PQYNPRDKDT | KIAKRMAVLI | FTDFMCMAPI | SFYALSALMN | KPLITVTNSK | 660 |
| 661 | ILLVLFYPLN | SCANPFLYAI | FTKAFQRDVF | ILLSKFGICK | RQAQAYQGQR | VCPNNSTGIQ | 720 |
| 721 | IQKIPQDTRQ | SLPNMQDTYE | LLGNSQLAPK | LQGQISEEYK | QTAL | | 764 |

FIG. 25A  TSHR260 (wild type): activity of the load and elution pools of before and after purification by ion exchange chromatography
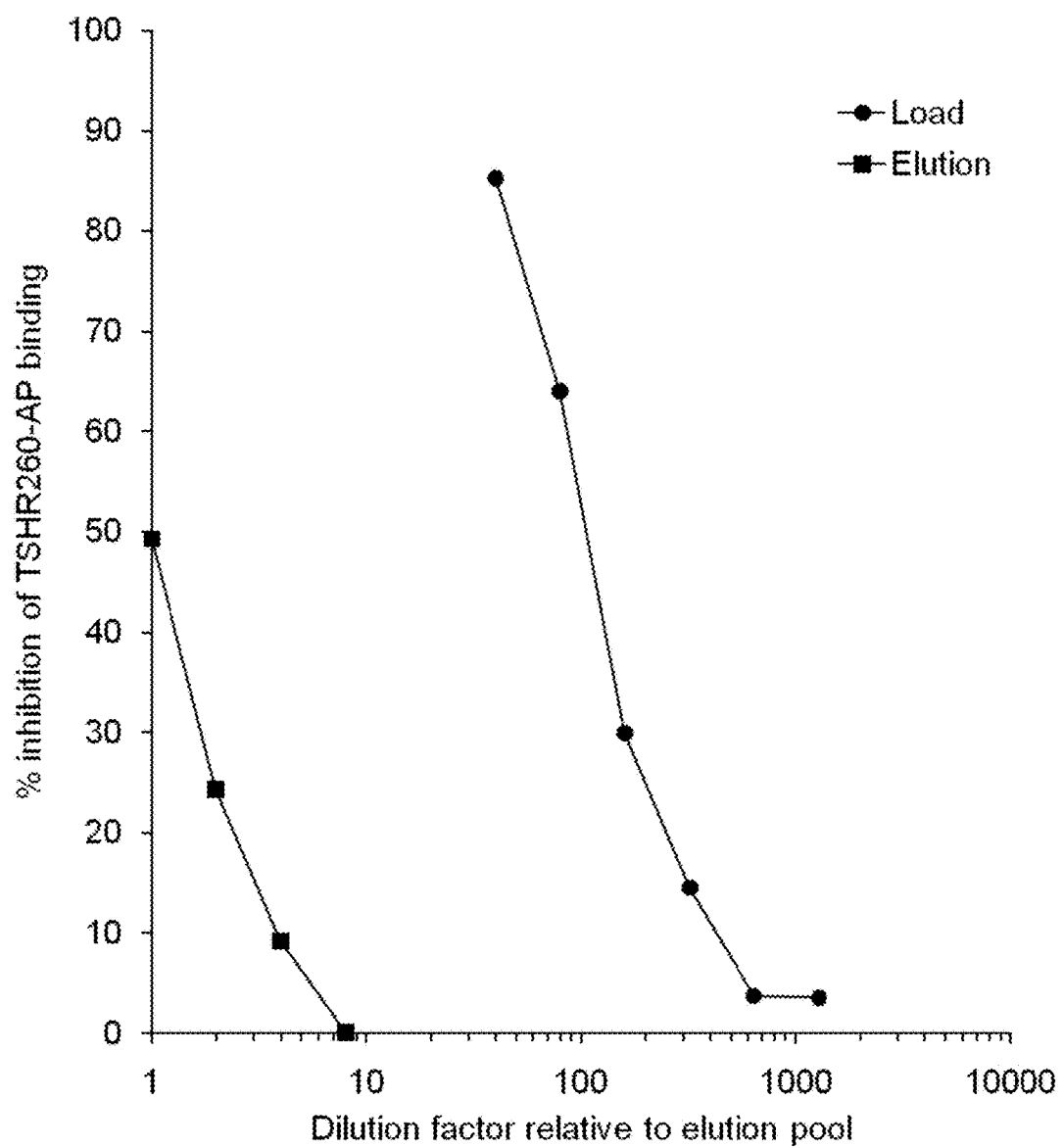

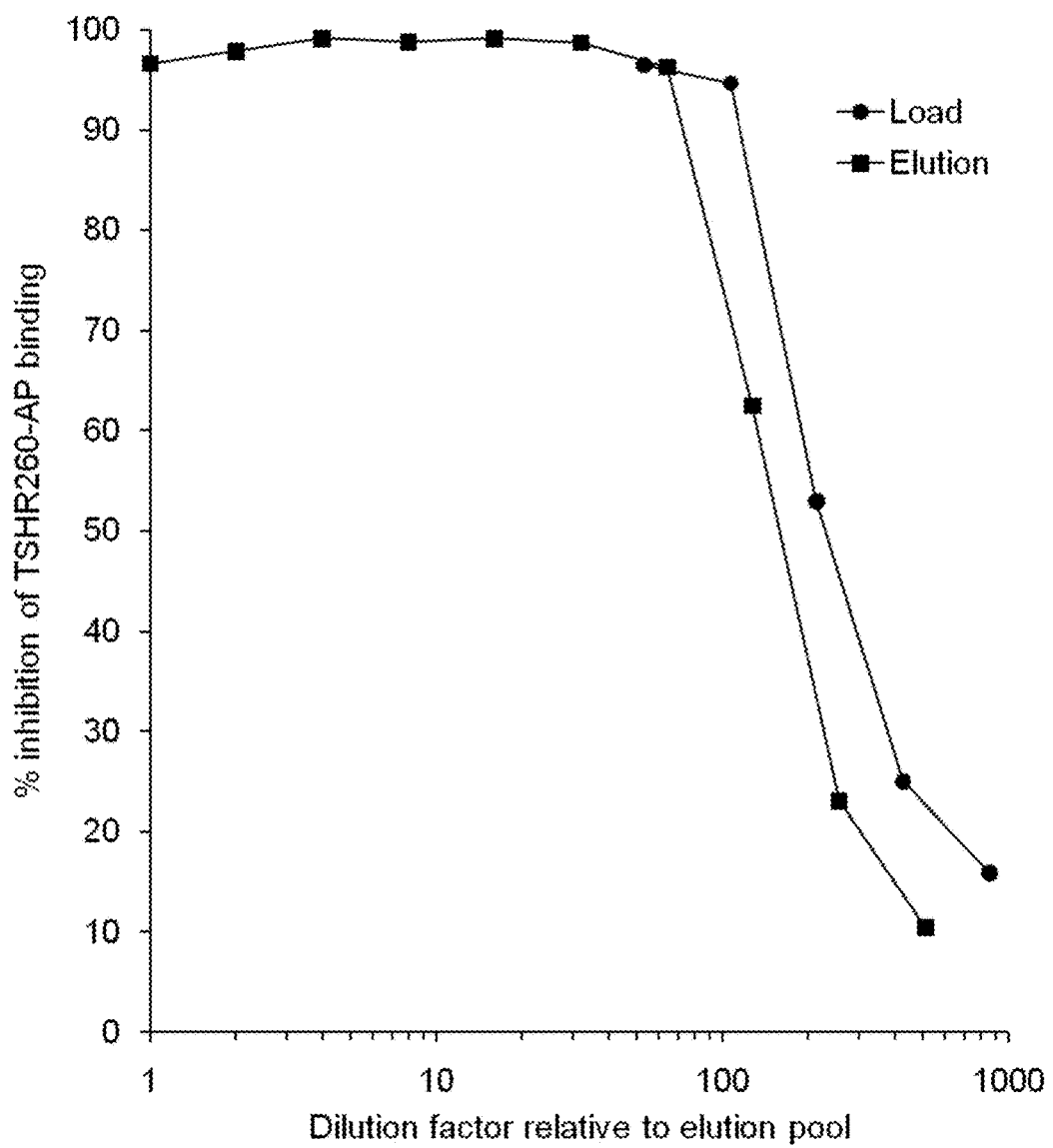
FIG. 25B  TSHR260 (wild type) in complex with 14C4 IgG: activity of the load and elution pools of before and after purification by ion exchange chromatography

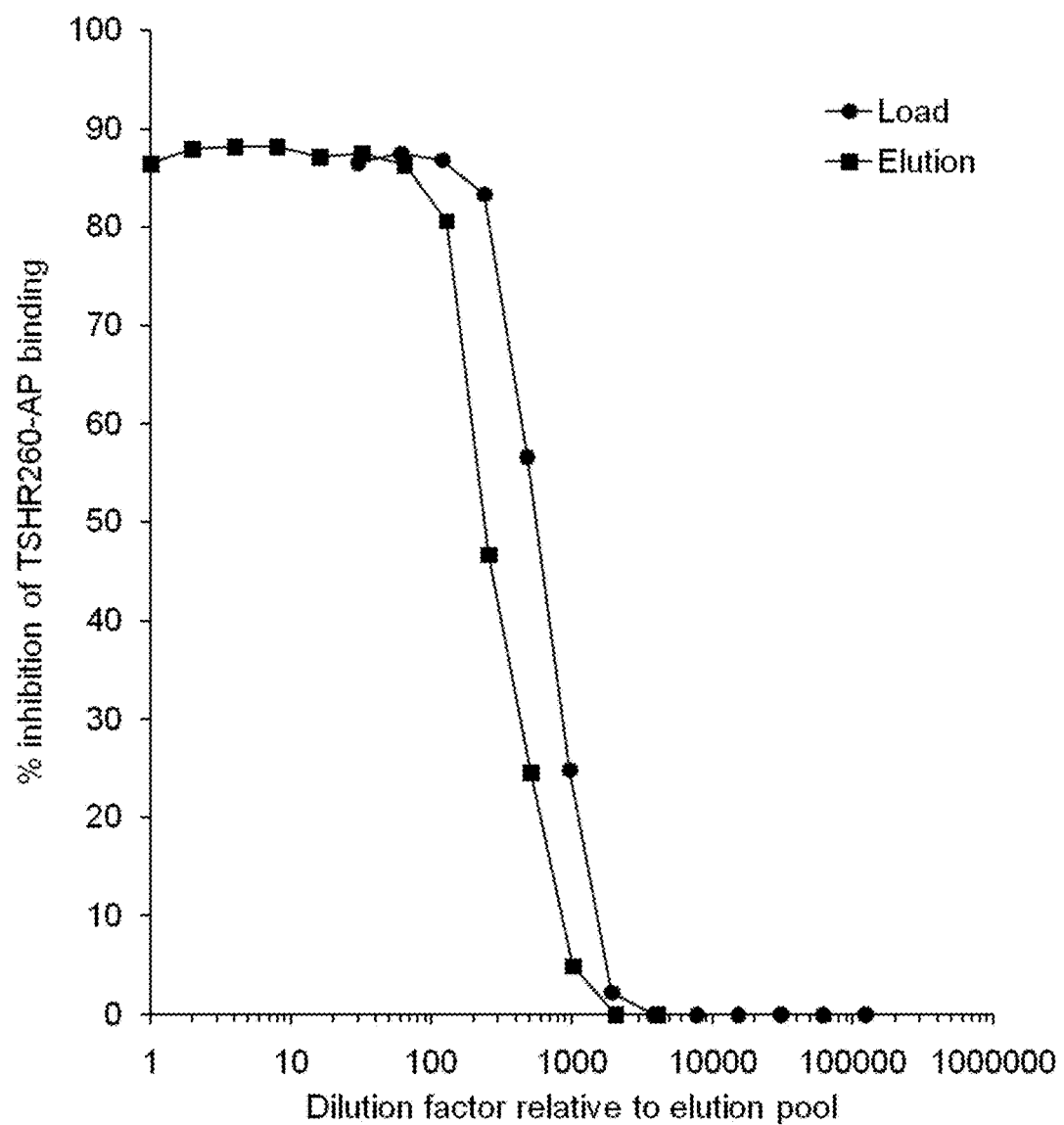
FIG. 25C  TSHR260 (wild type) in complex with 25E1 IgG: activity of the load and elution pools of before and after purification by ion exchange chromatography FIG. 25D    TSHR260 (wild type) in complex with 2H11 IgG: activity of the load and elution pools of before and after purification by ion exchange chromatography
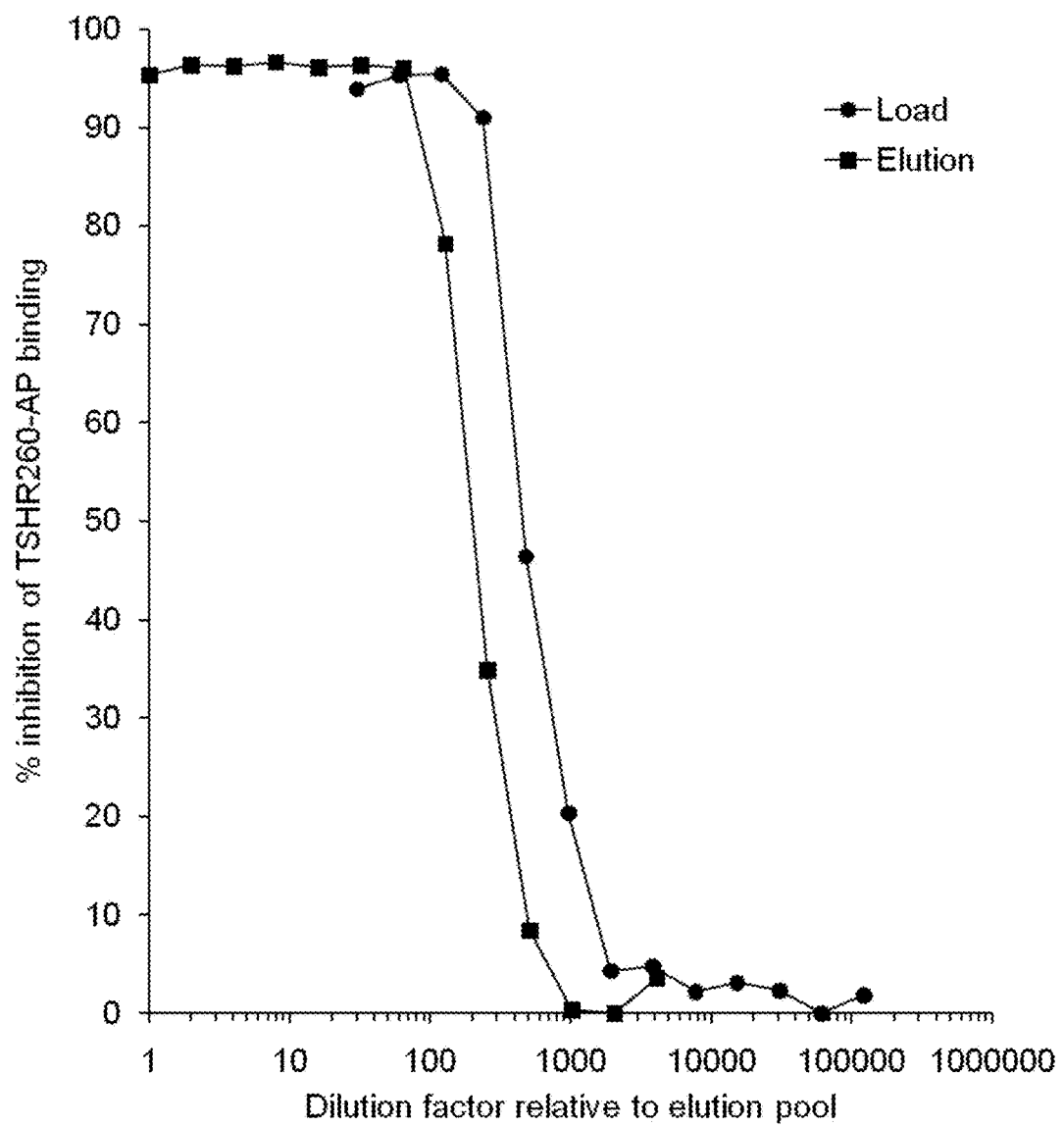

FIG. 25E  TSHR260 (wild type) in complex with 23H4 IgG: activity of the load and elution pools of before and after purification by ion exchange chromatography
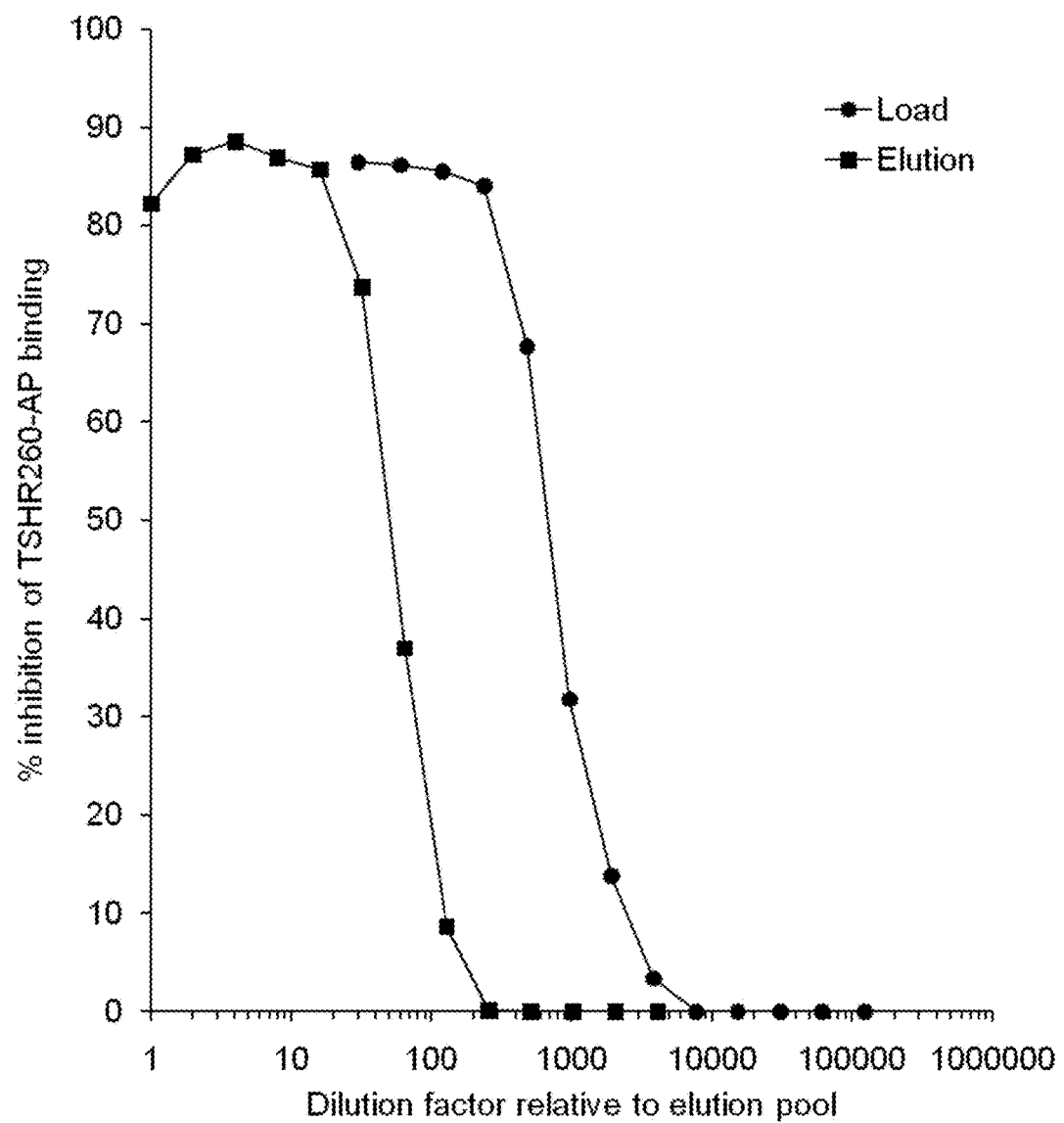

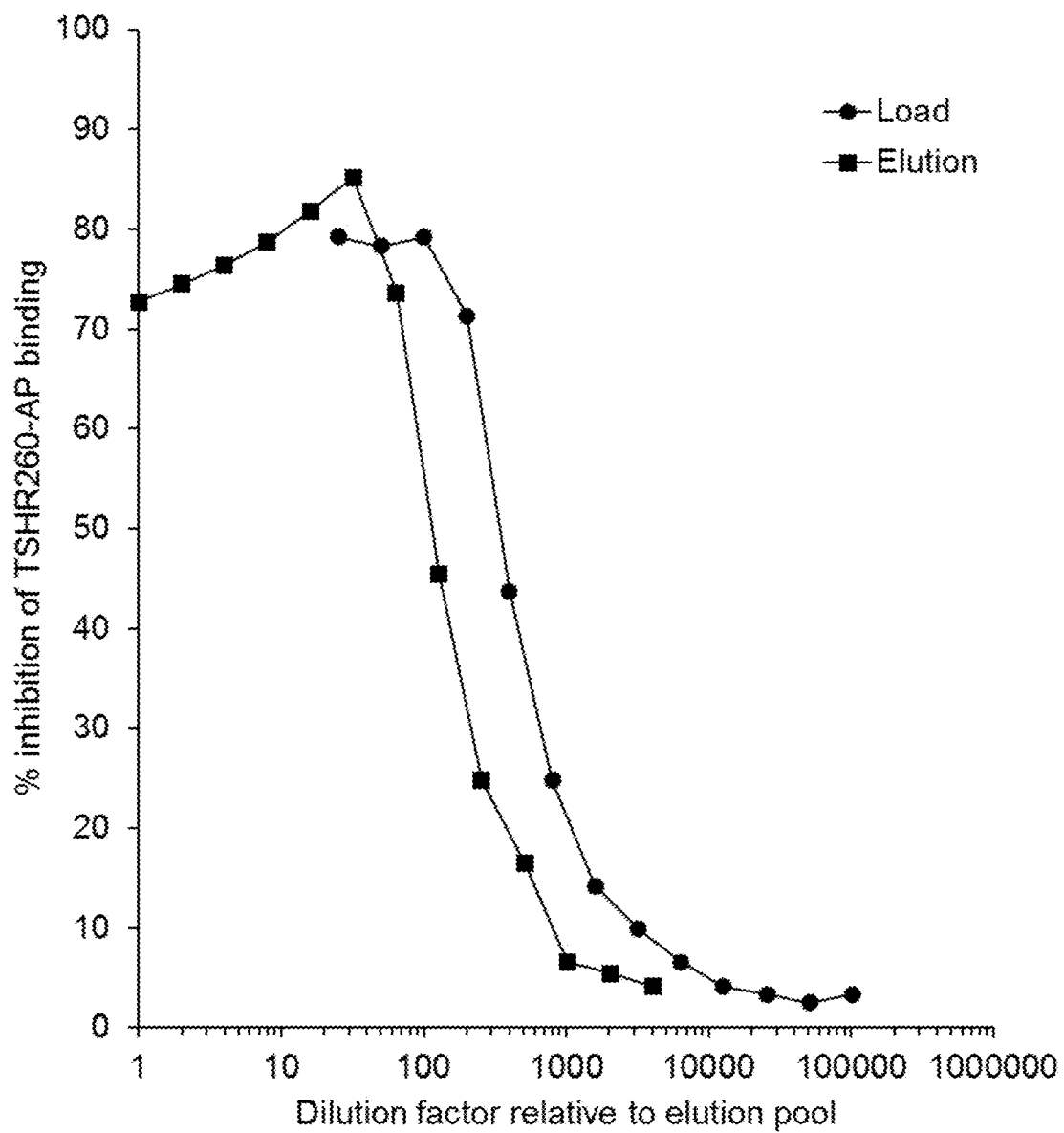
FIG. 25F  TSHR260 (wild type) in complex with 36F11 IgG: activity of the load and elution pools of before and after purification by ion exchange chromatography FIG. 25G   TSHR260 (wild type) in complex with 9B7 IgG: activity of the load and elution pools of before and after purification by ion exchange chromatography
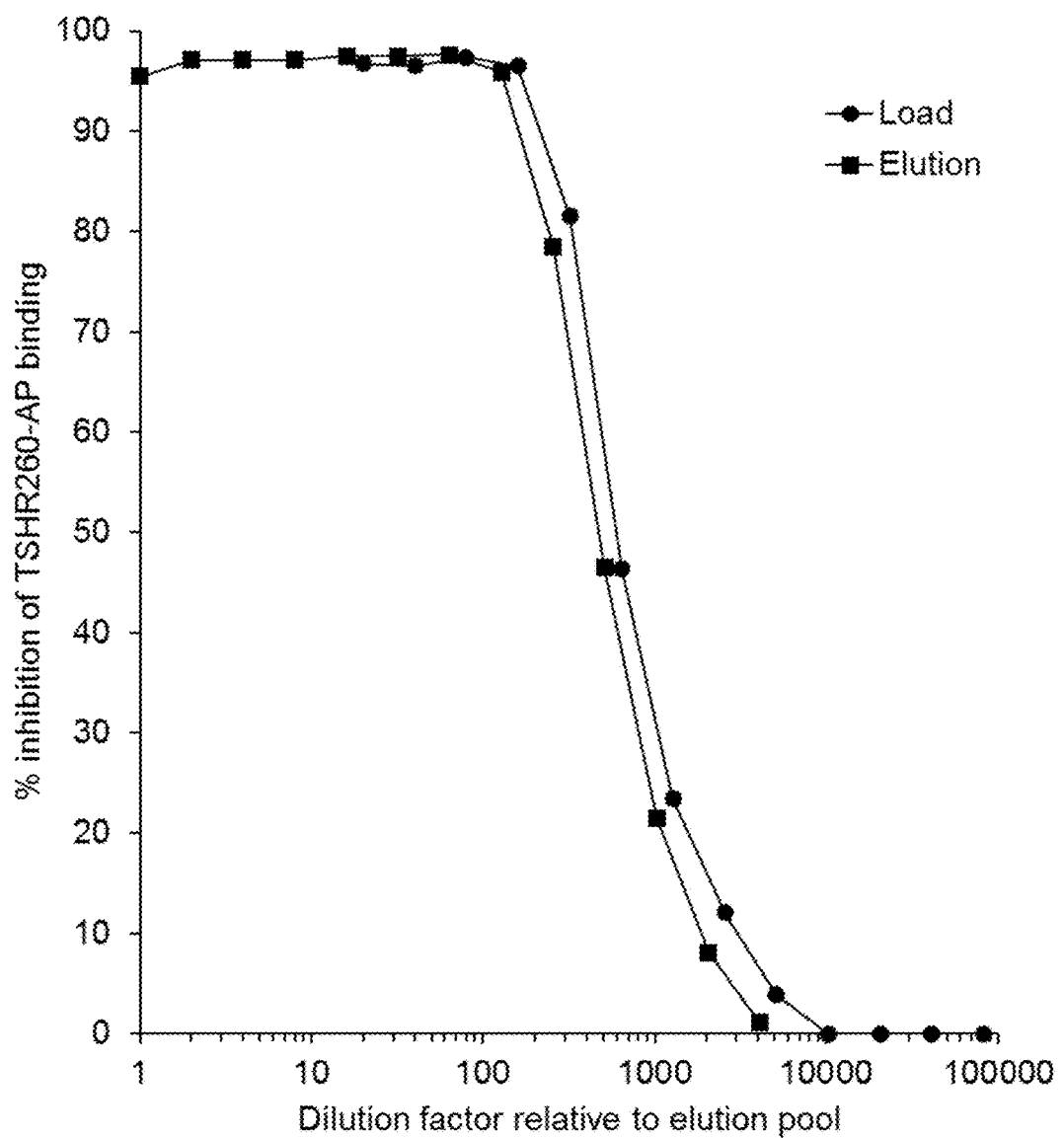

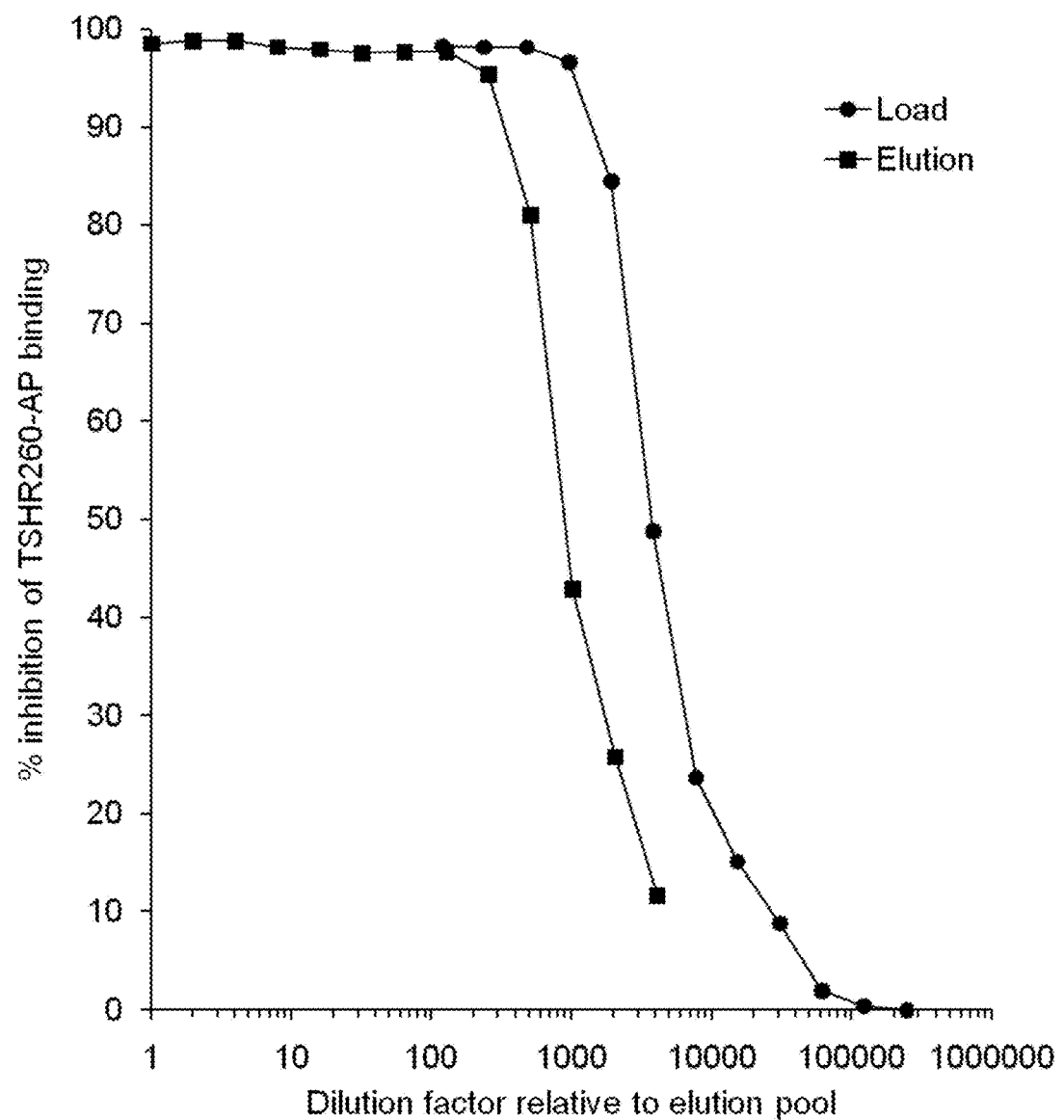
FIG. 25H  TSHR260-JMG55: activity of the load and elution pools of before and after purification by ion exchange chromatography

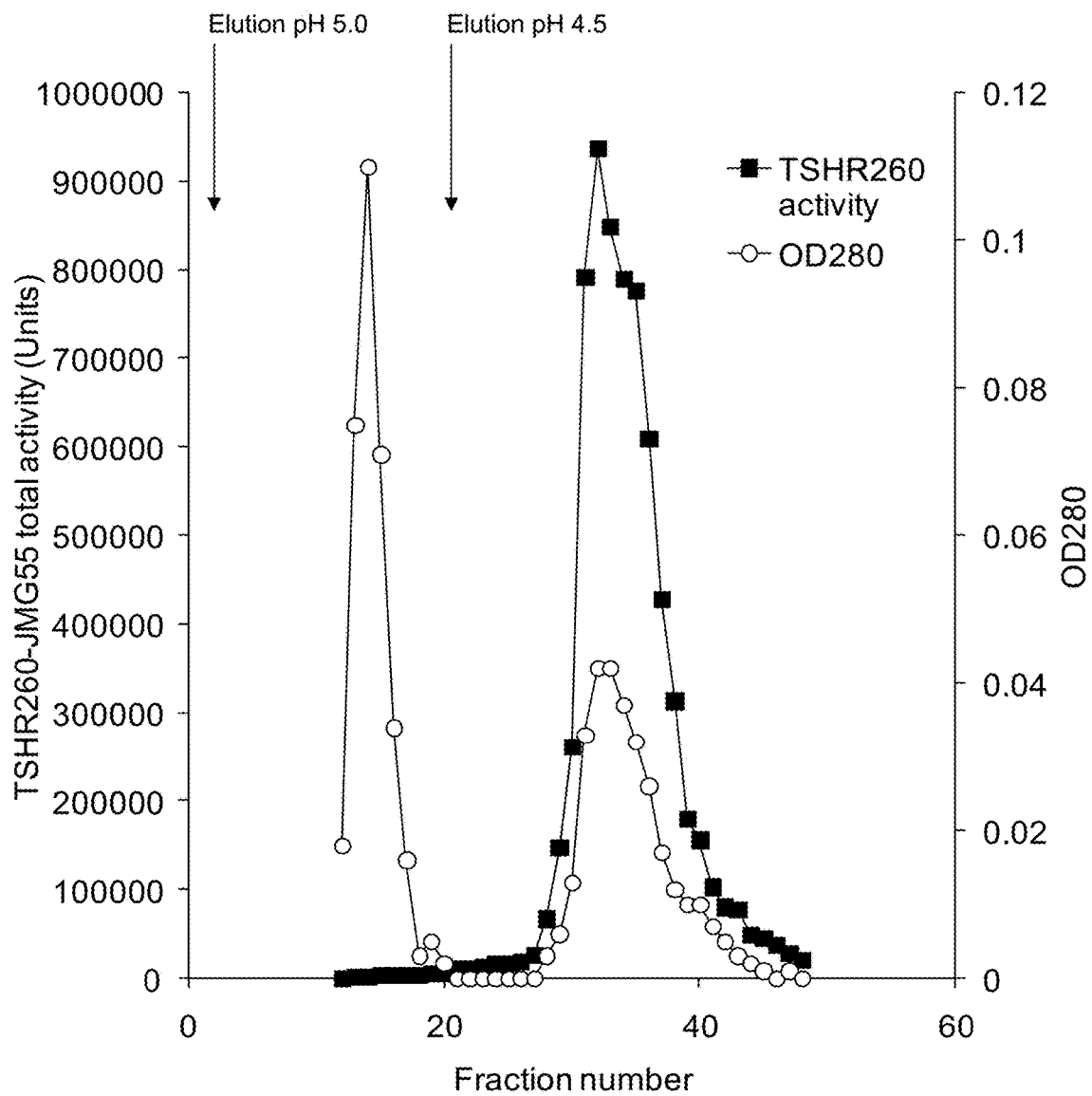
FIG. 26 Purification of TSHR260-JMG55 by 14C4-affinity chromatography: TSHR260 activity and total protein concentration (OD280) in the elution fractions.

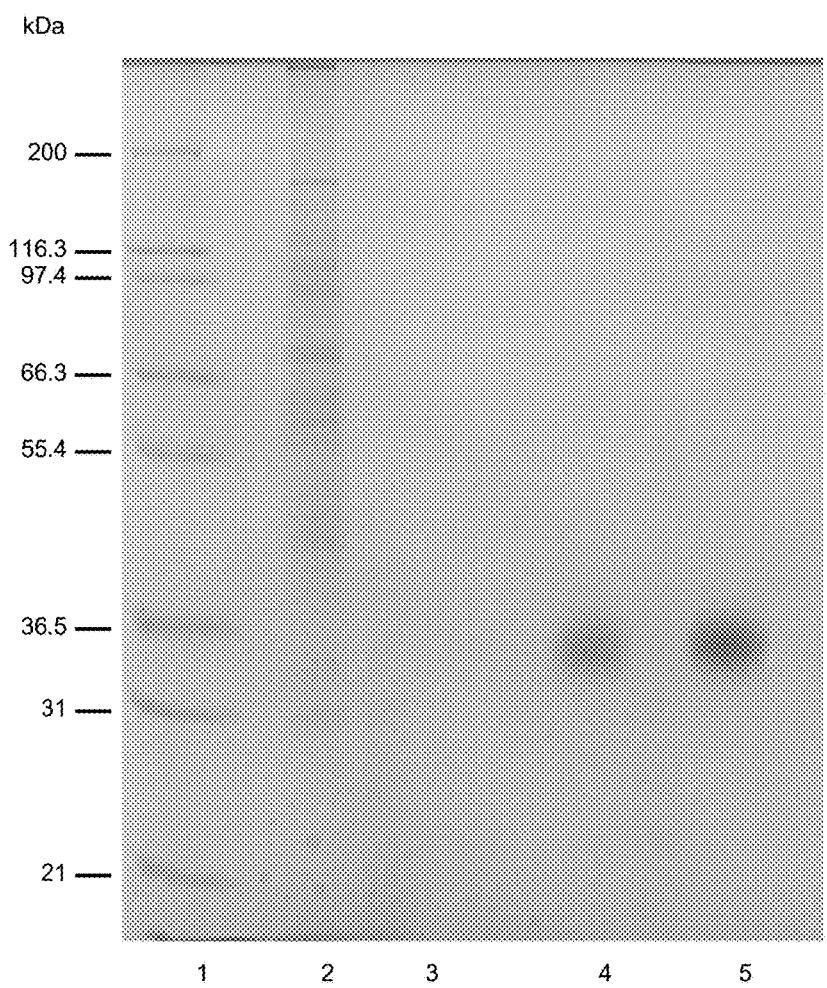

FIG. 27 Purified TSHR260-JMG55-5.0 (low specific activity) and purified TSHR260-JMG55-4.5 (high specific activity) after three rounds of column purification (cation exchange, 14C4-affinity and nickel-affinity chromatography) – 12% SDS-PAGE gel.

1) Molecular Weight Marker; 2) TSHR260 (wild type) culture supernatant control; 3) Insect cell culture media negative control; 4) Purified TSHR260-JMG55-5.0 (2.4 μg) and 5) TSHR260-JMG55-4.5 (3.0 μg).

FIG. 28A   Deglycosylation of TSHR260-JMG55-4.5 with Endoglycosidase F3 – 12% non-reduced SDS-PAGE gel.

A   0 mU and 40 mU of Endoglycosidase F3 per mg TSHR260-JMG55-4.5

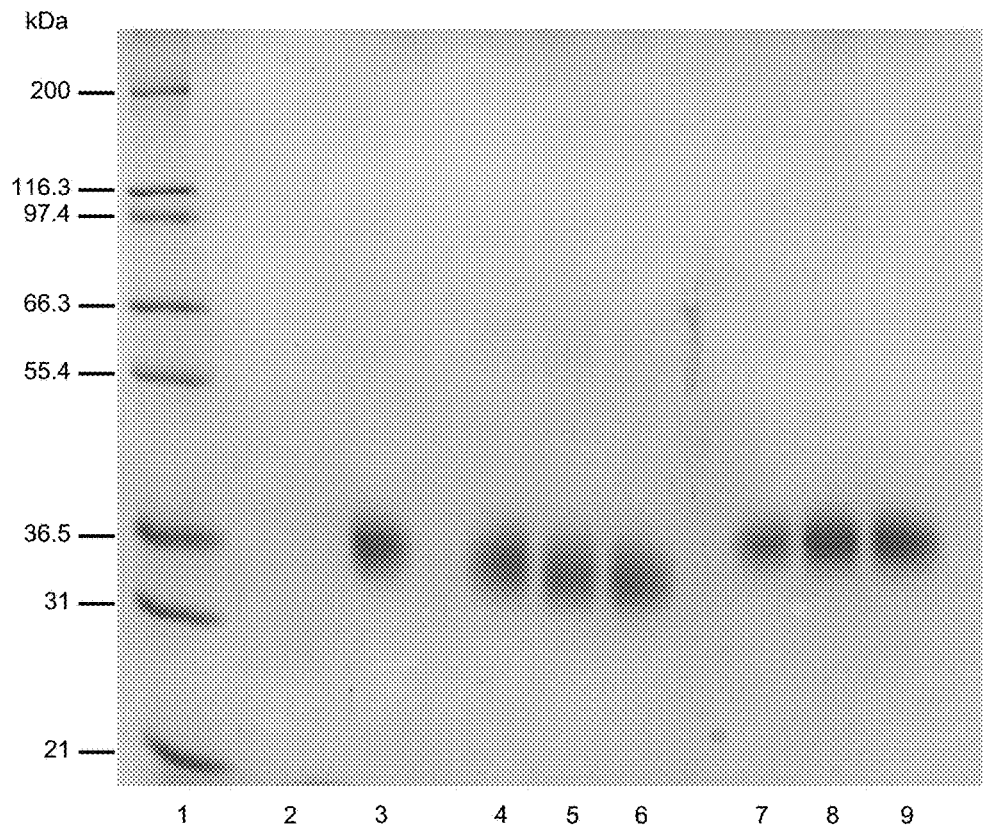

1) Molecular Weight Markers; 2) Insect cell culture media negative control; 3) Nickel-affinity purified TSHR260-JMG55-4.5 (untreated); 4-6) purified TSHR260-JMG55-4.5 treated with 40 mU Endoglycosidase F3 per mg of TSHR260-JMG55 after 24 h (lane 4), 72 h (lane 5) and 120 h (lane 6); 7-9) purified TSHR260-JMG55-4.5 with 0 mU Endoglycosidase F3 after 24 h (lane 7), 72 h (lane 8) and 120 h (lane 9).

FIG. 28B    Deglycosylation of TSHR260-JMG55-4.5 with Endoglycosidase F3 – 12% non-reduced SDS-PAGE gel.

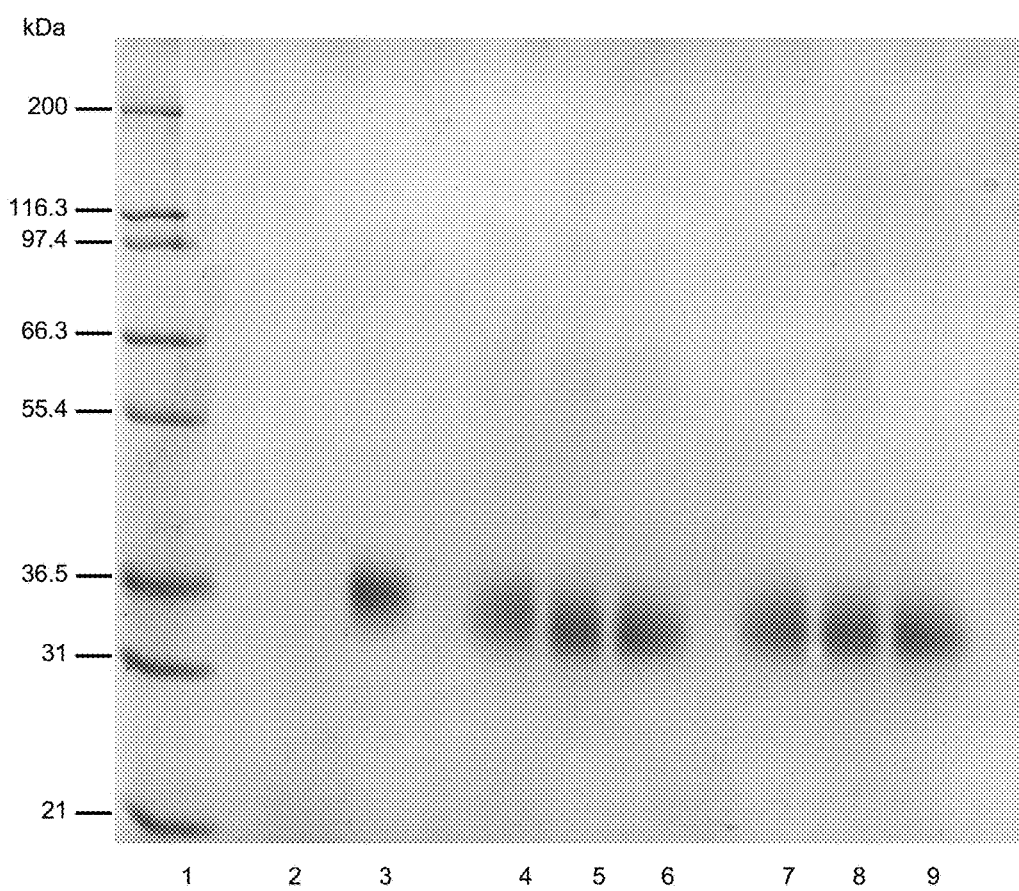

1) Molecular Weight Markers; 2) Insect cell culture media negative control; 3) Nickel-affinity purified TSHR260-JMG55-4.5 (untreated); 4-6) purified TSHR260-JMG55-4.5 treated with 60 mU Endoglycosidase F3 per mg of TSHR260-JMG55-4.5 after 24 h (lane 4), 72 h (lane 5) and 120 h (lane 6); 7-9) purified TSHR260-JMG55-4.5 with 80 mU Endoglycosidase F3 per mg of TSHR260-JMG55-4.5 after 24 h (lane 7), 72 h (lane 8) and 120 h (lane 9).

FIG. 29 DNA sequences of thermostabilising single amino acid mutations made in the TMD of TSHR-JMG55.

| Mutation | DNA sequence (3'-5') | SEQ ID No |
|---|---|---|
| E409K | $T_{1204}$CCGATGAGTTCAACCCGTGT$A_{1225}A_{1226}G_{1227}$GACATAATGGGCTACAAGTTC$_{1248}$ | 69 |
| D410K | $G_{1207}$ATGAGTTCAACCCGTGTGAA$A_{1228}A_{1229}G_{1230}$ATAATGGGCTACAAGTTCCTG$_{1251}$ | 70 |
| H443N | $C_{1306}$TGCTTATTCTCCTCACCAG$C_{1327}A_{1328}C_{1329}$TACAAACTGAACGTCCCCCGC$_{1350}$ | 71 |
| L452Y | $A_{1333}$AACTGAACGTCCCCCGCTTT$T_{1354}A_{1355}C_{1356}$ATGTGCAACCTGGCCTTTGCG$_{1377}$ | 72 |
| N455A | $G_{1342}$TCCCCCGCTTTCTCATGTGC$G_{1363}C_{1364}C_{1365}$CTGGCCTTTGCGGATTTCTGC$_{1386}$ | 73 |
| M463V | $C_{1366}$TGGCCTTTGCGGATTTCTGC$G_{1387}T_{1388}G_{1389}$GGGATGTACCTGCTCCTCATC$_{1410}$ | 74 |
| Y466F | $G_{1375}$CGGATTTCTGCATGGGGATGT$T_{1396}T_{1397}C_{1398}$CTGCTCCTCATCGCCTCTGTA$_{1419}$ | 75 |
| L467P | $G_{1378}$ATTTCTGCATGGGGATGTAC$C_{1399}C_{1400}C_{1401}$CTCCTCATCGCCTCTGTAGAC$_{1422}$ | 76 |
| T477I | $A_{1408}$TCGCCTCTGTAGACCTCTAC$A_{1429}T_{1430}C_{1431}$CACTCTGAGTACTACAACCAT$_{1452}$ | 77 |
| Q489H | $T_{1444}$ACAACCATGCCATCGACTGG$C_{1465}A_{1466}C_{1467}$ACAGGCCCTGGGTGCAACACG$_{1488}$ | 78 |
| K565L | $G_{1672}$TGGGAATAAGTAGCTATGCC$C_{1693}T_{1694}G_{1695}$GTCAGTATCTGCCTGCCCATG$_{1716}$ | 79 |
| V595I | $A_{1762}$CGCTCAACATAGTTGCCTT$CA_{1783}T_{1784}C_{1785}$ATCGTCTGCTGCTGTTATGTG$_{1806}$ | 80 |
| C600R | $G_{1777}$CCTTCGTCATCGTCTGCTGC$A_{1798}G_{1799}G_{1800}$TATGTGAAGATCTACATCACA$_{1821}$ | 81 |
| Y601F | $T_{1780}$TCGTCATCGTCTGCTGCTGT$T_{1801}T_{1802}C_{1803}$GTGAAGATCTACATCACAGTC$_{1824}$ | 82 |
| I648L | $T_{1921}$CATTCTATGCTCTGTCAGCA$C_{1942}T_{1943}G_{1944}$CTGAACAAGCCTCTCATCACT$_{1965}$ | 83 |
| K660D | $C_{1957}$TCATCACTGTTAGCAACTCC$G_{1978}A_{1979}C_{1980}$ATCTTGCTGGTACTCTTCTAT$_{2001}$ | 84 |
| Y667V | $A_{1978}$AAATCTTGCTGGTACTCTTC$G_{1999}T_{2000}G_{2001}$CCACTTAACTCCTGTGCCAAT$_{2022}$ | 85 |
| S671A | $G_{1990}$TACTCTTCTATCCACTTAAC$G_{2011}C_{2012}C_{2013}$TGTGCCAATCCATTCCTCTAT$_{2034}$ | 86 |
| Y678L | $T_{2011}$CCTGTGCCAATCCATTCCTC$C_{2032}T_{2033}G_{2034}$GCTATTTTCACCAAGGCCTTC$_{2055}$ | 87 |
| Y678A | $T_{2011}$CCTGTGCCAATCCATTCCT$CG_{2032}C_{2033}C_{2034}$GCTATTTTCACCAAGGCCTTC$_{2055}$ | 88 |

Twenty single TSHR mutations increased the thermostability of TSHR-JMG55 in at least two of the three stability assays A, B and C (Figure 14). These single mutations were used in combination to further improve the thermostability of TSHR-JMG55.

The mutated nucleotides are in bold. The subscript numbers are the positions of the nucleotides in the TSHR nucleotide sequence.

FIG. 30 Protein sequences of thermostabilising single amino acid mutations made in the TMD of TSHR-JMG55.

| Mutation | Protein sequence | SEQ ID No |
|---|---|---|
| E409K | $S_{402}$DEFNPC$K_{409}$DIMGYK$F_{416}$ | 89 |
| D410K | $D_{403}$EFNPCE$E_{410}$IMGYKF$L_{417}$ | 90 |
| H443N | $L_{436}$LILLTS$N_{443}$YKLNVP$R_{450}$ | 91 |
| L452Y | $K_{445}$LNVPRF$Y_{452}$MCNLAF$A_{459}$ | 92 |
| N455A | $V_{448}$PRFLMC$A_{455}$LAFAD$FC_{462}$ | 93 |
| M463V | $L_{456}$AFADFC$V_{463}$GMYLL$LI_{470}$ | 94 |
| Y466F | $A_{459}$DFCMGM$F_{466}$LLLIAS$V_{473}$ | 95 |
| L467P | $D_{460}$FCMGMY$P_{467}$LLIASV$D_{474}$ | 96 |
| T477I | $I_{470}$ASVDLY$I_{477}$HSEYYN$H_{484}$ | 97 |
| Q489H | $Y_{482}$NHAIDW$H_{489}$TGPGCN$T_{496}$ | 98 |
| K565L | $V_{558}$GISSYA$L_{565}$VSICLP$M_{572}$ | 99 |
| V595I | $T_{588}$LNIVAF$I_{595}$IVCCCY$V_{602}$ | 100 |
| C600R | $A_{593}$FVIVCC$R_{600}$YVKIYI$T_{607}$ | 101 |
| Y601F | $F_{594}$VIVCCC$F_{601}$VKIYIT$V_{608}$ | 102 |
| I648L | $S_{641}$FYALSA$L_{648}$LNKPLI$T_{655}$ | 103 |
| K660D | $L_{653}$ITVSNS$D_{660}$ILLVLF$Y_{667}$ | 104 |
| Y667V | $K_{660}$ILLVLF$V_{667}$PLNSCA$N_{674}$ | 105 |
| S671A | $V_{664}$LFYPLN$A_{671}$CANPFL$Y_{678}$ | 106 |
| Y678L | $S_{671}$CANPFL$L_{678}$AIFTKA$F_{685}$ | 107 |
| Y678A | $S_{671}$CANPFL$A_{678}$AIFTKA$F_{685}$ | 108 |

Twenty single TSHR mutations increased the thermostability of TSHR-JMG55 in at least two of the three stability assays A, B and C (Figure 14). These single mutations were used in combination to further improve the thermostability of TSHR-JMG55.

The

GLYCOPROTEIN HORMONE RECEPTOR MUTATIONS

CROSS-REFERENCE TO RELATED APPLICATIONS

This application is a filing under 35 U.S.C. 371 of International Application No. PCT/GB2015/000171 filed Jun. 11, 2015, entitled "Glycoprotein Hormone Receptor Mutation," which claims priority to Great Britain Patent Application No. 1410409.5 filed Jun. 11, 2014, which applications are incorporated by reference herein in their entirety.

FIELD OF THE INVENTION

The present invention relates generally to glycoprotein hormone receptors, particularly but not exclusively to the thyroid stimulating hormone (TSH) receptor (TSHR). The invention relates to mutations, especially single point mutations, that improve the thermostability of such receptor, particularly TSHR, preparations. Further, the invention relates to single point mutations combined together to even further improve the stability of such preparations. The invention also relates to methods using thermostable glycoprotein hormone receptor, including TSHR, preparations to detect the presence of autoantibodies, such as TSHR autoantibodies (TRAbs), for diagnosis, monitoring and prediction of diseases associated with autoimmunity, especially TSHR autoimmunity.

BACKGROUND

The TSH Receptor

The TSHR is a member of the G-protein coupled receptor (GPCR) family and consists of three domains: the extracellular leucine-rich repeat domain (LRD), the hinge region and a transmembrane domain (TMD) with an intracellular C-terminus (Nunez Miguel R et al (2004) Thyroid 14: 991-1011). TSHR260 is a subdomain of TSHR consisting of residues 22-260 and encompassing most of the LRD (Sanders J et al (2007) Thyroid 17:395-410). The TSHR260 shows similar binding to TRAbs as the full-length TSHR (Rees Smith B et al (2009) Hormone and Metabolic Research 41: 448-455 and WO 2010/073012).

In the thyroid, the TSHR is present on the basal membrane of thyroid follicular epithelial cells. Binding of TSH to the TSHR starts activation of the TSHR signalling cascade which involves binding of G-proteins to the TSHR followed by stimulation of the cyclic AMP pathway and synthesis of thyroid hormones (thyroxine; T4 and triiodothyronine; T3) (Sanders J et al (1997) Ballière's Clinical Endocrinology and Metabolism. Ed TF Davies 11: 451-479; pub Ballière Tindall, London and Latif R et al (2009) Endocrinology and Metabolism Clinics of North America 38: 319-341).

Autoimmune Thyroid Disease

Autoimmune thyroid disease is one of the most common autoimmune conditions with a prevalence rate of 600 to 1000 per 100,000 (Jacobson D L et al (1997) Clinical Immunology and Immunopathology 84: 223-243 and Cooper G S et al (2009) Journal of Autoimmunity 33: 197-207). The major thyroid autoantigens targeted by the autoimmune system are thyroid peroxidase (TPO), thyroglobulin (Tg) and the TSHR. TPO autoantibodies (TPOAbs) and thyroglobulin autoantibodies (TgAbs) are serological markers of thyroid autoimmunity in different forms of AITD including, Hashimoto's thyroiditis, Graves' disease and post-partum thyroiditis (PPT) (Rees Smith B et al (2007) Thyroid 17: 923-938). TRAbs are markers of TSHR autoimmunity, in particular, Graves' disease. Furthermore TRAbs are responsible for the pathology of Graves' disease. There are two main types of TRAbs; stimulating type and blocking type (Rees Smith B et al (2007) supra and Rees Smith B et al (2009) supra).

Thyroid stimulating autoantibodies bind to the TSHR and mimic the actions of TSH thereby stimulating the thyroid to produce high levels of T4 and T3; these autoantibodies are also described as TRAbs with stimulating activity or TSH agonist activity (Rees Smith B et al (2007) supra). The feedback control mechanism of thyroid function is no longer effective in the presence of thyroid stimulating autoantibodies and the patients present with clinical symptoms of a hyperactive thyroid characterised by excess of thyroid hormones in serum and their metabolic consequences. This condition is known as Graves' disease. TRAbs with stimulating activity may also interact with the TSHRs in retro-orbital tissue and contribute to the development of the eye signs of Graves' disease (Seethalakshimi, I and Bahn R (2012) Best Pract Res Clin Endocrinol Metab 26:281-289 and Rees Smith B, Sanders J and Furmaniak J (2008) Biomarkers Med 2: 567-576). A human monoclonal autoantibody which acts as a powerful thyroid stimulator (hMAb TSHR1; also referred to as M22) has been described in detail in EP 1565493B1. The structure of the complex of M22 Fab bound to TSHR260 has been solved by X-ray crystallography at 2.55 Å resolution as described in WO 2008/025991A1. Analysis of the structure of the TSHR260-M22 complex provides detailed information about the receptor and the stimulating autoantibody residues involved in interactions with each other.

A further human monoclonal autoantibody with potent thyroid stimulating activity (K1-18) is described in WO 2010/073012.

Blocking type TRAbs occur less frequently in patients with AITD than stimulating autoantibodies. Blocking type autoantibodies bind to the TSHR, prevent TSH from binding to the receptor but have no ability to stimulate TSHR activity. Consequently, formation and secretion of thyroid hormones (T4 and T3) is greatly reduced and the patients with this type of TRAb present with clinical symptoms of under-active thyroid (hypothyroidism). Blocking type autoantibodies are known as TRAbs with blocking activity or TSH antagonist activity (Rees Smith B et al (1988) Endocrine Reviews 9: 106-121 and Rees Smith B et al (2007) supra). A human autoantibody to the TSHR with TSH antagonist activity (5C9) has been described in detail in WO 2008/099185A1 and a further human monoclonal autoantibody with powerful TSHR blocking activity (K1-70) has been described in WO 2010/073012. The structure of K1-70 Fab in complex with TSHR260 has been solved by X-ray crystallography as described in Sanders P et al (2011) Journal of Molecular Endocrinology 46: 81-99. The TSHR260-K1-70 structure shows the binding arrangements between the TSHR and the TSHR blocking autoantibody at the molecular level. Comparison of the TSHR260-M22 and TSHR260-K1-70 structures provides a unique insight into the similarities and differences in the interactions of a stimulating and a blocking autoantibody with the TSHR (Nunez Miguel R et al (2012) Journal of Molecular Endocrinology 49: 137-151). TSHR-R255 emerged as a key amino acid residue forming strong interactions with M22 but not K1-70 consistent with the reported importance of R255 for the stimulating activity of various human and animal TSHR antibodies and stimulating antibodies in patient sera (Sanders J et al (2006) Thyroid 16: 1195-1206 and WO 2006/016121).

Methods to Detect TSHR Antibodies

It is well documented in the art that patient TRAbs with stimulating or blocking activity bind to regions on the TSHR LRD overlapping with each other and with the TSH binding site. However, there are subtle differences in the TSHR residues in contact with autoantibodies present in different sera (Rees Smith B et al (2007) supra). It is also documented that human monoclonal autoantibodies M22 and K1-70 are representative of TRAbs in patients with AITD (Sanders J et al (2007) supra, Rees Smith B et al (2009) supra, Evans M et al (2010) Clinical Endocrinology 73: 404-412, Núñez Miguel et al (2012) supra). The principles of TSHR interaction with TSH and TRAbs have been employed in different assays to detect patient TSHR autoantibodies.

Measurements of TRAbs are important in the diagnosis and management of Graves' disease and other thyroid disorders. Currently four types of assay are used to measure TRAbs:— a) competitive binding assays which measure the ability of patient serum TRAbs to inhibit the binding of TSH or human monoclonal TRAbs to preparations of TSH receptor;
b) bioassays which measure the ability of TRAbs to stimulate cells expressing the TSH receptor in culture;
c) immunoprecipitation of labelled TSH receptor preparations with TRAbs; and
d) Bridge type assays in which divalent TRAbs bind to TSHR coated onto ELISA plate wells with one arm and to liquid phase TSHR260-alkaline phosphatase fusion protein (TSHR260-AP) with the other arm to form a bridge.

Measurement of TSH receptor autoantibodies using such assays are described in references:—

Sanders J et al (1997) supra.
Sanders J et al (1999) Journal of Clinical Endocrinology and Metabolism 84: 3797-3802.
Rees Smith B et al (2004) Thyroid 14: 830-835
Rees Smith B et al (2009) supra.

Strategies to Improve TSHR Stability

We have appreciated that proteins such as TSHR and TSHR260 have poor stability and are denatured during purification. Accordingly, more thermostable proteins, for example more thermostable TSHR260 and full length TSHR, would have a number of applications including:

a) Enabling production of highly purified TSHR260 and full length TSHR.
b) Designing improved assays for detection of TRAbs.
c) Enabling crystallisation of highly purified TSHR260 free from stabilising antibodies.
d) Designing drugs whereby crystals of ligand-free TSHR260 are soaked into fragment libraries followed by X-ray crystallography to identify novel drug scaffolds.
e) Designing strategies to obtain increased thermostability of regions of full length TSHR outside TSHR260.

Natural proteins are stable enough in their native environment to function, but are often not optimally thermostable under the range of conditions required for industrial uses. Protein engineering methods, particularly mutagenesis, have been used to improve the thermostability of both soluble proteins and membrane proteins. Previous strategies for improving the thermostability of proteins by mutagenesis have involved one of two approaches: (i) testing a small number of rationally-designed mutations, or (ii) testing a large number of mutations produced either randomly or systematically (Dodevski I and Plückthun A (2011) Journal of Molecular Biology 408: 519-655; Serrano-Vega M J et al (2008) Proceedings of the National Academy of Sciences of the USA 105: 877-882) for thermostabilising effects on the protein.

The present invention describes mutations introduced particularly into TSHR, and especially into TSHR260, following the work of the present inventors to identify mutations that are most likely to improve the thermostability (Table 1):

In β-sheets, the position and environment of amino acid residues plays an important role in the formation and stability of β-sheets with periodicity of polar and nonpolar residues important for determining secondary structure (Xiong H et al (1995) Proceedings of the National Academy of Sciences of the USA 92: 6349-6353). The preferred residue periodicity for β-strands is 0+0−0+0—where "0" is a non-polar residue such as Ile or Thr, "+" is a positive residue, preferably Arg and "−" is a negative residue, preferably Asp.

The leucine rich domain (LRD) has a general consensus sequence of the leucine rich repeat (LRR) motif, LxxLxLxxNxLxxLpxxoFxxLxx, where "L" is Leu, Ile, Val or Phe, "N" is Asn, Thr, Ser or Cys, "o" is non-polar and "x" is a non-conserved residue (Matsushima N et al (2010) BMC Microbiology 10: 235-245). Residues can be mutated to conform to this motif.

Amino acids which tend to stabilise or destabilise proteins have been identified either computationally, by comparing the sequences of homologous proteins in mesophilic and thermophilic organisms or the amino acid composition of their proteomes, or experimentally, by measuring the thermodynamic properties of mutants. Different residues have different stabilising effects depending on whether they are at the surface or the core of the protein (Yokota K et al (2006) Science and Technology of Advanced Materials 7: 255-262) or their position in secondary structure elements (Xiong H, et al (1995) supra; Vogt G et al (1997) Journal of Molecular Biology 269: 631-643; Minor D L and Kim P S (1994) Nature 367: 660-663 and Minor D L and Kim P S (1994) Nature 371: 264). Stabilising residues include Glu, Lys, Arg and Tyr residues on the surface and Ala in the core; while Gln, Met, Cys and Ser and Asn tend to be destabilising (Cambillau C and Claverie J-M (2000) Journal of Biological Chemistry 275: 32383-32386; Kim C A and Berg J M (1993) Nature 362:267-270; Kumar S et al (2000) Journal of Biomolecular Structure & Dynamics 17 Suppl 1: 79-85; Minor D and Kim P S 1994a+b supra; Montanucci L et al (2008) Bioinformatics 24: i190—i195; Pack S P and Yoo Y J (2004) Journal of Biotechnology 111: 269-277; Smith C K et al (1994) Biochemistry 33: 5510-5517; Szilágy A and Závodsky P (2000) Structure 8: 493-504; Vogt G et al (1997) supra; Yokota K et al (2006) supra).

Thermophilic organisms tend to have more charged residues and less polar uncharged residues compared to mesophilic organisms (Cambillau C and Claverie J-M (2000) supra). The number and arrangement of ion pairs plays a large role in improving the thermostability of proteins (Vetriani C D L et al (1998) Proceedings of the National Academy of Sciences of USA 95: 12300-12305; Kumar S et al (2000) supra; Montanucci et al (2008) supra; Szilágy A and Závodsky P (2000) supra). This probably explains the high frequency of Glu and Lys in thermophilic proteins.

Mutation of residues to the consensus sequence of homologues of a protein in different organisms can be used to identify possible thermostabilising mutations. This has been used to produce more thermostable mutants of a wide range of proteins including immunoglobulin domains, GroEL minichaperones, p53 and phytase with increases in apparent melting point ($T_m$) of 5° C. to 36° C. (reviewed in Lehmann M and Wyss M (2001) Current Opinion in Biotechnology 12: 371-375). Residues with the appropriate backbone torsion angles can be mutated to either Pro, to improve the rigidity and therefore stability of the protein, or to Gly, to reduce the strained torsion angles in residues in the left-hand helical conformation (Vielle C and Ziekus G J (2001) Microbiology and Molecular Biology Reviews 65:1-43).

Computational modelling can be used to predict the effect of mutations on the thermostability of the protein, although the results obtained are variable.

The novel strategy to improve the thermostability of particularly TSHR and fragments thereof such as TSHR260 described in this invention used rational-scanning mutagenesis of the polypeptide TSHR260 (amino acid residues M22-L260), where every residue was mutated to another amino acid determined by a combination of rational approaches (listed above), coupled to a thermostability assay. The novel strategy described involved four steps: (i) site-directed mutagenesis by PCR to obtain the mutants, (ii) expression of the TSHR260 mutants by transient transfection of CHO-K1 cells, (iii) assessment of protein expression and thermostability, (iv) analysis of thermostability curves of the most stable mutants identified in (iii).

The most thermostabilising single mutations were combined to make double, triple, quadruple, quintuple and hextuple mutants of TSHR260, which increase the thermostability of TSHR260 even further.

The single and combined mutations that increased the thermostability of TSHR260 were also found to increase the thermostability of full length TSHR as well.

Similarly, thermostabilising mutations were identified in the transmembrane domain (TMD) of the TSHR. The 6 mutations from the most stable hextuple TSHR260 mutant were expressed as full length TSHR in combination with the thermostabilising TMD mutations. The thermostability of these full-length TSHR mutants was tested using analysis of thermostability curves and the most thermostabilising mutations in the TMD were combined to further increase the thermostability of the full length TSHR.

Full-length TSHR mutants and fragments thereof with improved thermostability can be used in assays to detect TSHR autoantibodies in patient sera and can be purified in an active form.

Related Previous Patent Applications

The invention described in EP 1565493B1 provides details about the properties of a human monoclonal autoantibody (M22 or hMAb TSHR1) with powerful stimulating activity and its interaction with the TSHR. The interactions between M22 Fab and the TSHR LRD have been solved at the molecular level from the X-ray diffraction analysis (2.55 Å resolution) of the complex between the two molecules as described in WO 2008/025991A1.

WO 2006/016121A1 discloses a mutated TSHR preparation including at least one point mutation which can be used in the differential screening and identification of patient serum stimulating TSHR autoantibodies, patient serum blocking TSHR autoantibodies and TSH in a sample of body fluid from a patient being screened.

Generation and characterisation of a mouse MAb (9D33) with TSHR blocking activity is described in WO 2004/050708A2. 9D33 binds to the TSHR with high affinity ($2 \times 10^{10}$ L/mol) and is an effective antagonist of TSH, hMAb TSHR1 (M22) and patient serum TRAbs with stimulating or blocking activities.

WO 2008/099185A1 discloses the isolation and characterisation of a human MAb (5C9) to the TSHR that is an effective antagonist of TSH and of stimulating TRAbs in patient sera. 5C9 has been found unexpectedly to inhibit TSHR constitutive activity, that is to say the production of cyclic AMP by the TSHR in a test system in the absence of thyroid stimulating hormone or M22. Furthermore, 5C9 has been found to inhibit increases in TSHR basal activity (i.e. activity in the absence of TSH) associated with TSHR activating mutations.

WO 2010/073012 discloses the isolation and characterisation of a further human monoclonal autoantibody (K1-18) with powerful stimulating activity and a human monoclonal autoantibody (K1-70) that is a potent TSHR antagonist from the peripheral blood lymphocytes of a patient. K1-18 and K1-70 have the characteristics of TRAbs with stimulating and blocking activities respectively found in patients' sera. The invention provides the first evidence that TRAbs with opposing activities (stimulation and blocking) can be present at the same time in a single patient's serum. Further the invention described in WO 2010/073012 describes a novel assay to measure TRAbs based on the bridging principle whereby divalent antibodies bind to the TSHR coated onto an ELISA plate well with one arm and to liquid phase TSHR260-alkaline phosphatase with the other arm to form a bridge.

SUMMARY OF THE INVENTION

The invention relates generally but not exclusively to the TSHR, and particularly but not exclusively to the TSHR sequence between the residues 22-260 (TSHR260) (FIGS. 3 and 4; SEQ ID Nos 3 and 4). A further aspect of the invention relates in particular to amino acid mutations in TSHR260, in particular to designing amino acid mutations using a novel rational-scanning mutagenesis approach, where every residue is mutated to another amino acid determined by a combination of rational approaches. Further, the invention relates to high-throughput methods to generate and test numerous mutants. One aspect of the invention relates to producing particularly but not exclusively TSHR260 containing single amino acid mutations characterised by greater thermostability relative to the wild type TSHR260 (TSHR260-WT).

Another aspect of the invention relates to designing, producing and testing the combinations of two single amino acid mutations to generate TSHR260 containing double mutations. One aspect of the invention relates to particularly but not exclusively TSHR260 containing double mutations characterised by greater thermostability relative to TSHR260 containing a single mutation and to TSHR260-WT.

Another aspect of the invention relates to designing, producing and testing of particularly but not exclusively TSHR260 containing triple, quadruple, quintuple and hextuple combinations of single amino acid mutations. These aspects of the invention relate to generating particularly but not exclusively mutated TSHR260 characterised by increased thermostability relative to TSHR260 containing a lower number of mutations and to TSHR260-WT.

In one aspect the invention describes a successful approach to identify stabilising mutations in the TSHR sequence that would not have been discovered had only a small number of residues been selected by rational approaches or computational modelling.

In one aspect the invention relates to the important biological activity of TSHR260. The biological activity relates to the ability to bind TSHR autoantibodies, in particular the TSHR stimulating human monoclonal autoantibody M22. The invention describes specific and novel single, double, triple, quadruple, quintuple and hextuple mutations that increase the thermostability of the TSHR260 measured by way of the ability of TSHR260 to bind M22. These aspects of the invention relate to novel mutated TSHR260 preparations which have increased thermostability and retain the ability to bind M22 and other TSHR autoantibodies.

In another aspect of the invention the novel single and combined mutations that increased the thermostability of TSHR260 were also, surprisingly, found to increase the thermostability of full length TSHR (FIGS. 1 and 2; SEQ ID Nos 1 and 2). The mutations in full length TSHR while increasing the thermostability of the TSHR did not affect its biological activity (i.e. ability of ligands to stimulate the TSHR) or its ability to bind TRAbs.

Further aspects of the invention relate to design and development of improved methods for detection of TSHR autoantibodies. In one aspect of the invention, particularly but not exclusively TSHR260 preparations stable in aqueous solution are employed to bind TSHR autoantibodies present in body fluids in an assay kit format. In another aspect of the invention, stable preparations of the full-length TSHR containing the stabilising mutations are employed to bind TSHR autoantibodies present in body fluids in an assay kit format. In a further aspect, stable full-length TSHRs provide improved means to detect TSHR bioactivity in response to binding to TSH or TSHR stimulating antibodies. This bioactivity could be, but is not limited to, stimulation of cyclic AMP production in cell lines expressing stable TSHR.

Further applications of the stable preparations of the TSHR could relate to new opportunities to neutralise TSHR autoantibodies present in the body fluids of patients with AITD. These applications could be, but are not limited to, contacting the body fluids with, for example, the stable TSHR260 preparations or, for example, the stable full-length TSHR preparations in vitro or in vivo. In addition, TSHR preparations containing fewer amino acids than TSHR260 can be stabilised by the same mutations as could TSHR preparations containing sequences intermediate to TSHR260 and full length TSHR. Although preparations of human TSHR are usually preferred, TSHR preparations of other species can be stabilised in the same way. Even further aspects of the invention open new opportunities to improve the stability of other similar proteins, in particular the other glycoprotein hormone receptors (FSHR and LHR (FIG. 11; SEQ ID Nos 57 and 58 respectively).

DESCRIPTION OF THE INVENTION

According to one aspect of the present invention, there is provided a mutant thyroid stimulating hormone receptor (TSHR) or fragment thereof comprising one or more mutations, wherein the mutant TSHR has increased thermostability with respect to the equivalent wild type TSHR or fragment. The mutations are preferably point mutations. In the following, where used, the word "mutant" refers to both full length TSHR and any fragment thereof, such as the fragment TSHR260 (FIGS. 3 and 4; SEQ ID Nos 3 and 4). Thermostability is discussed and defined further below.

Suitably, a TSHR fragment is one which is an antigenic fragment, and in particular is one which retains the ability to bind TSHR autoantibodies, in particular the TSHR stimulating human monoclonal autoantibody M22. Suitable fragments include TSHR260, as well as sequences of smaller lengths and those of intermediate length between TSHR260 and full length TSHR. TSHR418 (residues 22 to 418) is another example of such a fragment.

In one aspect of the invention, the mutant TSHR or fragment thereof is a full-length TSHR or comprises at least 70% or more, at least 80% or more, or at least 90% or more, of the length of full-length TSHR as measured by the number of amino acids present in the mutant compared to full-length TSHR.

Preferably, the one or more mutation is within the extracellular leucine-rich repeat domain (LRD) of the TSHR or fragment thereof. More preferably, the one or more mutation is within residues 22 to 260 (TSHR260) of the TSHR or fragment thereof.

In a preferred aspect, a mutant TSHR or fragment thereof according to the invention is from a mammalian species, particularly one which is from, or is derived from, human TSHR (SEQ ID Nos 1 and 2). However, any other suitable species may be used, and other such species include monkey, porcine, bovine, cat, dog, mouse, rat, sheep or horse TSHR (SEQ ID Nos 47-56 respectively).

Preferably a mutant TSHR or fragment thereof according to the invention binds TSHR autoantibodies, particularly the TSHR autoantibody M22, K1-70 or K1-18.

In one aspect, the invention provides a mutant TSHR or fragment thereof wherein the thermostability (as further defined herein) of the mutant as determined by its half-life at 42° C. is 1.5 times greater or more than the half-life of the equivalent wild type TSHR or fragment. Preferably, the thermostability of the mutant as determined by the half-life at 42° C. is 1.7, or 2, or 3, or 3.5, or 5 times greater or more than the half-life of the equivalent wild type TSHR or fragment. The figures above apply in particular, but not exclusively, to mutants comprising only one single point mutation.

The half-life of the mutant TSHR or fragment thereof (such as TSHR260), as compared to the half-life of the equivalent wild type TSHR or fragment thereof, is suitably measured in a binding assay which determines the amount of mutant TSHR or fragment thereof (or equivalent wild type protein) that retains the ability to bind an antibody or autoantibody to the TSHR at the test temperature.

A mutant TSHR or fragment thereof according to the invention may comprise any number of single point mutations, but we prefer to use from one to six single point mutations. In a preferred aspect of the invention the mutant contains one, two, three, four, five, or six point mutations selected from any one of the following mutations: P28E, L59F, T62V, H63C, L64Y, R112P, P142I, D143P, D151E, S166T, I167F, P168Y, V169R, N170W, T179C, I253R and R255Y (FIGS. 5 and 6; SEQ ID Nos 11-25, 27-43, 45 and 46 respectively). However, it will be understood that different point mutations from those above could be selected if desired, and one aspect of the present invention is the provision of a binding assay which enables the thermostability of any particular point mutation, or combination of point mutations, to be determined. In one aspect of the invention, the mutant contains only one single point mutation.

In another aspect, a mutant TSHR or fragment thereof according to the invention contains a double point mutation (that is, two single point mutations only). Preferably, the thermostability of such double point mutants as determined by the half-life at 42° C. is 3.5, or 5, or 7, or 9 times greater or more than the half-life of the equivalent wild type TSHR or fragment. Alternatively, the thermostability of such double point mutants as determined by its half-life at 50° C. is 3, or 5, or 6, or 8 or 10 times greater or more than the half-life of the equivalent wild type TSHR or fragment.

In a further aspect, a mutant TSHR or fragment thereof according to the invention contains a triple point mutation (that is, three single point mutations only). Preferably, the thermostability of such triple point mutations as determined by the half-life at 50° C. is 9, or 12, or 15 times greater or more than the half-life of the TSHR260 mutant comprising the single point mutation I253R (SEQ ID No 45). The TSHR260 mutant comprising the single point mutation I253R can be compared to wild type TSHR260 (TSHR260-WT), so as to enable a comparison between the more thermostable mutations (often comprising three of more single point mutations) and wild type TSHR260 (for which meaningful measurements of half-life at higher temperatures are difficult). TSHR260-I253R improved the thermostability 3.0±0.4 times over TSHR260-WT at 42° C., i.e. increased the half-life of TSHR260 at 42° C. by 53±6 minutes (See, for example the data in Tables 3 and 7). It also improved the thermostability at 50° C. by 2.85±0.13 times over TSHR260-WT.

In a further aspect, a mutant TSHR or fragment thereof according to the invention contains a quadruple point mutation (that is, four single point mutations only). Preferably, the thermostability of such quadruple point mutants as determined by the half-life at 50° C. is 20, or 30, or 50 times greater or more than the half-life of the TSHR260 mutant comprising the single point mutation I253R. Alternatively, the thermostability of such quadruple point mutants as determined by its half-life at 55° C. is 12, or 20, or 30 times greater or more than the half-life of the TSHR260 mutant comprising the single point mutation I253R.

In a further aspect, a mutant TSHR or fragment thereof according to the invention contains a quintuple point mutation (that is, five single point mutations only). Preferably, the thermostability of such quintuple point mutants as determined by the half-life at 55° C. is 40, or 70, or 100 times greater or more than the half-life of the TSHR260 mutant comprising the single point mutation I253R.

In a further aspect, a mutant TSHR or fragment thereof according to the invention contains a hextuple point mutation. Preferably, the thermostability of such hextuple point mutants as determined by the half-life at 55° C. is 500, or 750, or 900 times greater or more than the half-life of the TSHR260 mutant comprising the single point mutation I253R. Alternatively, the thermostability of such hextuple mutants as determined by its half-life at 60° C. is 3 times greater or more than the half-life of the TSHR260 mutant comprising the quadruple point mutation I253R+D143P+R112P+D151E (herein referred to as JMG45 (SEQ ID Nos 45, 36, 34 and 37 respectively), which has a predicted thermostability at 60° C. of 174 times that of TSHR260-WT) or at 55° C. is 1.2 times greater or more than the half-life of the TSHR260 mutant comprising the quadruple point mutation I253R+D143P+R112P+D151E. Full length TSHR mutants may be used if desired, in any aspect of the invention. Human, mouse or porcine full length TSHR mutants are particularly preferred, and have been shown to have good thermostability. In a further aspect, a mutant TSHR according to the invention is a full-length TSHR mutant, wherein the thermostability of the mutant as determined by its half-life at 50° C. is 3, or 5, times greater or more than the half-life of the equivalent wild type full length TSHR.

In a preferred aspect, a full length TSHR mutant comprises three or more point mutations within residues 22 to 260 (TSHR260) of the TSHR.

In a particularly preferred aspect of the invention, a mutant TSHR or fragment thereof consists of, or consists essentially of, the subdomain TSHR260 of the TSHR receptor. Consisting essentially of in this context means that suitably there is at least 80% sequence identity to TSHR260, preferably 90% sequence identity, more preferably 95% sequence identity.

In one aspect, a mutant TSHR or fragment thereof of the invention preferably contains a single point mutation from any of: P28E, L59F, T62V, H63C, L64Y, R112P, P142I, D143P, D151E, S166T, I167F, P168Y, V169R, N170W, T179C, I253R and R255Y. As will be understood by those in the art, "P28E" refers to mutation of the amino acid proline (P) to glutamic acid (E) at sequence position 28 of the TSHR, and so forth.

In another aspect, a mutant TSHR or fragment thereof according to the invention contains two point mutations, one of which is I253R (SEQ ID No 45) and the second of which is: P28E, L59F, T62V, H63C, L64Y, R112P, P142I, D143P, D151E, S166T, I167F, P168Y, V169R, N170W, T179C, or R255Y.

In another aspect, a mutant TSHR or fragment thereof according to the invention contains three point mutations, one of which is I253R (SEQ ID No 45), the second of which is D143P (SEQ ID No 36) and the third of which is one of P28E, L59F, T62V, H63C, L64Y, R112P, P142I, D151E, S166T, P168Y, V169R and N170W.

In another aspect, a mutant TSHR or fragment thereof according to the invention contains four point mutations, one of which is I253R, the second of which is D143P and the third of which is R112P (SEQ ID No 34), and a fourth of which is one of L59F, H63C, D151E, S166T, V169R and N170W.

In another aspect, a mutant TSHR or fragment thereof according to the invention contains five point mutations, one of which is I253R, the second of which is D143P, the third of which is R112P, a fourth of which is D151E (SEQ ID No 37) or H63C (SEQ ID No 32) and a fifth of which is one of L59F, (H63C or D151E), S166T and V169R (SEQ ID Nos 30, 32, 37, 38 and 41 respectively).

In another aspect, a mutant TSHR or fragment thereof according to the invention contains six mutations, one of which is I253R, the second of which is D143P, the third of which is R112P, a fourth of which is D151E, a fifth of which is H63C and a sixth of which is either S166T or V169R.

In another aspect, a mutant TSHR or fragment thereof according to the invention may contain from one, two, three, four, five, or six point mutations selected from any of: P28E, L59F, T62V, H63C, L64Y, R112P, P142I, D143P, D151E, S166T, I167F, P168Y, V169R, N170W, T179C, I253R and R255Y.

In one preferred aspect, the mutant TSHR or fragment thereof consists of TSHR260 and the equivalent wild type consists of wild type TSHR260.

A particularly preferred feature of the mutants of the invention is that the binding of monoclonal TSHR antibodies, particularly autoantibodies, to the mutant is unaffected, or substantially unaffected, when compared with the binding of the same monoclonal TSHR antibodies or autoantibodies to the equivalent wild type TSHR or fragment.

The invention also provides a mutant TSHR or fragment thereof according to the invention for use in medicine. There are potentially a number of medical and therapeutic uses of the mutants of the invention. For example, the invention provides a mutant TSHR or fragment thereof according to the invention for use in the detection of TSHR monoclonal autoantibodies and patient TRAbs. Also provided is a mutant TSHR or fragment thereof according to the invention for use in a therapeutically effective amount for absorbing circulating patient TRAbs.

The invention also provides the use of a mutant TSHR or fragment thereof according to the invention for small-molecule fragment screening to identify new scaffolds for small molecule drugs.

The invention also provides an in vitro method of treating an autoimmune disease associated with an immune reaction to the TSH receptor in a subject, which method comprises passing a sample of the subject's blood through a solid phase column having bound thereto a mutant TSHR or fragment thereof according to the invention, and absorbing the circulating TRAbs in the said blood onto the said mutant TSHR or fragment thereof.

The invention also provides a mutant TSHR or fragment thereof according to the invention wherein the mutant comprises a detectable label. The label may, for example, be selected from the group consisting of enzymatic labels, isotopic labels, chemiluminescent labels, fluorescent labels and dyes. Such labels may be added in any suitable way, for example, via gene fusion using an appropriate construct (as described further below) or by chemical labelling. Those skilled in the art will be familiar with the relevant techniques needed, and the identity of suitable labels.

In a preferred aspect, the label comprises an alkaline phosphatase (AP) label or a biotin label. Most preferably, an alkaline phosphatase label is employed.

In a preferred aspect, the labelled mutant consists of, or consists essentially of, the subdomain TSHR260 of the TSHR receptor. Certain preferred mutants are those consisting of the subdomain TSHR260 of the TSHR receptor and an alkaline phosphatase (AP) label, denoted herein as TSHR260-AP-X, wherein "X" indicates the one or more amino acid mutations in the mutant.

The labelled mutant or fragment thereof may comprise any one or more of the amino acid point mutations described herein. The mutations may be introduced into the wild type TSHR or fragment thereof either before or after the labelling, as will be understood by those skilled in the art.

The invention also provides a mutant thyroid stimulating hormone receptor (TSHR) or fragment thereof comprising one or more mutations within the transmembrane domain (TMD), wherein the mutant TSHR has increased thermostability with respect to the equivalent wild type TSHR or fragment.

Preferably, mutant TSHR or fragment thereof is a full-length TSHR or comprises at least 70% or more, or at least 80% or more, or at least 90% or more, of the length of full-length TSHR as measured by the number of amino acids present in the mutant compared to full-length TSHR.

In a preferred aspect, mutant TSHR or fragment with the one or more TMD mutations further comprises one or more further mutations which are not in the transmembrane domain, which one or more further mutations are according to the invention as described herein. The one or more further mutations may, for example, be in the TSHR260 subdomain accordingly to aspects of the invention described herein.

Preferably, the further mutations comprise at least two or more further mutations which are not in the transmembrane domain. Preferably, such mutations are in the TSHR260 subdomain.

In one aspect, the said further mutations comprise the hextuple point mutation H63C+R112P+D143P+D151E+V169R+I253R (TSHR-JMG55) (SEQ ID Nos 32, 34, 36, 37, 41 and 45 respectively).

Preferably, the invention provides a mutant thyroid stimulating hormone receptor (TSHR) or fragment thereof wherein the one or more mutations within the transmembrane domain (TMD) provide increased thermostability with respect to the equivalent mutant thyroid stimulating hormone receptor (TSHR) or fragment thereof which comprises only the said further mutations which are not in the transmembrane domain. The "equivalent" mutant thyroid stimulating hormone receptor (TSHR) here would thus be identical to the mutant in question, and thus comprise the same mutations except that it would lack any of the further mutations in the transmembrane domain. The term "equivalent" as used throughout the specification in similar contexts has the same meaning, mutatis mutandis.

In one aspect, the invention provides a mutant thyroid stimulating hormone receptor (TSHR) or fragment thereof comprising one or more mutations within the transmembrane domain (TMD) wherein the thermostability of the mutant as determined by its half-life at 33° C. is 1.2 times greater or more, or 1.3 times greater or more, than the half-life of the equivalent TSHR or fragment which comprises only the said further mutations which are not in the transmembrane domain.

In another aspect, the invention provides a mutant thyroid stimulating hormone receptor (TSHR) or fragment thereof comprising one or more mutations within the transmembrane domain (TMD) wherein the thermostability of the mutant as determined by its half-life at 33° C. is 1.2 times greater or more, or 1.3 times greater or more, than the half-life of the TSHR mutant comprising the hextuple mutation H63C+R112P+D143P+D151E+V169R+I253R (TSHR-JMG55).

Preferably, in the above aspects, the thermostability of the mutant as determined by its half-life at 33° C. is 2 times greater or more, or 3 times greater or more, or 5 times greater or more. Thermostability is defined generally below, but may for example be measured by stability assay A, B, or C shown in FIGS. 14b, c and d respectively.

Preferably, a mutant thyroid stimulating hormone receptor (TSHR) or fragment thereof according to the invention contains two point mutations in the transmembrane domain (TMD), wherein the thermostability of the mutant as determined by its half-life at 33° C. as measured by stability assay C shown in FIG. 14d is 1.1 times greater or more than the half-life of the equivalent TSHR or fragment which comprises only a single point mutation in the transmembrane domain (TMD) selected from T477I (SEQ ID No 97), V595I (SEQ ID No 100) or I648L (SEQ ID No 103).

In another preferred aspect, a mutant thyroid stimulating hormone receptor (TSHR) or fragment thereof according to the invention contains two point mutations in the transmembrane domain (TMD), wherein the thermostability of the mutant as determined by its half-life at 55° C. as measured by stability assay A or stability assay B shown in FIGS. 14b and 14c respectively is 1.5 times greater or more than the half-life of the equivalent TSHR or fragment which comprises only a single point mutation in the transmembrane domain (TMD) selected from T477I, V595I or I648L.

Preferably, a mutant thyroid stimulating hormone receptor (TSHR) or fragment thereof according to the invention is such that at least one of the said two point mutations in the TMD is selected from T477I, V595I, and I648L.

Preferably, a mutant TSHR or fragment thereof according to the invention having a mutation within the transmembrane domain (TMD) contains a single point mutation from any of: E409K, D410K, H443N, L452Y, N455A, M463V, Y466F, L467P, T477I, Q489H, K565L, V595I, C600R, Y601F, I648L, K660D, Y667V, S671A, Y678L, Y678A (SEQ ID Nos 89-108 respectively). Two or more of these mutations may also be combined.

Preferably, a mutant TSHR or fragment thereof according to the invention having a mutation within the transmembrane domain (TMD) contains two point mutations, one of which is T477I or V595I or I648L and the second of which is a different mutation selected from E409K, D410K, H443N, L452Y, N455A, M463V, Y466F, L467P, T477I, Q489H, K565L, V595I, C600R, Y601F, I648L, K660D, Y667V, S671A, Y678L, Y678A.

In another aspect, the invention also provides a method of purifying a mutant thyroid stimulating hormone receptor (TSHR) or fragment thereof comprising one or more mutations, wherein the mutant TSHR has increased thermostability with respect to the equivalent wild type TSHR or fragment, which method comprises:
i) purifying a composition comprising the mutant or fragment thereof by column chromatography;
ii) collecting the purified mutant or fragment thereof.

The composition may be any suitable composition or formulation containing mutant protein to be purified. For example, it may comprise an aqueous solution. It may comprise culture supernatant—for example, supernatant derived from cell cultures used to produce the mutant proteins.

The mutant TSHR or fragment thereof to be purified may be, for example, any one of the mutant TSHR or fragment thereof proteins according to the invention described herein. Preferably, the mutant consists of, or consists essentially of, the subdomain TSHR260 of the TSHR receptor and preferably may also comprise one of the following set of mutations:
1) I253R (FIGS. 5 and 6; SEQ ID Nos 27 and 45)
2) D143P+I253R (FIGS. 5 and 6; SEQ ID Nos 18, 27, 36 and 45)
3) R112P+D143P+I253R (FIGS. 5 and 6; SEQ ID Nos 16, 18, 27, 34, 36 and 45)
4) R112P+D143P+D151E+I253R (FIGS. 5 and 6; SEQ ID Nos 16, 18, 19, 27, 34, 36, 37 and 45)
5) R112P+D143P+D151E+V169R+I253R (FIGS. 5 and 6; SEQ ID Nos 16, 18, 19, 23, 27, 34, 36, 37, 41 and 45)
6) H63C+R112P+D143P+D151E+V169R+I253R (FIGS. 5 and 6; SEQ ID Nos 14, 16, 18, 19, 23, 27, 32, 34, 36, 37, 41 and 45)
7) H63C+R112P+D143P+V169R+I253R (FIGS. 5 and 6; SEQ ID Nos 14, 16, 18, 23, 27, 32, 34, 36, 41 and 45)
8) H63C+R112P+D143P+S166T+I253R (FIGS. 5 and 6; SEQ ID Nos 14, 16, 18, 20, 27, 32, 34, 36, 38 and 45).

Preferably, the column chromatography comprises an ion-exchange chromatography such as a cation-exchange or anion-exchange chromatography. Standard chromatography equipment and processes may be used, and such will be clear to those skilled in the art. Surprisingly, we have found that mutant proteins according to the present invention and described herein can, in fact, owing to their increased thermostability, be purified in the above way, unlike their wild type equivalents. This forms an aspect of the present invention.

Preferably, the purification method of the invention further comprises, either before or after step i), purifying a composition comprising the mutant or fragment thereof by affinity chromatography. Any suitable affinity chromatography may be used, but in a preferred aspect the affinity chromatography comprises antibody affinity chromatography and/or metal-ion affinity chromatography. One or both may be used.

In a particularly preferred aspect, the purification method of the invention described above comprises:
i) purifying a composition comprising the mutant or fragment thereof by cation-exchange or anion-exchange column chromatography;
ii) further purifying the mutant or fragment thereof by antibody affinity chromatography;
iii) optionally further purifying the mutant or fragment thereof by metal-ion affinity chromatography;
iv) collecting the purified mutant or fragment thereof.

Preferably, the antibody in step (ii) is an antibody, preferably a monoclonal antibody, which binds a conformational epitope within the TSHR extracellular domain. Any suitable antibody may be used. 14C4 is one preferred mouse monoclonal antibody.

In a preferred aspect, step (iii) above comprises using nickel-affinity chromatography, although other suitable metal-ion affinity chromatography columns may be used.

In another preferred aspect, a method of purification according to the invention wherein the affinity chromatography is antibody affinity chromatography and also comprises elution with elution buffer at pH 4.5+/−0.2, optionally preceded by elution with elution buffer at pH 5.0+/−0.2.

Preferably, in the purification method of the invention, the mutant consists of, or consists essentially of, the subdomain TSHR260 of the TSHR receptor. Preferably the mutant comprises the following set of mutations: H63C+R112P+D143P+D151E+V169R+I253R.

In a further aspect, according to the present invention purification of the mutant TSHR or fragment thereof does not require antibody bound to, or in complex with, the mutant or fragment thereof. The invention provides mutants of increased stability such that functional, active protein may be produced via purification without the need to stabilise the mutant of fragment thereof during purification with antibody bound or complexed to it.

In one aspect of the invention, particularly but not exclusively TSHR260 preparations, especially TSHR260-JMG55 preparations, which are stable in aqueous solution, are purified to obtain a preparation with high activity in the TSHR260 binding ELISA (shown in FIG. 12a).

The increased thermostability of the mutant TSHR proteins according to the invention allows for their purification, for example by the purification methods described herein. Such purification of active protein has hitherto been unachievable. Accordingly, the invention provides TSHR proteins, including TSHR260 proteins, at a level of purity and activity not previously achievable. These are novel products. "Purified" mutant TSHR or a fragment thereof as used herein is intended to refer to a mutant TSHR or fragment thereof which has been subjected to at least one purification step. The purification step or steps may be any suitable purification for purifying protein, and such will be clear to those skilled in this field. For example, the purification steps described and claimed herein may be used, but other suitable purifications are not excluded and may be used if desired.

According to another aspect of the present invention, there is provided purified mutant TSHR or fragment thereof according to the invention described herein obtained by the purification method of the invention described herein. The mutant TSHR of fragments thereof are also obtainable by the purification method of the invention. It is possible that other methods of purification may be used to produce the purified mutants of the present invention.

In a related aspect, therefore, the invention also provides a purified mutant TSHR or fragment thereof according to the invention described herein characterised in that the activity of the said purified mutant in a TSHR activity assay is greater than the activity of the unpurified mutant from culture supernatant as measured in the same TSHR activity assay. The supernatant will preferably be from a suitable cell culture used to express and secrete the mutant protein (as for example described herein). The TSHR activity assay may be any suitable assay which is capable of giving a measure of the activity of the mutant being tested, provided that exactly the same assay using the same conditions (i.e an identical assay) is used for both the unpurified and purified samples. Examples of a number of suitable assays are given herein, as will be clear to those skilled in the art. Particularly suitable assays are those shown in FIGS. 12*a*, 12*d*, and 13*c*.

The activity in the TSHR activity assay may be expressed in any suitable way, for example as the amount of activity per volume of sample—for example units per ml. Suitably, the activity is the specific activity of the mutant as measured in units of activity per quantity of protein—for example, units per mg.

In a preferred aspect, the invention provides a purified mutant TSHR or fragment thereof according to the invention described herein characterised in that the activity of the said purified mutant in a TSHR activity assay is 500 fold or greater compared to the activity of the unpurified mutant from culture supernatant as measured in the same TSHR activity assay. The activity may in fact be higher, for example the activity may be 1000 fold or greater, or 5000 fold or greater, compared to the activity of the unpurified mutant from culture supernatant as measured in the same TSHR activity assay. Preferably, the activity is expressed or measured as specific activity in units per mg of protein.

Preferably, the activity of the unpurified mutant is measured from the culture supernatant harvested directly from the culture, without any dilution or concentration of the supernatant, although it will be understood this may be done if desired—such will not affect the activity measured when expressed in terms of specific activity in units per mg of protein.

Preferably, the TSHR activity assay measures the ability of the said mutant to bind TSHR antibody or autoantibody. Any suitable antibody or autoantibody may be used, and suitable TSHR autoantibodies include M22, K1-70 or K1-18 (as described herein).

Preferably, the TSHR activity assay comprises mutant to be tested bound directly or indirectly to an ELISA plate. Preferably, the mutant to be tested is bound or coated indirectly on to an ELISA plate. For example, this may be achieved using antibody which binds TSHR but does not interfere with normal binding of the TSHR itself. Preferably, the antibody is a monoclonal antibody, which binds a conformational epitope within the TSHR extracellular domain. Any suitable antibody may be used. 14C4 is one preferred mouse monoclonal antibody, but others may be used, as will be understood.

In a preferred aspect, the TSHR activity assay comprises an assay as shown in FIG. 12*a* or FIG. 13*c*. If the mutant whose activity is to be tested is capable of being bound directly to an ELISA plate, then an assay of the type shown in FIG. 12*d* may be used. Preferably, purified mutant TSHR or fragment thereof according to the invention consists of, or consists essentially of, the subdomain TSHR260 of the TSHR receptor and comprises one of the following set of mutations:

1) I253R (FIGS. 5 and 6; SEQ ID Nos 27 and 45)
2) D143P+I253R (FIGS. 5 and 6; SEQ ID Nos 18, 27, 36 and 45)
3) R112P+D143P+I253R (FIGS. 5 and 6; SEQ ID Nos 16, 18, 27, 34, 36 and 45)
4) R112P+D143P+D151E+I253R (FIGS. 5 and 6; SEQ ID Nos 16, 18, 19, 27, 34, 36, 37 and 45)
5) R112P+D143P+D151E+V169R+I253R (FIGS. 5 and 6; SEQ ID Nos 16, 18, 19, 23, 27, 34, 36, 37, 41 and 45)
6) H63C+R112P+D143P+D151E+V169R+I253R (FIGS. 5 and 6; SEQ ID Nos 14, 16, 18, 19, 23, 27, 32, 34, 36, 37, 41 and 45)
7) H63C+R112P+D143P+V169R+I253R (FIGS. 5 and 6; SEQ ID Nos 14, 16, 18, 23, 27, 32, 34, 36, 41 and 45)
8) H63C+R112P+D143P+S166T+I253R (FIGS. 5 and 6; SEQ ID Nos 14, 16, 18, 20, 27, 32, 34, 36, 38 and 45).

In a particularly preferred aspect, the invention provides a purified mutant TSHR or fragment thereof according to the invention as described herein wherein the mutant comprises the set of mutations: H63C+R112P+D143P+D151E+V169R+I253R (FIGS. 5 and 6; SEQ ID Nos 14, 16, 18, 19, 23, 27, 32, 34, 36, 37 41 and 45).

The purified mutant TSHR or fragment thereof according to the invention may also comprise a detectable label as described herein.

Also provided is a mutant thyroid stimulating hormone receptor (TSHR) or fragment thereof according to the invention described herein, wherein the mutant or fragment thereof is deglycosylated and retains activity, for example as measured in a TSHR activity assay. Examples of such assays are described herein, and also above in relation to the activity of purified mutants. Any suitable TSHR activity assay may be used For example, the assays shown in FIG. 12*a* or 13*c* may be used to measure activity. The activity is preferably at least 70% or more, at least 80% or more, or at least 90% or more, the activity of the non-deglycosylated mutant or fragment thereof. In some cases, the activity may be hardly diminished at all, or may be the same as, or essentially the same as, the activity of the non-deglycosylated mutant or fragment thereof.

In principle, deglycosylation may be applied to any one of the mutant thyroid stimulating hormone receptor (TSHR) or fragments thereof described and claimed herein, although we prefer that the mutant comprises at least a double point mutation. A certain level of stability is required, and testing of the kind described herein will be able to determine the activity of the mutant protein after deglycosylation in each case. We expect mutants having at least a double point mutation, or in some cases at least a triple point mutation, to be capable of being deglycosylated, whilst retaining sufficient activity. As will be understood, deglycosylation removes the sugar residues from the protein, and enables more ready crystallisation. Any suitable deglycosylation process may be used, and one suitable technique is described in detail below.

A deglycosylated mutant according to the invention preferably consists of, or consists essentially of, the subdomain TSHR260 of the TSHR receptor and comprises one of the following set of mutations:
1) I253R (FIGS. 5 and 6; SEQ ID Nos 27 and 45)
2) D143P+I253R (FIGS. 5 and 6; SEQ ID Nos 18, 27, 36 and 45)
3) R112P+D143P+I253R (FIGS. 5 and 6; SEQ ID Nos 16, 18, 27, 34, 36 and 45)
4) R112P+D143P+D151E+I253R (FIGS. 5 and 6; SEQ ID Nos 16, 18, 19, 27, 34, 36, 37 and 45)
5) R112P+D143P+D151E+V169R+I253R (FIGS. 5 and 6; SEQ ID Nos 16, 18, 19, 23, 27, 34, 36, 37, 41 and 45)
6) H63C+R112P+D143P+D151E+V169R+I253R (FIGS. 5 and 6; SEQ ID Nos 14, 16, 18, 19, 23, 27, 32, 34, 36, 37, 41 and 45)
7) H63C+R112P+D143P+V169R+I253R (FIGS. 5 and 6; SEQ ID Nos 14, 16, 18, 23, 27, 32, 34, 36, 41 and 45)
8) H63C+R112P+D143P+S166T+I253R (FIGS. 5 and 6; SEQ ID Nos 14, 16, 18, 20, 27, 32, 34, 36, 38 and 45),
although as stated above deglycosylation can in principle be applied to any one of the mutants described and claimed herein.

There is also provided a method, including a diagnostic method, for detecting analyte autoantibodies to the TSHR, the method comprising contacting a sample of analyte autoantibody with a mutant thyroid stimulating hormone receptor (TSHR) or fragment thereof according to the invention described herein. Use of TSHR260 mutants, especially those labelled with alkaline phosphatase, are particularly preferred. TSHR260 comprising the point mutations H63C+R112P+D143P+D151E+V169R+I253R (JMG55) is especially preferred.

The analyte antibodies may come from any suitable source. Preferably, the sample of analyte autoantibodies has been isolated from a subject believed to contain such analyte autoantibodies. The sample may be from any species, including human—for example, human patient sera. Suitably, the sample comprises human or animal patient sera.

The invention also provides a method, including a diagnostic method, for detecting analyte autoantibodies to the TSHR, which method comprises:
a) providing a sample, for example a sample of body fluid, from a subject;
b) providing one or more first sources of TSHR or a fragment thereof;
c) providing one or more second sources of TSHR wherein the second source is a mutant thyroid stimulating hormone receptor (TSHR) or a fragment thereof according to the invention;
d) contacting said first and second sources of TSHR simultaneously or successively with said sample, for example a sample of body fluid, whereby said antibodies to the TSHR form one or more complexes comprising [TSHR of first source]-[TSHR antibody]-[TSHR of second source];
e) prior to, or concurrent with or subsequent to step (d), providing immobilising means whereby said first source of TSHR as present in a complex as formed in step (d) is immobilised to a solid support prior to, or concurrent with, or subsequent to step (d);
f) prior to, or concurrent with or subsequent to step (d) providing direct or indirect detectable labelling means whereby said second source of TSHR as present in the complex as formed in step (d) is provided with such direct or indirect labelling means prior to, or concurrent with or subsequent to step (d); and
g) detecting the presence of complexes formed in (d) according to (e) so as to provide an indication of the presence of TSHR antibodies in said sample of body fluid.

The first source of TSHR may be any suitable form of TSHR (wild type or mutated), including full-length TSHR, or fragments, including TSHR260, although preferably the first source of TSHR provided in (b) is full length TSHR, including one or more epitopes of a TSH receptor or a polypeptide comprising one or more epitopes of a TSH receptor. If desired, the first source of TSHR provided in (b) is a mutant TSHR or a fragment thereof according to the invention described herein. Both the first and second sources of TSHR in the methods of the invention may therefore, if desired, be a mutant TSHR or a fragment thereof according to the invention as described and claimed herein.

In a preferred aspect, the mutant TSHR or fragment thereof consists of, or consists essentially of, the subdomain TSHR260 of the TSHR receptor, although may in principle be any of the mutant TSHRs or fragments thereof disclosed herein.

The labelling means may comprise any suitable means of labelling the second source of TSHR, and suitable means and their methods of application and use will be known to those in the art. The label may, for example, be selected from the group consisting of enzymatic labels, isotopic labels, chemiluminescent labels, fluorescent labels and dyes. Such labels may be added in any suitable way, for example, via gene fusion using an appropriate construct (as described further below) or by chemical labelling. Those skilled in the art will be familiar with the relevant techniques needed, and the identity of suitable labels.

In a preferred aspect, the label comprises an alkaline phosphatase (AP) label or a biotin label. Most preferably, an alkaline phosphatase label is employed.

In a preferred aspect, the labelled mutant consists of, or consists essentially of, the subdomain TSHR260 of the TSHR receptor. Certain preferred mutants are those consisting of the subdomain TSHR260 of the TSHR receptor and an alkaline phosphatase (AP) label, denoted herein as TSHR260-AP-X, wherein "X" indicates the one or more amino acid mutations in the mutant.

Preferably, the labelling means comprises an alkaline phosphatase (AP) label.

Preferably, the mutant is directly labelled with the labelling means—for example, a TSHR260 directly chemically labelled with alkaline phosphatase (AP) label or a biotin.

In a preferred aspect, the immobilising means whereby said first source of TSHR is immobilised to a solid support, comprises a monoclonal antibody, recombinant antibody, synthetic antibody or fragment thereof. An example is the antibody 4E31 (described herein), but any suitable antibody may be used.

The solid support may be any suitable support, but is preferably a plate, for example an ELISA plate, or an ELISA plate well.

The invention also provides a kit for detecting analyte autoantibodies to the TSHR, which kit comprises:
a) one or more first sources of TSHR or a fragment thereof;
b) one or more second sources of TSHR wherein the second source is a mutant thyroid stimulating hormone receptor (TSHR) or a fragment thereof according to the invention described herein;
c) means for contacting said first and second sources of TSHR simultaneously or successively with a sample believed to contain analyte autoantibodies to the TSHR whereby said antibodies to the TSHR form one or more complexes comprising [TSHR of first source]-[TSHR antibody]-[TSHR of second source];

d) immobilising means for immobilising said first source of TSHR as present in a complex as formed in (c) to a solid support prior to, or concurrent with, or subsequent to (c);

e) detectable labelling means for directly or indirectly labelling said second source of TSHR as present in the complex as formed in (c) labelled prior to, or concurrent with, or subsequent to, formation of said complex; and f) means for detecting the presence of complexes formed in (c) so as to provide an indication of the presence of TSHR antibodies in said sample.

The kit may, for example, comprise any one or more of the features described above in relation to the corresponding method.

In particular, if desired, the first source of TSHR provided in (a) is a mutant TSHR or a fragment thereof according to the invention described herein. Both the first and second sources of TSHR in kits according to the invention may therefore, if desired, be a mutant TSHR or a fragment thereof according to the invention as described and claimed herein. The invention also provides a solid support having directly or indirectly bound thereto a mutant thyroid stimulating hormone receptor (TSHR) or a fragment thereof according to the invention described herein.

Preferably, the solid support according to the invention has bound thereto a mutant thyroid stimulating hormone receptor (TSHR) or a fragment thereof which consists of, or consists essentially of, the subdomain TSHR260 of the TSHR receptor.

In a preferred aspect, a solid support according to the invention has bound thereto a mutant thyroid stimulating hormone receptor (TSHR) or a fragment thereof comprising one of the following set of mutations:

1) I253R (FIGS. 5 and 6; SEQ ID Nos 27 and 45)
2) D143P+I253R (FIGS. 5 and 6; SEQ ID Nos 18, 27, 36 and 45)
3) R112P+D143P+I253R (FIGS. 5 and 6; SEQ ID Nos 16, 18, 27, 34, 36 and 45)
4) R112P+D143P+D151E+I253R (FIGS. 5 and 6; SEQ ID Nos 16, 18, 19, 27, 34, 36, 37 and 45)
5) R112P+D143P+D151E+V169R+I253R (FIGS. 5 and 6; SEQ ID Nos 16, 18, 19, 23, 27, 34, 36, 37, 41 and 45)
6) H63C+R112P+D143P+D151E+V169R+I253R (FIGS. 5 and 6; SEQ ID Nos 14, 16, 18, 19, 23, 27, 32, 34, 36, 37, 41 and 45)
7) H63C+R112P+D143P+V169R+I253R (FIGS. 5 and 6; SEQ ID Nos 14, 16, 18, 23, 27, 32, 34, 36, 41 and 45)
8) H63C+R112P+D143P+S166T+I253R (FIGS. 5 and 6; SEQ ID Nos 14, 16, 18, 20, 27, 32, 34, 36, 38 and 45).

The invention thus provides the use, in particular, of stable purified mutants of TSHR260, especially TSHR260-JMG55, directly coated onto ELISA plate wells for detection of TSHR monoclonal autoantibodies and patient serum TRAbs. Such mutants may comprise a detectable label such as an alkaline phosphatase (AP) label, if desired.

Suitably, the mutant thyroid stimulating hormone receptor (TSHR) or a fragment thereof is directly bound to the said solid support.

In a preferred aspect, the support is an ELISA plate comprising one or more wells.

The invention also provides a kit comprising a solid support according to the invention.

The invention also provides the use of a solid support according to the invention or a kit according to the invention comprising the solid support, for detecting TSHR monoclonal autoantibodies or patient TRAbs.

DESCRIPTION OF THE DRAWINGS

TSHR molecules and methods in accordance with the invention will now be described, by way of example only, with reference to the accompanying drawings, FIGS. 1 to 30, in which:

FIG. 1 shows the DNA sequence of the human (wild type) TSHR (SEQ ID No 1).

FIG. 2 shows the amino acid sequence of the human (wild type) TSHR (SEQ ID No 2).

FIG. 3 shows the DNA sequence of the human (wild type) TSHR260 fragment (SEQ ID No 3).

FIG. 4 shows the amino acid sequence of the human (wild type) TSHR260 fragment (SEQ ID No 4).

FIG. 5 shows the DNA sequence of thermostabilising TSHR single mutations (SEQ ID Nos 11-28).

FIG. 6 shows the amino acid sequence of thermostabilising TSHR single mutations (SEQ ID Nos 29-46).

FIGS. 7A-7E show representative examples of the results of a TSHR260 thermostability assay for TSHR260 mutants heated at (a) 42° C., (b) 50° C., (c) 50° C., (d) 55° C. and (e) 60° C.

FIG. 8 shows the thermostability of full-length TSHR mutants by heating on a 14C4 $Fab_2$ plate at 50° C.

FIG. 9 illustrates the TSHR260 domain in cartoon format and shows the position of native residues of the most thermostabilising mutations in stick conformation.

FIGS. 10A-10C show the alignment of TSHR amino acid sequences from human, grivet monkey, rhesus monkey, porcine, bovine, cat, dog, mouse, rat, sheep, horse (SEQ ID Nos 2, 47-56 respectively).

FIGS. 11A-11B show the alignment of the human TSHR amino acid sequence with human FSHR and human LHR (SEQ ID Nos 2, 57 and 58 respectively).

FIGS. 12A-12D show diagrams of assays involving TSHR260: (a) TSHR260-binding assay; (b) TSHR260 thermostability assay; (c) inhibition of M22-POD binding to TSHR260 and (d) TSHR260-JMG55 coated ELISA plate well assay.

FIGS. 13A-13C show diagrams of assays involving TSHR260-AP: (a) TSHR260-AP bridge ELISA; (b) TSHR260-AP thermostability assay and (c) TSHR260-AP bridge inhibition ELISA.

FIGS. 14A-14E show diagrams of assays involving TSHR: (a) TSHR-binding assay; (b) TSHR stability assay A; (c) TSHR stability assay B; (d) TSHR stability assay C and (e) inhibition of M22-POD binding to TSHR.

FIG. 15 shows the DNA sequence of TSHR260-AP (SEQ ID No 59)

FIG. 16 shows the amino acid sequence of TSHR260-AP (SEQ ID No 60)

FIG. 17 shows the DNA sequence of porcine (wild type) TSHR (SEQ ID No 61).

FIG. 18 shows the amino acid sequence of porcine (wild type) TSHR (SEQ ID No 62).

FIG. 19 shows the DNA sequence of mouse (wild type) TSHR (SEQ ID No 63).

FIG. 20 shows the amino acid sequence of mouse (wild type) TSHR (SEQ ID No 64).

FIG. 21 shows the DNA sequence of porcine (mutated) TSHR (SEQ ID No 65).

FIG. 22 shows the amino acid sequence of porcine (mutated) TSHR (SEQ ID No 66).

FIG. 23 shows the DNA sequence of mouse (mutated) TSHR (SEQ ID No 67).

FIG. 24 shows the amino acid sequence of mouse (mutated) TSHR (SEQ ID No 68).

FIGS. 25A-25H show the activity as measured by the bridge inhibition ELISA assay illustrated in FIG. 13(c) of the load and elution pools for purification of (a) TSHR260 (wild type), (b) TSHR260 (wild type) in complex with 14C4 IgG, (c) TSHR260 (wild type) in complex with 25E1 IgG, (d) TSHR260 (wild type) in complex with 2H11 IgG, (e) TSHR260 (wild type) in complex with 23H4 IgG, (0 TSHR260 (wild type) in complex with 36F11 IgG, (g) TSHR260 (wild type) in complex with 9B7 IgG and (h) TSHR260-JMG55 on either streamline DEAE or streamline HST matrices.

FIG. 26 shows the distribution of TSHR260-JMG55 activity in the elution fractions after 14C4-affinity chromatography of streamline HST purified TSHR260-JMG55.

FIG. 27 shows a stained 12% non-reduced SDS-PAGE gel of purified TSHR260-JMG55-5.0 (low specific activity) and purified TSHR260-JMG55-4.5 (high specific activity) after 3 rounds of column purification (streamline HST, 14C4-affinity and nickel-affinity chromatography). Lane 1: Molecular Weight Markers; lane 2: TSHR260 (wild type) culture supernatant control; lane 3: Insect cell culture media control; lane 4: purified TSHR260-JMG55-5.0 (2.4 µg) and lane 5: purified TSHR260-JMG55-4.5 (3.0 µg).

FIGS. 28A-28B show deglycosylation of purified TSHR260-JMG55-4.5 using Endoglycosidase F3 at different concentrations (stained 12% non-reduced SDS-PAGE gel). (A) Lane 1: Molecular Weight Markers; Lane 2: Insect cell culture media negative control; Lane 3: Nickel-affinity purified TSHR260-JMG55-4.5 (untreated); Lanes 4-6: 40 mU Endoglycosidase F3/mg of TSHR260-JMG55-4.5 after 24 h, 72 h and 120 h incubation respectively; Lanes 7-9: 0 mU Endoglycosidase F3/mg of TSHR260-JMG55-4.5 after 24 h, 72 h and 120 h incubation respectively. (B) Lane 1: Molecular Weight Markers; Lane 2: Insect cell culture media negative control; Lane 3: Nickel-affinity purified TSHR260-JMG55-4.5 (untreated); Lanes 4-6: 60 mU Endoglycosidase F3/mg of TSHR260-JMG55-4.5 after 24 h, 72 h and 120 h incubation respectively; lanes 7-9: 80 mU Endoglycosidase F3/mg of TSHR260-JMG55-4.5 after 24 h, 72 h and 120 h incubation respectively.

FIG. 29 shows the DNA sequence of thermostabilising single amino acid mutations made in the TMD of TSHR-JMG55 (SEQ ID Nos 69-88).

FIG. 30 shows the amino acid sequence of thermostabilising single amino acid mutations made in the TMD of TSHR-JMG55 (SEQ ID Nos 89-108).

METHODS

Computational Modelling of TSHR260 Mutations

Computational modelling was performed with Discovery studios v3.5 (Accelrys Software Inc, Accelrys Ltd, Cambridge, CB4 OWN, UK) using the Calculate Mutation Energy Stability protocol. The crystal structure of TSHR260-M22 Fab complex (PDB code: 3G04; Available from the RCSB Protein Databank at wwwscsb.org/pdb/explore/explore.do?structureId=3go4) was used as the initial model for all mutations to ensure that mutations which do not disturb the binding of M22 to TSHR260 were chosen. Each residue in the TSHR260 structure was mutated to each of the other 19 possible amino acids and the mutation energy data collected and compared.

The computational modelling data was used in conjunction with other predictions of stabilising mutations to estimate which target residue is most likely to be stabilising for each position. These other predictions were based on a number of factors:
1. Torsion angles of the residues predicting favourable conformations for Pro or Gly amino acids.
2. Consensus sequence of TSHR from other organisms and other glycoproteins
3. Position of the residue in the LRR and/or β-sheets.
4. Position of the residue in the surface or core of the protein.

Primer Design

Primers were designed to introduce point mutations into TSHR260 using the PrimerX website (www.bioinformatics.org/primerx/index.htm). The protein-based primer design option was used, using the QuikChange SDM protocol, and choosing primer pairs such that their overhang was between two and ten residues. Primers had melting temperatures between 73° C. and 84° C. (ideally greater than 76° C.), were between 27 and 49 base pairs in length and had a GC content between 33% and 70% (ideally greater than 40%). Primers were ordered in 96-well format, in 10 µM aqueous solution from Sigma Genosys, Haverhill, CB9 8QP, UK.

Mutagenesis, Plasmid DNA Preparation and Purification

The TSHR260-6His template construct (coding amino acids 1-260 of the human TSHR; see FIGS. 3 (SEQ ID No 3) and 4 (SEQ ID No 4) for the nucleotide sequence and amino acid sequence respectively of the wild type TSHR 260) was previously amplified using full-length human TSHR as template (Oda Y et al (1998) Journal of Molecular Endocrinology 20: 233-244) with the addition of a six His tag at the C terminus. Residues 1-260 of TSHR were amplified from the full-length TSHR with two primers 5'-cactgcaggatccaaatgaggccggcggacttg-3' (SEQ ID No 5) and 5'-cagtcctctagattatcagtgatggtggtggtgatggttaagagtcca-ggtgttcttgctat-3' (SEQ ID No 6) which add a BamHI restriction site at the N terminus, and a one amino acid linker (Asn), a six His tag, a stop codon and an XbaI restriction site to the C terminus of human TSHR amino acids 1-260. The PCR product was cloned into pcDNA3.1+using BamHI and XbaI restriction sites.

Mutations in the TSHR260 sequence (FIG. 5; SEQ ID Nos 11 to 28 and FIG. 6; SEQ ID No 29 to 46) were generated by site-directed mutagenesis using the polymerase chain-reaction (PCR) with the QuikChange II methodology (Agilent Technologies UK Ltd, Stockport, SK8 3GR). Mutagenesis was performed in 96-well plate format using KOD hot start polymerase kit (Novagen from VWR International, Lutterworth, LE17 4XN, UK). Using TSHR260-6His as the template, or the appropriate TSHR260 mutants in the vector pcDNA3.1+, 50 µL PCR reactions were set up so that the final concentration in each reaction was: 1×KOD buffer, 0.2 mM dNTPs, 1.5 mM $MgSO_4$, 0.02 U/µL KOD hot start polymerase, 9% v/v DMSO (Sigma Aldrich, Poole, BH12 4QH), 0.2 ng/µL template DNA, 0.3 µM forward primer and 0.3 µM reverse primer. The following PCR program was run: 2 minutes denaturation at 94° C.; 18 cycles of 15 s denaturation at 94° C., 1 minute annealing at 68° C., 8 minutes elongation at 68° C.; followed by a final step of elongation at 68° C. for 7 minutes. The template was digested by incubation with 2 µL DpnI (Fisher Scientific, Loughborough, LE11 5RG) at 37° C. for at least 3 h.

1 μL of the PCR reaction was added to 30 μL XL1 blue competent cells in 1.5 mL microtubes or 96-well cell culture cluster round bottom plates (Nunc A/S, Roskilde, Denmark) and incubated on ice for 30 minutes. Cells were heat-shocked at 42° C. for 90 s, transferred to ice and 200 μL Luria Broth (LB) media added. Cells were incubated at 37° C. for 1 hour before being spread on LB agar plates containing ampicillin (100 μg/mL). When more than 30 transformations were performed simultaneously, LB agar containing ampicillin (100 μg/mL) poured into Q-tray plates with 48 divisions (Molecular Dimensions, Newmarket, CB8 7SQ, UK) were used. Plates were incubated at 37° C. overnight to allow colonies to grow.

Two colonies from each transformation were picked and grown at 37° C. overnight in 7 mL LB media with 100 μg/mL ampicillin in 15 mL Falcon tubes or 24-well deep-well blocks (Promega UK Ltd, Southampton, SO16 7NS, UK). Plasmid DNA was extracted from the cell pellet of the overnight cultures using the Qiagen PlasmidPlus 96 Mini-prep Kit (Qiagen Ltd, Manchester, M15 6SH, UK) or Wizard PlusMiniprep DNA purification System (Promega) and the mutated TSHR260 cDNA was sequenced by Source Bioscience (Cambridge, CB4 0WU, UK) to confirm the presence of the desired mutations. Stocks of E coli strains containing the mutant TSHR260-6His were maintained at −70° C. after addition of glycerol (14% final concentration) to an aliquot of the overnight culture.

Introduction of Specific Amino Acid Mutations into the Full Length Human TSHR Sequence Using PCR The TSHR full length nucleotide sequence (Oda Y et al (1998) supra) was cloned into pcDNA5.1/FRT vector (Invitrogen) using BamHI and XhoI restriction sites following standard cloning procedures. Mutations in the full length sequence were generated by site directed mutagenesis using the PCR with the QuikChange II methodology as described above for the TSHR260 mutations, except mutagenesis was performed in 0.2 mL PCR tubes instead of a 96 well plate format. The PCR reaction was transformed, expanded and the mutations verified by sequencing as described above for TSHR260 PCR products. See FIGS. 1 (SEQ ID No 1) and 2 (SEQ ID No 2) for the nucleotide sequence and amino acid sequence respectively of full length wild type TSHR.

Transient Transfections of TSHR260 Mutants into CHO-K1 Cells Using Freestyle Max Reagent One day prior to transfection, 1.5×10$^5$ CHO-K1 cells/well were plated out into 24-well cell culture plates (Nunc). For each well to be transfected, 5 μL TSHR260-6His mutant in pcDNA3.1+(0.2 μg/μL) was mixed with 20 μL Optipro SFM (Life Technologies, Paisley, PA4 9RF, UK). 2.5 Freestyle Max reagent (Life Technologies) diluted in 22.5 μL Optipro SFM was added to each DNA/Optipro SFM mixture and incubated at room temperature for 10-20 minutes. 40 μL DNA/Freestyle Max mix was added to CHO-K1 cells in a 24-well plate and incubated at 37° C. for 40-48 h. Thereafter expressed TSHR protein secreted into the media was harvested by centrifugation at 13000 rpm for 2 minutes to remove the cell debris and the supernatant stored at −70° C.

The TSHR260-WT standard was made by transfecting an 80 cm$^2$ flask containing 90% confluent CHO-K1 cells with TSHR260-6His in pcDNA3.1+. 20 μL TSHR260-6His in pcDNA3.1+(1 μg/μL) was added to 480 μL Optipro SFM (Life Technologies). 50 μL Freestyle Max reagent (Life Technologies) diluted in 450 μL Optipro SFM was added to the DNA/Optipro SFM mixture and incubated at room temperature for 10-20 minutes. 1 mL DNA/Freestyle Max mix was added to the 80 cm$^2$ flask of CHO-K1 cells and incubated at 37° C. for 40-48 h. Thereafter expressed TSHR260-6His protein secreted into the media was harvested by centrifugation at 3000 rpm for 30 minutes to remove the cell debris and the supernatant stored at −70° C. This was defined as 100 U/mL. Further TSHR260-WT standard samples were diluted to be the same concentration as the first TSHR260-WT standard, as detected in the TSHR260-binding assay (see below).

Transfection of Full Length TSHR Constructs into CHO Cells Using the Flp-In System A confluent flask of Flp-In-CHO cells (Invitrogen, Paisley, PA4 9RF, UK; O'Gorman, S., Fox, D. T., and Wahl, G. M. (1991) Science 251: 1351-1355) was used to seed 24 well plate wells at 1×10$^5$-1.5×10$^5$ cells/well in DMEM (Invitrogen), 10% foetal calf serum (FCS) (Invitrogen), 1× L-Glutamine (Invitrogen) and 1×non-essential amino acids (NEAA) (Invitrogen) with no antibiotics. The cells were incubated overnight at 37° C., 5% CO$_2$ and >95% humidity.

The pcDNA5.1/FRT TSHR DNA (described above) and pOG44 DNA (Invitrogen) were diluted to give 0.01 μg/mL and 0.1 μg/mL solutions, respectively in sterile water. The pOG44 DNA and the TSHR DNA were mixed at 3 different concentrations: (1) 9 μL of pOG44, 10 μL TSHR DNA and 31 μL optimem I (Invitrogen); (2) 8 μL pOG44, 20 μL TSHR DNA and 22 μL optimem I; (3) 9.5 μL pOG44, 5 μL TSHR DNA and 35.5 μL Optimem I and incubated at room temp for 5 min. 50 μL of 1:25 diluted lipofectamine (Invitrogen) in optimem I was added to each tube (1-3 above) and incubated for 20 min at room temp. Each incubation mixture was then added to 1 well (in a 24 well plate) of 95% confluent Flp-In-CHO cells and incubated overnight under conditions described above. The culture media was then removed and changed for DMEM, 10% FCS, 1× L-glutamine, 1×NEAA and 1× penicilin (100 u/mL)/streptomycin (100 μg/mL) (Invitrogen) and incubation continued overnight. The cells were then detached from the well using 1×trypsin/EDTA solution (Invitrogen) and split into 4 new wells and grown in the media as above with addition of 600 μg/mL of hygromycin (Invitrogen).

The cells transfected with both, the pOG44 plasmid DNA and pcDNA5.1/FRT TSHR are capable of inserting the TSHR into the Flp-In-CHO cell genome and conferring hygromycin resistance on the cell so it will be able to grow in hygromycin selection media. The Flp-In system from Invitrogen is so designed that the TSHR in our constructs will be inserted into the FRT site in the Flp-In-CHO cells by the pOG44. The Flp-In-CHO cells contain one Flp-In site per cell therefore the TSHR DNAs will be inserted in the same place in the genome in each experiment and it will be present as one copy per cell. This system has the advantage that screening colonies of cells for those with optimum expression levels (followed by cell cloning to find a stable cell line) is not necessary. Consequently, cells expressing mutated TSHR that grows in the hygromycin selection media can be expanded quickly and used in different assays.

Antibodies Used in TSHR260 Binding Assay

14C4

The 14C4 TSHR mouse monoclonal antibody used in the TSHR260-binding assay was prepared by cDNA immunisation. Briefly, six- to eight-week old NMRI (out bred) mice were injected intramuscularly with 100 μL of 10 μM cardiotoxin five days before intramuscular immunisation with 100 μg of full-length TSHR cDNA (pRC/CMVhTSHR; Oda et al (1998) supra). TSHR DNA immunisation was repeated at three week intervals for a total of five injections (Hasan et al (1999) J. Immunol. Methods 229:1-22). The mouse bleeds were tested for the presence of TSHR antibodies by inhibition of $^{125}$I-labelled TSH binding to the TSHR (assay manufactured by RSR Ltd, Cardiff, UK). Monoclonal antibodies were produced using the spleen cells from the mouse with the highest TSHR antibody titres in the serum. Isolated spleen cells were mixed in a 1:2 ratio with a mouse myeloma cell line (X63_Ag8.653; ECACC Porton Down, UK) and fused using 10% DMSO and 50% PEG (Sigma Aldrich, Poole, UK) according to previously described methods (de St Groth, S. F., & Scheidegger. D. (1980). *Journal of immunological methods* 35, 1-21.). Cells were cultured in DMEM (supplemented with 20% fetal calf serum containing HAT to select for hybrids) and plated into 48-well plates. To obtain 14C4, supernatants from the cell cultures were screened for TSHR antibodies by immunoprecipitation of $^{125}$I-TSH labelled TSHR complexes. In these assays the full-length TSHR is labelled using $^{125}$I-TSH to form a $^{125}$I-TSH-TSHR complex. The $^{125}$I-TSH-TSHR complex is bound by antibodies which are capable of binding to the TSHR at the same time as TSH. The complex can then be precipitated using standard PEG precipitation techniques and the radioactivity in the pellet measured. The cells from the positive wells were recloned two times by limiting dilution to obtain clones expressing the required monoclonal antibody. 14C4 IgG binds to a conformational epitope on the convex surface of the TSHR allowing TSH or patient TRAb to bind to the concave surface of the TSHR at the same time. 14C4 is available from RSR Ltd, Cardiff, UK (www.rsrltd.com).

M22 Protein Data Bank (PDB) Accession Number 3G04 (www.rcsb.org/pdb/explore/explore.do?structureId=3go4)

M22 (hMAb TSHR1) is a human thyroid stimulating monoclonal autoantibody which was obtained from peripheral blood lymphocytes from a patient with Graves' disease (Sanders et al (2003) Lancet 362: 126-128). Briefly, lymphocytes were isolated from 20 mL of peripheral blood of a 19-year old man with hyperthyroidism and high levels of TSHR autoantibodies (due to Graves' disease). The lymphocytes were infected with Epstein Barr virus and fused with a mouse/human hybrid cell line (K6H6/B5; ECACC, Porton Down, UK) using standard techniques (Hayakawa N et al (2002) Autoimmunity 35: 343-55). The cells were plated out in 48-well plates and the supernatants screened by the inhibition of $^{125}$I-TSH binding to TSHR coated tubes (assay RSR Ltd, Cardiff, UK). Positive wells were then recloned by limiting dilution until a single colony producing high concentrations of TSHR autoantibody M22 was isolated. M22 (hMAb TSHR1) is well known in the art as the WHO 2$^{nd}$ International Standard for Thyroid Stimulating Antibody NIBSC code: 08/204 (Burns C et al (2010) WHO International Collaborative Study of the proposed 2$^{nd}$ International Standard for Thyroid Stimulating Antibody, Expert Committee on Biological Standardization, Geneva 18 to 22 Oct. 2010, WHO/BS/10.214, Available at: www.who.int/biologicals/expert_committee/BS_2142_Thyroid_ Stimulating_Autoantibody.pdf). M22 (hMAb TSHR1) is available to purchase from RSR Ltd, Cardiff, UK (Supra).

Thermostability

In the context of the present invention, thermostability is, generally speaking, the ability of the mutant TSHR or fragment thereof (such as a TSHR260 mutant) to retain its normal biological activity after being exposed to a given temperature for a defined time period. Suitably, it can be determined by the percentage of active mutant protein remaining after the temperature exposure. One suitable measure of the amount of active mutant protein is the percentage of mutant protein that retains the ability to bind an antibody or autoantibody to the TSHR in a binding assay. The amount of active mutant protein remaining after exposure to a given temperature can thus be measured as a function of time and a thermostability curve at that temperature obtained—for example as shown in FIG. 7. The half-life of the mutant protein—that is, the time taken for the amount of active protein to fall to 50% of its initial value (i.e. 50% is inactive or denatured)—can thus be derived. The half-life of the mutant protein gives a convenient quantitative measure of the thermostability of the protein, and this can be compared with the half-life of the equivalent non-mutated TSHR or fragment thereof (i.e. wild type TSHR or fragments thereof such as wild type TSHR260) in order to assess whether there has been an increase or decrease in thermostability.

A suitable binding assay may, for example, comprise a plate having bound thereto a mutant TSHR or fragment thereof to be tested, and a labelled antibody or autoantibody to TSHR, and such an assay forms part of the present invention. The mutant to be tested is suitably bound to the plate in such a way so as not to interfere with binding of the antibody to the mutant protein. The mutant may, for example, be bound to the plate using any suitable antibody, and one such antibody is 14C4 as described above. The amount of labelled antibody bound can be used to indicate the amount of active mutant protein, as will be clear to those skilled in the art. Preferably, a labelled monoclonal autoantibody to TSHR is employed, such as M22 (as described above), to bind to the mutant protein being assayed. The principle of such an assay is, for example, shown in FIGS. 12a and 12b, FIGS. 13a and 13b, and FIGS. 14a, b, c and d. Whilst the specific details of the assays shown in the above Figures vary, the thermostability of the mutant protein in each case can be derived by comparing mutant protein and wild type by measuring the amount of protein that retains the ability to bind an antibody or autoantibody (such as M22) to the TSHR.

In the present invention, the terms "thermostability" and "thermostable" (and all related terms such as "increased thermostability") are to be understood in a quantitative sense as referring to the half-life of the mutant TSHR or fragment thereof (such TSHR260), as compared to the half-life of the equivalent wild type TSHR or fragment thereof, as measured under identical conditions in a binding assay which determines the amount of mutant TSHR or fragment thereof (or equivalent wild type protein) that retains the ability to bind an antibody or autoantibody to the TSHR at the test temperature. Preferably, the autoantibody used to test this binding ability of the mutant is M22, K1-70 or K1-18.

Any suitable binding assay which allows a determination of the half-life of the mutant TSHR or fragment thereof as described above may be used. For the purposes of the present invention, we have employed specific binding assays of this type and these are described fully below. These binding assays can in principle be employed to determine the thermostability of any mutant TSHR or fragment (whether full-length, TSHR260, or a sequence length shorter or longer than TSHR260).

For fragments of the TSHR, such as TSHR260 mutants, we have employed the thermostability protocol and TSHR260-binding assay described below to determine thermostability. Whilst the invention has been described primarily with respect to TSHR260 mutants, it will be understood that the thermostability protocol and binding assay can be used in the same way with other TSHR fragments of varying sequence lengths.

With respect to full-length TSHR and full-length mutants, we have employed a similar, but modified, binding assay as described under "*Thermostability of full-length TSHR and mutants coated on 14C4-Fab$_2$ ELISA plates*" and "*Thermostability of full-length TSHR mutants*" below. In this assay, the main difference is that the full-length sample is bound to the plate before heating to the test temperature.

TSHR260-Binding Assay

Maxisorp 96-well ELISA plate (Nunc) wells were coated with 150 µL aliquots of 1 µg/mL 14C4 Fab$_2$ (Jeffreys J et al (2002) Thyroid 12: 1051-1061 and Sanders J et al (2007) supra) in coating buffer (15 mM Na$_2$CO$_3$, 35 mM NaHCO$_3$, 1.5 mM NaN$_3$, 0.01 g/L Phenol Red, pH9.2), incubated at room temperature for 3 h and then at 4° C. overnight. Wells were washed three times with wash buffer (50 mM NaCl; 20 mM Tris pH 7.8; 1% v/v Triton X-100) and 150 µL test sample (TSHR260-6His harvested from transiently transfected CHO-K1 cells) was applied to each well and incubated at room temperature for 1 h to allow the TSHR260 to bind to 14C4-Fab$_2$. The wells were then washed and incubated with 75 of assay buffer (50 mM NaCl, 20 mM Tris pH7.8, 1% v/v Triton X-100, 1 g/L BSA, 50 mg/L normal mouse IgG) and 75 µL of healthy blood donor serum pool (NPS) for 1 h at room temperature at 500 shakes per minute on an ELISA plate shaker. Thereafter the contents of the wells were emptied, the wells washed and 100 µL of M22 Fab-peroxidase conjugate (M22-POD, RSR Ltd, Cardiff, CF23 8HE, UK) added to each well. After 25 minutes incubation at room temperature without shaking the plate wells were washed again followed by addition of 100 µL of tetramethylbenzidine and a further incubation of 25 minutes at room temperature without shaking. The reaction was stopped by addition of 50 µL of 0.5 M H$_2$SO$_4$ and the absorbance of each well read at 450 nm on an ELISA plate reader (FIG. 12*a*).

Binding and Stability Screen

TSHR260-6His samples harvested from transiently transfected CHO-K1 cells were diluted ¼ in CHO-K1 media ((-)DMEM, 10% FBS, 2× Glutathione, 1× Pen/Strep, 1×NEAA). For each sample, a 100 µL aliquot was heated at 42° C. for 30 min, while a second identical sample was kept on ice. Samples were then diluted ⅕ in TAT buffer (50 mM NaCl, 10 mM Tris pH7.8, 1% v/v Triton X-100, 1 g/L BSA, 0.2 g/L sodium azide) and 150 µL aliquots were applied in duplicate to the TSHR260-binding assay (FIG. 12*a*), which was performed as above. The amount of TSHR protein detected (see TSHR260 binding assay above) was expressed as i) a percentage of the TSHR260-WT standard and ii) the fraction of active TSHR protein remaining after heating. This was compared to the fraction of TSHR260-WT standard remaining after heating to give the mutant stability as a percentage of TSHR260-WT standard stability. Where the amount of active TSHR protein detected was too high or too low to be accurately determined, the binding assay was repeated at different dilutions of TSHR260 mutant.

Thermostability of TSHR260 Mutants

TSHR260 mutants transiently expressed in CHO-K1 cells and harvested from the supernatant as above, were diluted to 25% TSHR260-WT standard (see above) in CHO-K1 media. 100 µL aliquots were heated for between 0 and 30 days at 37° C. or between 0 and 3 hours at 42° C., 50° C., 55° C. or 60° C. Samples were then diluted ⅕ in TAT buffer (87.5 µL sample+350 µL TAT buffer) and 150 µL aliquots were applied in duplicate to the TSHR260-binding assay described above (FIG. 12*b*). Assay data were plotted against time and fitted to an exponential curve and the half-life ($t_{1/2}$) of the mutants calculated and compared to TSHR260-WT, TSHR260-I253R or TSHR260-JMG45 (defined in Table 5).

Dot Blot Assay to Determine the Total Amount (Active Plus Inactive) of TSHR Expressed The expression levels of TSHR260 mutants were determined by Dot Blot assays using the Bio-Dot Microfiltration Apparatus (Bio-Rad Laboratories Ltd, Hemel Hempstead, HP2 7DX, UK). 50 µL aliquots of TSHR260-6His preparations harvested from transfected cell cultures as described above were applied to the Bio-Dot apparatus and allowed to enter the nitrocellulose membrane by gravity-flow. The samples were followed with 50 µL phosphate buffered saline (PBS, 8 g/L NaCl, 1.15 g/L disodium hydrogen phosphate, 0.2 g/L potassium dihydrogen phosphate, 0.2 g/L potassium chloride, pH7.4) by gravity flow. The samples on the membrane were then washed with 400 µL wash buffer (0.5% (v/v) Tween in PBS), applying vacuum to pull the wash buffer through the membrane. The membrane was then removed from the Bio-Dot apparatus and blocked by incubation with 0.1 mg/L polyvinyl acetate in PBS for 1 minute, with gentle shaking. The membrane was washed with wash buffer (3× three minutes, room temperature, with shaking) and incubated with the primary antibody, a TSHR monoclonal antibody, 18C5-IgG (0.01 mg/mL) or 8E2-IgG (0.02 mg/mL) (Jeffreys J et al (2002) supra) diluted in antibody buffer (180 g/L D-glucose, 10% (v/v) Foetal calf serum, 10% (v/v) ~87% glycerol, 0.5% (v/v) Tween in PBS) for 1 h with shaking at room temperature. The membrane was again washed with wash buffer (3× three minutes, room temperature, with shaking), after which it was incubated with a secondary antibody, Goat anti-mouse HRP (0.04 µg/mL, Sigma) in PBS for 1 hour with shaking at room temperature. After washing the membrane again with wash buffer (3× three minutes, room temperature, with shaking), the membrane was incubated with chemiluminescence substrate, Super Signal West Pico Stable Peroxide (ThermoScientific) and Super Signal West Pico Luminal Enhancer (ThermoScientific).

18C5-IgG and 8E2-IgG bind to linear epitopes of TSHR260 therefore their binding is not affected by unfolding of the TSHR protein. The 18C5-IgG recognises the linear epitope formed by TSHR residues 246-260, while the 8E2-IgG binds to a linear epitope on the N-terminus of TSHR260, residues 36-42. Using the two antibodies in combination enables the detection of TSHR260 on the blots irrespective of potential changes in TSHR protein folding following mutagenesis (i.e. detection of active plus inactive TSHR).

Thermostability of Full-Length TSHR and Mutants Coated on 14C4-Fab$_2$ ELISA Plates.

For testing 'on-plate' stability of full length wild type TSHR and mutated TSHR (JMG37, JMG45 and JMG52) 96-well Maxisorp ELISA plates (Nunc) were coated as follows. 14C4 Fab$_2$ was diluted to 1 µg/mL in coating buffer and 150 µL was aliquoted into each well of the 96-well ELISA plate. This was incubated for 3 h at room temperature followed by an overnight incubation at 4° C. ELISA plate wells were washed three times with wash buffer to remove any unbound antibody. Wild type and mutated TSHR samples were removed from −80° C., allowed to thaw at room temperature and placed on ice (0° C.). The TSHR samples were then diluted in TAT buffer. 150 µL of each dilution was pipetted into four ELISA plate wells and incubated overnight at 4° C. Plates were washed three times with wash buffer to remove any TSHR that had not bound to the 14C4 Fab$_2$. TAT buffer was added to each well (150 µL) and an adhesive plate cover was then applied to seal the wells. Each plate was then placed in an incubator set at 42° C. or 50° C. One strip (8 wells) of the 96-well plate was removed from each plate after 5, 10, 15, 20, 30, 45, 60, 90, 120 and 180 minutes and inserted in to a spare ELISA plate rack, which was then kept on ice. After the 180-minute time course was complete the receptor dilution buffer was aspirated from the ELISA wells.

Assay buffer was then added to each well (75 µL) followed by healthy blood donor serum pool (75 µL) and incubated for 1 hour at room temperature (20-25° C.) at 500 shakes per minute on an ELISA plate shaker. Well contents were discarded and washed once with wash buffer and 100 µL of M22-POD (RSR Ltd) was added to each well. After a 25-minute incubation at room temperature without shaking, plate wells were washed twice with wash buffer then once with water. 100 µL tetramethylbenzidine was then added to each well and incubated for 25 minutes. The reaction was stopped with 50 µl 0.5 M H$_2$SO$_4$ and the absorbance of each well was read at 450 nm on an ELISA plate reader (Stability assay A, FIG. 14b).

M22-POD, K1-18-POD and K1-70-POD Binding to TSHR260 and Full-Length TSHR Mutants Maxisorp ELISA plate (Nunc) wells were coated with 150 µL aliquots of 1 µg/mL 14C4 Fab$_2$ in coating buffer, incubated at room temperature for 3 hours and then at 4° C. overnight. TSHR260 mutants were diluted in CHO-K1 media and then diluted ⅕ in TAT buffer. Alternatively, full-length TSHR mutants were diluted in TAT buffer. Wells were washed and 150 µL TSHR260 or full-length TSHR test sample was applied to each well and incubated at room temperature for 1 hour to allow the TSHR260 or full-length TSHR to bind to 14C4-Fab$_2$. The wells were then washed and incubated with 75 µL of assay buffer and 75 µL of healthy blood donor serum for 1 hour at room temperature at 500 shakes per minute on an ELISA plate shaker. Thereafter the contents of the wells were emptied, the wells washed and incubated with 100 µL of M22-POD (RSR Ltd), K1-18 peroxidase conjugate (K1-18-POD; RSR Ltd) or K1-70 peroxidase conjugate (K1-70-POD; RSR Ltd) at a range of concentrations between 10 µg/mL and 1 ng/mL. After 25 minutes incubation at room temperature without shaking, the plate wells were washed again followed by addition of 100 µL of tetramethylbenzidine and a further incubation of 25 minutes at room temperature without shaking. The reaction was stopped by addition of 50 µL of 0.5 M H2504 and the absorbance of each well read at 450 nm on an ELISA plate reader. For non-specific binding, CHO-K1 media was diluted in TAT buffer and applied as negative controls to the wells as for the TSHR260 mutants or the full-length TSHR mutants and treated in the same way, including incubation with varying concentrations of M22-POD, K1-18 POD or K1-170 POD. GraphPad Prism (GraphPad Software, Inc., La Jolla, Calif., USA) was used to plot the binding curves for M22-POD, K1-18-POD and K1-70-POD, correcting for non-specific binding by subtracting the OD450 of the negative CHO-K1 controls from the OD450 of the TSHR260 or TSHR samples incubated with the matching concentrations of M22-POD, K1-18 POD or K1-70 POD. Non-linear regression (one-site specific binding saturation curve) was used to calculate the equilibrium binding constant ($K_d$), which is the concentration of ligand (M22-POD, K1-18-POD or K1-70-POD) at which half of the receptor (full length TSHR or TSHR260 mutants) is bound to ligand. $K_d$ is equivalent to $1/K_a$, where $K_a$ is the affinity constant (FIG. 12a and FIG. 14a).

M22 IgG, K1-18 IgG, K1-70 IgG and TRAb Positive Patient Sera Inhibition of M22-POD Binding to TSHR260 Mutants in the TSHR260-Binding Assay.

ELISA plate (Nunc) wells were coated with 150 µL aliquots of 1 µg/mL 14C4 Fab$_2$ in coating buffer, incubated at room temperature for 3 h and then at 4° C. overnight. TSHR260-WT, TSHR-JMG37, TSHR-JMG45, TSHR-JMG52 and TSHR-JMG55 were diluted in media, followed by ⅕ dilution in TAT buffer. Wells were washed and 150 µL full length TSHR test sample was applied to each well and incubated at room temperature for 1 h to allow the TSHR260 to bind to 14C4-Fab$_2$. The wells were then washed and incubated with 75 µL of assay buffer and 75 µL of TRAb positive patient sera or M22 IgG, K1-18 IgG or K1-70 IgG diluted in NPS (1000 ng/mL to 0.1 ng/mL) for 1 h at room temperature at 500 shakes per minute on an ELISA plate shaker. Thereafter the contents of the wells were emptied, the wells washed and 100 µL of 89.5 ng/mL M22-POD (RSR Ltd) added to each well. After 25 minutes incubation at room temperature without shaking, the plate wells were washed again followed by addition of 100 µL of tetramethylbenzidine and a further incubation of 25 minutes at room temperature without shaking. The reaction was stopped by addition of 50 µL of 0.5 M H$_2$SO$_4$ and the absorbance of each well read at 450 nm on an ELISA plate reader (FIG. 12c).

M22 IgG, K1-18 IgG, K1-70 IgG and TRAb Positive Patient Sera Inhibition of M22-POD Binding to Full-Length TSHR Mutants.

ELISA plate (Nunc) wells were coated with 150 µL aliquots of 1 µg/mL 14C4 Fab$_2$ in coating buffer, incubated at room temperature for 3 h and then at 4° C. overnight. Full-length TSHR-WT, TSHR-JMG37, TSHR-JMG45 and TSHR-JMG52 were diluted in TAT buffer. Wells were washed and 150 µL full length TSHR test sample was applied to each well and incubated at 4° C. overnight to allow the full-length TSHR mutants to bind to 14C4-Fab$_2$. The wells were then washed and incubated with 75 µL of assay buffer and 75 µL of TRAb positive patient sera or M22 IgG, K1-18 IgG or K1-70 IgG diluted in NPS (1000 ng/mL to 0.1 ng/mL) for 1 h at room temperature at 500 shakes per minute on an ELISA plate shaker. Thereafter the contents of the wells were emptied, the wells washed and 100 µL of 89.5 ng/mL M22-POD (RSR Ltd) added to each well. After 25 minutes incubation at room temperature without shaking, the plate wells were washed again followed by addition of 100 µL of tetramethylbenzidine and a further incubation of 25 minutes at room temperature without shaking. The reaction was stopped by addition of 50 µL of 0.5 M H$_2$SO$_4$ and the absorbance of each well read at 450 nm on an ELISA plate reader (FIG. 14e).

Analysis of TSHR Stimulation

Transfection of mutated TSHR constructs into Chinese hamster ovary (CHO) cells using the Flp-In system is described in WO2006/016121A.

The ability of TSH, monoclonal TRAbs (M22 and K1-18) and patient sera to stimulate production of cyclic AMP in CHO cells transfected with the human TSHR was tested as described in WO2004/050708A2. CHO cells expressing the TSHR mutants were seeded into 96-well plates at 2-3×10$^5$ cells per well and grown for 48 hours until 100% confluent. The test samples (TSH, M22-Fab, K1-18 IgG or patient sera) were added (100 µL diluted in cyclic AMP assay buffer i.e. NaCl free Hank's Buffered Salts solution containing 1 g/L glucose, 20 mM HEPES, 222 mM sucrose, 15 g/L bovine serum albumin and 0.5 mM 3-isobutyl-1-methylxanthine, pH 7.4) and incubated for 1 hour at 37° C. After removal of test solutions, cells were lysed by incubation with 200 µL lysis buffer (0.37% HCl, 1% (v/v) Triton X-100) for 30 minutes with shaking at room temperature and cyclic AMP concentration in the lysates assayed using Direct cyclic AMP Elisa kits from Enzo Life Sciences. Results are expressed as pmol/mL of cyclic AMP in the cell lysate (200 µL). These experiments were compared to similar experiments carried out using CHO cells expressing wild type TSHR. Each assay was performed at least twice. GraphPad Prism was used to fit a dose-response curve to the TSH, M22 and K1-18 data using non-linear regression. This enabled calculation of the EC50 of each agonist (TSH or monoclonal TRAb), i.e. the concentration of agonist which gives a response halfway between the maximum and baseline cyclic AMP concentration.

Alignment of the Human TSHR Protein Sequence to TSHR Protein Sequences from Other Organisms and with the Human FSHR and the Human LHR Sequences The protein sequences for TSHR from grivet monkey, rhesus monkey, porcine, bovine, cat, dog, mouse, rat, sheep and horse (FIG. 10; SEQ ID Nos 47-56) and the protein sequences from human FSHR (FIG. 11; SEQ ID No 57) and human LHR (FIG. 11; SEQ ID No 58) were obtained from the Uniprot database and aligned to the protein sequence of human TSHR (FIG. 2; SEQ ID No 2) using DNAStar MegAlign (v. 9.1, DNAStar, Madison, Wis., USA).

Production of TSHR260-Alkaline Phosphatase (TSHR260-AP) Construct

One example of a labelled mutant according to the invention (TSHR260 comprising an alkaline phosphatase label) is described below, although it will be understood that different labels and different length mutant TSHRs (including full-length TSHR) may be used if desired. Other labels may, for example, be selected from the group consisting of enzymatic labels, isotopic labels, chemiluminescent labels, fluorescent labels and dyes, and such are known in the art. Such labels may be added in any suitable way, for example, via gene fusion using an appropriate construct (as described further below) or by chemical labelling. Those skilled in the art will be familiar with the relevant techniques needed for any particular label. Biotin labelling, involving any suitable biotinylation process, may be used.

The methods used to produce a TSHR260-alkaline phosphate (AP) construct have been described in WO2010/073012A2 to which reference can be made for further details.

The TSHR260 construct (coding amino acids 1-260 of the human TSHR; amino acids 1-21 being the leader sequence) (FIGS. 3 and 4; SEQ ID Nos 3 and 4 for the nucleotide and amino acid sequences respectively of the wild type TSHR260) was amplified using full-length human TSHR as the template (Oda Y, et al 1998. Journal of Molecular Endocrinology 20: 233-244) and joined to the coding sequence of a secreted alkaline phosphatase (excluding the 17 amino acid alkaline phosphatase leader sequence) using the cloning vector pSEAP2-basic (Clontech) as the template. Two PCR reactions were carried out, the first used the full-length TSHR amplified with specific primers (Primer 1—cactgcgaat tcaaaatgag gccggcggac ttgctg (SEQ ID No 7); Primer 2—gttctcctcc tcaactggga tgatgttaag agtccaggtg tttcttgc (SEQ ID No 8) (Sigma Genosys) which added an EcoRI restriction site at the N-terminus, and a 1 amino acid linker (Asparagine) and the first 8 amino acids (excluding the 17 amino acid C-leader sequence) of the secreted alkaline phosphatase at the C-terminus. The second PCR was carried out using the cloning vector pSEAP2-basic amplified with the primers (Primer 3—gcaagaaaca cctggactct taacatcatc ccagttgagg aggagaac (SEQ ID No 9); Primer 4—taatacgact cactataggg (SEQ ID No 10)) which adds amino acids 254-260 of the TSHR and a 1 amino acid linker (Asparagine) to the N-terminus of the secreted alkaline phosphatase and a 6 histidine tag, a stop codon and an XhoI restriction site at the C-terminus of the secreted alkaline phosphatase gene. The PCR reactions were carried out for 30 cycles of 1 minute at 94° C., 1 minute at 40° C. and 1 minute at 72° C. followed by 7 minutes at 72° C. The PCR products were run on 1% agarose gels and the DNA extracted using a Geneclean II kit (Anachem Ltd, Luton) following the manufacturer's instructions. Purified PCR products 1 and 2 were then used to set up a third PCR to construct the whole TSHR260-alkaline phosphatase gene. The PCR 3 reaction contained 200 ng of PCR 1 product and 200 ng of PCR 2 product and PCR 3 was carried out for 7 cycles at 94° C. for 1.5 minutes, 65° C. for 1.5 minutes and 72° C. for 1.5 minutes. The temperature was then increased to 94° C. again for 2 minutes and primer 1 and primer 4 added followed by 30 cycles of 94° C. for 1 minute, 52° C. for 1 minute and 72° C. for 2 minutes. The PCR 3 product was cloned into pFastBac1 using EcoRI and XhoI restriction sites and the presence of the mutation was verified using sequencing by the Sanger-Coulson method (Sanger F et al 1997. Proceedings of the National Academy of Sciences of the USA 74: 5463-5467). Recombinant DNA was made using the Bac to Bac Baculovirus expression system (Invitrogen, UK) and transfected into Sf-9 cells to obtain and amplify recombinant baculovirus stock as described in WO2008/025991A1. TSHR260-AP was expressed in insect cells as described in WO2008/025991A1.

Production of TSHR260-AP Construct Containing Stabilising Amino Acid Mutations

The methods used to introduce specific mutations into the TSHR sequence of the TSHR260-AP construct (FIGS. 15 and 16; SEQ ID Nos 59 and 60) are as described above for the TSHR260 mutations. TSHR mutations (FIGS. 5 and 6; SEQ ID Nos 14, 16, 18, 19, 20, 23, 27, 32, 34, 36, 37, 38, 41 and 45) were introduced sequentially into the TSHR260-AP construct resulting in eight separate constructs (TSHR260-AP-I253R, TSHR260-AP-JMG22, TSHR260-AP-JMG37, TSHR260-AP-JMG45, TSHR260-AP-JMG52, TSHR260-AP-JMG55, TSHR-AP-JMG57 and TSHR260-AP-JMG58) detailed below. Amino acid residue numbering refers to the position that the amino acid is found in the native wild type TSHR sequence:

TSHR260-AP-I253R=TSHR260-
　AP+I253R　　　　　　　　　　(FIGS. 5 and 6; SEQ ID
　　　　　　　　　　　　　　　　　　　Nos 27 and 45)

TSHR260-AP-JMG22=TSHR260-
　AP+D143P+I253R　　　　　　(FIGS. 5 and 6; SEQ ID
　　　　　　　　　　　　　　　　Nos 18, 27, 36 and 45)

TSHR260-AP-JMG37=TSHR-
　260AP+R112P+D143P+ I253R　(FIGS. 5 and 6; SEQ ID Nos
　　　　　　　　　　　　　　　　16, 18, 27, 34, 36 and 45)

TSHR260-AP-JMG45=TSHR260-AP+R112P+
　D143P+
　D151E+I253R　　　　　　　　(FIGS. 5 and 6; SEQ ID Nos
　　　　　　　　　　　　　　　16, 18, 19, 27, 34, 36, 37 and 45)

TSHR260-AP-JMG52=TSHR260-AP+R112P+
　D143P+D151E+V169R+
　I253R　　　　　　　　　　　　(FIGS. 5 and 6; SEQ ID Nos
　　　　　　　　　　　　　16, 18, 19, 23, 27, 34, 36, 37, 41 and 45)

TSHR260-AP-JMG55=TSHR260-AP+H63C+
　R112P+D143P+D151E+V169R+
　I253R　　　　　　　　　　　　(FIGS. 5 and 6; SEQ ID Nos 14, 16,
　　　　　　　　　　　　18, 19, 23, 27, 32, 34, 36, 37, 41 and 45)

TSHR260-AP-JMG57=TSHR260-AP+H63C+
　R112P+D143P+
　V169R+I253R　　　　　　　　(FIGS. 5 and 6; SEQ ID
　　　　　　　　　　　　Nos 14, 16, 18, 23, 27, 32, 34, 36, 41 and 45)

TSHR260-AP-JMG58=TSHR260-AP+H63C+
　R112P+D143P+
　S166T+I253R　　　　　　　　(FIGS. 5 and 6; SEQ ID Nos
　　　　　　　　　　　　14, 16, 18, 20, 27, 32, 34, 36, 38 and 45).

Antibodies Used in the TSHR260-AP Bridge ELISA

4E31

The 4E31 antibody is a mouse monoclonal antibody to residues 603-764 of the C-terminus of the TSHR (C-TSHR) which can be used to immobilise the full-length TSHR onto ELISA plate wells (EP 1021721B1, Bolton et al., (1999 supra). For the immunisation of mice, C-TSHR was expressed in *Escherichia coli* as a fusion protein with glutathione S-transferase (GST) using standard protocols (Oda Y et al., (1998) supra). The 3' end of cDNA (1809 to 2295 bp) coding for the last 162 amino acids was cloned in frame with the GST fusion protein in pGEX2T vector (Pharmacia Biotech, St. Albans ALI 3AW UK). An overnight culture of *E. coli* (strain UT580) transformed with pGEX-2T/C-TSHR plasmid was diluted ⅕ into 2×YTG medium (16 g/L Tryptone, 10 g/L yeast extract, 5 g/L NaCl, 20 g/L glucose, pH 7.0), incubated for 3 hours at 30° C. Thereafter, isopropyl-3-D-thiogalactopyranoside (IPTG) was added to a final concentration of 1 mM in order to induce C-TSHR/GST fusion protein expression, followed by incubation for a further three hours. The bacterial pellets were resuspended in PBS (8 g/L NaCl, 0.2 g/L KCl, 1.44 g/L $Na_2HPO_4$, 0.24 g/L $KH_2PO_4$ pH 7.4) containing 1% (v/v) Triton X-100 and sonicated three times for one minute on ice. The inclusion bodies were pelleted, washed in 4M urea, solubilised in 8M urea and separated on 9% polyacrylamide gels (SDS-polyacrylamide electrophoresis, SDS-PAGE) under reducing conditions. The C-TSHR/GST fusion protein (MW 44 kDa) was electroeluted from polyacrylamide gel slices in 0.1 M $NaHCO_3$ and 0.1% SDS pH 7.8, dialysed against 50 mM Tris-HCl pH 8.0 and stored in aliquots at −70° C.

The 4E31 antibody was prepared by immunisation with electroeluted C-TSHR/GST fusion protein. Briefly, BALB C mice were immunised with 50 μg C-TSHR/GST per mouse per injection until the titre of TSHR antibody was high. The mouse bleeds were tested using an immunoprecipitation assay based on 355-labelled TSHR produced in an in vitro transcription/translation system (Prentice et al., (1997) Journal of Clinical Endocrinology and Metabolism, 84:1288-1292). Mouse spleen cells were fused with mouse myeloma cell line (X63_Ag8.653; ECACC Porton Down, UK) and cloned to produce a stable hybridoma secreting the monoclonal antibody using standard techniques (Oda et al., (1998) supra). 4E31 is available for purchase from RSR Ltd, Cardiff, UK (supra).

K1-70

K1-70 is a blocking type human monoclonal autoantibody to the TSHR which was obtained from the peripheral blood lymphocytes of a patient with hypothyroidism (Evans et al, (2010) Clinical Endocrinology 73: 404-412; EP2367850). Briefly, lymphocytes were isolated from 20 mL of peripheral blood of a 54 year old patient with hypothyroidism and high levels of TSHR antibodies. The lymphocytes were infected with Epstein Barr virus and fused with a mouse/human hybrid cell line (K6H6/B5; ECACC, Porton Down, UK) using standard techniques (Hayakawa N et al., (2002) supra). The cells were plated out in 48-well plates and the supernatants screened using an assay based on inhibition of $^{125}$I-TSH binding to TSHR coated tubes (assay kit available from RSR Ltd, Cardiff, UK). Positive wells were then recloned by limiting dilution until a single colony producing high concentrations of TSHR autoantibody K1-70 was isolated. K1-70 is available for purchase from RSR Ltd, Cardiff, UK (supra)

M22

As detailed above in "Antibodies used in TSHR260 binding assay"

Bridge ELISA Based on TSHR260-AP

A bridge ELISA was used based on the method described previously (FIG. 13a, Rees Smith, B et al (2009) supra; WO2010/073012A2). This ELISA was based on the ability of divalent TSHR antibodies to bind with one antigen binding site to TSHR coated onto an ELISA plate well and with the other antigen binding site to TSHR260-AP in liquid phase i.e. forming a bridge. TSHR in the form of full-length detergent-solubilised receptor expressed in CHO cells was coated onto ELISA plate wells via 4E31, a C-terminal antibody as described previously (Bolton, J et al (1999) supra). In the assay 75 μL of start buffer (50 mM NaCl; 20 mM Tris pH 7.8; 1 g/L BSA; 50 mg/L normal mouse IgG; 1% Triton X-100 pH 7.8) and 75 μL of test sample (patient sera or monoclonal antibodies diluted in a pool of healthy blood donor serum or diluted in assay buffer [50 mM NaCl, 20 mM Tris pH 7.8, 1% Triton X-100, 1 g/L BSA]) were added to the ELISA plate wells coated with the full-length detergent solubilised TSHR and incubated for 2 hours at room temperature with shaking (500 rpm). Then the contents of the wells were removed, the wells washed 3 times with wash buffer (50 mM NaCl, 20 mM Tris pH 7.8, 1% Triton X-100) followed by addition of 100 μL of TSHR260-AP (diluted in wash buffer containing 0.2 g/L $MgCl_2\text{-}6H_2O$ and 2 g/L BSA). After incubation for 1 hour at room temperature with shaking (500 rpm) the wells were emptied, washed (3 times) and 100 μL of p-nitrophenyl phosphate (pNpp) substrate (Europa Bioproducts Ltd, Ely, Cambridge UK) added and the plate incubated in the dark for 45 minutes. Thereafter 100 μL of stop solution (1 M NaOH) was added and the absorbance read at 405 nm in an ELISA plate reader. The results were expressed as $OD_{405\ nm}$ absorbance values and concentration of TRAb in each sample calculated using a standard curve prepared with the human monoclonal TSHR autoantibody K1-70.

Thermostability of TSHR260-AP Mutants

TSHR260-AP mutants (see "Production of TSHR260-AP construct containing stabilising amino acid mutations" for SEQ ID Nos) expressed in insect cells and harvested from the supernatant as above, were diluted in wash buffer containing 0.2 g/L $MgCl_2\text{-}6H_2O$ and 2 g/L BSA to give an appropriate absorbance in the TSHR260-AP bridge ELISA (FIG. 13b). 150 μL aliquots were heated for between 0 and 3 hours at 50° C., 60° C. or 65° C. 100 μL of sample was applied in duplicate to the TSHR260-AP bridge ELISA described above (FIG. 13b). Assay data were plotted against time and fitted to an exponential curve and half-life ($t_{1/2}$) of the mutants calculated and compared to TSHR260-AP WT (FIGS. 15 and 16; SEQ ID Nos 59 and 60), TSHR260-AP-JMG22 or TSHR260-AP-JMG45 (defined above in "Production of TSHR260-AP construct containing stabilising amino acid mutations").

TSHR260 Bridge Inhibition ELISA

The TSHR260 bridge ELISA described above can be modified to form an inhibition ELISA for the detection of uncomplexed TSHR260 and TSHR260-Mab complexes (FIG. 13c). In the assay 75 μL of start buffer (as described for TRAb ELISA; Bolton J, et al (1999) supra) and 75 μL of 1 μg/mL M22 IgG or 1 μg/mL K1-70 IgG were added to the ELISA plate wells coated with full-length detergent-solubilised TSHR and incubated for 30 minutes at room temperature with shaking (500 rpm). Then the contents of the wells were removed, the wells washed with wash buffer (50 mM NaCl, 20 mM Tris pH 7.8, 1% Triton X-100) followed by addition of 100 μL of test sample (i.e. unlabelled TSHR260 or TSHR260-Mab complexes) per well. After incubation for 1 hour at room temperature with shaking (500 rpm) the contents of the wells were removed and the wells washed with wash buffer and 100 μL of TSHR260-AP (diluted in wash buffer containing 0.2 g/L $MgCl_2\text{-}6H_2O$ and 2 g/L BSA) was added. After incubation for 30 minutes at room temperature with shaking (500 rpm) the wells were emptied, washed (3 times) and 100 µL of p-nitrophenyl phosphate (pNpp) substrate (Europa Bioproducts Ltd, Ely, Cambridge UK) added and the plate incubated for 45 minutes. Thereafter 50 µL of stop solution (1 M NaOH) was added and the absorbance read at 405 nm in an ELISA plate reader. The inhibition of labelled TSHR260 (i.e. TSHR260-AP) binding by test sample containing unlabelled TSHR260 was expressed as: 100×(1−ratio of absorbance 405 nm of test sample to absorbance 405 nm of buffer alone).

For ease of comparison of the TSHR260 activity in the different volumes of the initial starting material and the eluted TSHR260 pools after purification on either anion or cation exchange chromatography the activity of each test sample was expressed as a dilution factor relative to the undiluted elution material.

Production of Monoclonal Antibodies to the Convex Surface of Human TSHR

The 2H11, 25E1, 23H4, 9B7 and 36F11 TSHR mouse monoclonal antibodies to the convex surface of the TSHR used in the partial purification of TSHR260 were prepared by cDNA immunisation. Briefly, six- to eight-week old OF1 (out bred) mice were injected intramuscularly with 100 µl of 10 □M cardiotoxin five days before intramuscular immunisation with 100 µg of full-length TSHR cDNA (pRC/CMVhTSHR; Oda et al (1998) supra). TSHR DNA immunisation was repeated at three week intervals for a total of five injections (Hasan et al (1999) J. Immunol. Methods 229:1-22). The mouse bleeds were tested for the presence of antibodies to the convex surface of the TSHR by inhibition of Biotin-labelled 14C4 IgG binding to the TSHR (assay manufactured by RSR Ltd, Cardiff, UK). Monoclonal antibodies were produced using the spleen cells from the mouse with the highest TSHR antibody titres in the serum. Isolated spleen cells were fused with a mouse myeloma cell line (Sp2/O—Ag14) using standard procedures (de St Groth, S. & Scheidegger, D. (1980). Journal of *Immunological Methods* 35, 1-21.). Cells were cultured in DMEM (supplemented with 15% foetal calf serum containing HAT to select for hybrids) and plated into 96-well plates. To obtain antibodies to the convex surface of the TSHR, supernatants from the cell cultures were screened by inhibition of Biotin labelled 14C4 IgG binding to the TSHR coated onto ELISA plate wells. In these assays the full-length TSHR is bound to an ELISA plate well using 4E31 (an antibody to the C terminus of the TSHR), the TSHR antibodies in the culture supernatant bind to the immobilised TSHR and wells that contain antibodies to the convex surface of the TSHR (i.e. overlapping with the 14C4 binding site) inhibit binding of biotin labelled 14C4 to the TSHR. The cells from the positive wells were recloned two times by limiting dilution to obtain clones expressing the required monoclonal antibody.

Preparation of TSHR260 and TSHR260-JMG55

High-Five™ insect cells (BTI-TN-5B1-4 from Invitrogen) were maintained in Insect Xpress media (Lonza). 2 L or 0.2 L shake-flasks were seeded at a cell density of approximately $1.00 \times 10^6$ cells/mL and incubated overnight at 27° C. at 110 rpm (after which time the temperature was reduced to 23° C.). Cells were infected using the Bac to Bac system (Invitrogen) with baculovirus stock at a multiplicity of infection (MOI) of 0.012 pfu/mL. Culture supernatants containing either TSHR260 (FIG. 4; SEQ ID No 4) or TSHR260-JMG55 were harvested 120 hours post infection by centrifugation at 500 g for 10 minutes at 4° C. One tablet of Complete protease inhibitors (Roche Diagnostics, Lewes, UK) was added per 200 mL of supernatant, before storing at −70° C. until purification.

Preparation of TSHR260 in the Presence of Different Monoclonal Antibodies

High-Five™ insect cells were cultured and infected as above for TSHR260 except that 2 mg/L of TSHR monoclonal antibody (14C4, 2H11, 25E1, 36F11, 9B7 or 23H4 IgG) was added to the culture media after approximately 96 hours. Culture supernatants containing TSHR260-TSHR Mab complexes were harvested 120 hours post infection by centrifugation at 500 g for 10 minutes at 4° C. One tablet of Complete protease inhibitors (Roche Diagnostics, Lewes, UK) was added per 200 mL of supernatant, before storing at −70° C. until purification by either anion or cation exchange chromatography depending on the PI of the individual complex.

Purification of TSHR260

Culture supernatant containing TSHR260 (100 mL) was diluted 1:1 with HPLC grade water and adjusted to pH 9.0 using 2M Tris and loaded onto 15 mL of Streamline DEAE matrix for purification by anion exchange chromatography. The column was washed with 10 mM Tris-HCl (pH 9.0), 50 mM NaCl, followed by elution with 500 mM NaCl and 10 mM Tris-HCl (pH 9.0). The eluted material was dialysed into 50 mM NaCl, 10 mM Tris-HCl pH 8.0. The presence of the TSHR260 in the elution fractions was confirmed by Western blotting analysis using a mouse monoclonal antibody (10 µg/mL) reactive with a TSHR epitope within amino acids 246-260 (TSHR MAb 18C5, Jeffreys J et al (2002) supra) and the activity measured in the TSHR260 bridge inhibition ELISA (FIG. 13c).

Purification of TSHR260 in the Presence of 14C4, 2H11, 25E1, 23H4, 36F11 or 9B7 TSHR Monoclonal Antibodies Culture supernatant containing TSHR260-14C4-IgG complex (200 mL) was diluted 1:1 with HPLC grade water, adjusted to pH 9.0 using 2M Tris and loaded onto 15 mL of Streamline DEAE matrix and purified by anion exchange chromatography as above for uncomplexed TSHR260.

Culture supernatant containing TSHR260-2H11-IgG, TSHR260-25E1-IgG, TSHR260-23H4-IgG, TSHR260-36F11-IgG or TSHR260-9B7-IgG complex (600 mL) was adjusted to pH 6.3 with 500 mM NaH$_2$PO$_4$ and loaded onto 10 mL of Streamline Direct HST matrix for purification by cation exchange chromatography. The column was washed with 50 mM NaH$_2$PO$_4$ (pH 6.0), 50 mM NaCl followed by 50 mM NaH$_2$PO$_4$ (pH 7.0), 50 mM NaCl then eluted in 50 mM NaH$_2$PO$_4$ (pH 8.0), 50 mM NaCl. The presence of TSHR260 in the elution fractions was confirmed by Western blotting analysis using a mouse monoclonal antibody 18C5 (10 µg/mL) reactive with a TSHR epitope within amino acids 246-260 (TSHR-MAb 18C5, Jeffreys J et al (2002) supra) and the activity measured in the TSHR260 bridge inhibition ELISA (FIG. 13c).

Purification of TSHR260-JMG55

An equivalent purification to that described below may be used for other mutants according to the invention. TSHR260-JMG55 was purified by three rounds of column chromatography using: a) Cation exchange chromatography on Streamline Direct HST matrix; b) Monoclonal antibody affinity chromatography on 14C4 coupled to sepharose and c) Nickel-affinity chromatography. Culture supernatant containing TSHR260-JMG55 (12 L) was adjusted to pH 6.0 with 500 mM sodium phosphate (NaH$_2$PO$_4$). Tween 80 was added to a final concentration of 0.015% v/v and the culture supernatant was loaded onto 75 mL of Streamline Direct HST matrix in a Streamline 25 expanded bed chromatography system (GE Healthcare). Two further batches of 12 L were processed in the same way in separate experiments.

The column was washed with 50 mM $NaH_2PO_4$ (pH 6.0), 50 mM NaCl containing 0.015% v/v Tween 80, followed by 100 mM NaCl, 50 mM Tris-HCl (pH 7.0) containing 0.015% v/v Tween 80 then eluted with 100 mM NaCl, 50 mM Tris-HCl (pH 8.0) containing 0.015% v/v Tween 80. The presence of the TSHR260-JMG55 in the elution fractions was confirmed by Western blotting analysis using a mouse monoclonal antibody 8E2 (10 μg/mL) reactive with a TSHR epitope within amino acids 36-42 (TSHR-MAb 8E2, Jeffreys J et al (2002) supra) and the activity measured in the TSHR260-binding assay (FIG. 12a). Samples were also analysed in the TSHR260 bridge inhibition ELISA for comparison with the streamline purifications of the TSHR260 and TSHR260-IgG complexes (FIG. 13c).

TSHR260-JMG55 was purified further by affinity chromatography using a mouse monoclonal antibody 14C4 that binds to a conformational epitope within amino acids 22-261 of the TSHR extracellular domain (Jeffreys J et al (2002) supra), coupled to CNBr-activated sepharose 4B (Sigma). In particular, TSHR260-JMG55 pooled from the three Streamline column elutions was loaded onto a 7 mL 14C4-affinity column, washed with 100 mM NaCl, 50 mM Tris-HCL (pH 8.0) containing 0.015% v/v Tween 80. The 14C4-affinity column was sequentially eluted with elution buffer (100 mM NaCl, 100 mM citrate, 0.015% v/v Tween 80) at pH 5.0 followed by elution buffer at pH 4.5. Elution fractions were collected into an equal volume of neutralisation buffer (0.5 mM Tris-HCl, pH 8.0, 0.015% v/v Tween 80) followed by dialysis into 100 mM NaCl, 50 mM Tris-HCl, pH 8.0 containing 0.015% v/v Tween 80. Fractions eluted at pH 5.0 (TSHR260-JMG55-5.0) and fractions eluted at pH 4.5 (TSHR260-JMG55-4.5) were pooled and dialysed separately. The presence of the TSHR260-JMG55 in the elution fractions was confirmed by Western blotting analysis using a mouse monoclonal antibody 8E2 (10 μg/mL) and the activity measured using the TSHR260-binding assay (FIG. 12a).

Dialysed TSHR260-JMG55-4.5 was further purified using nickel-affinity chromatography. The TSHR260-JMG55 was adjusted to a final concentration of 10 mM imidazole, pH 8.0 and loaded onto a NiNTA-HiTrap 1 mL Immobilised Metal Affinity Column (IMAC) HP column (GE Healthcare) using an Äkta 10 platform (GE Healthcare), washed with 10 mM imidazole (pH 8.0) in wash buffer (100 mM NaCl, 50 mM Tris-HCl (pH 8.0), 0.015% v/v Tween 80) and eluted with 150 mM imidazole (pH 8.0) in wash buffer. The eluted TSHR260-JMG55-4.5 was pooled and dialysed into 100 mM NaCl, 50 mM Tris-HCL (pH 8.0) containing 0.015% v/v Tween 80 and stored at −70° C. The presence of TSHR260-JMG55 in the elution fractions was confirmed by Western blotting analysis using a mouse monoclonal antibody 8E2 (10 μg/mL) and the activity analysed in the TSHR260-binding assay (FIG. 12a). The concentration of purified TSHR260-JMG55-4.5 was calculated from the absorbance at 280 nm on the basis that 1 absorbance unit is equivalent to 1.43 mg/mL of TSHR260-JMG55 (this extinction coefficient was obtained using DNASTAR Protean V.9.1.0). The concentration was confirmed by densitometric analysis using Image Lab software (Bio-Rad) of material run on a 12% non-reduced SDS-PAGE gel stained with SimplyBlue SafeStain (Invitrogen).

Dialysed TSHR260-JMG55-5.0 was also further purified using IMAC nickel-affinity chromatography. The TSHR260-JMG55-5.0 was loaded onto a NiNTA HiTrap column (GE Healthcare) using an Äkta 10 platform (GE Healthcare), washed with wash buffer then eluted with 150 mM imidazole (pH 8.0) in wash buffer. The eluted TSHR260 JMG55-5.0 was then dialysed into 100 mM NaCl, 50 mM Tris-HCL (pH 8.0) and 0.015% v/v Tween 80. The presence of the TSHR260-JMG55 in the elution fractions was confirmed by Western blotting analysis using a mouse monoclonal antibody 8E2 (10 μg/mL) and the activity analysed in the TSHR260-binding assay (FIG. 12a). The concentration of purified TSHR260-JMG55-5.0 was calculated from the absorbance at 280 nm on the basis that 1 absorbance unit is equivalent to 1.43 mg/mL of TSHR260-JMG55 (this extinction coefficient was obtained using DNASTAR Protean V.9.1.0). The concentration was confirmed by densitometric analysis using Image Lab software (Bio-Rad) of material run on a 12% non-reduced SDS-PAGE gel stained with SimplyBlue SafeStain (Invitrogen).

TSHR260-JMG55-4.5 Coated ELISA Plate Well Assay

Maxisorp 96-well ELISA plate (Nunc) wells were coated with 150 μL aliquots of 4 μg/mL or 0.4 μg/mL purified JMG55-TSHR260-4.5 in coating buffer (15 mM $Na_2CO_3$, 35 mM $NaHCO_3$, 1.5 mM $NaN_3$, 0.01 g/L Phenol Red, pH9.2 containing 5 μg/mL BSA), and incubated at 4° C. overnight. Wells were washed three times with wash buffer (50 mM NaCl; 20 mM Tris pH 7.8; 1% v/v Triton X-100) followed by 1 hour incubation with 250 μL post-coat buffer (154 mM NaCl, 58 mM sucrose, 3 g/L BSA, 0.2 g/L sodium azide). Wells were washed three times with wash buffer, and incubated with 75 μL of assay buffer (50 mM NaCl, 20 mM Tris pH7.8, 1% v/v Triton X-100, 1 g/L BSA) and 75 μL of healthy blood donor serum pool (NPS) for 1 h at room temperature at 500 shakes per minute on an ELISA plate shaker. Thereafter the contents of the wells were emptied, the wells washed and 100 μL of either M22 Fab-peroxidase conjugate (M22-POD, RSR Ltd, Cardiff, CF23 8HE, UK), K1-70 IgG-peroxidase conjugate (K1-70-POD) or K1-18 IgG-peroxidase conjugate (K1-18-POD) at a range of concentrations (0.25 to 7.5 μg/mL) added to each well. After 25 minutes incubation at room temperature without shaking, the plate wells were washed again followed by addition of 100 μL of tetramethylbenzidine and a further incubation of 25 minutes at room temperature without shaking. The reaction was stopped by addition of 50 μL of 0.5 M $H_2SO_4$ and the absorbance of each well read at 450 nm on an ELISA plate reader (FIG. 12d).

Deglycosylation of TSHR260-JMG55-4.5

Deglycosylation may be applied as described below to other mutants according to the invention. Deglycosylation reactions were performed using Endoglycosidase F3 (Endo F3, Sigma) and 5 μg of TSHR260-JMG55-4.5 at 0 mU/mg, 40 mU/mg, 60 mU/mg and 80 mU/mg (Endo F3:TSHR260-JMG55-4.5 ratio) in 50 mM sodium acetate buffer (pH 4.5) at 20° C. for 24 h, 72 h and 120 h. The reactions were analysed on 12% non-reduced SDS-PAGE by staining with SimplyBlue SafeStain (Invitrogen) and western blotting using the TSHR mouse monoclonal antibody 8E2. Any change in the molecular weight of the TSHR260-JMG55-4.5 was determined using Mark12 molecular weight markers (Invitrogen). The activity of TSHR260-JMG55-4.5 was determined by TSHR260-binding assay (FIG. 12a) after deglycosylation.

Introduction of Specific Amino Acid Mutations into Full-Length Mouse and Porcine TSHR Sequences Using PCR The porcine TSHR full-length nucleotide sequence (FIG. 17; SEQ ID No 61) was cloned from a porcine thyroid cDNA library (EP 1021721B1). Briefly total RNA was prepared from 2.5 g of porcine thyroid tissue using the acid phenol guanidine method (P Chomczynski, N Sacchi; Single step method of RNA isolation by guanidinium thiocyanate-phenol-chloroform extraction; Analytical Biochemistry 1987; 162: 156-159). mRNA was prepared using a Dynal bead mRNA purification kit (Dynal Biotec Ltd; Wirral, CH62 3QL, UK). This mRNA was used to make a cDNA library using ZapExpress cDNA Gigapack Cloning Kit III (Stratagene Ltd., Cambridge CB4 4DF UK). Four degenerate oligonucleotides were made to known TSHR sequences (mouse, rat, human, dog and bovine) and two fragments of porcine TSHR amplified using PCR. These were sequenced to verify their homology with TSHR cDNA and used to screen the cDNA library for full-length porcine TSHR clones. Three full-length clones were obtained and fully sequenced. The coding sequence of the porcine TSHR cDNA was cloned into the BamHI and NotI restriction sites of the pcDNA5.1/FRT vector (Invitrogen) using standard cloning procedures. Amino acid sequence see FIG. 18 (SEQ ID No 62).

The mouse TSHR full-length nucleotide sequence (FIG. 19; SEQ ID No 63) was synthesised with a BamHI restriction site at the 5' terminus and a NotI restriction site at the 3' terminus (Geneart, Life Technologies, Paisley, UK) and cloned into pcDNA5.1/FRT vector (Invitrogen) using standard cloning procedures. Amino acid sequence see FIG. 20 (SEQ ID No 64).

Mutations in full-length mouse and porcine TSHR sequences were generated by site-directed mutagenesis using PCR with QuikChange II methodology as described for human TSHR260 above. See FIGS. 21 and 22 (SEQ ID Nos 65 and 66) for the nucleotide and amino acid sequences, respectively of mutated porcine TSHR and FIGS. 23 and 24 (SEQ ID Nos 67 and 68) for the nucleotide and amino acid sequences, respectively of mutated mouse TSHR. See Table 54 for the JMG55 equivalent amino acid mutations in the porcine and mouse TSHRs.

Stable transfections of the full-length TSHR constructs into Flp-In CHO cells were carried out as detailed above in "Transfection of full-length TSHR constructs into CHO cells using the Flp-In system".

Thermostability of Full-Length Mouse and Porcine TSHR (Wild Type and Mutants)

The thermostability of full-length mouse and porcine TSHR wild type and mutants was tested in stability assay B (FIG. 14c), involving TSHR bound to 4E31-coated plates heated at 55° C., as described below in "*Thermostability of full-length TSHR mutants*" (FIG. 14c).

Analysis of Mouse and Porcine Wild Type and Mutated TSHR in Response to Stimulation by TSH and by M22

Transfection of wild type and mutated TSHR constructs into Chinese hamster ovary (CHO) cells using the Flp-In system is described in WO2006/016121A.

The ability of TSH and the thyroid stimulating monoclonal antibody M22 to stimulate production of cyclic AMP in CHO cells expressing the wild type and mutated mouse and porcine TSHR was tested as described above in "Analysis of TSHR stimulation" for the human TSHR.

Preparation of Detergent Solubilised Full-Length Wild Type and Mutated TSHR

CHO cells expressing full-length wild type or mutated TSHR (human, porcine or mouse) were grown to confluence, detached from 175 cm$^2$ cell culture flasks and the cell pellet washed with 50 mM NaCl, 10 mM Tris-HCl, pH7.5 containing 1 mM phenylmethylsulfonylfluoride (PMSF), then homogenised in the same buffer. The cell membranes after centrifugation at 12000 g for 30 min at 4° C. were solubilised in the same buffer (4 mL of buffer for approximately 4×10$^8$ cells) as used for homogenisation except for addition of 1% Triton X-100. The solubilised receptor preparations were centrifuged at 90000 g for two hours at 4° C. and the supernatant stored at −70° C.

Analysis of TSH Binding to Full-Length Wild Type and Mutated TSHR

Maxisorp assay tubes (Nunc) were coated with 200 µL aliquots of 10 µg/mL 4E31-Fab$_2$ in coating buffer (15 mM Na$_2$CO$_3$, 35 mM NaHCO$_3$, 1.5 mM NaN$_3$, 0.01 g/L Phenol Red, pH 9.2), incubated at 37° C. for 90 min and then overnight at 4° C. Wells were washed 3 times with assay buffer (50 mM NaCl; 20 mM Tris-HCl pH 7.8, 1% Triton-X-100). Full-length TSHR preparations were diluted in assay buffer and 200 µL aliquots incubated in the 4E31-coated tubes overnight at 4° C. Wells were washed 3 times with assay buffer. Unlabelled TSH in 50 µL in assay buffer, 50 µL of $^{125}$I-labelled TSH (30,000 cpm in assay buffer) and 50 µL of start buffer (50 mM NaCl; 20 mM Tris-HCl pH 7.8, 1% Triton-X-100, 1 g/L BSA, 50 mg/L normal mouse IgG) were applied to the coated tubes and incubated for 2 hours at room temperature with gentle shaking, washed twice with 1 mL of assay buffer and counted in a gamma counter. The concentration of TSH bound vs. bound/free was plotted (G Scatchard (1949) Annals of the New York Academy of Sciences 51: 660-672) to derive the association constants.

Thermostabilising Mutations in the TMD of the TSHR-JMG55

Further to the thermostabilising mutations identified in the LRD of the TSHR, the sequence of the TMD of TSHR-JMG55 was examined to determine whether further thermostabilising mutations may be identified in this domain of the TSHR. Three principles were used to predict possible thermostabilising mutations in the TMD of the TSHR: i) the consensus sequence of TSHR homologues in other organisms was used to identify possible thermostabilising mutations; ii) mutations that cause lower basal cAMP signalling activity of TSHR (retrieved from the SSFA database (www.ssfa-gphr.de); Kreuchwig A et al (2013) Mol Endocrinol. 8: 1357-63) were examined as these may stabilise the inactive conformation of TSHR which, for GPCRs, is more thermostable than the active conformation; and iii) mutations that have been identified as thermostabilising in other GPCRs, namely β$_1$-adrenoceptor (PAR, Serrano-Vega et al (2008) *PNAS* 105: 877-82; Miller J L and Tate C G (2011) J. Mol. Bio. 413: 628-38), A$_{2A}$ adenosine receptor (A2AR; Dore A S et al (2011) Structure 19: 1283-93), NTS$_1$ neurotensin receptor (NTS$_1$R; Egloff P et al (2014) *PNAS* 111: E655-62; Shibata Y et al (2009) J. Mol. Bio. 390: 262-277) and corticotrophin-releasing factor receptor-1 (CRF$_1$R; Hollenstein K et al (2013) Nature 499: 438-443), were transferred to TSHR. In total 56 possible thermostabilising mutations were identified: 10 TSHR consensus mutations, 19 TSHR inactivating mutations, 26 GPCR thermostabilising mutations and one mutation, Y601A, that is both inactivating in TSHR and thermostabilising in the β$_1$-adrenoceptor (Table 59).

The TSHR-JMG55 full-length nucleotide sequence was cloned into pcDNA3.1(+) vector (Invitrogen) using BamHI and XhoI restriction sites following standard cloning procedures. Mutations in the full-length TSHR-JMG55 sequence were generated by site directed mutagenesis using PCR with the QuikChange II methodology as described above for the TSHR260 mutations. The PCR reaction was transformed, expanded and the mutations verified by sequencing as described above for TSHR260 PCR products. Larger quantities of plasmid DNA were obtained by growing 50 mL cultures in LB media with ampicillin (100 µg/mL). Plasmid DNA was extracted from the cell pellet of the overnight cultures using the Qiagen Plasmid Plus Midi Kit (Qiagen Ltd, Manchester, M15 6SH, UK).

Transient Transfections of Full-Length TSHR Mutants into CHO-K1 Cells Using Freestyle Max Reagent One day prior to transfection, $2.2 \times 10^5$ CHO-K1 cells/well were plated out into 90 mm cell culture dishes (Nunc). For each 90 mm dish to be transfected, 30 µg TSHR-JMG55 mutant in pcDNA3.1(+) was mixed with 600 µL Optipro SFM (Life Technologies, Paisley, PA4 9RF, UK). 60 Freestyle Max reagent (Life Technologies) diluted in 540 µL Optipro SFM was added to each DNA/Optipro SFM mixture and incubated at room temperature for 10-20 minutes. 1200 DNA/Freestyle Max mix was added to CHO-K1 cells in a 90 mm dish and incubated at 37° C. for 40-48 h. CHO-K1 cells expressing TSHR-TMD mutants were harvested by rinsing the cell mono-layer with 4 mL PBS, and then harvesting the cells in 1 mL PBS using scraping to dislodge the cells. The cells were centrifuged in 1.5 mL vials at 13 000 rpm for 1 minute, the supernatant discarded and the cell pellet stored at −70° C. When required, each cell pellet was solubilised by suspension in 1 mL solubilisation buffer (50 mM NaCl, 10 mM Tris pH 7.8, 1% v/v Triton X-100, Complete protease inhibitors (Roche)), and incubated on ice for at least 30 minutes. This material was then used immediately or stored at −70° C.

The TSHR-JMG55 standard was made by transfecting 80 cm² flasks containing 90% confluent CHO-K1 cells with TSHR-JMG55 in pcDNA3.1+. For each 80 cm² flask, 40 µg TSHR-JMG55 in pcDNA3.1 was mixed with 800 µL Optipro SFM (Life Technologies), then 80 µL Freestyle Max reagent (Life Technologies) diluted in 720 µL Optipro SFM was added to the DNA/Optipro SFM mixture and incubated at room temperature for 10-20 minutes. 1.6 mL DNA/Freestyle Max mix was added to each 80 cm² flask of CHO-K1 cells and incubated at 37° C. for 40-48 h. CHO-K1 cells expressing TSHR-JMG55 standard were harvested from each 80 cm² flask by rinsing the cell mono-layer with 10 mL PBS, and then harvesting the cells in 2 mL PBS using scraping to dislodge the cells. Cells from all the flasks were pooled and aliquoted in 1 mL aliquots in 1.5 mL vials. The cells were centrifuged at 13 000 rpm for 1 minute, the supernatant discarded and the cell pellet stored at −70° C. When required, each cell pellet was solubilised by suspension in 500 µL solubilisation buffer (50 mM NaCl, 10 mM Tris pH 7.8, 1% v/v Triton X-100, Complete protease inhibitors (Roche)), and incubated on ice for at least 30 minutes. This material was then used immediately or stored at −70° C. TSHR-JMG55 standard was diluted so that it gave the same activity in TSHR-binding assays (described below in "TSHR-binding assay", FIG. 14a) with 14C4-coated ELISA plate wells as TSHR260-WT standard gave in TSHR260-binding assays (FIG. 12a) with 14C4-coated ELISA plate wells as defined in "*Transient transfections of TSHR260 mutants into CHO-K1 cells using Freestyle Max reagent*". This was defined as having a 14C4-activity of 100 U/mL. Similarly, the same sample assayed in the TSHR binding assay to 4E31-coated ELISA plate wells (FIG. 14a) was used to define a 4E31-activity of 100 U/mL. Further TSHR-JMG55 standard samples were diluted to the same concentration as the first TSHR-JMG55 standard, as detected in the TSHR-binding assays with 14C4- and 4E31-coated ELISA plate wells, respectively.

Antibodies Used in the TSHR-Binding Assay

4E31

As detailed above in "Antibodies used in the TSHR260-AP Bridge ELISA"

14C4

As detailed above in "Antibodies used in TSHR260 binding assay"

M22

As detailed above in "Antibodies used in TSHR260 binding assay"

TSHR-Binding Assay

Maxisorp 96-well ELISA plate (Nunc) wells were coated with 150 µL aliquots of 1 µg/mL 14C4-Fab$_2$ (Jeffreys J et al (2002) supra and Sanders J et al (2007) supra) or 1 µg/mL 4E31-Fab$_2$ (EP 1021721B1, Bolton et al (1999) supra) in coating buffer (15 mM Na$_2$CO$_3$, 35 mM NaHCO$_3$, 1.5 mM NaN$_3$, 0.01 g/L Phenol Red, pH9.2), incubated at room temperature for 3 h and then at 4° C. overnight. Wells were washed three times with wash buffer (50 mM NaCl; 20 mM Tris pH 7.8; 1% v/v Triton X-100) and 150 µL test sample (TSHR harvested from transiently transfected CHO-K1 cells), diluted in TAT buffer (50 mM NaCl, 10 mM Tris pH7.8, 1% v/v Triton X-100, 1 g/L BSA, 0.2 g/L sodium azide) was applied to each well and incubated at room temperature for 1 h or at 4° C. overnight to allow the TSHR to bind to 14C4-Fab$_2$ or 4E31-Fab$_2$ coated plates.

The wells were then washed and incubated with 75 µL of assay buffer (50 mM NaCl, 20 mM Tris pH7.8, 1% v/v Triton X-100, 1 g/L BSA, 50 mg/L normal mouse IgG) and 75 µL of healthy blood donor serum pool (NPS) for 1 h at room temperature at 500 shakes per minute on an ELISA plate shaker. Thereafter the contents of the wells were emptied, the wells washed and 100 µL of M22 Fab-peroxidase conjugate (M22-POD, RSR Ltd, Cardiff, CF23 8HE, UK) added to each well. After 25 minutes incubation at room temperature without shaking the plate wells were washed again followed by addition of 100 µL of tetramethylbenzidine and a further incubation of 25 minutes at room temperature without shaking. The reaction was stopped by addition of 50 µL of 0.5 M H$_2$SO$_4$ and the absorbance of each well read at 450 nm on an ELISA plate reader (FIG. 14a).

For each mutant, their activity in assays bound to both 14C4-coated plates and 4E31-coated plates was measured and compared to a TSHR-JMG55 standard diluted to have the same activity bound to the 14C4-coated plates as the TSHR260-WT standard bound to the 14C4-coated plates in the TSHR260-binding assay (100 U/mL) as defined in "*Transient transfections of TSHR260 mutants into CHO-K1 cells using Freestyle Max reagent*" and "*Transient transfections of full-length TSHR mutants into CHO-K1 cells using Freestyle Max reagent*".

Thermostability of Full-Length TSHR Mutants

The thermostability of TSHR mutants was measured in three different ways: A) Heating TSHR mutants bound to 14C4-coated ELISA plate wells (FIG. 14b); B) Heating TSHR mutants bound to 4E31-coated ELISA plate wells (FIG. 14c); and C) Heating TSHR mutants in solution and then binding them to 4E31-coated ELISA plate wells for the assay (FIG. 14d).

Thermostability assays A and B: Maxisorp 96-well ELISA plate (Nunc) wells were coated with 150 µL aliquots of 1 µg/mL 14C4-Fab$_2$ (thermostability assay A) or 1 µg/mL 4E31-Fab$_2$ (thermostability assay B) in coating buffer, incubated at room temperature for 3 h and then at 4° C. overnight. Wells were washed three times with wash buffer and 150 µL test sample (TSHR harvested from transiently transfected CHO-K1 cells), diluted in TAT buffer was applied to each well and incubated at 4° C. overnight to allow the TSHR to bind to 14C4- or 4E31-coated ELISA plate wells. Plates were washed three times with wash buffer to remove any TSHR that had not bound to the 14C4-Fab$_2$ or 4E31-Fab$_2$. TAT buffer was added to each well (150 μL) and an adhesive plate cover was then applied to seal the wells. Each plate was then placed in a water bath set at 45° C. or 55° C. One strip (8 wells) of the 96-well plate was removed from each plate after periods of up to 180 minutes and inserted in to a spare ELISA plate rack, which was then kept on ice. After the 180-minute time course was complete the receptor dilution buffer was aspirated from the ELISA plate wells and the TSHR-binding assay (FIG. 14a) described above was continued. Assay data were plotted against time and fitted to an exponential curve and the half-life ($t_{1/2}$) of the mutants calculated and compared to TSHR-JMG55 or another TSHR mutant.

Thermostability assay C: Maxisorp 96-well ELISA plate (Nunc) wells were coated with 150 aliquots of 1 μg/mL 4E31-Fab$_2$ in coating buffer, incubated at room temperature for 3 h and then at 4° C. overnight. TSHR mutants transiently expressed in CHO-K1 cells were diluted in solubilisation buffer. 100 μL aliquots were heated between 0 and 2 hours at 33° C. or 40° C. Samples were then diluted ¼ in TAT buffer (83.3 μL sample+250 μL TAT buffer) and 150 μL aliquots were applied in duplicate to 4E31-coated ELISA plate wells that had been washed three times with wash buffer and the TSHR-binding assay (FIG. 14a) was carried out as described above. Assay data were plotted against time and fitted to a two-phase exponential decay equation. The percentage of active TSHR mutant remaining after heating for 10, 30 and 120 min was calculated and compared to TSHR-JMG55 or another TSHR mutant to give a survival ratio at 10, 30 and 120 min.

Results
Single Mutations

In our experiments, 239 single mutants of TSHR260 have been prepared and expressed. In particular, each residue from Met22 to Leu260 was mutated to the amino acid estimated to be the most thermostabilising for each position (Table 1). These mutants have been screened for binding and stability in the TSHR260-binding assay (FIG. 12a, b, Table 2). The half-life at 42° C. of the 64 best candidates identified in the screen were determined and compared to wild-type TSHR260 (TSHR260-WT, average $t_{1/2}$=30.7±1.1 minutes), to give the difference in half-life between the mutant and TSHR260-WT ($\Delta t_{1/2}$) and the stability ratio between the half-life of the mutant and the half-life of TSHR260-WT (Table 3). These thermostability curves identified 17 mutations (P28E, L59F, T62V, H63C, L64Y, R112P, P142I, D143P, D151E, S166T, I167F, P168Y, V169R, N170W, T179C, I253R and R255Y) (FIGS. 5 and 6; SEQ ID Nos 11-25, 27-43, 45 and 46) that significantly improve the thermostability of the TSHR260-WT by at least 60%, which gives a 17-minute increase in the half-life of the protein at 42° C. (Table 3). The best single mutant, I253R (SEQ ID No 45), improved the thermostability 3.0±0.4 times over TSHR260-WT at 42° C., i.e. increased the half-life of TSHR260 at 42° C. by 53±6 minutes (FIG. 7a). It also improved the thermostability at 50° C. by 2.85±0.13 times over TSHR260-WT.

Surprisingly, the 17 mutations that had the best thermostabilising effect were distributed throughout the TSHR260 structure (FIG. 9), although most are on the convex surface or edges between the convex and concave surfaces of the LRD. Seven are on the convex surface, (P142I, D143P, S166T, I167F, P168Y, V169R, and N170W), six are on the edges of the LRD (T62V, H63C, L64Y, R112P, T179C, R255Y); only three are on the concave surface (L59F, D151E and I253R) and P28E is not visible in the crystal structure. Leu59 and Ile253 are on the concave side but do not interact with M22-Fab in the crystal structure (PDB code 3G04; Sanders J et al (2007) supra). Of these thermostabilising mutants, Asp151 is the only residue that interacts directly with M22-Fab forming a salt-bridge as shown in the crystal structure. Consequently, Asp151 was mutated to another negative amino acid, Glu, to maintain the salt-bridge interactions.

Dot Blot Results (to Determine Total Amount of TSHR Expressed, i.e. Active Plus Inactive TSHR)

The amount of TSHR260 detected in the TSHR260-binding assay varied for different mutants (between 0% and 1000% of TSHR260-WT) and consequently the total amount of each mutant expressed was measured using a Dot Blot assay. The results of Dot Blot assays are shown in Table 4. The level of expression measured by the Dot Blot assay was defined relative to TSHR260-WT and compared to the results of the TSHR260-binding assay, which was also defined relative to TSHR260-WT. The ratio between the TSHR260-binding assay results and the Dot Blot results was calculated (TSHR260-binding Dot Blot) to determine when there was a large discrepancy between the total amount of TSHR260 detected in the Dot Blot assay and the amount of active TSHR260 detected in the TSHR260-binding assay.

Double Mutants

Double mutants of TSHR260 have been made by adding the mutations P142I (SEQ ID No 35) and I253R (SEQ ID No 45) to the best stabilising mutations as shown in Table 5; Mutants JMG1-JMG15 and JMG31 are double mutants with P142I. Mutants JMG15-JMG29 are double mutants with I253R. Although P142I had a large thermostabilising impact, improving the thermostability of TSHR260 5-fold, it was expressed at very low levels. This low expression level was also observed in the case of the double mutants which included P142I. Therefore further mutagenesis and thermostability assays were continued with I253R mutants only.

Similar to P142I, the single mutants, T62V, L64Y, P142I, I167F, P168Y, N170W and T179C had low expression levels (Table 4) which were also observed in the double and triple mutants containing these mutations. As a practical matter, these were not used for further mutant combinations.

The stability of the double mutations was measured at both 42° C. (Table 6) and at 50° C. (Table 7). All of the double mutations tested improved the thermostability relative to TSHR260-WT and the single mutant TSHR260-I253R. The most thermostable double mutant was JMG22 (I253R+D143P) (SEQ ID Nos 45 and 36 respectively), which improved the thermostability of TSHR260-WT 9.3±0.5 times at 42° C. and 15.1±0.7 times at 50° C. to give a half-life of 261±45 min and 23.8±0.7 minutes, respectively (FIG. 7a, b).

Triple Mutants

Mutants JMG30-JMG42 are triple mutants of TSHR260 with the mutation D143P (SEQ ID No 36) added to the most stabilising double mutations (Table 5). Two triple mutants, I167F+D143P+I253R and T179C+D143P+I253R, were not made because their respective double mutants JMG25 (I167F+I253R) and JMG29 (T179C+I253R) showed poor expression levels.

Thermostability curves were established for the triple mutants at 50° C. and compared to the thermostability of I253R at 50° C. (Table 8). The most thermostable triple mutant was JMG37 (I253R+D143P+R112P) (SEQ ID Nos 45, 36 and 34 respectively), which had a half-life of 69±3 minutes at 50° C. and was 16.6±0.5 times more thermostable than TSHR260-I253R (FIG. 7b, c).

Quadruple Mutants

Mutants JMG43-JMG48 are quadruple mutants of TSHR260 with the mutation R112P (SEQ ID No 34) added to the most thermostabilising triple mutants (Table 5). Thermostability curves were determined for the quadruple mutants at 50° C. and 55° C. and compared to the thermostability of I253R at these temperatures (Table 8 and Table 9). The most thermostable quadruple mutant was JMG45 (I253R+D143P+R112P+D151E) (SEQ ID Nos 45, 36, 34 and 37 respectively), which had a half-life of 226±31 minutes at 50° C., and was 58±6 times more thermostable than TSHR260-I253R (FIG. 7c). At 55° C. it had a half-life of 27±3 minutes and was 54±7 times more thermostable than TSHR260-I253R (FIG. 7d). At 60° C. it had a half life of 2.40±0.16 minutes.

Quintuple Mutants

Mutants JMG49-JMG52 are quintuple mutants of TSHR260 in which D151E (SEQ ID No 37) was added on to the quadruple mutants (Table 5). The most thermostable quintuple mutant was JMG52 (I253R+D143P+R112P+D151E+V169R) (SEQ ID Nos 45, 36, 34, 37 and 41 respectively) (Table 9 and Table 10). It had a half-life of 66±12 minutes at 55° C. and was 125.1±0.6 times more thermostable than TSHR260-I253R (FIG. 7d). At 60° C. it had a half-life of 7.1±0.6 minutes and was 3.0±0.2 times more thermostable than TSHR260-JMG45 (FIG. 7e).

Hextuple Mutants

The hextuple mutations were made by adding an S166T (SEQ ID No 38) or V169R (SEQ ID No 41) mutation on to the quintuple mutant JMG50 to give JMG54 (I253R+D143P+R112P+D151E+H63C+S166T) (SEQ ID Nos 45, 36, 34, 37, 32 and 38 respectively) and JMG55 (I253R+D143P+R112P+D151E+H63C+V169R) (SEQ ID Nos 45, 36, 34, 37, 32 and 41 respectively) (Table 5 and Table 10). They were too thermostable at 55° C. to be accurately measured and so thermostability was measured at 60° C. (FIG. 7e). JMG54 had a half-life of 9.6±1.5 minutes at 60° C. and was 4.0±0.4 times more thermostable than TSHR260-JMG45. JMG55 had a half-life of 13±3 minutes at 60° C. and was 5.2±0.9 times more thermostable than TSHR260-JMG45. JMG55 is 5.2 times more thermostable than TSHR260-JMG45, which is 56 times more thermostable than TSHR260-I253R, which in turn is 3.1 times more thermostable than TSHR260-WT. Comparison of other thermostability ratios suggests that component stability ratios can be multiplied to obtain the overall thermostability ratio (Table 12). Therefore JMG55 is approximately 900 times more thermostable than TSHR260-WT.

Thermostability at 37° C.

The thermostability of the most stable single, double, triple, quadruple, quintuple and hextuple TSHR260 mutants (I253R, JMG22 (I253R+D143P), JMG37 (I253R+D143P+R112P), JMG45 (I253R+D143P+R112P+D151E), JMG52 (I253R+D143P+R112P+D151E+V169R) and JMG55 (I253R+D143P+R112P+D151E+V169R+H63C)) was measured at 37° C. relative to TSHR260-WT. The half-life of the mutants was calculated from the thermostability curves at 37° C. and is shown in Table 11. Table 11 also shows the stability ratios for each mutant compared to TSHR260-WT. These are consistent with the stability ratios observed at other temperatures (Table 12).

Comparing the Thermostability of the Most Thermostable Mutants at a Range of Temperatures The stability ratios of mutants compared to TSHR260-WT do not change greatly at different temperatures i.e. 42° C. and 50° C. Above 50° C. TSHR260-WT is so unstable it cannot be used as a reference preparation. Consequently a more suitable mutant was chosen instead. The stability ratios obtained with this more stable mutant as reference were then multiplied by the stability ratio of the stable reference mutant compared to TSHR260-WT (Table 12). For example, JMG37 is 12.0±0.9 times more thermostable than I253R at 55° C., which is 3.1 times more thermostable than TSHR260-WT. Therefore JMG37 is calculated to be 12.0× 3.1=37±3 times more thermostable than TSHR260-WT at 55° C., which corresponds well to the measured thermostability ratio relative to TSHR260-WT at 37° C. (34±5 times).

Thermostability of Full-Length TSHR and Mutants Coated on 14C4 Plates.

The thermostability of full-length TSHR-WT (SEQ ID No 2), TSHR-JMG37 (SEQ ID Nos 45, 36, 34), TSHR-JMG45 (SEQ ID Nos 45, 36, 34, 37), TSHR-JMG52 (SEQ ID Nos 45, 36, 34, 37, 41) and TSHR-JMG55 (SEQ ID Nos 45, 36, 34, 37, 32, 41) bound to ELISA plates coated with 14C4-Fab$_2$ was determined by heating the plates at 42° C. or 50° C. Unexpectedly, the full-length TSHR mutants, TSHR-JMG37, TSHR-JMG45, TSHR-JMG52 and TSHR-JMG55 were considerably more thermostable than TSHR-WT (Table 13, Table 14). At 50° C., TSHR-WT has a half-life of 33 minutes, TSHR-JMG37 has a half-life of 110 minutes and is 3.4 times more thermostable than TSHR-WT, TSHR-JMG45 has a half-life of 173 minutes and is 5.3 times more thermostable that TSHR-WT, TSHR-JMG52 has a half-life of 175 minutes and is 5.4 times more thermostable that TSHR-WT and TSHR-JMG55 is 6.9 times more thermostable than TSHR-WT with a half-life of 226 minutes (FIG. 8)

M22-POD, K1-18-POD and K1-70-POD Binding to TSHR260 and Full-Length TSHR Mutants M22-POD, K1-18 POD and K1-70 POD binding to TSHR260 mutants and full-length TSHR has been tested by varying the concentration of TRAb-peroxidase conjugate (i.e. M22-POD, K1-18 POD or K1-70 POD) binding to ELISA plates coated with TSHR260 mutants or full-length TSHR mutants and detecting the binding of TRAb-peroxidase conjugate by incubation with the substrate tetramethylbenzidine. The binding constant ($K_d$), which is the concentration of ligand (TRAb-peroxidase) at which half of the receptor (TSHR or TSHR260 mutants) is bound to ligand, was determined relative to the binding constant of TSHR260-WT or full-length TSHR-WT as appropriate. The mutations tested did not affect the binding of full-length TSHR or TSHR260 to any of M22-POD, K1-18-POD or K1-70-POD (Table 15 to Table 21).

K1-18 IgG and K1-70 IgG Inhibition of M22-POD Binding to TSHR260 Mutants and Full-Length TSHR Mutants Incubating the receptor (TSHR260 mutants and full-length TSHR mutants), with varying concentration of K1-18 IgG and K1-70 IgG, which bind to the same site as M22, before incubation with M22-POD, measures inhibition of M22-POD binding and indicates whether the receptor-antibody interactions have been affected by the thermostabilising mutations. K1-18 IgG and K1-70 IgG inhibit the binding of M22-POD to the TSHR260 mutants and the full-length TSHR mutants to a similar extent as to TSHR260-WT and full-length TSHR-WT respectively. These results show that the mutations have not affected binding of the monoclonal TSHR antibodies to TSHR260 or full-length TSHR (Table 22 to Table 25).

Inhibition of M22-POD Binding to TSHR260 and Full-Length TSHR Mutants by TRAb Positive Patient Sera To determine whether the thermostabilised mutants of TSHR260 and full-length TSHR are suitable for use in assays to detect TRAbs in patient sera, the ability of patient sera to inhibit the binding of M22-POD to TSHR260-WT, TSHR260-JMG52, TSHR260-JMG55 full-length TSHR-WT, TSHR-JMG45 and TSHR-JMG52 was measured (FIG. 12c, FIG. 14e). The patient sera inhibited the binding of M22-POD to TSHR260-JMG52 and TSHR260-JMG55 similarly to TSHR260-WT (Table 27, Table 29). Furthermore, the patient sera inhibited the binding of M22-POD to full-length TSHR-JMG45 and full-length TSHR-JMG52 similarly to full-length TSHR-WT (Table 28, Table 29). Therefore, the thermostable TSHR260 or full length TSHR mutants are suitable for use in assays to detect TRAb in patient sera.

Analysis of TSHR Stimulation

The stimulation of full-length TSHR and full-length TSHR mutants (expressed in FlpIn CHO cells) by TSH, M22 Fab and K1-18 IgG, was determined by measuring the amount of cyclic AMP produced using a range of different concentrations of TSH, M22-Fab or K1-18 IgG. In each assay, the stimulation of the TSHR mutants was compared to the stimulation of TSHR-WT detected in the same assay. The EC50, i.e. the concentration of agonist (TSH, M22-Fab, or K1-18 IgG) which produces 50% of the maximum stimulation response, was calculated for each mutant and compared to TSHR-WT (Table 30 to Table 39). Surprisingly, the mutations did not have a marked effect on cyclic AMP production in response to stimulation by TSH, M22 or K1-18, although there was a small increase in EC50 of M22 for the quadruple mutant TSHR-JMG45 (I253R+D143P+R112P+D151E), the quintuple mutant TSHR-JMG52 (I253R+D143P+R112P+D151E+V169R) and the hextuple mutant TSHR-JMG55 (I253R+D143P+R112P+D151E+V169R+H63C), relative to TSHR-WT (Table 38).

Stimulation of full-length TSHR-WT, TSHR-JMG45 and TSHR-JMG52 by TRAb positive patient sera was also measured and compared to the effects of healthy blood donor sera. The stimulation of the mutated full-length TSHRs by patient sera was very similar to the stimulation of TSHR-WT (Table 40 and Table 41).

Transferability of Thermostabilising Human TSHR Mutations to TSHR from Other Species and Other Glycoprotein Hormone Receptors.

There is a high sequence homology (86-97.5% sequence identity) between the TSHR sequences currently available from different mammalian species. This suggests that most of the thermostabilising mutations identified in the human TSHR (hTSHR), will be thermostabilising in these homologues. Table 42 shows that most of the amino acids mutated in the human TSHR to improve thermostability are conserved across species. Pro28, Leu59, Thr62, Leu64, Arg112, Pro142, Asp143, Asp151, Ser166, Pro168, Asn170, Thr179 and Ile253 are conserved across all species (Table 42). In the case of thermostabilising mutation H63C, position 63 is Gln in dog TSHR and Arg in both Rhesus monkey and Grivet monkey rather than His. As these residues are quite different to both His and Cys, it is difficult to predict whether mutation to Cys may still be thermostabilising. Regarding thermostabilising mutation I167F, in mouse, rat and sheep, position 167 is Val rather than Ile. As Ile and Val are both similar aliphatic amino acids, it is likely that mutation to Phe may still be thermostabilising. In the case of thermostabilising mutation V169R, position 169 is Ala in porcine, bovine, cat, dog, sheep and horse TSHR sequences, which is similar to the aliphatic Val present in human, therefore it is expected that mutation to Arg will also be thermostabilising in these TSHRs. In contrast, in mouse and rat, the residue 169 is Glu, which is a charged residue like Arg, therefore mutation to Arg may not have as dramatic a stabilising effect as in the human TSHR. Regarding thermostabilising mutation R255Y, mouse and rat have Lys at position 255, rather than Arg present in the other TSHR sequences, which are both positively charged amino acids. Therefore mutation to Tyr may still be thermostabilising at position 255.

There is lower sequence identity between hTSHR (SEQ ID No 2) and the other glycoproteins hFSHR (SEQ ID No 57) (50% sequence identity) and hLHR (SEQ ID No 58) (53.3% sequence identity). However, sequence alignment (FIG. 11) indicates that many of the thermostabilising mutated residues in hTSHR correspond to the same or similar residues in the hFSHR and hLHR. Consequently, many thermostabilising mutations are likely to be transferable (Table 43). In the FSHR it is expected that T56V, L58Y, N106P, P136I, D137P, Q145E, I160F, N163W, S172C and R247Y will be thermostabilising. In the LHR, the corresponding mutations P33E, L56F, V61Y, K109P, P139I, D140P, I164F, P165Y, N167W, S176C and I249R are predicted to be thermostabilising.

Further Thermostabilising TSHR260-Mutants

Two more thermostable quintuple TSHR260 mutants have been made and tested for thermostability: TSHR260-JMG57 (I253R+D143P+R112P+V169R+H63C) (SEQ ID Nos 45, 36, 34, 41 and 32 respectively) and TSHR260-JMG58 (I253R+D143P+R112P+S166T+H63C) (SEQ ID Nos 45, 36, 34, 38 and 32 respectively) have a half-life at 55° C. of 40±2 min and 31.4±0.4 min respectively and are 1.64±0.07 and 1.28±0.05 times more thermostable than the quadruple mutant TSHR260-JMG45. TSHR260-JMG57 and TSHR260-JMG58 also maintain the ability to detect patient sera in inhibition of M22-POD binding assays (FIG. 12c, Table 44).

M22 IgG, K1-70 IgG and K1-18 IgG Binding to Alkaline Phosphatase Labelled TSHR260 Mutants in the Bridge ELISA The assay (FIG. 13a) relies on the bivalent properties of human monoclonal stimulating type TSHR autoantibodies (M22 IgG and K1-18 IgG) and the human monoclonal blocking type TSHR autoantibody (K1-70 IgG) to form a bridge between immobilised full-length wild type TSHR and alkaline phosphatase labelled TSHR260 mutants (TSHR260-AP-I253R, TSHR260-AP-JMG22, TSHR260-AP-JMG37, TSHR260-AP-JMG45, TSHR260-AP-JMG52, TSHR260-AP-JMG55, TSHR260-AP-JMG57 and TSHR260-AP-JMG58) (see "Production of TSHR260-AP construct containing stabilising amino acid mutations" for SEQ ID Nos). When diluted in a pool of healthy blood donor serum, M22 IgG, K1-70 IgG and K1-18 IgG all bound to the TSHR260-AP mutants and to wild type TSHR260-AP in a similar dose dependent manner (Table 45 a-c; e-g). Furthermore, when diluted in assay buffer, M22 IgG, K1-70 IgG and K1-18 IgG all bound to the TSHR260-AP mutants and to wild type TSHR260-AP in a similar dose dependent manner (Table 46a-c; e-g). A negative control human monoclonal autoantibody to GAD (5B3 IgG) diluted in healthy blood donor serum or assay buffer was tested for binding (Table 45d and Table 46d). No binding was seen between 5B3 IgG (negative control antibody) and either the wild type TSHR260-AP or TSHR260-AP mutants, (absorbance values of 0.0016-0.033 for dilutions in healthy blood donor serum and 0.001-0.034 for dilutions in assay buffer). These experiments demonstrated the ability of human monoclonal TSHR autoantibodies with either stimulating or blocking activity to bind to alkaline phosphatase labelled TSHR260 mutants.

TRAb Positive and TRAb Negative Sera Binding to Alkaline Phosphatase Labelled TSHR260 Mutants in the Bridge ELISA Twelve TRAb positive patient sera (G1-G12) and eleven TRAb negative patient sera (N1-N11) were tested for their ability to bind bivalently and form a bridge between immobilised full-length TSHR and alkaline phosphatase labelled TSHR260 (TSHR260-AP) mutants (TSHR260-AP-I253R, TSHR260-AP-JMG22, TSHR260-AP-JMG37, TSHR260-AP-JMG45, TSHR260-AP-JMG52, TSHR260-AP-JMG55, TSHR260-AP-JMG57 and TSHR260-AP-JMG58) (FIG. 13a). Binding of TRAb positive and TRAb negative sera was similar for both the wild type and mutant TSHR260-AP (Table 47a). Using the K1-70 IgG standard curve to calculate TRAb concentrations for each patient serum showed that TRAb concentrations calculated for the mutant TSHR260-AP constructs compared well to the average of the wild type TSHR260-AP assays (Table 47b). Performing Pearson correlation of assay results obtained with each TSHR260-AP mutant compared to the average TRAb concentration determined with wild type TSHR260-AP gave good r-values (Table 47c), demonstrating that patient sera TRAb bind to wild type TSHR260-AP and the TSHR260-AP mutants in a similar way.

Thermostability of TSHR260-AP Mutants

TSHR260-AP mutant half-lives ($t_{1/2}$) were calculated by fitting an exponential curve to the time course data (0 h-3 h) for each TSHR260-AP construct at each temperature, using duplicate measurements (FIG. 13b). The half-life of each construct at each temperature tested is shown in Table 48. The half-life for each TSHR260-AP mutant was compared to the half-life for TSHR260-AP-JMG45 (65° C.), TSHR260-AP-JMG22 (60° C.) or TSHR260-AP-WT (50° C.). From this a predicted stability ratio could be calculated to show the overall stability of each TSHR260-AP mutant compared to TSHR260-AP-WT. TSHR260-AP-JMG22, TSHR260-AP-JMG45 and TSHR260-AP-JMG55 had half-lives of approximately 11-fold, 66-fold and 165-fold greater than TSHR260-AP-WT, respectively. Although the increase in stability between TSHR260-AP-WT and the TSHR260-AP mutants was reduced compared to TSHR260 without the alkaline phosphatase fusion protein, the thermostability of the TSHR260-AP constructs were greater than the equivalent constructs without alkaline phosphatase. The half-life of TSHR260-AP-WT at 50° C. was 2.9-fold greater than the half-life of wild type TSHR260 (without alkaline phosphatase). Similarly, at 60° C. TSHR260-AP-JMG45 and TSHR260-AP-JMG55 had half-lives of 3.2-fold and 1.5-fold greater, respectively, than the equivalent TSHR260 constructs without alkaline phosphatase.

Purification of Wild Type TSHR260

After purification using anion exchange chromatography the eluted wild type TSHR260 pool contained approximately 80-fold less activity in the TSHR260 bridge inhibition ELISA than the initial material loaded onto the anion exchange column (FIG. 25a). These results confirm that the wild type TSHR260 is inherently unstable during purification with an 80-fold loss of activity after only one round of anion exchange chromatography purification.

Purification of Wild Type TSHR260 in Complex with TSHR Monoclonal Antibodies (14C4, 2H11, 25E1, 23H4, 36F11 or 9B7)

Previously we have shown that TSHR260 (wild type) can be stabilised, purified and crystallised when in complex with the human monoclonal thyroid stimulating autoantibody M22 (WO 2008/025991A1). However M22 binds to the TSHR260 fragment with high affinity ($5 \times 10^{10}$ L/mol), is not easily dissociated and inhibits binding of patient serum autoantibodies to the TSHR260 fragment (EP 1565493B1, Nakatake et al. (2006) Thyroid, 16: 1077-1084). Therefore the formation and purification of a complex of TSHR260-M22 cannot be used as a purification method for uncomplexed TSHR260 for use in assay systems to detect binding of patient autoantibodies to the TSHR or for other purposes.

Purification of the wild type TSHR260 in complex with 14C4 IgG, 25E1 IgG, 2H11 IgG, 36F11 IgG or 9B7 IgG (TSHR monoclonal antibodies to the convex surface of the TSHR which do not compete with M22 for binding to TSHR) by ion exchange chromatography showed similar activity (less than 2-fold decrease) in the eluted material relative to the load material after analysis in the TSHR260-AP bridge inhibition ELISA (FIG. 13c, FIGS. 25b, c, d, f and g respectively). However 23H4 IgG (a further monoclonal antibody to the convex surface of the TSHR) was less effective at stabilising the wild type TSHR260 with the eluted material following cation exchange chromatography containing approximately 15-fold less activity than the initial material loaded onto the column, measured in the TSHR260 bridge inhibition ELISA (FIG. 25e). These experiments show that purification of the wild type TSHR260 in complex with different TSHR mouse monoclonal antibodies (14C4, 2H11, 25E1 or 23H4, 36F11 IgG or 9B7 IgG; which bind to the convex surface of the TSHR away from the binding sites of patient serum autoantibodies) was able to stabilise the wild type TSHR260 during one round of ion exchange chromatography.

Purification of TSHR260-JMG55

Initial purification by cation exchange chromatography of 36 Litres of insect cell culture supernatant containing TSHR260-JMG55 showed a 529-fold increase in the specific activity of the TSHR260-JMG55 from 30 U/mg to 15,872 U/mg measured in the TSHR260 binding assay (FIG. 12a, Table 49). Units of TSHR260-JMG55 are defined relative to TSHR260 standard as described in "*Transient transfections of TSHR260 mutants into CHO-K1 cells using Freestyle Max reagent*".

Analysis of the initial load material and the eluted pool from the streamline column in the TSHR260 bridge inhibition ELISA (FIG. 13c) showed similar activity (approximately 3-4 fold decrease in total activity) in the eluted pool relative to the load material (FIG. 25h).

Further purification of TSHR260-JMG55 using a TSHR MAb 14C4 affinity column resulted in the purification of two different forms of TSHR260-JMG55 (FIG. 26). Elution of the 14C4-affinity column at pH 5.0 gave purified TSHR260-JMG55-5.0 which had a low specific activity of 12,041 U/mg while elution at pH 4.5 gave purified TSHR260-JMG55-4.5 which had a high specific activity of 11,443,46 U/mg (Table 49). A final purification of the high activity TSHR260-JMG55-4.5 using nickel affinity chromatography increased the specific activity of the purified protein to 6,414,000 U/mg giving an overall purification level of 213,708 compared to the initial culture supernatant (Table 49 and Table 50a). In contrast, final purification of the low activity TSHR260-JMG55-5.0 using nickel affinity chromatography gave a specific activity of 20,361 U/mg for the purified protein giving an overall purification level of 679 compared to the initial culture supernatant (Table 49 and Table 50b).

The two forms of the purified TSHR260-JMG55 ran as single bands of approximately 34 kDa on a 12% non-reduced SDS PAGE (FIG. 27). After the final purifications 0.665 mg of high specific activity TSHR260-JMG55-4.5 (6,414,000 U/mg) and 0.927 mg of low specific activity TSHR260-JMG55-5.0 (20,361 U/mg) were obtained.

K1-18-POD, K1-70-POD and M22-POD bound to purified JMG55-TSHR260-4.5 coated ELISA plate wells in a dose dependant manner (Table 51).

Deglycosylation of TSHR260-JMG55-4.5

Incubation of purified TSHR260-JMG55-4.5 in deglycosylation buffer without Endo F3 for 1, 3 and 5 days at 20° C. showed no reduction in the molecular weight (FIG. 28A). In contrast deglycosylation of TSHR260-JMG55-4.5 with Endo F3 at 40 mU/mg, 60 mU/mg or 80 mU/mg resulted in a maximum reduction in molecular weight of approximately 2 kDa at 120 h, 72 h and 24 h respectively (FIGS. 28A and 28B). Analysis of the activity of the deglycosylated TSHR260-JMG55-4.5 after 120 h incubation at 20° C. was determined in the TSHR260-binding assay (FIG. 12a) and compared to the activity of the untreated purified TSHR260-JMG55-4.5 material stored at −70° C. (Table 52). Incubation of TSHR260-JMG55-4.5 with no enzyme (0 mU/mg), 40 mU/mg, 60 mU/mg or 80 mU/mg gave 111%, 100%, 104% and 104% of the activity of the untreated purified TSHR260-JMG55-4.5 material respectively.

The purified TSHR260-JMG55-4.5 protein retained its activity and was stable after three rounds of column chromatography (streamline HST, 14C4 affinity and nickel affinity chromatography) and removal of approximately 2 kDa of sugar residues by deglycosylation with Endo F3.

In contrast to the wild type TSHR260, the TSHR260-JMG55 mutated TSHR can be successfully purified by three rounds of column chromatography (streamline HST, 14C4 affinity followed by nickel affinity chromatography) without the addition of a TSHR monoclonal antibody to form a stable complex. Two different forms of active TSHR260-JMG55 have been purified from the culture supernatant, a high specific activity form (TSHR260-JMG55-4.5) which had a specific activity of 6,414,000 U/mg and a low specific activity form which had a specific activity of 20,361 U/mg (315-fold lower). The observation that deglycosylated, purified TSHR260-JMG55-4.5 was active in the TSHR260-binding assay further confirmed the increased stability of the mutated TSHR fragment.

Transferability of Thermostable Human TSHR Mutations to Mouse and Porcine TSHR

The equivalent mutations of the most thermostable human TSHR mutant, JMG55 (I253R+D143P+R112P+D151E+V169R+H63C), were transferred to mouse TSHR (I253R+D143P+R112P+D151E+E169R+H63C) (FIG. 23; SEQ ID No 67 for nucleotide sequence and FIG. 24; SEQ ID No 68 for amino acid sequence) and porcine TSHR (I253R+D143P+R112P+D151E+A169R+H63C) (FIG. 21; SEQ ID No 65 for nucleotide sequence and FIG. 22; SEQ ID No 66 for amino acid sequence) (Table 54). Five of the six mutated residues are identical in human, mouse and porcine TSHR, Only residue 169 differs between species: in human TSHR it is valine, in mouse TSHR it is glutamic acid and in porcine TSHR it is alanine. For both mouse and porcine TSHR residue 169 was mutated to arginine as in human TSHR-JMG55. The full-length mutant mouse TSHR and porcine TSHR were compared to the respective full-length wild type TSHR with respects to thermostability, binding affinities for $^{125}$I-TSH and responsiveness to stimulation when transfected into CHO cells Thermostability of Full-Length Wild Type and Mutated Mouse, Porcine and Human TSHR The thermostability of full-length wild type and mutated mouse, porcine and human TSHR was measured in stability assay B at 45° C. (FIG. 14c). Stability assay B involves binding TSHR mutants to 4E31-coated plates overnight and then heating the plates at 45° C. in a water bath for up to three hours. The percentage of active TSHR remaining after heating is measured in the TSHR-binding assay (FIG. 14a, Table 55).

The mutations increased the thermostability of mouse TSHR 6.3 times, (from a half-life of 2.15 min to 13.6 min). There was a similar increase in the thermostability of porcine TSHR (from a half-life of 3.6 min to 12.1 min to give a 3.34-fold improvement in thermostability). Mutated human TSHR (TSHR-JMG55, half-life of 184 min) was 39 times more thermostable than wild type human TSHR (half-life of 4.8 min). This shows that the thermostabilising mutations found in human TSHR are transferable to TSHR from other species and improve their thermostability, however the improvement in thermostability is not as great as the improvement in thermostability observed for human TSHR-JMG55.

Stimulation of Mouse and Porcine Wild Type and Mutated TSHR Expressed in CHO Cells Stimulation of full-length wild type mouse and porcine TSHRs and full-length mouse and porcine TSHR-JMG55 equivalent mutants (Table 54) (expressed in Flp-In CHO cells) by TSH and M22 Fab, was assessed by measuring the amount of cyclic AMP produced with a range of different concentrations of the two TSHR agonists (TSH or M22-Fab). In each assay, the stimulation of the TSHR mutant was compared to stimulation of TSHR-WT (measured in the same assay). The EC50, i.e. the concentration of agonist which produces 50% of the maximum stimulation response, was calculated for each mutant and compared to TSHR-WT (Table 56 and Table 57). Similar to the full-length human TSHR-WT and full-length human TSHR-JMG55 mutation, the JMG55 equivalent mutations did not have a marked effect on cyclic AMP production in response to stimulation by TSH or M22 compared to the equivalent mouse or porcine TSHR-WT.

Binding Affinity of 125I-TSH to Solubilised Full-Length Human, Mouse and Porcine TSHR, Wild Type and Mutated $^{125}$I-TSH binding to human, mouse and porcine wild type TSHRs (expressed in CHO cells and detergent solubilised) gave similar affinity constants of $1.80 \times 10^9$ L/mol, $1.58 \times 10^9$ L/mol and $1.99 \times 10^9$ L/mol respectively (Table 58). $^{125}$I-TSH binding to detergent solubilised full-length mutated human (JMG55), mouse and porcine TSHR (JMG55 equivalent; Table 54) also showed similar affinity constants ($0.98 \times 10^9$ L/mol, $0.87 \times 10^9$ L/mol and $1.25 \times 10^9$ L/mol respectively) to the wild type TSHRs. This indicated that the binding of TSH to the full-length TSHR was unaffected by the JMG55 equivalent TSHR mutations in different TSHR species.

Thermostability Effects of Single Mutations to the Transmembrane Domain (TMD) of TSHR-JMG55

In total 56 possible thermostabilising mutations in the transmembrane domain of TSHR were identified: 10 TSHR consensus mutations, 19 TSHR inactivating mutations, 26 GPCR thermostabilising mutations and one mutation (Y601A) that is both inactivating in the TSHR and thermostabilising in the $\beta_1$-adrenoceptor (Table 59). These single mutations were added to full-length TSHR-JMG55, which already contains six thermostabilising mutations (I253R, D143P, R112P, D151E, H63C and V169R) (SEQ ID Nos 45, 36, 34, 37, 32 and 41) located in the LRD, The mutants showed different relative levels of activity in the assays when bound to 14C4-coated plates or 4E31-coated plates (FIG. 14a). This suggests that some of the mutations affect binding of the TSHR to these antibodies. For this reason the activity of the mutants in both forms of the assay were tested and the samples were diluted appropriately to give similar OD450 readings (between 2.0 and 2.5 OD450) in each assay. D460A and S505A did not have high enough activity to determine their thermostability. Due to low activity in the 14C4 thermostability assay (A), the thermostability of C600R could only be determined in the 4E31 thermostability assays (B and C).

The thermostability of full-length TSHR-JMG55 and mutants bound to ELISA plates coated with 14C4-Fab$_2$ or 4E31-Fab$_2$ was measured in three different ways. Stability assay A involves binding TSHR mutants to 14C4-coated ELISA plate wells by overnight incubation at 4° C. and then heating the wells at 55° C. in a water bath for up to two hours (FIG. 14b). Similarly, stability assay B involves binding TSHR mutants to 4E31-coated ELISA plate wells by incubation overnight at 4° C. and then heating the wells at 55° C. in a water bath for up to two hours (FIG. 14c). In contrast, stability assay C involves heating the TSHR mutants in solution at 33° C. for up to two hours followed by binding to a 4E31-coated ELISA plate wells (FIG. 14d). In all cases the percentage of active TSHR remaining after heating is measured in the TSHR-binding assay (FIG. 14a).

TSHR260 wild type and TSHR260 mutants are small, globular domains of the TSHR. In this relatively simple case the inactivation of the protein by heat over time accurately fits a single-phase exponential decay curve from which the half-life ($t_{1/2}$) is calculated. However, the full-length TSHR is a multi-domain protein and therefore there exist transition states between the folded and unfolded state of the protein. Therefore, in stability assay C where the protein is heated in solution (FIG. 14d), the TSHR unfolding is better modelled as two-phase decay, i.e. the decay of the protein is the sum of two decay processes, one fast and one slow, giving rise to two parameters "half-life (slow)" and "half-life (fast)" that describe the unfolding process and a third parameter, "PercentFast", what percentage of the decay process is described by the fast decay process. It is more complicated to directly compare three parameters, and therefore the comparisons have been made on the percentage of active TSHR remaining after heating for 10, 30 and 120 minutes. Alternatively, an apparent half-life is estimated by determining the time point at which the TSHR has lost 50% of its activity. In the case of stability assays A and B (FIG. 14a and FIG. 14b), one of the TSHR domains is tethered to the plate by the antibodies 14C4 or 4E31. This leads to a heat-inactivation process which more closely resembles single-phase exponential decay and thus a half-life for TSHR mutants in these assays can be determined and compared. For all assays the thermostability of TSHR-JMG55 is measured in the same experiment and used to determine the half-life ratio of each TSHR mutant.

Surprisingly, most of the mutations tested were thermostabilising in at least one of the stability assays (half-life ratio≥1.3). Only two of the 54 mutations assayed, C599S and I622A were neutral or destabilising in all three thermostability assays (Table 60). The twenty most thermostabilising mutations of TSHR-JMG55 are E409K, D410K, H443N, L452Y, N455A, M463V, Y466F, L467P, T477I, Q489H, K565L, V595I, C600R, Y601F, I648L, K660D, Y667V, S671A, Y678L and Y678A (FIG. 29, 30, SEQ IDs 69 to 88 (DNA) and 89 to 108 (protein)). They increase the stability of TSHR-JMG55 up to 4.5-fold in stability assay A, up to 1.6-fold in stability assay B, and up to 15-fold in stability assay C.

Thermostability of Double Mutations in the TMD of TSHR-JMG55

Three of the single TSHR-JMG55 TMD mutants, T477I, V595I and I648L (FIG. 30; SEQ ID Nos 97, 100 and 103 respectively), were selected for further mutagenesis as they increased the thermostability considerably in all three thermostability assays. These three mutations were combined with each other and with the other most thermostabilising single mutations (n=17) to form double mutants of TSHR-JMG55 (Table 61 and FIGS. 29 and 30; SEQ ID Nos 69-88 and SEQ ID Nos 89-108, respectively). Mutants JMG59 to JMG73 are combinations with T477I, mutants JMG74 to JMG92 are combinations with V595I and JMG93 to JMG111 are combinations with I648L. JMG66 and JMG82 are identical (JMG55+T477I+V595I), JMG68 and JMG101 are identical (JMG55+T477I+I648L) and JMG87 and JMG104 are identical (JMG55+V595I+I648L). The construct JMG85 (JMG55+V595I+C600R) was not made as the mutations V595I and C600R are too close together and would be likely to interfere with each other.

All of these double mutants, JMG59 to JMG111 were assayed in thermostability assay C format (FIG. 14d) and compared to the thermostability of single mutants T477I, V595I or I648L in the same assay (Table 62). Five out of the fifteen T477I double mutants (JMG59 to JMG73) were thermostabilising relative to T477I (defined as a half-life ratio ≥1.1). Twelve out of the eighteen V595I double mutants (JMG74 to JMG92) were thermostabilising relative to V595I and twelve of nineteen I648L double mutants (JMG93 to JMG111) were thermostabilising relative to I648L (JMG111 was not active enough to be tested in the thermostability assays). JMG87 [JMG55 (SEQ ID Nos 45, 36, 34, 37, 32, 41)+V595I (SEQ ID No 100)+I648L (SEQ ID No 103)], JMG90 [JMG55 (SEQ ID Nos 45, 36, 34, 37, 32, 41)+V595I (SEQ ID No 100)+S671A (SEQ ID No 106)] and JMG91 [JMG55 (SEQ ID Nos 45, 36, 34, 37, 32, 41)+V595I (SEQ ID No 100)+Y678L (SEQ ID No 107)] were the most thermostabilising V595I mutants in thermostability assay C.

Because the V595I double mutants (JMG74 to JMG92) were the most thermostabilising and did not have as great a difference in activities in the 14C4 and 4E31 assays as those observed for the T477I double mutants, the JMG74 to JMG92 mutants were further analysed in stability assays A and B (FIG. 14b, c; Table 63). All of these mutants were thermostabilising in at least one of these thermostability assays relative to V595I. The half-life in stability assay A increased from 27 min at 55° C. for TSHR-JMG55-V595I to 59 min for JMG82 (JMG55+V595I+T477I) [JMG55 (SEQ ID Nos 45, 36, 34, 37, 32, 41)+V595I (SEQ ID No 100)+T477I (SEQ ID No 97)]. The most thermostable mutant in stability assay B was JMG84 (JMG55+V595I+K565L) [JMG55 (SEQ ID Nos 45, 36, 34, 37, 32, 41)+V595I (SEQ ID No 100)+K565L (SEQ ID No 99)] with a half-life at 55° C. of 38 min, a 2.4-fold improvement on the 18 min half-life of TSHR-JMG55-V595I. However, JMG91 (JMG55+V595I+Y678L) and JMG84 (JMG55+V595I+K565L) were selected as the mutants with the best all-round thermostability in all three thermostability assays. In stability assay A, JMG91 has a half-life of 48 min at 55° C., a 1.8 times improvement of TSHR-JMG55-V595I, in stability assay B it has a half-life of 30 min at 55° C. which is a 1.7 times improvement of TSHR-JMG55-V595I and in stability assay C, it has a half-life of 108 min at 33° C. which is a 2.1 times improvement over TSHR-JMG55-V595I. This is equivalent to survival of 80%, 64% and 49% after 10, 30 and 120 min respectively at 33° C., which is an increase in stability of 1.3, 1.1 and 1.3 times respectively. In stability assay A, JMG84 has a half-life of 44 min at 55° C., a 1.6 times improvement of TSHR-JMG55-V595I, in stability assay B it has a half-life of 38 min at 55° C. which is a 2.4 times improvement of TSHR-JMG55-V595I and in stability assay C, it has a half-life of 102 min at 33° C. which is a 1.6 times improvement over TSHR-JMG55-V595I. This is equivalent to survival of 72%, 60% and 48% after 10, 30 and 120 min respectively at 33° C., which is an increase in stability of 1.1, 1.1 and 1.4 times respectively.

Thermostability of Triple Mutations in the TMD of TSHR-JMG55

TSHR-JMG91 and TSHR-JMG84 were combined with 15 single mutations that were thermostabilising in the double TSHR mutant thermostability assays (Table 61). Due to the increased thermostability of these mutants, in stability assay C, the solubilised TSHR mutants were heated at 40° C. instead of 33° C. used previously. While some of the triple mutants are thermostabilising relative to the double mutants TSHR-JMG91 (JMG55+V595I+Y678L) or TSHR-JMG84 (JMG55+V595I+K565L) in stability assays A and B, only the triple TMD mutants of full length TSHR-JMG55 built on TSHR-JMG84 (JMG127 to JMG142) are thermostabilising in thermostability assay C at 40° C. (Table 64). The overall most thermostabilising of the triple mutants of TSHR-JMG55 is TSHR-JMG131 (JMG55+V595I+K565L+ N455A) [JMG55 (SEQ ID Nos 45, 36, 34, 37, 32, 41)+ V595I (SEQ ID No 100)+K565L (SEQ ID No 99)+N455A (SEQ ID No 93)]. In stability assay A, TSHR-JMG131 has a half-life at 55° C. of 60 minutes, which is a 1.5-fold improvement of the 38±4 minute half-life of TSHR-JMG84. In stability assay B at 55° C., TSHR-JMG131 has a 32 minute half-life, which is a 1.1 times improvement of the 23±7 minute half-life of TSHR-JMG84. In stability assay C at 40° C., TSHR-JMG131 has a half-life of 47 minutes which is a 3.5-fold increase in thermostability over TSHR-JMG84, which has a half-life of 14±3 minutes at 40° C.

M22-POD, K1-70-POD and K1-18-POD Binding to TSHR TMD Mutants

M22-POD, K1-18-POD and K1-70-POD binding to full-length TSHR mutants, TSHR-JMG55, TSHR-JMG55-V595I, TSHR-JMG84 (JMG55+V595I+K565L) and TSHR-JMG91 (JMG55+V595I+Y678L), has been tested by varying the concentration of TRAb-peroxidase conjugate (i.e. M22-POD, K1-18 POD or K1-70 POD) binding to ELISA plates coated with TSHR mutants and detecting the binding of TRAb-peroxidase conjugate by incubation with the substrate tetramethylbenzidine (FIG. 14a). The binding constant ($K_d$), i.e. the concentration of ligand (TRAb-peroxidase) at which half of the receptor is bound to ligand, was determined (Table 65). The mutations tested did not affect the binding of TSHR mutants to any of M22-POD, K1-18-POD or K1-70-POD relative to TSHR-JMG55 (Table 65 to Table 67).

Inhibition of M22-POD Binding to Full-Length TSHR-JMG55 Mutants by M22 IgG, K1-18 IgG, K1-70 IgG or TRAb Positive Patient Sera Inhibition of M22-POD binding to full-length TSHR-JMG55 mutants TSHR-JMG55, TSHR-JMG55-V595I, TSHR-JMG84 (JMG55+V595I+K565L) and TSHR-JMG91 (JMG55+V595I+Y678L) was determined by incubating the TSHR mutants with M22 IgG, K1-18 IgG, K1-70 IgG or TRAb positive patient sera before incubation with M22-POD (FIG. 14e). M22 IgG, K1-18 IgG, K1-70 IgG and TRAb positive patient sera inhibit the binding of M22-POD to the full-length TSHR mutants to a similar extent as to TSHR-JMG55. These results show that the mutations have not affected binding of the monoclonal TSHR antibodies to full-length TSHR (Table 68 to Table 70). Similarly, the TRAb positive patient sera show similar inhibition of M22-POD binding to the TSHR-JMG55 mutants as to TSHR-JMG55 (Table 71). Therefore, these full-length TSHR mutants are suitable for use in assays to detect TRAb in patient sera.

Transferability of Thermostabilising Human TSHR Mutations in the TMD Region to TSHR from Other Species and Other Glycoprotein Hormone Receptors.

Table 72 shows that most of the amino acids located in the TMD that have been mutated in the human TSHR to improve thermostability are conserved across human, mouse and porcine TSHR. Glu409, Asp410, His443, Leu452, Asn455, Met463, Tyr466, Leu467, Thr477, Gln489, Lys565, Cys600, Tyr601, Lys660, Tyr667, Ser671 and Tyr678 are conserved across all species. Residue 595 is Val in human and mouse, but Thr in porcine. Mutation of Thr595 to Ile in porcine TSHR is likely to be thermostabilising. Residue 648 is Ile in human but Leu in mouse and porcine. Therefore mouse and porcine TSHR already have the target residue of the I648L thermostabilising mutation in hTSHR. Mutation to Val, another aliphatic residue may alter the thermostability.

The sequence alignment of human TSHR (SEQ ID No 2), FSHR (SEQ ID No 57) and LHR (SEQ ID No 58) (FIG. 11) indicates that many of the thermostabilising mutated residues in hTSHR correspond to the same or similar residues in the hFSHR and hLHR. Consequently, most of the thermostabilising mutations located in the TMD of TSHR are likely to be thermostabilising when transferred to the equivalent residues of FSHR and LHR (Table 73). The only differences are: His443, which is Gln391 in FSHR and Arg388 in LHR; Met463, which is Ile411 in FSHR; Ile648, which is Ser596 in FSHR and Ala593 in LHR; and Tyr667 which is His615 in FSHR and Tyr612 in LHR. Some of these equivalent mutations may still be thermostabilising.

SUMMARY AND CONCLUSIONS

This invention presents a novel approach to improving the thermostability of glycoprotein hormone receptor proteins such as the TSHR based on rational-scanning mutagenesis. Here, the approach of rationally designing a few stabilising mutations has been combined with the power of the scanning mutagenesis approach of mutating every residue in a protein to alanine to identify thermostabilising positions in the TSHR sequence. In the rational-scanning mutagenesis approach, for each position in the TSHR protein the most probable stabilising mutation (predicted by the present inventors by a combination of computational and rational methods) has been produced and tested for thermostabilising properties. In this invention high-throughput methods have enabled us to generate and screen many mutants to identify the most thermostabilising mutations. This has enabled the identification of more thermostabilising mutations in the TSHR sequence than would have been possible otherwise. The methods described in the invention could also be applied to improve thermostability of other proteins. The method of the invention has in particular enabled the identification of 17 greatly thermostabilising mutations of TSHR260 (P28E, L59F, T62V, H63C, L64Y, R112P, P142I, D143P, D151E, S166T, I167F, P168Y, V169R, N170W, T179C, I253R and R255Y) (FIGS. 5 and 6; SEQ ID Nos 11-25, 27-43, 45 and 46) that have been successfully combined to produce more thermostable TSHR260 mutants which improve the thermostability of TSHR260 up to 900 times. These mutants still bind TSHR stimulating human autoantibody M22 in a similar manner to TSHR260-WT. The thermostability of the most stable single (TSHR260-I253R) (SEQ ID No 45), double (TSHR260-JMG22: I253R (SEQ ID No 45)+D143P (SEQ ID No 36)), triple (TSHR260-JMG37: I253R (SEQ ID No 45)+D143P (SEQ ID No 36)+R112P (SEQ ID No 34)), quadruple (TSHR260-JMG45: I253R (SEQ ID No 45)+D143P (SEQ ID No 36)+R112P (SEQ ID No 34)+D151E (SEQ ID No 37)), quintuple (TSHR260-JMG52: I253R (SEQ ID No 45)+D143P (SEQ ID No 36)+R112P (SEQ ID No 34)+D151E (SEQ ID No 37)+V169R (SEQ ID No 41)) and hextuple (TSHR260-JMG55: I253R (SEQ ID No 45)+D143P (SEQ ID No 36)+R112P (SEQ ID No 34)+D151E (SEQ ID No 37)+V169R (SEQ ID No 41)+H63C (SEQ ID No 32)) TSHR260 mutants improve the thermostability of the TSHR260 by approximately 3.1, 13, 42, 174, 450, 700 and 900 times respectively. Furthermore, in the case of full-length TSHR, the triple (TSHR-JMG37: I253R+D143P+R112P), quadruple (TSHR-JMG45: I253R+D143P+R112P+D151E), quintuple (TSHR-JMG52 I253R+D143P+R112P+D151E+V169R) and hextuple (TSHR260-JMG55: I253R+D143P+R112P+D151E+V169R+H63C) TSHR mutants improve the thermostability relative to full-length wild-type TSHR.

The mutations do not affect binding of the monoclonal TSHR antibodies (M22, K1-18 and K1-70) to TSHR260 or full length TSHR. Further, TRAb positive patient sera inhibit the binding of M22-POD to the TSHR260 mutants and full-length TSHR mutants to the same extent as to wild-type TSHR260 and full-length TSHR respectively. Even further, M22-Fab, K1-18 IgG and TSH stimulate the production of cyclic AMP in full length TSHR mutants expressed in Flp-In CHO cells in a similar way to that seen for the wild-type TSHR.

Increasing the thermostability of TSHR preparations, especially TSHR260, has enabled purification of the mutants, in particular the most thermostable mutant of TSHR260, TSHR260-JMG55 (I253R+D143P+R112P+D151E+V169R+H63C; SEQ ID Nos 45, 36, 34, 37, 41 and 32 respectively), to homogeneity while retaining its activity without the need for an antibody bound to it to maintain the folded state of TSHR260. This is the first time conformationally active TSHR260 has been purified without antibodies bound to it. After deglycosylation of the purified material using Endoglycosidase F3, the TSHR260-JMG55 was still active. Both the purified and the deglycosylated TSHR260-JMG55 material can be used in improved assays to detect TSHR autoantibodies in patient sera.

These thermostabilising mutations were also transferable, for example to the fusion protein TSHR260-AP, which consists of the detectable label alkaline phosphatase joined to TSHR260 for use in assays. The thermostabilising TSHR260-AP mutants, TSHR260-AP-JMG22 (I253R+D143P; SEQ ID Nos 45 and 36), TSHR260-AP-JMG45 (I253R+D143P+R112P+D151E; SEQ ID Nos 45, 36, 34 and 37) and TSHR260-AP-JMG55 (I253R+D143P+R112P+D151E+V169R+H63C; SEQ ID Nos 45, 36, 34, 37, 41 and 42) improve the thermostability of TSHR260-AP approximately 11-, 66-, or 165-fold respectively. These TSHR260-AP mutants are still able to bind TRAb antibodies (M22, K1-18, K1-70 and TRAb positive patient sera) to the same extent as wild-type TSHR260-AP. These constructs are valuable for use in the TSHR260-AP bridge ELISA for detecting TSHR autoantibodies in patient sera. Other detectable labels may also be used and it is expected that the thermostabilising mutations identified for TSHR260 and full-length TSHR will also increase the thermostability of these labelled constructs and therefore enable their use in a wide range of applications.

Many of the thermostabilising mutations disclosed in this invention are surprising and would not have been predicted by computational modelling or examination of the structure alone.

The experiments described as part of the present invention have highlighted the limited usefulness of using modelling software. The computationally predicted thermostabilities of mutants were mainly used in two situations. Firstly, when there was more than one option for rational mutagenesis, Discovery Studios was used to predict which mutation was likely to be most thermostabilising in a specific position. Secondly, when there was no clear rational mutation for a single residue, Discovery Studios software was used to predict the most thermostabilising, or, if all the mutations were destabilising, the least destabilising mutation. The software has been of some use in identifying many thermostabilising mutations that may not have been tested otherwise (e.g. H63C, S84F, P142I, D143P, P168Y, N170W and R255Y). However, for some residues, mutagenesis to any other amino acid was predicted to be destabilising. In these cases the least destabilising prediction out of many destabilising mutations was chosen. Surprisingly, some of these were found to be some of the most stabilising mutations (e.g. T62V, L64Y, P142I and I167F). There are also many cases of mutations that were predicted to be stabilising that were actually destabilising, illustrating the limitations of computational modelling and the requirement for experimental studies, which has now been possible using the methods disclosed in the present invention.

One of the most successful strategies of the invention has been the removal and introduction of proline residues into the structure. In total, 5/23 (22%) of the mutations to or from proline (i.e. P28E, R112P, P142I, D143P and P168Y) stabilise TSHR260 considerably, however it can also be very disruptive to the structure with 8/23 mutants (35%) expressed at very low levels or not at all. Proline, with its five-membered ring, has a very rigid structure with the backbone dihedral angle φ constrained to −63°±15° and the torsion angles of the residue preceding the proline residue constrained too. This decreased flexibility of the protein backbone gives it the lowest conformational entropy so that where the geometry is favourable, replacing an amino acid with proline produces a more thermostable TSHR. However, where the geometry is unfavourable, a proline residue can introduce strain into the structure by confining the torsion angles. Substituting such a proline residue with another more flexible amino acid, releases the strain producing a more thermostable residue.

A second successful strategy of the invention has been the mutation of surface residues to charged residues. P28E, D151E, V169R and I253R have all involved the introduction or change of a charged residue to the surface of the protein. In particular, V169R and I253R, involve the mutation of aliphatic surface residues to the analogous residue in hFSHR, which in both cases is Arg.

Further stabilising mutations of full-length TSHR were identified in the transmembrane domain (TMD) of TSHR. The twenty most thermostabilising mutations identified in the TMD region of TSHR are: E409K, D410K, H443N, L452Y, N455A, M463V, Y466F, L467P, T477I, Q489H, K565L, V595I, C600R, Y601F, I648L, K660D, Y667V, S671A, Y678L and Y678A (FIGS. 29 and 30; SEQ ID Nos 69-88 (DNA) and SEQ ID Nos 89-108 (protein)). They increase the stability of TSHR-JMG55 up to 4.5-fold in stability assay A, up to 1.6-fold in stability assay B, and up to 15-fold in stability assay C. They have been combined to form double (e.g. TSHR-JMG91 (JGM55 (SEQ ID Nos 45, 36, 34, 37, 32 and 41)+V595I (SEQ ID No 100)+Y678L (SEQ ID No 107)) and TSHR-JGM84 (JGM55 (SEQ ID Nos 45, 36, 34, 37, 32 and 41)+V595I (SEQ ID No 100)+K565L (SEQ ID No 99)) and triple mutants (e.g. TSHR-JMG131 (JMG55 (SEQ ID Nos 45, 36, 34, 37, 32 and 41)+V595I (SEQ ID No 100)+K565L (SEQ ID No 99)+N455A (SEQ ID No 93)) with mutations located in the TMD which further increase the thermostability of full-length TSHR.

An immediate and key outcome of the invention is production for the first time of thermostable TSHR preparations. This opens up new opportunities to apply the effect of the mutations to the stability of the full-length TSHR and other TSHR preparations consisting of shorter sequences. Such TSHR preparations will be useful for the production of improved, manual and automated assay systems (for detection of patient TRAbs) which can be run at higher temperatures. Furthermore, thermostable TSHR preparations can be purified and the availability of such pure preparations will have important implications for studies on the structure of the TSHR and development of new therapeutics.

Tables

TABLE 1

Single amino acid mutations in TSHR260

| Mutation | Reason for mutation | Mutation | Reason for mutation |
| --- | --- | --- | --- |
| G21D | surface | L64Y | DS |
| M22K | consensus sequence | R65K | consensus sequence |
| G23R | consensus sequence | T66V | DS |
| C24E | surface | I67L | DS |
| S25P | consensus sequence | P68Q | consensus sequence |
| S26D | surface | S69P | torsion angles |
| P27T | natural variant - hypothyroid | H70R | consensus sequence |
| P28E | surface | A71C | DS |
| C29E | surface | F72Y | DS |
| E30D | surface | S73E | surface |
| C31I | β-sheet | N74H | DS |
| H32I | DS | L75W | DS |
| Q33E | β-sheet, surface | P76E | surface |
| E34W | DS | N77E | surface |
| E35D | consensus sequence | I78V | core |
| D36E | surface | S79L | DS |
| F37R | surface | R80W | DS |
| R38I | DS | I81L | DS |
| V39I | β-sheet | Y82F | DS |
| T40D | β-sheet | V83L | consensus sequence |
| C41I | β-sheet | S84F | DS |
| K42R | surface | I85Y | DS |
| D43E | surface | D86N | DS |
| I44L | DS | V87D | surface |
| Q45H | consensus sequence | T88E | surface |
| R46I | DS | L89A | core |
| I47F | DS | Q90E | surface |
| P48I | DS | Q91D | DS |
| S49C | DS | L92W | DS |
| L50I | DS | E93D | surface |
| P51R | DS | S94E | surface |
| P52T | natural variant | H95G | torsion angles |
| S53I | DS | S96A | surface |
| T54I | DS | F97Y | surface |
| Q55W | DS | Y98W | surface |
| T56I | DS | N99G | torsion angles |
| L57I | β-sheet | L100I | LRR |
| K58F | DS | S101I | DS |
| L59F | consensus sequence | K102R | surface |
| I60E | surface | V103L | LRR |
| E61W | DS | T104I | DS |
| T62V | DS | H105F | DS |
| H63C | DS | I106W | DS |
| E107Q | DS | F153T | β-sheet |
| I108W | DS | F154Y | DS |

TABLE 1-continued

Single amino acid mutations in TSHR260

| Mutation | Reason for mutation | Mutation | Reason for mutation |
| --- | --- | --- | --- |
| R109Y | DS | I155F | DS |
| N110W | DS | L156F | LRR |
| T111I | β-sheet | E157Q | DS |
| R112P | torsion angles | I158L | LRR |
| N113S | consensus sequence | T159R | β-sheet |
| L114W | DS | D160E | β-sheet |
| T115L | consensus sequence | N161I | DS |
| Y116F | consensus sequence | P162E | surface |
| I117L | LRR | Y163E | surface |
| D118E | surface | M164I | LRR |
| P119E | surface | T165S | LRR |
| D120E | surface | S166T | β-sheet |
| A121Y | DS | I167F | LRR |
| L122F | LRR | P168Y | DS |
| K123R | surface | V169R | surface |
| E124D | surface | N170W | DS |
| L125I | LRR | A171S | consensus sequence |
| P126W | DS | F172W | DS |
| L127C | DS | Q173E | surface |
| L128W | DS | G174I | DS |
| K129R | surface | L175F | LRR |
| F130T | surface | C176V | LRR |
| L131I | LRR | N177E | surface |
| G132W | DS | E178D | surface |
| I133F | LRR | T179C | surface |
| F134Y | DS | L180I | LRR |
| N135F | DS | T181I | DS |
| T136Y | DS | L182I | LRR |
| G137N | DS | K183R | natural variant, β-sheet |
| L138F | LRR | L184I | LRR |
| K139R | consensus sequence | Y185F | DS |
| M140V | consensus sequence | N186L | DS |
| F141Y | DS | N187Q | DS |
| P142I | DS | G188D | DS |
| D143P | DS | F189Y | DS |
| L144I | LRR | T190I | DS |
| T145F | DS | S191E | β-sheet |
| K146V | DS | V192I | consensus sequence |
| V147I | consensus sequence | Q193H | DS |
| Y148W | DS | G194P | torsion angles |
| S149Q | DS | Y195H | consensus sequence |
| T150I | DS | A196R | DS |
| D151E | surface | F197W | DS |
| I152V | consensus sequence | N198P | torsion angles |
| G199Q | surface | L230F | DS |
| T200Q | DS | L231I | LRR |
| K201W | DS | D232N | DS |
| L202I | LRR | V233I | LRR |
| D203E | β-sheet | S234M | DS |
| A204I | β-sheet | Q235Y | consensus sequence |
| V205I | LRR | T236N | LRR |
| Y206F | DS | S237I | DS |
| L207I | LRR | V238L | LRR |
| N208R | DS | T239C | disulphide, DS |
| K209Y | DS | A240S | surface |
| N210I | DS | L241I | LRR |
| K211R | surface | P242L | DS |
| Y212I | DS | S243P | DS |
| L213F | DS, LRR | K244W | DS |
| T214I | DS | G245L | DS |
| V215E | surface | L246F | LRR |
| I216F | LRR | E247C | DS |
| D217P | LRR | H248S | consensus sequence |
| K218N | consensus sequence | L249E | surface |
| D219W | DS | K250C | DS |
| A220F | DS | E251C | DS |
| F221D | DS | L252I | LRR, β-sheet |
| G222D | DS | I253R | surface |
| G223P | DS | A254L | LRR, DS |
| V224I | LRR | R255Y | DS |
| Y225H | consensus sequence | N256Y | DS |
| S226W | DS | T257N | LRR |
| G227A | torsion angles | W258I | LRR, β-sheet |
| P228L | LRR | T259S | LRR |
| S229T | β-sheet | L260C | disulphide |

Reasons for carrying out the particular mutations are as follows: Torsion angles—mutations of residues with the correct backbone structure for mutation to Pro or Gly determined by examination of the torsion angles of the backbone of the TSHR260 crystal structure; Consensus—mutations to the consensus sequence of either TSHR across different species, or the three glycoprotein hormone receptors. Also, one naturally occurring TSHR variant P27T that is reported to cause hypothyroidism; β-sheet—mutagenesis of β-strand residues so that the alternating polar, non-polar periodicity is maintained, core residues mutated to Ile, surface residues mutated to Thr, Asp or Arg. LRR—mutations to conform to the general consensus sequence of the leucine rich repeat motif, LxxLxLxxNxLxxLpxxoFxxLxx, where "L" is Leu, Ile, Val or Phe, "N" is Asn, Thr, Ser or Cys, "o" is non-polar and "x" is a non-conserved residue (Matsushima, Miyashita, Mikami, & Kuroki, 2010); Surface—surface residues mutated to Glu (or Asp if already Glu), nature of charged residues are maintained by mutating Arg to Lys and Lys to Arg; Core—mutations of core residues, Ile and Ala to Val, Gly to Gln, other residues to Ala. DS— mutations that were predicted to be stabilising by molecular modelling with Discovery Studios software.

TABLE 2

Effect of single mutations on the stability of TSHR260 as assessed in an assay based on binding of M22-peroxidase to TSHR260 (TSHR260-binding assay)

| Mutation | Binding in TSHR260 assay (% WT std) | Stability screen (% WT stability) | Mutation | Binding in TSHR260 assay (% WT std) | Stability screen (% WT stability) |
|---|---|---|---|---|---|
| WT | 100 | 100 | E61W | 69 | 77 |
| M22K | 72 | 135 | T62V | 16 | 123 |
| G23R | 307 | 78 | H63C | 153 | 143 |
| C24E | 71 | 82 | L64Y | 20 | 142 |
| S25P | 86 | 140 | R65K | 5 | 97 |
| S26D | 59 | 142 | T66V | 33 | 87 |
| P27T | 124 | 129 | I67L | 57 | 79 |
| P28E | 24 | 216 | P68Q | 26 | 40 |
| C29E | 62 | 90 | S69P | 243 | 82 |
| E30D | 40 | 152 | H70R | 43 | 81 |
| C31I | 195 | 138 | A71C | 42 | 69 |
| H32I | 175 | 104 | F72Y | 45 | 35 |
| Q33E | 241 | 83 | S73E | 196 | 64 |
| E34W | 49 | 140 | N74H | 31 | 71 |
| E35D | 246 | 129 | L75W | 13 | 0 |
| D36E | 226 | 103 | P76E | 79 | 91 |
| F37R | 33 | 46 | N77E | 48 | 81 |
| R38I | 164 | 135 | I78V | 37 | 0 |
| V39I | 110 | 121 | S79L | 19 | 0 |
| T40D | 25 | 93 | R80W | 12 | 0 |
| C41I | 8 | 250 | I81L | 23 | 0 |
| K42R | 61 | 172 | Y82F | 85 | 102 |
| D43E | 22 | 0 | V83L | 80 | 102 |
| I44L | 14 | 89 | S84F | 154 | 108 |
| Q45H | 0 | — | I85Y | 397 | 145 |
| R46I | 0 | — | D86N | 25 | 154 |
| I47F | 5 | 79 | V87D | 40 | 141 |
| P48I | 9 | 34 | T88E | 59 | 110 |
| S49C | 0 | — | L89A | 35 | 109 |
| L50I | 9 | 0 | Q90E | 244 | 73 |
| P51R | 0 | — | Q91D | 44 | 96 |
| P52T | 10 | 171 | L92W | 9 | 0 |
| S53I | 35 | 118 | E93D | 98 | 83 |
| T54I | 82 | 82 | S94E | 83 | 96 |
| Q55W | 41 | 74 | H95G | 23 | 57 |
| T56I | 172 | 126 | S96A | 70 | 85 |
| L57I | 102 | 92 | F97Y | 14 | 66 |
| K58F | 78 | 136 | Y98W | 52 | 104 |
| L59F | 200 | 209 | N99S | 56 | 75 |
| I60E | 54 | 118 | L100I | 7 | 205 |
| S101I | 116 | 130 | L144I | 42 | 96 |
| K102R | 88 | 244 | T145F | 0 | — |
| V103L | 271 | 159 | K146V | 0 | — |
| T104I | 94 | 162 | V147I | 284 | 66 |
| H105F | 38 | 0 | Y148W | 129 | 50 |
| I106W | 6 | 223 | S149Q | 0 | — |
| E107Q | 54 | 92 | T150I | 140 | 76 |
| I108W | 7 | 54 | D151E | 426 | 153 |
| R109Y | 21 | 47 | I152V | 242 | 90 |
| N110W | 45 | 78 | F153T | 75 | 101 |
| T111I | 41 | 122 | F154Y | 0 | — |
| R112P | 351 | 167 | I155F | 0 | — |
| N113S | 149 | 146 | L156F | 0 | — |

TABLE 2-continued

Effect of single mutations on the stability of TSHR260 as assessed in an assay based on binding of M22-peroxidase to TSHR260 (TSHR260-binding assay)

| Mutation | Binding in TSHR260 assay (% WT std) | Stability screen (% WT stability) | Mutation | Binding in TSHR260 assay (% WT std) | Stability screen (% WT stability) |
|---|---|---|---|---|---|
| L114W | 9 | 170 | E157Q | 44 | 0 |
| T115L | 37 | 90 | I158L | 47 | 0 |
| Y116F | 96 | 129 | T159R | 23 | 60 |
| I117L | 60 | 54 | D160E | 0 | — |
| D118E | 79 | 68 | N161I | 0 | — |
| P119E | 57 | 49 | P162E | 16 | 130 |
| D120E | 128 | 55 | Y163E | 23 | 0 |
| A121Y | 20 | 0 | M164I | 449 | 136 |
| L122F | 332 | 49 | T165S | 87 | 58 |
| K123R | 228 | 59 | S166T | 690 | 170 |
| E124D | 365 | 62 | I167F | 16 | 189 |
| L125I | 31 | 0 | P168Y | 21 | 248 |
| P126W | 6 | 0 | V169R | 696 | 212 |
| L127C | 187 | 66 | N170W | 44 | 205 |
| L128W | 0 | — | A171S | 0 | — |
| K129R | 205 | 71 | F172W | 0 | — |
| F130T | 16 | 81 | Q173E | 0 | — |
| L131I | 0 | — | G174I | 0 | — |
| G132W | 0 | — | L175F | 0 | — |
| I133F | 122 | 34 | C176V | 0 | — |
| F134Y | 205 | 76 | N177E | 34 | 96 |
| N135F | 2 | 0 | E178D | 37 | 0 |
| T136Y | 0 | — | T179C | 10 | 208 |
| G137N | 0 | — | L180I | 193 | 90 |
| L138F | 1 | 0 | T181I | 0 | — |
| K139R | 216 | 203 | L182I | 13 | 95 |
| M140V | 5 | 0 | K183R | 77 | 66 |
| F141Y | 0 | — | L184I | 10 | 117 |
| P142I | 5 | 201 | Y185F | 42 | 33 |
| D143P | 562 | 214 | N186L | 0 | — |
| N187Q | 0 | — | V224I | 36 | 59 |
| G188D | 0 | — | Y225H | 243 | 115 |
| F189Y | 0 | — | S226W | 21 | 33 |
| T190I | 59 | 61 | G227A | 0 | — |
| S191E | 271 | 159 | P228L | 0 | — |
| V192I | 241 | 102 | S229T | 0 | — |
| Q193H | 70 | 77 | L230F | 280 | 128 |
| G194P | 238 | 156 | L231I | 12 | 55 |
| Y195H | 32 | 99 | D232N | 0 | — |
| A196R | 0 | — | V233I | 0 | — |
| F197W | 0 | — | S234M | 3 | 0 |
| N198P | 0 | — | Q235Y | 123 | 109 |
| G199Q | 0 | — | T236N | 0 | — |
| T200Q | 0 | — | S237I | 6 | 0 |
| K201W | 0 | — | V238L | 225 | 141 |
| L202I | 0 | — | T239C | 10 | 80 |
| D203E | 77 | 60 | A240S | 160 | 161 |
| A204I | 9 | 0 | L241I | 141 | 81 |
| V205I | 2 | — | P242L | 0 | — |
| Y206F | 31 | 0 | S243P | 9 | 0 |
| L207I | 0 | — | K244W | 0 | — |
| N208R | 0 | — | G245L | 0 | 0 |
| K209Y | 0 | — | L246F | 0 | — |
| N210I | 5 | — | E247C | 5 | 0 |
| K211R | 124 | 76 | H248S | 58 | 66 |
| Y212I | 0 | — | L249E | 0 | — |
| L213F | PCR | 0 | K250C | 24 | 91 |
| T214I | 0 | — | E251C | 165 | 144 |
| V215E | 164 | 111 | L252I | 144 | 142 |
| I216F | 19 | 0 | I253R | 978 | 178 |
| D217P | 4 | 0 | A254L | 54 | 84 |
| K218N | 132 | 105 | R255Y | 188 | 177 |
| D219W | 5 | 0 | N256Y | 11 | 59 |
| A220F | 0 | — | T257N | 74 | 71 |
| F221W | 4 | 0 | W258I | 123 | 89 |
| G222D | 106 | 56 | T259S | 104 | 67 |
| G223P | 2 | 0 | L260C | 20 | 22 |

For each TSHR260 mutation expressed in CHO-K1 cells, M22-binding in the TSHR260 assay (FIG. 12a) is expressed as a percentage of TSHR260-WT and the stability, determined by the proportion of active protein remaining after heating at 42° C. for 30 min (FIG. 12b), is expressed as a percentage of the TSHR260-WT stability (% WT). The stability screen results of mutations which increase the stability are in bold. These mutations were tested in the thermostability assay to determine the half-life of the mutant (FIG. 12b). M22 is a human monoclonal autoantibody to the TSHR.

TABLE 3

Half-life of TSHR260 mutants at 42° C. determined in the TSHR260-binding assay

| Mutation | $t_{1/2}$ at 42° C. (min) | $\Delta t_{1/2}$ relative to WT (min) | Stability ratio relative to WT at 42° C. | n |
|---|---|---|---|---|
| WT | 30.9 ± 1.1 | 0.0 ± 1.1 | 1 ± 0 | 24 |
| M22K | 27 ± 4 | −3 ± 9 | 1.0 ± 0.3 | 2 |
| G23R | 25.8 ± 0.8 | −10.3 ± 1.1 | 0.72 ± 0.02 | 3 |
| S25P | 25 ± 4 | 1 ± 2 | 1.05 ± 0.10 | 2 |
| S26D | 31.3 ± 1.2 | 7.8 ± 0.6 | 1.34 ± 0.05 | 2 |
| P27T | 33 ± 2 | 2 ± 2 | 1.11 ± 0.11 | 3 |
| P28E | 58.9 ± 0.2 | 30 ± 4 | 2.1 ± 0.3 | 2 |
| E30D | 39 ± 4 | 5.2 ± 1.2 | 1.16 ± 0.06 | 2 |
| C31I | 31.1 ± 1.8 | 3 ± 5 | 1.14 ± 0.20 | 2 |
| Q33E | 27.9 | −11 | 0.72 | 1[a] |
| E35D | 25 ± 4 | −5 ± 4 | 0.85 ± 0.10 | 2 |
| R38I | 33.7 ± 0.8 | 2 ± 2 | 1.07 ± 0.08 | 2 |
| K42R | 28 | 3 | 1.11 | 1[a] |
| I47F | 24 | −3.7 | 0.87 | 1[a] |
| P52T | 27.1 | 2 | 1.08 | 1[a] |
| S53I | 36.5 ± 0.8 | 3 ± 6 | 1.11 ± 0.19 | 2 |
| T56I | 26.8 | −4 | 0.86 | 1[a] |
| K58F | 29.4 ± 1.2 | 2 ± 5 | 1.08 ± 0.18 | 2 |
| L59F | 47 ± 5 | 18 ± 4 | 1.61 ± 0.12 | 5 |
| T62V | 74 ± 14 | 49 ± 13 | 2.9 ± 0.4 | 2 |
| H63C | 70 ± 7 | 37 ± 7 | 2.2 ± 0.2 | 4 |
| L64Y | 113 ± 7 | 80 ± 13 | 3.7 ± 0.9 | 2 |
| T66V | 30 ± 6 | −3 ± 6 | 0.92 ± 0.19 | 2 |
| S69P | 32 ± 3 | −1.6 ± 1.8 | 0.95 ± 0.06 | 3 |
| H70R | 27.8 | −7 | 0.81 | 1[a] |
| P76E | 25.9 | −7 | 0.79 | 1[a] |
| S84F | 44 ± 5 | 10 ± 6 | 1.30 ± 0.18 | 5 |
| I85Y | 38 ± 2 | 2.8 ± 1.8 | 1.08 ± 0.05 | 5 |
| D86N | 39.7 | 15 | 1.59 | 1[a] |
| V87D | 41 | 17 | 1.7 | 1[a] |
| Q90E | 32 ± 4 | −4 ± 5 | 0.92 ± 0.16 | 3 |
| S101I | 38 ± 4 | 2 ± 3 | 1.06 ± 0.09 | 3 |
| K102R | 30.3 ± 1.4 | −4.6 ± 1.8 | 0.87 ± 0.04 | 2 |
| V103L | 34 ± 4 | −1 ± 6 | 0.99 ± 0.16 | 2 |
| T104I | 31.5 ± 1.6 | −6 ± 3 | 0.84 ± 0.07 | 3 |
| R112P | 62 ± 7 | 27 ± 7 | 1.8 ± 0.2 | 4 |
| N113S | 21.5 | −20 | 0.52 | 1[a] |
| Y116F | 24.3 | −10.6 | 0.7 | 1[a] |
| K139R | 30.6 | 6 | 1.23 | 1[a] |
| P142I | 134 ± 20 | 109 ± 19 | 5.5 ± 0.8 | 2 |
| D143P | 80 ± 9 | 55 ± 9 | 3.2 ± 0.4 | 2 |
| D151E | 53.2 ± 1.4 | 27.9 ± 1.8 | 2.11 ± 0.09 | 2 |
| I152V | 34.1 | 4 | 1.14 | 1[a] |
| P162E | 13.4 | −14 | 0.48 | 1[a] |
| M164I | 34 | 6 | 1.22 | 1[a] |
| S166T | 49 ± 2 | 23 ± 3 | 1.85 ± 0.15 | 2 |
| I167F | 72 ± 8 | 44 ± 8 | 2.6 ± 0.3 | 2 |
| P168Y | 74 ± 18 | 49 ± 17 | 2.9 ± 0.5 | 3 |
| V169R | 56 ± 9 | 32 ± 9 | 2.3 ± 0.4 | 2 |
| N170W | 70 ± 13 | 47 ± 14 | 3.1 ± 0.7 | 2 |
| T179C | 60 ± 7 | 35 ± 7 | 2.4 ± 0.3 | 3 |
| S191E | 42.5 ± 1.6 | 14 ± 3 | 1.52 ± 0.15 | 2 |
| G194P | 42 ± 2 | 13.7 ± 0.6 | 1.49 ± 0.01 | 2 |
| V205I | 12 | −12.2 | 0.49 | 1[a] |
| V215E | 32.8 ± 0.2 | 3 ± 3 | 1.11 ± 0.13 | 2 |
| K218N | 24.3 | −7 | 0.78 | 1[a] |
| Y225H | 34.2 ± 0.5 | 5.4 ± 1.6 | 1.19 ± 0.07 | 2 |
| L230F | 31 ± 3 | 3.8 ± 0.5 | 1.14 ± 0.03 | 2 |
| Q235Y | 26.1 | −5 | 0.85 | 1[a] |
| V238L | 38 ± 0.6 | 8 ± 2 | 1.3 ± 0.1 | 2 |
| A240S | 32 ± 2 | 7.73 ± 0.11 | 1.32 ± 0.03 | 2 |
| E251C | 30.2 | −2 | 0.94 | 1[a] |
| L252I | 30 ± 4 | 2.04 ± 0.04 | 1.07 ± 0.01 | 2 |
| I253R | 81 ± 3 | 53 ± 6 | 3.0 ± 0.4 | 3 |
| R255Y | 42 ± 3 | 17.8 ± 1.1 | 1.73 ± 0.02 | 2 |

The half-life of each mutant is determined by heating aliquots at 42° C. assaying at intervals over a period of two hours (FIG. 12b). The amount of active TSHR protein was determined by TSHR260-binding assay and plotted against time. In each experiment, the thermostability (half-life, $t_{1/2}$) of TSHR260-WT was measured and used to determine the difference in half-life ($\Delta t_{1/2}$) and half-life ratio compared to the half-life of TSHR260-WT in the same experiment. In bold are the most thermostabilising mutants, which were used to make double mutants. n is the number of times the half-life was measured in independent experiments for each sample. Results are expressed as mean±standard error of the mean (SEM) for experiments repeated at least twice. [a]Experiments that have only been performed a single time (assayed in duplicate) do not have SEM associated with them.

TABLE 4

Analysis of the levels of expression of TSHR260 mutants relative to TSHR260-WT, as measured by the Dot Blot assay (total amount of TSHR mutant. i.e. active plus inactive), and their activity in the TSHR260-binding assay relative to TSHR260-WT

| Mutation | Dot Blot assay (% WT) | TSHR260-binding assay (% WT) | TSHR260-binding/Dot Blot (Ratio) | Classification | Stability ratio at 42° C. (WT ratio) or * stability screen data (% WT) |
| --- | --- | --- | --- | --- | --- |
| WT | 100 | 100 | 1.00 | a | 1.00 |
| Neg | 2 | 0 | 0.00 | — | — |
| M22K | 30 | 88 | 2.97 | b | 0.87 |
| G23R | 370 | 345 | 0.93 | a | 0.71 |
| C24E | 43 | 37 | 0.86 | a | *82 |
| S25P | 173 | 65 | 0.38 | c | 1.02 |
| S26D | 270 | 73 | 0.27 | c | 1.33 |
| P27T | 201 | 133 | 0.66 | a | 1.04 |
| P28E | 121 | 25 | 0.20 | c | 1.97 |
| C29E | 142 | 62 | 0.44 | a | *90 |
| E30D | 132 | 38 | 0.29 | c | 1.14 |
| C31I | 32 | 195 | 6.10 | b | 1.04 |
| H32I | 199 | 175 | 0.88 | a | *104 |
| Q33E | 403 | 241 | 0.60 | a | 0.72 |
| E34W | 55 | 49 | 0.89 | a | *140 |
| E35D | 358 | 246 | 0.69 | a | 0.82 |
| D36E | 420 | 226 | 0.54 | a | *103 |
| F37R | 65 | 33 | 0.51 | a | *46 |
| R38I | >420 | 164 | <0.39 | c | 1.03 |
| V39I | 141 | 110 | 0.78 | a | *121 |
| T40D | 85 | 24 | 0.29 | c | *93 |
| C41I | 4 | 8 | 2.21 | — | *250 |
| K42R | 35 | 61 | 1.76 | a | 1.11 |
| D43E | 58 | 22 | 0.38 | c | *0 |
| I44L | 288 | 14 | 0.05 | c | *89 |
| Q45H | 232 | 0 | 0.00 | c | — |
| R46I | 0 | 0 | 0.00 | — | — |
| I47F | nd | 5 | nd | — | 0.87 |
| P48I | 18 | 11 | 0.62 | — | *34 |
| S49C | 93 | 0 | 0.00 | c | — |
| L50I | 72 | 9 | 0.12 | c | *0 |
| P51R | 9 | 0 | 0.00 | — | — |
| P52T | 49 | 7 | 0.14 | c | 1.08 |
| S53I | 28 | 40 | 1.43 | a | 1.06 |
| T54I | 116 | 82 | 0.71 | a | *82 |
| Q55W | 13 | 41 | 3.13 | b | *74 |
| T56I | 220 | 172 | 0.78 | c | 0.86 |
| L57I | 155 | 102 | 0.66 | a | *92 |
| K58F | nd | 78 | nd | — | 1.07 |
| L59F | 87 | 171 | 1.96 | a | 1.58 |
| I60E | >420 | 54 | <0.13 | c | *118 |
| E61W | 67 | 69 | 1.02 | a | *77 |
| T62V | 5 | 9 | 1.78 | — | 2.91 |
| H63C | 34 | 172 | 5.04 | b | 1.99 |
| L64Y | 3 | 10 | 3.50 | — | 3.28 |
| R65K | 10 | 5 | 0.49 | — | *97 |
| T66V | nd | 33 | nd | — | 0.91 |
| I67L | 46 | 57 | 1.22 | a | *79 |
| P68Q | 48 | 26 | 0.55 | a | *40 |
| S69P | 44 | 234 | 5.30 | b | 0.96 |
| H70R | 69 | 43 | 0.63 | a | 0.81 |
| A71C | 26 | 42 | 1.60 | a | *69 |
| F72Y | 4 | 45 | 10.93 | b | *35 |
| S73E | 86 | 196 | 2.28 | a | *64 |
| N74H | 82 | 31 | 0.38 | c | *71 |
| L75W | 8 | 13 | 1.60 | — | *0 |
| P76E | 75 | 79 | 1.06 | a | 0.79 |
| N77E | 35 | 48 | 1.37 | a | *81 |
| I78V | 46 | 39 | 0.84 | a | *0 |
| S79L | 20 | 19 | 0.93 | a | *0 |
| R80W | 36 | 12 | 0.32 | a | *0 |
| I81L | 13 | 23 | 1.83 | a | *0 |
| Y82F | 112 | 85 | 0.76 | a | *102 |
| V83L | 118 | 80 | 0.68 | a | *102 |
| S84F | 159 | 191 | 1.20 | a | 1.13 |
| I85Y | 359 | 309 | 0.86 | a | 1.06 |
| D86N | 7 | 30 | 4.46 | b | 1.59 |
| V87D | 195 | 45 | 0.23 | c | 1.66 |
| T88E | 200 | 59 | 0.29 | c | *110 |
| L89A | 14 | 35 | 2.46 | a | *109 |
| Q90E | 98 | 244 | 2.49 | a | 0.90 |
| Q91D | 12 | 44 | 3.63 | b | *96 |
| L92W | 6 | 9 | 1.53 | — | *0 |
| E93D | 133 | 98 | 0.74 | a | *83 |
| S94E | 85 | 83 | 0.98 | a | *96 |
| H95G | 20 | 23 | 1.15 | a | *57 |
| S96A | 104 | 70 | 0.68 | a | *85 |
| F97Y | 4 | 14 | 4.04 | — | *66 |
| Y98W | 33 | 52 | 1.60 | a | *104 |
| N99G | 14 | 56 | 3.93 | b | *75 |
| L100I | 2 | 10 | 5.44 | — | *205 |
| S101I | 12 | 116 | 9.79 | b | 1.00 |
| S101L | 8 | 109 | 13.16 | b | 1.21 |
| K102R | 68 | 88 | 1.29 | a | 0.88 |
| K102L | 8 | 13 | 1.60 | — | *81 |
| V103L | 109 | 271 | 2.49 | b | 0.95 |
| T104I | 59 | 94 | 1.61 | a | 0.83 |
| H105F | 24 | 38 | 1.59 | a | *0 |
| I106W | 3 | 6 | 1.97 | — | *223 |
| E107Q | 18 | 54 | 2.98 | b | *92 |
| I108W | 1 | 7 | 5.03 | — | *54 |
| R109Y | 8 | 21 | 2.55 | a | *47 |
| N110W | 15 | 45 | 2.95 | b | *78 |
| T111I | 10 | 41 | 4.10 | b | *122 |
| R112P | 123 | 351 | 2.86 | b | 1.65 |
| N113S | 94 | 149 | 1.59 | a | 0.52 |
| L114W | 2 | 9 | 4.54 | — | *170 |
| T115L | 50 | 37 | 0.75 | a | *90 |
| Y116F | 137 | 96 | 0.70 | a | 0.70 |
| I117L | >420 | 60 | <0.14 | c | *54 |
| D118E | 144 | 79 | 0.55 | a | *68 |
| P119E | >420 | 57 | <0.14 | c | *49 |
| D120E | >420 | 128 | <0.30 | c | *55 |
| A121Y | 15 | 20 | 1.31 | — | *0 |
| L122F | >420 | 332 | <0.79 | a | *49 |
| K123R | >420 | 228 | <0.54 | a | *59 |
| E124D | >420 | 365 | <0.87 | a | *62 |
| L125I | 180 | 31 | 0.17 | c | *0 |
| P126W | 5 | 6 | 1.38 | — | *0 |

TABLE 4-continued

Analysis of the levels of expression of TSHR260 mutants relative to TSHR260-WT, as measured by the Dot Blot assay (total amount of TSHR mutant. i.e. active plus inactive), and their activity in the TSHR260-binding assay relative to TSHR260-WT

| Mutation | Dot Blot (% WT) | TSHR260-binding assay (% WT) | TSHR260-binding/Dot Blot (Ratio) | Classification | Stability ratio at 42° C. (WT ratio) or * stability screen data (% WT) |
|---|---|---|---|---|---|
| L127C | 210 | 187 | 0.89 | a | *66 |
| L128W | 4 | 0 | 0.00 | — | — |
| K129R | 131 | 205 | 1.56 | a | *71 |
| F130T | 159 | 16 | 0.10 | c | *81 |
| L131I | 30 | 0 | 0.00 | c | — |
| G132W | 9 | 0 | 0.00 | — | — |
| I133F | 210 | 122 | 0.58 | a | *34 |
| F134Y | 198 | 205 | 1.04 | a | *76 |
| N135F | 12 | 2 | 0.14 | — | *0 |
| T136Y | 1 | 0 | 0.00 | — | — |
| G137N | 6 | 0 | 0.00 | — | — |
| L138F | 1 | 1 | 0.58 | — | — |
| K139R | 187 | 166 | 0.89 | a | 1.23 |
| M140V | 20 | 7 | 0.36 | — | *0 |
| F141Y | 2 | 0 | 0.00 | — | — |
| P142I | 3 | 8 | 2.42 | — | 5.49 |
| D143P | 43 | 576 | 13.36 | b | 3.12 |
| L144I | 154 | 42 | 0.27 | c | *96 |
| T145F | 4 | 0 | 0.00 | — | — |
| K146V | 2 | 0 | 0.00 | — | — |
| V147I | 210 | 284 | 1.35 | a | *66 |
| Y148W | 204 | 129 | 0.63 | a | *50 |
| S149Q | 0 | 0 | 0.00 | — | — |
| T150I | 91 | 140 | 1.54 | a | *76 |
| D151E | 298 | 476 | 1.59 | a | 2.11 |
| I152V | 210 | 343 | 1.63 | a | 1.14 |
| F153T | 201 | 75 | 0.37 | c | *101 |
| F154Y | 3 | 0 | 0.00 | — | — |
| I155F | 18 | 0 | 0.00 | — | — |
| L156F | 2 | 0 | 0.00 | — | — |
| E157Q | >210 | 44 | <0.21 | c | *0 |
| I158L | >210 | 47 | <0.22 | c | *0 |
| T159R | 145 | 23 | 0.16 | c | *60 |
| D160E | 9 | 0 | 0.00 | — | — |
| N161I | 8 | 0 | 0.00 | — | — |
| P162E | 38 | 11 | 0.29 | c | 0.48 |
| Y163E | 98 | 23 | 0.24 | c | *0 |
| M164I | >210 | 523 | <2.49 | a | 1.22 |
| T165S | >210 | 87 | <0.41 | c | *58 |
| S166T | 266 | 682 | 2.56 | b | 1.87 |
| I167F | 4 | 18 | 5.23 | — | 2.50 |
| P168Y | 1 | 14 | 10.01 | — | 2.60 |
| V169R | 157 | 720 | 4.59 | b | 2.22 |
| N170W | 5 | 61 | 12.65 | b | 2.93 |
| A171S | 27 | 0 | 0.00 | c | — |
| F172W | 3 | 0 | 0.00 | — | — |
| Q173E | 5 | 0 | 0.00 | — | — |
| G174I | 4 | 0 | 0.00 | — | — |
| L175F | 4 | 0 | 0.00 | — | — |
| C176V | 20 | 0 | 0.00 | c | — |
| N177E | 22 | 34 | 1.56 | a | *96 |
| E178D | 85 | 37 | 0.44 | a | *0 |
| T179C | 2 | 8 | 4.68 | — | 2.37 |
| L180I | 132 | 193 | 1.46 | a | *90 |
| T181I | 44 | 0 | 0.00 | c | — |
| L182I | 69 | 13 | 0.18 | c | *95 |
| K183R | 143 | 77 | 0.54 | a | *66 |
| L184I | 17 | 10 | 0.57 | — | *117 |
| Y185F | 112 | 42 | 0.37 | c | *33 |
| N186L | 9 | 0 | 0.00 | — | — |
| N187Q | 5 | 0 | 0.00 | — | — |
| G188D | 13 | 0 | 0.00 | — | — |
| F189Y | 19 | 0 | 0.00 | — | — |
| T190I | 85 | 59 | 0.70 | a | *61 |
| S191E | 301 | 392 | 1.30 | a | 1.48 |
| V192I | 151 | 0 | 0.00 | c | — |
| Q193H | 183 | 59 | 0.32 | c | *77 |
| G194P | 293 | 329 | 1.12 | a | 1.49 |
| Y195H | 204 | 32 | 0.15 | c | *99 |
| A196R | 39 | 0 | 0.00 | c | — |
| F197W | 4 | 0 | 0.00 | — | — |
| N198P | 7 | 0 | 0.00 | — | — |
| G199Q | 28 | 0 | 0.00 | c | — |
| T200Q | 5 | 0 | 0.00 | — | — |
| K201W | 16 | 0 | 0.00 | — | — |
| L202I | 13 | 0 | 0.00 | — | — |
| D203E | 87 | 77 | 0.88 | a | *60 |
| A204I | 3 | 9 | 2.63 | — | *0 |
| V205I | 3 | 4 | 1.22 | — | 0.49 |
| Y206F | 133 | 31 | 0.23 | c | *0 |
| L207I | 17 | 0 | 0.00 | — | — |
| N208R | 25 | 0 | 0.00 | c | — |
| K209Y | 36 | 0 | 0.00 | c | — |
| K209R | 224 | 196 | 0.87 | a | 0.93 |
| N210I | 1 | 0 | 0.00 | — | — |
| K211R | 31 | 124 | 4.01 | b | *76 |
| Y212I | 18 | 0 | 0.00 | a | — |
| L213F | nd | nd | — | — | nd |
| T214I | 10 | 0 | 0.00 | — | — |
| V215E | 97 | 150 | 1.56 | a | 1.12 |
| I216F | 95 | 19 | 0.20 | c | *0 |
| D217P | 14 | 4 | 0.26 | — | *0 |
| K218N | >420 | 163 | <0.39 | c | 0.78 |
| D219W | 20 | 5 | 0.22 | a | *0 |
| A220F | 8 | 0 | 0.00 | — | — |
| F221W | 3 | 4 | 1.14 | — | *0 |
| G222D | >420 | 106 | <0.25 | c | *56 |
| G222L | 138 | 289 | 2.09 | a | 1.00 |
| G223P | 1 | 2 | 1.48 | — | *0 |
| V224I | 96 | 36 | 0.37 | c | *59 |
| Y225H | >420 | 279 | <0.66 | a | 1.19 |
| S226W | 58 | 21 | 0.37 | c | *33 |
| G227A | 2 | 0 | 0.00 | — | — |
| P228L | 5 | 0 | 0.00 | — | — |
| S229T | 3 | 0 | 0.00 | — | — |
| L230F | >420 | 338 | <0.81 | a | 1.13 |
| L231I | 50 | 12 | 0.24 | c | *55 |
| D232N | 42 | 0 | 0.00 | c | — |
| V233I | 20 | 0 | 0.00 | c | — |
| S234M | 26 | 3 | 0.11 | c | *0 |
| Q235Y | 71 | 142 | 2.00 | a | 0.85 |
| T236N | 22 | 0 | 0.00 | c | — |
| S237I | 7 | 6 | 0.86 | — | *0 |
| V238L | 286 | 264 | 0.92 | a | 1.32 |
| T239C | 3 | 16 | 5.18 | — | *80 |
| A240S | 78 | 136 | 1.75 | a | 1.33 |
| L241I | 84 | 141 | 1.68 | a | *81 |
| P242L | 8 | 0 | 0.00 | — | — |
| S243P | 61 | 9 | 0.15 | c | *0 |
| K244W | 5 | 0 | 0.00 | — | — |
| G245L | 0 | 0 | — | — | — |
| L246F | 0 | 0 | — | — | — |
| E247C | 18 | 7 | 0.40 | a | *0 |
| H248S | 64 | 58 | 0.90 | a | *66 |
| L249E | 0 | 0 | — | — | — |
| K250C | 0 | 24 | 103.88 | b | *91 |
| E251C | 74 | 199 | 2.69 | b | 0.94 |
| L252I | 104 | 175 | 1.69 | a | 1.07 |
| I253R | 381 | 902 | 2.37 | a | 2.93 |
| A254L | 25 | 54 | 2.11 | a | *84 |

TABLE 4-continued

Analysis of the levels of expression of TSHR260 mutants relative to TSHR260-WT, as measured by the Dot Blot assay (total amount of TSHR mutant. i.e. active plus inactive), and their activity in the TSHR260-binding assay relative to TSHR260-WT

| Mutation | Dot Blot assay (% WT) | TSHR260-binding assay (% WT) | TSHR260-binding/Dot Blot (Ratio) | Classification | Stability ratio at 42° C. (WT ratio) or * stability screen data (% WT) |
|---|---|---|---|---|---|
| R255Y | 31 | 175 | 5.70 | b | 1.74 |
| N256Y | 21 | 11 | 0.50 | a | *59 |
| T257N | 58 | 74 | 1.27 | a | *71 |
| W258I | 70 | 123 | 1.76 | a | *89 |
| T259S | 61 | 104 | 1.72 | a | *67 |
| L260C | 17 | 20 | 1.19 | a | *22 | nd = not determined.

The results of the Dot blot and the TSHR260-binding assay (FIG. 12a) were expressed as relative to the TSHR260-WT (% WT), respectively. Mutants are classified by the ratio between the TSHR260-binding assay and the dot Blot assay (total TSHR mutant protein) as follows: (a) little or no difference between the TSHR260-binding data and the Dot Blot expression data; (b) TSHR260-binding is considerably greater than the Dot Blot expression (TSHR260-binding/Dot Blot>2.5); or (c) Dot Blot expression is considerably greater than the TSHR260-binding (TSHR260-binding/Dot Blot<0.4). Where both the TSHR260-binding assay results and the Dot Blot results are low (less than 20% WT), these are not classified. Stability ratio is based on the half-life of the mutants, but where this was not measured, the stability screen data (as a percentage of TSHR260-WT (% WT)), where the mutants were heated at 42° C. for 30 minutes, is listed (*).

TABLE 5

Combination of single TSHR260 mutations to produce double, triple, quadruple, quintuple and hextuple TSHR260 mutants

| | Mutant name | Mutation 1 | Mutation 2 | Mutation 3 | Mutation 4 | Mutation 5 | Mutation 6 |
|---|---|---|---|---|---|---|---|
| Double Mutants | JMG1 | P142I | P28E | | | | |
| | JMG2 | P142I | L59F | | | | |
| | JMG3 | P142I | T62V | | | | |
| | JMG4 | P142I | H63C | | | | |
| | JMG5 | P142I | L64Y | | | | |
| | JMG6 | P142I | R112P | | | | |
| | JMG7 | P142I | D143P | | | | |
| | JMG8 | P142I | D151E | | | | |
| | JMG9 | P142I | S166T | | | | |
| | JMG10 | P142I | I167F | | | | |
| | JMG11 | P142I | P168Y | | | | |
| | JMG12 | P142I | V169R | | | | |
| | JMG13 | P142I | N170W | | | | |
| | JMG14 | P142I | T179C | | | | |
| | JMG15 | P142I | I253R | | | | |
| | JMG31 | P142I | R255Y | | | | |
| | JMG16 | I253R | P28E | | | | |
| | JMG17 | I253R | L59F | | | | |
| | JMG18 | I253R | T62V | | | | |
| | JMG19 | I253R | H63C | | | | |
| | JMG20 | I253R | L64Y | | | | |
| | JMG21 | I253R | R112P | | | | |
| | JMG22 | I253R | D143P | | | | |
| | JMG23 | I253R | D151E | | | | |
| | JMG24 | I253R | S166T | | | | |
| | JMG25 | I253R | I167F | | | | |
| | JMG26 | I253R | P168Y | | | | |
| | JMG27 | I253R | V169R | | | | |
| | JMG28 | I253R | N170W | | | | |
| | JMG29 | I253R | T179C | | | | |
| Triple Mutants | JMG30 | I253R | P142I | D143P | | | |
| | JMG32 | I253R | D143P | P28E | | | |
| | JMG33 | I253R | D143P | L59F | | | |
| | JMG34 | I253R | D143P | T62V | | | |
| | JMG35 | I253R | D143P | H63C | | | |
| | JMG36 | I253R | D143P | L64Y | | | |
| | JMG37 | I253R | D143P | R112P | | | |
| | JMG38 | I253R | D143P | D151E | | | |
| | JMG39 | I253R | D143P | S166T | | | |
| | JMG40 | I253R | D143P | P168Y | | | |
| | JMG41 | I253R | D143P | V169R | | | |
| | JMG42 | I253R | D143P | N170W | | | |
| Quadruple Mutants | JMG43 | I253R | D143P | R112P | L59F | | |
| | JMG44 | I253R | D143P | R112P | H63C | | |
| | JMG45 | I253R | D143P | R112P | D151E | | |
| | JMG46 | I253R | D143P | R112P | S166T | | |

TABLE 5-continued

Combination of single TSHR260 mutations to produce double, triple, quadruple, quintuple and hextuple TSHR260 mutants

| | Mutant name | Mutation 1 | Mutation 2 | Mutation 3 | Mutation 4 | Mutation 5 | Mutation 6 |
|---|---|---|---|---|---|---|---|
| | JMG47 | I253R | D143P | R112P | V169R | | |
| | JMG48 | I253R | D143P | R112P | N170W | | |
| Quintuple mutants | JMG49 | I253R | D143P | R112P | D151E | L59F | |
| | JMG50 | I253R | D143P | R112P | D151E | H63C | |
| | JMG51 | I253R | D143P | R112P | D151E | S166T | |
| | JMG52 | I253R | D143P | R112P | D151E | V169R | |
| | JMG57 | I253R | D143P | R112P | H63C | V169R | |
| | JMG58 | I253R | D143P | R112P | H63C | S166T | |
| Hextuple mutants | JMG53 | I253R | D143P | R112P | D151E | H63C | L59F |
| | JMG54 | I253R | D143P | R112P | D151E | H63C | S166T |
| | JMG55 | I253R | D143P | R112P | D151E | H63C | V169R |

Corresponding mutations in full length TSHR are defined as TSHR-JMGx where x is the respective mutation number in TSHR260.

TABLE 6

Thermostability of the TSHR260 double mutants measured at 42° C.

| Mutant name | Mutation 1 | Mutation 2 | TSHR260-binding levels (% WT) | $t_{1/2}$ at 42° C. (min) | $\Delta t_{1/2}$ (min) Relative to WT | Stability ratio Relative to WT | $\Delta t_{1/2}$ (min) Relative to I253R | Stability ratio Relative to I253R | n |
|---|---|---|---|---|---|---|---|---|---|
| WT std | | | 100 | 28 ± 2 | 0 ± 2 | 1.0 ± 0.0 | −60 ± 4 | 0.32 ± 0.01 | 10 |
| I253R | I253R | | 836 | 88 ± 7 | 59 ± 5 | 3.8 ± 0.1 | 0 ± 0 | 1.0 ± 0.0 | 8 |
| JMG2 | P142I | L59F | 29 | 253 ± 133 | 221 ± 128 | 8 ± 3 | 159 ± 126 | 2.6 ± 1.2 | 2 |
| JMG4 | P142I | H63C | 14 | 275 ± 94 | 245 ± 87 | 9.2 ± 1.0 | 180 ± 87 | 2.9 ± 0.8 | 2 |
| JMG7 | P142I | D143P | 15 | 70 | 48 | 3.2 | −18 | 0.8 | 1[a] |
| JMG9 | P142I | S166T | 11 | 197 | 171 | 7.4 | 109 | 2.2 | 1[a] |
| JMG15 | P142I | I253R | 7 | 343 | 316 | 14 | 273 | 4.9 | 1[a] |
| JMG16 | I253R | P28E | 35 | 212 ± 60 | 174 ± 59 | 5.6 ± 1.4 | 102 ± 50 | 1.9 ± 0.4 | 2 |
| JMG17 | I253R | L59F | 1007 | 144 ± 26 | 118 ± 20 | 5.5 ± 0.1 | 71 ± 13 | 1.96 ± 0.01 | 2 |
| JMG19 | I253R | H63C | 433 | 231 ± 10 | 205 ± 5 | 9.1 ± 1.4 | 157 ± 3 | 3.2 ± 0.4 | 2 |
| JMG20 | I253R | L64Y | 63 | 159 ± 17 | 132 ± 16 | 6.3 ± 0.9 | 74 ± 32 | 2.0 ± 0.5 | 2 |
| JMG21 | I253R | R112P | 1041 | — | — | — | — | — | 0 |
| JMG22 | I253R | D143P | 1031 | 261 ± 45 | 233 ± 42 | 9.3 ± 0.5 | 183 ± 37 | 3.3 ± 0.2 | 2 |
| JMG23 | I253R | D151E | 1200 | 126 ± 1 | 103 ± 1 | 5.6 ± 0.4 | 55 ± 9 | 1.8 ± 0.2 | 2 |
| JMG24 | I253R | S166T | 1357 | 141 ± 6 | 115 ± 7 | 5.5 ± 0.5 | 59 ± 7 | 1.7 ± 0.1 | 2 |
| JMG26 | I253R | P168Y | 40 | 329 ± 209 | 296 ± 203 | 9 ± 5 | 227 ± 191 | 3.0 ± 1.5 | 2 |
| JMG27 | I253R | V169R | 1194 | 142 ± 11 | 117 ± 12 | 5.6 ± 0.7 | 60 ± 12 | 1.7 ± 0.2 | 2 |
| JMG28 | I253R | N170W | 20 | 271 ± 111 | 238 ± 104 | 7.9 ± 1.8 | 161 ± 101 | 2.4 ± 0.8 | 2 |
| JMG30 | I253R | PD142IP | 91 | 24 | −2 | 0.92 | −76 | 0.24 | 1[a] |

JMG1, JMG3, JMG5, JMG6, JMG8, JMG10, JMG11, JMG12, JMG13, JMG14, JMG18, JMG25, JMG29 and JMG31 showed too low binding in the TSHR260-binding assays so that determination of thermostability was not possible. The thermostability of JMG21 was not measured at 42° C. JMG30 is a triple mutant that was studied at only 42° C.

The half-life of each mutant is determined by heating aliquots at 42° C. assaying at intervals over a period of three hours (FIG. 12b). The amount of active TSHR protein was determined by TSHR260-binding assay and plotted against time. In each experiment, the thermostability of TSHR260-WT and TSHR260-I253R were measured and used to determine the difference in half-life ($\Delta t_{1/2}$) and half-life ratio compared to the half-life of TSHR260-WT and TSHR260-I253R in the same experiment. The most thermostabilising mutant with a good level of binding in the TSHR260-binding assays is in bold. n is the number of times the half-life was measured in independent experiments for each sample. Results are expressed as mean±SEM for experiments repeated at least twice. [a]Experiments that have only been performed a single time (assayed in duplicate) do not have SEM associated with them.

TABLE 7

Thermostability of the TSHR260 double mutants measured at 50° C.

| Mutant name | Mutation 1 | Mutation 2 | TSHR260-binding levels (% WT) | $t_{1/2}$ (min) | $\Delta t_{1/2}$ (min) Relative to WT | Stability ratio Relative to WT | $\Delta t_{1/2}$ (min) Relative to I253R | Stability ratio Relative to I253R | n |
|---|---|---|---|---|---|---|---|---|---|
| WT std | | | 100 | 1.43 ± 0.05 | 0 ± 0.05 | 1 ± 0 | −2.61 ± 0.12 | 0.35 ± 0.02 | 9 |
| I253R | I253R | | 827 | 4.18 ± 0.10 | 3.1 ± 0.2 | 2.85 ± 0.13 | 0 ± 0 | 1 ± 0 | 19 |
| JMG2 | P142I | L59F | 9 | 42 | 41 | 29 | 39 | 11 | 1[a] |
| JMG4 | P142I | H63C | 7 | 23 ± 3 | 22 ± 3 | 16 ± 3 | 23 ± 2 | 6.9 ± 1.5 | 2 |
| JMG9 | P142I | S166T | 7 | 4.82 ± 0.02 | 3.55 ± 0.03 | 3.80 ± 0.05 | 1.1 ± 0.3 | 1.30 ± 0.10 | 2 |
| JMG16 | I253R | P28E | 16 | 9.1 ± 1.5 | 7.7 ± 1.6 | 6.3 ± 1.4 | 4.7 ± 1.2 | 2.03 ± 0.19 | 2 |
| JMG17 | I253R | L59F | 833 | 6.03 ± 0.05 | 4.81 ± 0.09 | 5.0 ± 0.2 | 2.07 ± 0.12 | 1.52 ± 0.04 | 2 |
| JMG19 | I253R | H63C | 387 | 7.3 ± 1.0 | 6 ± 1 | 5.9 ± 0.6 | 3.3 ± 1.0 | 1.8 ± 0.2 | 2 |
| JMG20 | I253R | L64Y | 29 | 13.4 ± 0.3 | 11.8 ± 0.4 | 8.7 ± 0.7 | 9.5 ± 0.4 | 3.42 ± 0.17 | 2 |
| JMG21 | I253R | R112P | 1019 | 10.67 ± 0.02 | — | — | 6.07 ± 0.05 | 2.32 ± 0.03 | 2 |
| JMG22 | I253R | D143P | 860 | 23.8 ± 0.7 | 22.4 ± 1.5 | 15.1 ± 0.7 | 19.4 ± 0.7 | 5.5 ± 0.2 | 9 |
| JMG23 | I253R | D151E | 1113 | 9.0 ± 0.3 | 7.65 ± 0.06 | 6.6 ± 0.8 | 4.94 ± 0.06 | 2.21 ± 0.04 | 2 |
| JMG24 | I253R | S166T | 1348 | 9.5 ± 0.8 | 7.9 ± 0.8 | 6.0 ± 0.3 | 5.4 ± 0.6 | 2.31 ± 0.07 | 2 |
| JMG26 | I253R | P168Y | 25 | 15.0 ± 1.9 | 13.7 ± 1.9 | 11.3 ± 1.1 | 10.9 ± 1.3 | 3.67 ± 0.13 | 2 |
| JMG27 | I253R | V169R | 1203 | 15.8 ± 1.8 | 14.2 ± 1.9 | 10.1 ± 1.5 | 11.9 ± 1.9 | 4.0 ± 0.5 | 2 |
| JMG28 | I253R | N170W | 16 | 11 ± 5 | 10 ± 5 | 9 ± 4 | 7 ± 5 | 3.1 ± 1.7 | 2 |

JMG1, JMG3, JMG5, JMG6, JMG7, JMG8, JMG10, JMG11, JMG12, JMG13, JMG14, JMG15, JMG18, JMG25, JMG29 and JMG31 showed too low binding in the TSHR260-binding assays so that determination of thermostability was not possible. The thermostability of JMG21 was determined in the same experiment as only TSHR260-I253R, and not TSHR260-WT.

The half-life of each mutant is determined by heating aliquots at 50° C. assaying at intervals over a period of two hours (FIG. 12b). The amount of active TSHR protein was determined by TSHR260-binding assay and plotted against time. In each experiment, the thermostability of TSHR260-WT and TSHR260-I253R were measured and used to determine the difference in half-life ($\Delta t_{1/2}$) and half-life ratio compared to the half-life of TSHR260-WT and TSHR260-I253R in the same experiment. The most thermostabilising mutant with a good level of binding in the TSHR260-binding assay is in bold. n is the number of times the half-life was measured in independent experiments for each sample. Results are expressed as mean±SEM for experiments repeated at least twice. [a]Experiments (assayed in duplicate) that have only been performed a single time do not have SEM associated with them.

TABLE 8

Thermostability of the triple and quadruple TSHR260 mutants measured at 50° C.

| | Mutant name | Foundation mutant | Additional mutation | TSHR260-binding levels (% WT) | $t_{1/2}$ (min) | $\Delta t_{1/2}$ (min) Relative to I253R | Stability ratio Relative to I253R | n |
|---|---|---|---|---|---|---|---|---|
| | WT std | | | 100 | 1.43 ± 0.05 | −2.61 ± 0.12 | 0.35 ± 0.02 | 9 |
| | I253R | I253R | | 827 | 4.18 ± 0.10 | 0 ± 0 | 1 ± 0 | 19 |
| Triple mutants | JMG30 | JMG22 | P142I | 42 | 1.52 | −2.7 | 0.36 | 1[a] |
| | JMG32 | JMG22 | P28E | 8 | 56 | 51 | 13 | 1[a] |
| | JMG33 | JMG22 | L59F | 587 | 39 ± 4 | 35 ± 4 | 9.4 ± 0.7 | 2 |
| | JMG35 | JMG22 | H63C | 919 | 60 ± 4 | 56 ± 5 | 12.8 ± 1.1 | 2 |
| | JMG37 | JMG22 | R112P | 622 | 69 ± 3 | 65 ± 3 | 16.6 ± 0.5 | 7 |
| | JMG38 | JMG22 | D151E | 468 | 70.4 ± 1.1 | 65.5 ± 1.2 | 14.4 ± 0.6 | 2 |
| | JMG39 | JMG22 | S166T | 490 | 65 ± 3 | 60 ± 3 | 13.6 ± 1.3 | 2 |
| | JMG41 | JMG22 | V169R | 975 | 74 ± 3 | 69 ± 3 | 15.5 ± 1.4 | 2 |
| Quadruple mutants | JMG43 | JMG37 | L59F | 328 | 88 ± 3 | 84 ± 3 | 24.1 ± 1.9 | 2 |
| | JMG44 | JMG37 | H63C | 2333 | 131 ± 16 | 128 ± 16 | 34 ± 3 | 3 |
| | JMG45 | JMG37 | D151E | 323 | 226 ± 31 | 222 ± 31 | 58 ± 6 | 3 |
| | JMG46 | JMG37 | S166T | 400 | 151 ± 15 | 147 ± 15 | 35 ± 4 | 2 |
| | JMG47 | JMG37 | V169R | 462 | 123 ± 10 | 119 ± 10 | 29 ± 3 | 2 |

Foundation mutant refers to the double mutant JMG22 (I253R+D143P; Table 5) or triple mutant JMG37 (I253R+D143P+R112P; Table 5) on which the triple and quadruple mutants were based respectively. JMG34, JMG36, JMG40, JMG42 and JMG48 showed too low binding (<16% of TSHR260-WT) in the TSHR260-binding assays so that determination of their thermostability was not possible.

The half-life of each mutant is determined by heating aliquots at 50° C. assaying at intervals over a period of three hours (FIG. 12b). The amount of active TSHR protein was determined by TSHR260-binding assay and plotted against time. In each experiment, the thermostability of TSHR260-I253R was measured and used to determine the difference in half-life ($\Delta t_{1/2}$) and half-life stability ratio compared to the half-life of TSHR260-I253R in the same experiment. The most thermostabilising mutants are in bold. n is the number of times the half-life was measured in independent experiments for each sample. Results are expressed as mean±SEM for experiments repeated at least twice. [a]Experiments that have only been performed a single time (assayed in duplicate) do not have SEM associated with them.

Foundation mutant refers to the triple mutant JMG37 (I253R+D143P+R112P; Table 5), quadruple mutant JMG45 (I253R+D143P+R112P+D151E; Table 5) or quintuple mutant JMG50 (I253R+D143P+R112P+D151E+H62C;

TABLE 9

Thermostability of the quadruple quintuple and hextuple TSHR260 mutants measured at 55° C.

| | Mutant name | Foundation mutant | Additional mutation | TSHR260-binding levels (% WT) | $t_{1/2}$ (min) | $\Delta t_{1/2}$ (min) | Stability ratio Relative to I253R | n |
|---|---|---|---|---|---|---|---|---|
| | I253R | I253R | | 793 | 0.54 ± 0.05 | 0 ± 0 | 1 ± 0 | 6 |
| | JMG37 | JMG22 | R112P | 659 | 5.89 ± 0.11 | 5.4 ± 0.07 | 12.0 ± 0.9 | 2 |
| Quadruple | JMG43 | JMG37 | L59F | 322 | 7.5 ± 0.3 | 6.9 ± 0.4 | 13.8 ± 1.2 | 1[a] |
| Mutants | JMG44 | JMG37 | H63C | 2250 | 10.9 ± 0.3 | 10.3 ± 0.3 | 20.1 ± 1.4 | 1[a] |
| | JMG45 | JMG37 | D151E | 271 | 27 ± 2 | 27 ± 2 | 54 ± 7 | 4 |
| | JMG46 | JMG37 | S166T | 485 | 12.4 ± 0.9 | 12.0 ± 1.0 | 28 ± 4 | 1[a] |
| | JMG47 | JMG37 | V169R | 454 | 16.7 ± 1 | 16.3 ± 1.0 | 37 ± 5 | 1[a] |
| Quintuple | JMG49 | JMG45 | L59F | 194 | 41.8 ± 2.0 | 41.2 ± 1.9 | 78 ± 7 | 2 |
| Mutants | JMG50 | JMG45 | H63C | 930 | 58 ± 5 | 58 ± 5 | 110 ± 7 | 3 |
| | JMG51 | JMG45 | S166T | 300 | 25 ± 7 | 25 ± 7 | 49 ± 19 | 2 |
| | JMG52 | JMG45 | V169R | 241 | 66 ± 12 | 65 ± 11 | 125.1 ± 0.6 | 2 |
| Hextuple | JMG54 | JMG50 | S166T | 1235 | 837 ± 197 | 836 ± 197 | 1171 ± 316 | 1[a] |
| mutants | JMG55 | JMG50 | V169R | 1574 | 689 ± 147 | 688 ± 147 | 964 ± 239 | 1[a] |

Foundation mutant refers to the triple mutant JMG37 (I253R+D143P+R112P; Table 5), quadruple mutant (I253R+D143P+R112P+D151E; Table 5) or quintuple mutant JMG50 (I253R+D143P+R112P+D151E+H62C; Table 5) on which the resulting quadruple, quintuple and hextuple mutants were respectively based. JMG48 had no detectable binding in the TSHR260-binding assays so that determination of thermostability was not possible. The hextuple mutants, JMG54 and JMG55 were too stable to determine the half-life accurately at 55° C.

The half-life of each mutant is determined by heating aliquots at 55° C. assaying at intervals over a period of two hours (FIG. 12b). The amount of active TSHR protein was determined by TSHR260-binding assay and plotted against time. In each experiment, the thermostability of TSHR260-I253R and TSHR260-JMG37 was measured and used to determine the difference in half-life ($\Delta t_{1/2}$) and half-life stability ratio compared to the half-life of TSHR260-I253R in the same experiment. The most thermostabilising mutants are in bold. n is the number of times the half-life was measured in independent experiments for each sample. Results are expressed as mean±SEM for experiments repeated at least twice. [a]Experiments that have only been performed a single time (assayed in duplicate) do not have SEM associated with them.

Table 5) on which the resulting quadruple, quintuple and hextuple mutants were respectively based.

The half-life of each mutant is determined by heating aliquots at 60° C. assaying at intervals over a period of two hours (FIG. 12b). The amount of active TSHR protein was determined by TSHR260-binding assay and plotted against time. In each experiment, the thermostability of TSHR260-JMG45 was measured and used to determine the difference in half-life ($\Delta t_{1/2}$) and half-life stability ratio compared to the half-life of TSHR260-JMG45 in the same experiment. The most thermostabilising mutants are in bold. n is the number of times the half-life was measured in independent experiments for each sample. Results are expressed as mean±SEM for experiments repeated at least twice.

TABLE 11

Thermostability curves of TSHR260-WT, TSHR260-I253R, JMG22, JMF37, JMG45, JMG52, JMG54 and JMG55 measured at 37°.

| Mutant name | $t_{1/2}$ (h) | $\Delta t_{1/2}$ (h) | Stability ratio | n |
|---|---|---|---|---|
| WT | 3.5 ± 0.6 | 0 ± 0 | 1 ± 0 | 2 |
| I253R | 11.3 ± 0.3 | 7.8 ± 0.2 | 3.3 ± 0.4 | 2 |
| JMG22 | 38 ± 4 | 35 ± 5 | 11 ± 3 | 2 |
| JMG37 | 124 ± 32 | 120 ± 31 | 35 ± 4 | 2 |
| JMG45 | 150 | 147 | 48 | 1[a] |

TABLE 10

Thermostability of the quintuple and hextuple TSHR260 mutants measured at 60° C.

| | Mutant name | Foundation Mutant | Additional Mutation | TSHR260-binding levels (% WT) | $t_{1/2}$ (min) | $\Delta t_{1/2}$ (min) | Stability ratio Relative to JMG45 | n |
|---|---|---|---|---|---|---|---|---|
| | JMG45 | JMG37 | D151E | 500 | 2.40 ± 0.16 | 0 ± 0 | 1 ± 0 | 3 |
| Quintuple | JMG50 | JMG45 | H63C | 1122 | 4.50 ± 0.07 | 2.1 ± 0.2 | 1.90 ± 0.14 | 3 |
| mutants | JMG52 | JMG45 | V169R | 501 | 7.1 ± 0.6 | 4.7 ± 0.5 | 3.0 ± 0.2 | 3 |
| Hextuple | JMG54 | JMG50 | S166T | 899 | 9.6 ± 1.5 | 7.2 ± 1.4 | 4.0 ± 0.4 | 3 |
| mutants | JMG55 | JMG50 | V169R | 1452 | 13 ± 3 | 10 ± 3 | 5.2 ± 0.9 | 3 |

TABLE 11-continued

Thermostability curves of TSHR260-WT, TSHR260-I253R, JMG22, JMF37, JMG45, JMG52, JMG54 and JMG55 measured at 37°.

| Mutant name | $t_{1/2}$ (h) | $\Delta t_{1/2}$ (h) | Stability ratio | n |
|---|---|---|---|---|
| JMG52 | 249 | 246 | 80 | 1[a] |
| JMG54 | 204 | 201 | 65 | 1[a] |
| JMG55 | 358 | 355 | 115 | 1[a] |

The half-life of each mutant is determined by heating aliquots at 37° C. assaying at intervals over a period of 37 days (FIG. 12b). The amount of active TSHR protein was determined by TSHR260-binding assay and plotted against time. The difference in half-life ($\Delta t_{1/2}$) and half-life stability ratio compared to the half-life of TSHR260-WT measured in the same experiment is shown. n is the number of times the half-life was measured in independent experiments for each sample. Results are expressed as mean±SEM for experiments repeated at least twice. [a]Experiments that have only been performed a single time (assayed in duplicate) do not have SEM associated with them.

TABLE 12

Comparison of thermostability ratios of TSHR260 mutants at different temperatures

| | 37° C. | | 42° C. | | | 50° C. | | |
|---|---|---|---|---|---|---|---|---|
| Mutant name | $t_{1/2}$ (h) | Ratio (to WT) | $t_{1/2}$ (min) | Ratio (to WT) | Ratio (to I253R) | $t_{1/2}$ (min) | Ratio (to WT) | Ratio (to I253R) |
| WT | 3.5 ± 0.6 | 1 ± 0 | 30.7 ± 1.1 | 1 ± 0 | 0.321 ± 0.014 | 1.43 ± 0.05 | 1 ± 0 | 0.35 ± 0.02 |
| I253R | 11.3 ± 0.3 | 3.3 ± 0.4 | 88 ± 7 | 3.07 ± 0.13 | 1 ± 0 | 4.18 ± 0.10 | 2.85 ± 0.14 | 1 ± 0 |
| JMG22 | 38 ± 4 | 11 ± 3 | 261 ± 45 | 9.3 ± 0.5 | 3.3 ± 0.2 | 23.8 ± 0.7 | 15.1 ± 0.7 | 5.5 ± 0.2 |
| JMG37 | 124 ± 32 | 35 ± 4 | | | | 69 ± 3 | | 16.6 ± 0.5 |
| JMG45 | 150 | 48[a] | | | | 226 ± 31 | | 58 ± 6 |
| JMG52 | 249 | 80[a] | | | | | | |
| JMG54 | 204 | 65[a] | | | | | | |
| JMG55 | 358 | 115[a] | | | | | | |

| Mutant name | 55° C. | | 60° C. | | Predicted stability ratio to WT |
|---|---|---|---|---|---|
| | $t_{1/2}$ (min) | Ratio (to I253R) | $t_{1/2}$ (min) | Ratio (to JMG45) | |
| WT | | | | | 1 |
| I253R | 0.54 ± 0.05 | 1 ± 0 | | | 3.1 |
| JMG22 | | | | | 12 |
| JMG37 | 5.89 ± 0.11 | 12.0 ± 0.9 | | | 41 |
| JMG45 | 27 ± 2 | 54 ± 7 | 2.40 ± 0.16 | 1 ± 0 | 174[b] |
| JMG52 | 66 ± 12 | 125.1 ± 0.6 | 7.1 ± 0.6 | 3.0 ± 0.2 | ~450[b] |
| JMG54 | | | 9.6 ± 1.5 | 4.0 ± 0.4 | ~700[b] |
| JMG55 | | | 13 ± 3 | 5.2 ± 0.9 | ~900[b] |

Summary of results presented in Tables 6-11. Results are expressed as mean ± SEM for experiments repeated at least twice. a Experiments that have only been performed a single time (assayed in duplicate) do not have SEM associated with them. [b] These stability ratios are based on the stability ratios relative to I253R and JMG45 at 50° C.-60° C.

TABLE 13

Thermostability of full-length TSHR mutants at 42° C. on 14C4 plates

| Time heated at 42° C. (min) | TSHR-WT | | TSHR-JMG37 | | TSHR-JMG45 | | TSHR-JMG52 | |
|---|---|---|---|---|---|---|---|---|
| | OD450 | Active TSHR (% unheated sample) | OD450 | Active TSHR (% unheated sample) | OD450 | Active TSHR (% unheated sample) | OD450 | Active TSHR (% unheated sample) |
| 0 | 1.97 ± 0.07 | 100 | 1.87 ± 0.08 | 100 | 2.17 ± 0.03 | 100 | 1.93 ± 0.10 | 100 |
| 5 | 2.03 ± 0.07 | 103 | 1.87 ± 0.03 | 100 | 2.15 ± 0.02 | 99 | 1.95 ± 0.05 | 101 |
| 10 | 1.99 ± 0.02 | 101 | 1.85 ± 0.06 | 99 | 2.14 ± 0.03 | 99 | 1.98 ± 0.01 | 103 |
| 15 | 2.04 ± 0.04 | 104 | 1.84 ± 0.04 | 98 | 2.13 ± 0.04 | 98 | 1.96 ± 0.03 | 102 |
| 20 | 1.99 ± 0.03 | 101 | 1.74 ± 0.12 | 93 | 2.09 ± 0.05 | 96 | 1.90 ± 0.11 | 99 |
| 30 | 1.82 ± 0.10 | 93 | 1.78 ± 0.07 | 95 | 2.00 ± 0.06 | 92 | 1.89 ± 0.03 | 98 |
| 45 | 1.40 ± 0.16 | 71 | 1.72 ± 0.00 | 92 | 1.98 ± 0.04 | 91 | 1.81 ± 0.04 | 94 |
| 60 | 1.23 ± 0.08 | 63 | 1.66 ± 0.02 | 89 | 1.94 ± 0.06 | 89 | 1.78 ± 0.03 | 92 |
| 90 | 0.77 ± 0.08 | 39 | 1.51 ± 0.08 | 81 | 1.82 ± 0.11 | 84 | 1.62 ± 0.09 | 84 |
| 120 | 0.69 ± 0.07 | 35 | 1.45 ± 0.05 | 77 | 1.76 ± 0.03 | 81 | 1.56 ± 0.05 | 81 |
| 180 | 0.51 ± 0.04 | 26 | 1.14 ± 0.08 | 61 | 1.56 ± 0.05 | 72 | 1.47 ± 0.08 | 76 |

Results are expressed as both absorbance at 450 nm and as a percentage of the unheated sample's absorbance at 450 nm. Mean ± SD for quadruplicate measurements in a single experiment.

TABLE 14

Thermostability of full-length TSHR mutants at 50° C. on 14C4 plates

| Time heated at 50° C. (min) | TSHR-WT OD450 | TSHR-WT Active TSHR (% un-heated sample) | TSHR-JMG37 OD450 | TSHR-JMG37 Active TSHR (% un-heated sample) | TSHR-JMG45 OD450 | TSHR-JMG45 Active TSHR (% un-heated sample) | TSHR-JMG52 OD450 | TSHR-JMG52 Active TSHR (% un-heated sample) | TSHR-JMG55 OD450 | TSHR-JMG55 Active TSHR (% un-heated sample) |
|---|---|---|---|---|---|---|---|---|---|---|
| 0 | 2.42 ± 0.09 | 100 | 2.42 ± 0.08 | 100 | 2.54 ± 0.08 | 100 | 2.39 ± 0.18 | 100 | 2.42 ± 0.09 | 100 |
| 5 | 2.43 ± 0.06 | 100 | 2.42 ± 0.08 | 100 | 2.55 ± 0.06 | 100 | 2.36 ± 0.06 | 99 | 2.43 ± 0.06 | 100 |
| 10 | 2.40 ± 0.04 | 99 | 2.44 ± 0.06 | 101 | 2.57 ± 0.06 | 101 | 2.48 ± 0.04 | 104 | 2.40 ± 0.04 | 99 |
| 15 | 2.30 ± 0.11 | 95 | 2.51 ± 0.02 | 103 | 2.65 ± 0.02 | 104 | 2.56 ± 0.06 | 107 | 2.30 ± 0.11 | 95 |
| 20 | 2.17 ± 0.09 | 90 | 2.52 ± 0.02 | 104 | 2.73 ± 0.05 | 107 | 2.51 ± 0.12 | 105 | 2.17 ± 0.09 | 90 |
| 30 | 1.41 ± 0.08 | 58 | 1.95 ± 0.04 | 81 | 2.50 ± 0.06 | 98 | 2.43 ± 0.14 | 102 | 1.41 ± 0.08 | 58 |
| 45 | 1.06 ± 0.06 | 44 | 1.98 ± 0.12 | 82 | 2.43 ± 0.01 | 95 | 2.12 ± 0.18 | 89 | 1.06 ± 0.06 | 44 |
| 60 | 0.40 ± 0.02 | 16 | 1.47 ± 0.03 | 61 | 1.82 ± 0.01 | 71 | 1.96 ± 0.19 | 82 | 0.40 ± 0.02 | 16 |
| 90 | 0.27 ± 0.02 | 11 | 1.33 ± 0.09 | 55 | 1.70 ± 0.05 | 67 | 1.56 ± 0.22 | 65 | 0.27 ± 0.02 | 11 |
| 120 | 0.19 ± 0.03 | 8 | 1.07 ± 0.11 | 44 | 1.56 ± 0.06 | 61 | 1.53 ± 0.17 | 64 | 0.19 ± 0.03 | 8 |
| 180 | 0.15 ± 0.02 | 6 | 0.96 ± 0.09 | 39 | 1.51 ± 0.06 | 59 | 1.34 ± 0.16 | 56 | 0.15 ± 0.02 | 6 |
| 240 | 0.09 ± 0.02 | 4 | 0.74 ± 0.09 | 30 | 1.25 ± 0.04 | 49 | 1.21 ± 0.14 | 51 | 0.09 ± 0.02 | 4 |
| $t_{1/2}$ (min) | | 33 | | 110 | | 173 | | 175 | | 226 |
| Stability ratio | | 1.0 | | 3.4 | | 5.3 | | 5.4 | | 6.9 |

Results are expressed as both absorbance at 450 nm and as a percentage of the unheated sample's absorbance at 450 nm. Mean ± SD for quadruplicate measurements in a single experiment. Half-life at 50° C. and the stability ratio relative to full-length TSHR-WT for each mutant is listed.

TABLE 15

M22-POD binding to TSHR260 mutants.

| M22-POD (ng/mL) | TSHR260-WT OD450 | TSHR260-WT % Max | TSHR260-JMG37 OD450 | TSHR260-JMG37 % Max | TSHR260-JMG45 OD450 | TSHR260-JMG45 % Max |
|---|---|---|---|---|---|---|
| 179.0 | 2.94 ± 0.05 | 100.0 ± 1.6 | 3.13 ± 0.03 | 100.0 ± 1.0 | 2.69 ± 0.14 | 100.0 ± 5.1 |
| 89.5 | 2.34 ± 0.05 | 79.5 ± 1.7 | 2.50 ± 0.06 | 80.1 ± 1.8 | 1.91 ± 0.11 | 70.9 ± 3.9 |
| 44.8 | 1.55 ± 0.05 | 52.5 ± 1.8 | 1.62 ± 0.00 | 52.0 ± 0.1 | 1.18 ± 0.03 | 43.7 ± 1.1 |
| 22.4 | 0.89 ± 0.07 | 30.1 ± 2.2 | 0.87 ± 0.01 | 27.7 ± 0.2 | 0.67 ± 0.05 | 25.1 ± 1.8 |
| 11.2 | 0.50 ± 0.03 | 17.0 ± 1.0 | 0.42 ± 0.10 | 13.4 ± 3.3 | 0.34 ± 0.09 | 12.7 ± 3.5 |
| 5.6 | 0.24 ± 0.08 | 8.3 ± 2.8 | 0.22 ± 0.11 | 7.0 ± 3.5 | 0.15 ± 0.08 | 5.6 ± 2.8 |
| 2.8 | 0.09 ± 0.08 | 3.2 ± 2.8 | 0.07 ± 0.10 | 2.2 ± 3.1 | 0.05 ± 0.07 | 1.8 ± 2.8 |
| 0.0 | −0.05 ± 0.08 | −1.8 ± 2.6 | −0.05 ± 0.08 | −1.7 ± 2.4 | −0.05 ± 0.08 | −2.0 ± 2.8 |
| $K_d$ (ng/mL) | 82.7 | | 93.8 | | 136.6 | |
| $K_d$ (% WT) | 100 | | 113 | | 165 | |

| M22-POD (ng/mL) | TSHR260-JMG52 OD450 | TSHR260-JMG52 % Max | TSHR260-JMG55 OD450 | TSHR260-JMG55 % Max |
|---|---|---|---|---|
| 179.0 | 2.58 ± 0.06 | 100.0 ± 2.2 | 2.44 ± 0.11 | 100.0 ± 4.4 |
| 89.5 | 1.88 ± 0.11 | 72.9 ± 4.2 | 1.73 ± 0.11 | 70.9 ± 4.4 |
| 44.8 | 1.17 ± 0.13 | 45.2 ± 5.1 | 0.98 ± 0.04 | 40.2 ± 1.8 |
| 22.4 | 0.57 ± 0.05 | 22.2 ± 1.9 | 0.48 ± 0.04 | 19.7 ± 1.7 |
| 11.2 | 0.32 ± 0.06 | 12.5 ± 2.5 | 0.24 ± 0.07 | 10.0 ± 3.0 |
| 5.6 | 0.15 ± 0.07 | 5.7 ± 2.8 | 0.10 ± 0.07 | 4.0 ± 2.8 |
| 2.8 | 0.04 ± 0.07 | 1.7 ± 2.7 | 0.02 ± 0.08 | 1.0 ± 3.3 |
| 0.0 | −0.06 ± 0.08 | −2.1 ± 3.0 | −0.06 ± 0.08 | −2.3 ± 3.2 |
| $K_d$ (ng/mL) | 136.8 | | 184.3 | |
| $K_d$ (% WT) | 165 | | 223 | |

Results are expressed as absorbance at 450 nm, with non-specific binding subtracted, and a percentage of the maximum OD450 reading (% Max) for each mutant, Mean ± SD for duplicate measurements in a single experiment. $K_d$ was determined by fitting a saturation binding curve to the data with GraphPad Prism.

TABLE 16

K1-18-POD binding to TSHR260 mutants.

| K1-18-POD | TSHR260-WT | | TSHR260-I253R | | TSHR260-JMG22 | | TSHR260-JMG37 | |
|---|---|---|---|---|---|---|---|---|
| (μg/mL) | OD450 | % Max | OD450 | % Max | OD450 | % Max | OD450 | % Max |
| 10 | 2.61 ± 0.06 | 100 ± 2 | 1.91 ± 0.11 | 100 ± 6 | 2.16 ± 0.08 | 100 ± 4 | 2.76 ± 0.12 | 100 ± 4 |
| 7.5 | 2.50 ± 0.02 | 96 ± 1 | 1.84 ± 0.30 | 96 ± 16 | 2.29 ± 0.09 | 106 ± 4 | 2.86 ± 0.02 | 104 ± 1 |
| 5 | 2.61 ± 0.09 | 100 ± 3 | 2.13 ± 0.20 | 111 ± 10 | 2.10 ± 0.00 | 97 ± 0 | 2.74 ± 0.09 | 99 ± 0 |
| 2.5 | 2.18 ± 0.19 | 83 ± 7 | 1.68 ± 0.09 | 88 ± 4 | 1.75 ± 0.06 | 81 ± 3 | 2.45 ± 0.10 | 89 ± 3 |
| 1 | 1.24 ± 0.06 | 48 ± 2 | 0.93 ± 0.03 | 49 ± 2 | 0.99 ± 0.00 | 46 ± 0 | 1.35 ± 0.12 | 49 ± 4 |
| 0.75 | 0.98 ± 0.03 | 37 ± 1 | 0.73 ± 0.06 | 38 ± 3 | 0.80 ± 0.06 | 37 ± 3 | 1.16 ± 0.01 | 42 ± 0 |
| 0.5 | 0.72 ± 0.05 | 28 ± 2 | 0.21 ± 0.02 | 11 ± 1 | 0.54 ± 0.01 | 25 ± 1 | 0.87 ± 0.00 | 32 ± 0 |
| 0.25 | 0.39 ± 0.09 | 15 ± 3 | 0.42 ± 0.03 | 22 ± 2 | 0.28 ± 0.02 | 13 ± 1 | 0.61 ± 0.17 | 22 ± 6 |
| 0.1 | 0.12 ± 0.02 | 4 ± 1 | 0.08 ± 0.00 | 4 ± 0 | 0.11 ± 0.00 | 5 ± 0 | 0.19 ± 0.00 | 7 ± 0 |
| 0.01 | 0.02 ± 0.01 | 1 ± 0 | 0.01 ± 0.00 | 0 ± 0 | 0.01 ± 0.00 | 0 ± 0 | 0.03 ± 0.01 | 1 ± 0 |
| 0 | 0.01 ± 0.01 | 1 ± 0 | 0.01 ± 0.00 | 0 ± 0 | 0.04 ± 0.01 | 2 ± 0 | 0.10 ± 0.02 | 4 ± 1 |
| $K_d$ (μg/mL) | 1.45 | | 1.58 | | 1.72 | | 1.28 | |
| $K_d$ (% WT) | 100 | | 109 | | 119 | | 88.5 | |

| K1-18-POD | TSHR260-JMG45 | | TSHR260-JMG52 | | TSHR260-JMG55 | |
|---|---|---|---|---|---|---|
| (μg/mL) | OD450 | % Max | OD450 | % Max | OD450 | % Max |
| 10 | 2.36 ± 0.20 | 100 ± 8 | 2.29 ± 0.04 | 100 ± 2 | 2.79 ± 0.05 | 100 ± 2 |
| 7.5 | 2.34 ± 0.15 | 99 ± 6 | 2.32 ± 0.01 | 101 ± 0 | 2.86 ± 0.03 | 103 ± 1 |
| 5 | 2.30 ± 0.07 | 97 ± 3 | 2.43 ± 0.03 | 106 ± 0 | 2.68 ± 0.15 | 96 ± 5 |
| 2.5 | 1.82 ± 0.03 | 77 ± 1 | 2.16 ± 0.03 | 94 ± 2 | 2.34 ± 0.22 | 84 ± 8 |
| 1 | 1.13 ± 0.03 | 48 ± 1 | 1.28 ± 0.13 | 56 ± 6 | 1.24 ± 0.12 | 45 ± 4 |
| 0.75 | 0.90 ± 0.06 | 38 ± 3 | 0.97 ± 0.08 | 43 ± 4 | 1.04 ± 0.09 | 37 ± 3 |
| 0.5 | 0.56 ± 0.05 | 24 ± 2 | 0.56 ± 0.10 | 25 ± 4 | 0.76 ± 0.01 | 27 ± 0 |
| 0.25 | 0.33 ± 0.03 | 14 ± 1 | 0.36 ± 0.02 | 16 ± 1 | 0.40 ± 0.01 | 14 ± 0 |
| 0.1 | 0.11 ± 0.01 | 5 ± 0 | 0.14 ± 0.01 | 6 ± 0 | 0.14 ± 0.01 | 5 ± 0 |
| 0.01 | 0.02 ± 0.01 | 1 ± 1 | 0.02 ± 0.01 | 1 ± 0 | 0.02 ± 0.00 | 1 ± 0 |
| 0 | 0.01 ± 0.00 | 0 ± 0 | 0.00 ± 0.00 | 0 ± 0 | 0.02 ± 0.02 | 1 ± 1 |
| $K_d$ (μg/mL) | 1.30 | | 1.60 | | 0.936 | |
| $K_d$ (% WT) | 89.7 | | 110 | | 64.7 | |

Results are expressed as absorbance at 450 nm, with non-specific binding subtracted, and a percentage of the maximum OD450 reading (% Max) for each mutant, Mean ± SD for duplicate measurements in a single experiment. $K_d$ was determined by fitting a saturation binding curve to the data with GraphPad Prism.

TABLE 17

K1-70-POD binding to TSHR260 mutants.

| K1-70-POD | TSHR260-WT | | TSHR260-I253R | | TSHR260-JMG22 | | TSHR260-JMG37 | |
|---|---|---|---|---|---|---|---|---|
| (μg/mL) | OD450 | % Max | OD450 | % Max | OD450 | % Max | OD450 | % Max |
| 10 | 3.01 ± 0.02 | 100 ± 1 | 2.89 ± 0.06 | 100 ± 2 | 2.79 ± 0.05 | 100 ± 2 | 3.10 ± 0.03 | 100 ± 1 |
| 5 | 3.29 ± 0.06 | 110 ± 2 | 3.14 ± 0.01 | 109 ± 0 | 3.03 ± 0.07 | 108 ± 2 | 3.31 ± 0.01 | 107 ± 0 |
| 2.5 | 3.26 ± 0.03 | 109 ± 1 | 2.77 ± 0.23 | 96 ± 8 | 2.57 ± 0.20 | 92 ± 7 | 3.26 ± 0.01 | 105 ± 0 |
| 1 | 2.32 ± 0.28 | 77 ± 9 | 1.92 ± 0.18 | 66 ± 6 | 1.62 ± 0.06 | 58 ± 2 | 1.99 ± 0.45 | 64 ± 15 |
| 0.75 | 1.89 ± 0.12 | 63 ± 4 | 1.51 ± 0.28 | 52 ± 10 | 1.31 ± 0.01 | 47 ± 0 | 1.86 ± 0.07 | 60 ± 2 |
| 0.5 | 1.39 ± 0.02 | 46 ± 1 | 1.19 ± 0.02 | 41 ± 1 | 0.98 ± 0.03 | 35 ± 1 | 1.45 ± 0.04 | 47 ± 1 |
| 0.25 | 0.77 ± 0.05 | 25 ± 2 | 0.67 ± 0.04 | 23 ± 1 | 0.51 ± 0.01 | 18 ± 0 | 0.87 ± 0.04 | 28 ± 1 |
| 0.1 | 0.31 ± 0.02 | 10 ± 1 | 0.26 ± 0.00 | 9 ± 0 | 0.21 ± 0.00 | 8 ± 0 | 0.32 ± 0.00 | 10 ± 0 |
| 0.05 | 0.14 ± 0.02 | 5 ± 1 | 0.13 ± 0.00 | 4 ± 0 | 0.12 ± 0.01 | 4 ± 0 | 0.16 ± 0.01 | 5 ± 0 |
| 0.01 | 0.09 ± 0.10 | 3 ± 3 | 0.06 ± 0.03 | 2 ± 1 | 0.04 ± 0.01 | 1 ± 0 | 0.05 ± 0.03 | 2 ± 1 |
| 0 | 0.01 ± 0.00 | 0 ± 0 | 0.00 ± 0.01 | 0 ± 0 | 0.00 ± 0.02 | 0 ± 1 | 0.01 ± 0.01 | 0 ± 0 |
| $K_d$ (μg/mL) | 0.69 | | 0.88 | | 1.12 | | 0.74 | |
| $K_d$ (% WT) | 100 | | 128 | | 163 | | 107 | |

TABLE 17-continued

K1-70-POD binding to TSHR260 mutants.

| K1-70-POD (μg/mL) | TSHR260-JMG45 OD450 | % Max | TSHR260-JMG52 OD450 | % Max | TSHR260-JMG55 OD450 | % Max |
|---|---|---|---|---|---|---|
| 10 | 2.93 ± 0.08 | 100 ± 3 | 3.03 ± 0.04 | 100 ± 1 | 3.08 ± 0.06 | 100 ± 2 |
| 5 | 3.17 ± 0.06 | 108 ± 2 | 3.29 ± 0.03 | 109 ± 1 | 3.34 ± 0.04 | 109 ± 1 |
| 2.5 | 2.88 ± 0.01 | 98 ± 1 | 3.17 ± 0.03 | 105 ± 1 | 3.40 ± 0.01 | 110 ± 0 |
| 1 | 1.85 ± 0.09 | 63 ± 3 | 2.25 ± 0.02 | 74 ± 1 | 2.67 ± 0.01 | 87 ± 0 |
| 0.75 | 1.59 ± 0.02 | 54 ± 1 | 1.33 ± 0.03 | 44 ± 1 | 2.22 ± 0.02 | 72 ± 0 |
| 0.5 | 1.15 ± 0.07 | 39 ± 3 | 1.95 ± 0.06 | 64 ± 2 | 1.71 ± 0.01 | 56 ± 0 |
| 0.25 | 0.53 ± 0.01 | 18 ± 0 | 0.67 ± 0.02 | 22 ± 1 | 0.85 ± 0.06 | 28 ± 2 |
| 0.1 | 0.25 ± 0.03 | 8 ± 1 | 0.29 ± 0.01 | 10 ± 0 | 0.37 ± 0.01 | 12 ± 0 |
| 0.05 | 0.12 ± 0.00 | 4 ± 0 | 0.30 ± 0.00 | 10 ± 0 | 0.19 ± 0.00 | 6 ± 0 |
| 0.01 | 0.02 ± 0.01 | 1 ± 1 | 0.04 ± 0.01 | 1 ± 0 | 0.04 ± 0.01 | 1 ± 0 |
| 0 | 0.12 ± 0.01 | 0 ± 0 | −0.01 ± 0.00 | 0 ± 0 | 0.00 ± 0.00 | 0 ± 0 |
| $K_d$ (μg/mL) | 0.94 | | 0.72 | | 0.54 | |
| $K_d$ (% WT) | 137 | | 104 | | 78 | |

Results are expressed as absorbance at 450 nm, with non-specific binding subtracted, and a percentage of the maximum OD450 reading (% Max) for each mutant, Mean ± SD for duplicate measurements in a single experiment.
$K_d$ was determined by fitting a saturation binding curve to the data with GraphPad Prism.

TABLE 18

M22-POD binding to full-length TSHR mutant.

| M22-POD (ng/mL) | TSHR-WT OD450 | % Max | TSHR-JMG37 OD450 | % Max | TSHR-JMG45 OD450 | % Max | TSHR-JMG52 OD450 | % Max |
|---|---|---|---|---|---|---|---|---|
| 200 | 3.44 ± 0.03 | 100 ± 1 | 2.51 ± 0.07 | 100 ± 3 | 2.65 ± 0.14 | 100 ± 5 | 2.64 ± 0.06 | 100 ± 2 |
| 100 | 2.58 ± 0.05 | 75 ± 1 | 1.60 ± 0.02 | 64 ± 1 | 1.61 ± 0.09 | 61 ± 3 | 1.63 ± 0.01 | 61 ± 1 |
| 75 | 2.11 ± 0.07 | 62 ± 2 | 1.18 ± 0.04 | 47 ± 2 | 1.18 ± 0.04 | 45 ± 1 | 1.21 ± 0.03 | 46 ± 1 |
| 50 | 1.47 ± 0.06 | 43 ± 2 | 0.86 ± 0.06 | 34 ± 3 | 0.85 ± 0.02 | 32 ± 1 | 0.85 ± 0.05 | 32 ± 2 |
| 25 | 0.73 ± 0.01 | 21 ± 0 | 0.42 ± 0.01 | 17 ± 0 | 0.41 ± 0.01 | 16 ± 0 | 0.47 ± 0.08 | 18 ± 3 |
| 10 | 0.29 ± 0.01 | 8 ± 0 | 0.16 ± 0.01 | 6 ± 0 | 0.16 ± 0.01 | 6 ± 0 | 0.18 ± 0.00 | 7 ± 0 |
| 5 | 0.15 ± 0.01 | 4 ± 0 | 0.08 ± 0.00 | 3 ± 0 | 0.08 ± 0.00 | 3 ± 0 | 0.09 ± 0.01 | 3 ± 1 |
| 1 | 0.04 ± 0.00 | 1 ± 0 | 0.02 ± 0.00 | 1 ± 0 | 0.02 ± 0.00 | 1 ± 0 | 0.03 ± 0.01 | 1 ± 0 |
| 0 | 0.00 ± 0.00 | 0 ± 0 | 0.00 ± 0.00 | 0 ± 0 | 0.00 ± 0.00 | 0 ± 0 | 0.00 ± 0.00 | 0 ± 0 |
| $K_d$ (ng/mL) | 155 | | 371 | | 499 | | 430 | |
| $K_d$ (% WT $K_d$) | 100 | | 240 | | 323 | | 278 | |

Results are expressed as absorbance at 450 nm, with non-specific binding subtracted, and a percentage of the maximum OD450 reading (% Max) for each mutant, Mean ± SD for duplicate measurements in a single experiment.
$K_d$ was determined by fitting a saturation binding curve to the data with GraphPad Prism.

TABLE 19

K1-18-POD binding to full-length TSHR mutants.

| K1-18-POD (μg/mL) | TSHR-WT OD450 | % Max | TSHR-JMG37 OD450 | % Max | TSHR-JMG45 OD450 | % Max | TSHR-JMG52 OD450 | % Max |
|---|---|---|---|---|---|---|---|---|
| 200 | 2.59 ± 0.02 | 100 ± 1 | 2.84 ± 0.01 | 100 ± 0 | 2.82 ± 0.01 | 100 ± 0 | 2.93 ± 0.04 | 100 ± 1 |
| 100 | 2.34 ± 0.09 | 90 ± 3 | 2.80 ± 0.02 | 99 ± 1 | 2.77 ± 0.00 | 98 ± 0 | 3.04 ± 0.02 | 104 ± 1 |
| 75 | 1.48 ± 0.01 | 57 ± 0 | 1.91 ± 0.08 | 67 ± 3 | 1.84 ± 0.06 | 65 ± 2 | 2.43 ± 0.05 | 83 ± 2 |
| 50 | 0.70 ± 0.01 | 27 ± 0 | 0.95 ± 0.03 | 34 ± 1 | 0.66 ± 0.02 | 24 ± 1 | 1.27 ± 0.01 | 43 ± 0 |
| 25 | 0.53 ± 0.02 | 20 ± 1 | 0.74 ± 0.01 | 26 ± 0 | 0.90 ± 0.05 | 32 ± 2 | 0.96 ± 0.02 | 33 ± 1 |
| 10 | 0.36 ± 0.01 | 14 ± 0 | 0.49 ± 0.02 | 17 ± 1 | 0.46 ± 0.01 | 16 ± 0 | 0.62 ± 0.02 | 21 ± 1 |
| 5 | 0.17 ± 0.01 | 6 ± 0 | 0.24 ± 0.00 | 9 ± 0 | 0.22 ± 0.01 | 8 ± 1 | 0.32 ± 0.03 | 11 ± 1 |
| 1 | 0.07 ± 0.01 | 3 ± 0 | 0.09 ± 0.00 | 3 ± 0 | 0.08 ± 0.00 | 3 ± 0 | 0.16 ± 0.00 | 5 ± 0 |
| 0 | 0.01 ± 0.01 | 0 ± 1 | 0.02 ± 0.01 | 1 ± 0 | 0.02 ± 0.00 | 1 ± 0 | 0.02 ± 0.00 | 1 ± 0 |
| $K_d$ (μg/mL) | 5.3 | | 3.4 | | 3.8 | | 2.2 | |
| $K_d$ (% WT $K_d$) | 100 | | 64 | | 72 | | 41 | |

Results are expressed as absorbance at 450 nm, with non-specific binding subtracted, and a percentage of the maximum OD450 reading (% Max) for each mutant, Mean ± SD for duplicate measurements in a single experiment.
$K_d$ was detennined by fitting a saturation binding curve to the data with GraphPad Prism.

TABLE 20

K1-70-POD binding to full-length TSHR mutants.

| K1-70-POD | TSHR-WT | | TSHR-JMG37 | | TSHR-JMG45 | | TSHR-JMG52 | |
|---|---|---|---|---|---|---|---|---|
| (µg/ml) | OD450 | % Max | OD450 | % Max | OD450 | % Max | OD450 | % Max |
| 7.5 | 1.92 ± 0.17 | 100 ± 9 | 2.64 ± 0.02 | 100 ± 1 | 2.66 ± 0.08 | 100 ± 3 | 2.85 ± 0.02 | 100 ± 1 |
| 5 | 1.59 ± 0.12 | 83 ± 7 | 2.34 ± 0.01 | 89 ± 0 | 2.37 ± 0.06 | 89 ± 2 | 2.79 ± 0.00 | 98 ± 0 |
| 2.5 | 0.89 ± 0.09 | 46 ± 5 | 1.33 ± 0.04 | 50 ± 2 | 1.36 ± 0.06 | 51 ± 2 | 1.74 ± 0.01 | 61 ± 0 |
| 1 | 0.42 ± 0.02 | 22 ± 1 | 0.61 ± 0.01 | 23 ± 1 | 0.65 ± 0.01 | 24 ± 0 | 0.90 ± 0.07 | 31 ± 3 |
| 0.75 | 0.30 ± 0.03 | 16 ± 2 | 0.46 ± 0.01 | 17 ± 0 | 0.50 ± 0.03 | 19 ± 1 | 0.64 ± 0.04 | 22 ± 2 |
| 0.5 | 0.21 ± 0.03 | 11 ± 1 | 0.30 ± 0.02 | 11 ± 1 | 0.33 ± 0.01 | 12 ± 1 | 0.45 ± 0.03 | 16 ± 1 |
| 0.25 | 0.10 ± 0.02 | 5 ± 1 | 0.16 ± 0.01 | 6 ± 1 | 0.15 ± 0.01 | 6 ± 0 | 0.24 ± 0.01 | 8 ± 0 |
| 0.1 | 0.05 ± 0.00 | 3 ± 0 | 0.11 ± 0.00 | 4 ± 0 | 0.11 ± 0.00 | 4 ± 0 | 0.16 ± 0.02 | 6 ± 1 |
| 0 | 0.00 ± 0.00 | 0 ± 0 | 0.00 ± 0.01 | 0 ± 0 | 0.00 ± 0.00 | 0 ± 0 | 0.02 ± 0.00 | 1 ± 0 |
| $K_d$ (µg/mL) | 9.8 | | 7.4 | | 6.9 | | 4.1 | |
| $K_d$ (% WT $K_d$) | 100 | | 76 | | 70 | | 42 | |

Results are expressed as absorbance at 450 nm, with non-specific binding subtracted, and a percentage of the maximum OD450 reading (% Max) for each mutant, Mean ± SD for duplicate measurements in a single experiment.
$K_d$ was determined by fitting a saturation binding curve to the data with GraphPad Prism.

TABLE 21

Summary of effects of mutations (relative to TSHR60-WT or full-length TSHR-WT) on binding of M22-POD, K1-18 POD and K1-70 POD.

| Mutant | M22-POD binding | K1-18 POD binding | K1-70 POD binding |
|---|---|---|---|
| TSHR260-I253R | n.d. | Little change | Little change |
| TSHR260-JMG22 | n.d. | Little change | Little change |
| TSHR260-JMG37 | Little change | Little change | Little change |
| TSHR260-JMG45 | Little change | Little change | Little change |
| TSHR260-JMG52 | Little change | Little change | Little change |
| TSHR260-JMG55 | Little change | Little change | Little change |
| TSHR-JMG37 | Little change | Little change | Little change |
| TSHR-JMG45 | Little change | Little change | Little change |
| TSHR-JMG52 | Little change | Little change | Little change | n.d. = not determined.

TABLE 22

Inhibition by K1-18 IgG of M22-POD binding to TSHR260 mutants

| K1-18 IgG (ng/mL) | TSHR260-WT | | TSH260-JMG37 | | TSHR260-JMG45 | | TSHR260-JMG52 | | TSHR260-JMG55 | |
|---|---|---|---|---|---|---|---|---|---|---|
| | OD450 | Inhibition (%) | OD450 | Inhibition (%) | OD450 | Inhibition (%) | OD450 | Inhibition (%) | OD450 | Inhibition (%) |
| 1000 | 0.07 ± 0.00 | 97 ± 0 | 0.25 ± 0.03 | 89 ± 1 | 0.25 ± 0.01 | 88 ± 0 | 0.38 ± 0.02 | 79 ± 1 | 0.35 ± 0.02 | 78 ± 1 |
| 300 | 0.18 ± 0.02 | 93 ± 1 | 0.41 ± 0.06 | 82 ± 3 | 0.38 ± 0.05 | 82 ± 2 | 0.49 ± 0.03 | 73 ± 2 | 0.55 ± 0.02 | 67 ± 1 |
| 100 | 0.62 ± 0.06 | 75 ± 3 | 0.87 ± 0.06 | 62 ± 3 | 0.78 ± 0.03 | 62 ± 2 | 0.78 ± 0.06 | 57 ± 3 | 0.83 ± 0.02 | 49 ± 1 |
| 30 | 1.59 ± 0.17 | 35 ± 7 | 1.57 ± 0.14 | 32 ± 6 | 1.38 ± 0.15 | 33 ± 7 | 1.26 ± 0.23 | 30 ± 13 | 1.24 ± 0.05 | 24 ± 3 |
| 10 | 1.83 ± 0.05 | 26 ± 2 | 1.66 ± 0.04 | 28 ± 1 | 1.57 ± 0.21 | 24 ± 10 | 1.48 ± 0.13 | 17 ± 7 | 1.32 ± 0.05 | 19 ± 2 |
| 3 | 2.03 ± 0.14 | 18 ± 6 | 1.93 ± 0.01 | 16 ± 1 | 1.84 ± 0.16 | 11 ± 8 | 1.56 ± 0.09 | 13 ± 5 | 1.65* | −1* |
| 1 | 2.38 ± 0.28 | 3 ± 11 | 2.21 ± 0.20 | 5 ± 9 | 2.02 ± 0.02 | 2 ± 1 | 1.66 ± 0.12 | 8 ± 7 | 1.63 ± 0.03 | 1 ± 2 |
| 0 | 2.46 ± 0.01 | 0 ± 0 | 2.31 ± 0.03 | 0 ± 1 | 2.06 ± 0.05 | 0 ± 2 | 1.80 ± 0.01 | 0 ± 0 | 1.64* | 0* |

Results are presented as absorbance at 450 nm and a percentage of inhibition of M22-POD binding ± SD for duplicate measurements in a single experiment.
*From a single measurement.

TABLE 23

Inhibition by K1-70 IgG of M22-POD binding to TSHR260 mutants

| K1-70 IgG (ng/mL) | TSHR260-WT | | TSH260-JMG37 | | TSHR260-JMG45 | |
|---|---|---|---|---|---|---|
| | OD450 | Inhibition (%) | OD450 | Inhibition (%) | OD450 | Inhibition (%) |
| 1000 | 0.066 ± 0.014 | 97.2 ± 0.6 | 0.047 ± 0.008 | 97.9 ± 0.4 | 0.018 ± 0.001 | 99.04 ± 0.08 |
| 300 | 0.109 ± 0.013 | 95.4 ± 0.5 | 0.130 ± 0.001 | 94.30 ± 0.03 | 0.069 ± 0.004 | 96.3 ± 0.2 |
| 100 | 0.34 ± 0.02 | 85.8 ± 0.9 | 0.388 ± 0.012 | 82.9 ± 0.5 | 0.241 ± 0.008 | 87.1 ± 0.5 |
| 30 | 1.045 ± 0.011 | 55.8 ± 0.4 | 1.069 ± 0.006 | 52.9 ± 0.2 | 0.80 ± 0.03 | 57.4 ± 1.4 |

TABLE 23-continued

Inhibition by K1-70 IgG of M22-POD binding to TSHR260mutants

| | | | | | | |
|---|---|---|---|---|---|---|
| 10 | 1.61 ± 0.09 | 32 ± 4 | 1.51 ± 0.06 | 33 ± 3 | 1.18 ± 0.02 | 37.1 ± 1.2 |
| 1 | 2.22 ± 0.03 | 6.1 ± 1.1 | 2.1 ± 0.3 | 10 ± 14 | 1.47 ± 0.06 | 21 ± 3 |
| 0.1 | 2.38 ± 0.05 | −0.6 ± 1.9 | 1.99 ± 0.08 | 13 ± 4 | 1.77 ± 0.10 | 5 ± 5 |
| 0 | 2.4 ± 0.2 | 0.0 ± 10 | 2.27 ± 0.07 | 0 ± 3 | 1.87 ± 0.04 | 0 ± 2 |

| K1-70 IgG | TSHR260-JMG52 | | TSHR260-JMG55 | |
|---|---|---|---|---|
| (ng/mL) | OD450 | Inhibition (%) | OD450 | Inhibition (%) |
| 1000 | 0.024 ± 0.004 | 98.7 ± 0.2 | 0.02* | 99.3* |
| 300 | 0.10 ± 0.04 | 95 ± 2 | 0.072 ± 0.012 | 97.5 ± 0.4 |
| 100 | 0.29 ± 0.03 | 84.0 ± 1.5 | 0.38 ± 0.05 | 87.0 ± 1.7 |
| 30 | 0.86 ± 0.05 | 53 ± 3 | 1.5 ± 0.3 | 48 ± 9 |
| 10 | 1.23 ± 0.02 | 32.4 ± 1.2 | 2.14 ± 0.15 | 26 ± 5 |
| 1 | 1.58 ± 0.11 | 13 ± 6 | 2.71 ± 0.05 | 6.7 ± 1.7 |
| 0.1 | 1.65 ± 0.10 | 9 ± 6 | 2.77 ± 0.06 | 4.6 ± 2.0 |
| 0 | 1.82 ± 0.06 | 0 ± 3 | 2.91 ± 0.04 | 0.0 ± 1.3 |

Results are presented as absorbance at 450 nm and a percentage of inhibition of M22-POD binding ± SD for duplicate measurements in a single experiment.
*From a single measurement.

TABLE 24

Inhibition by K1-18 IgG of M22-POD binding to full-length TSHR mutants

| K1-18 IgG | TSHR-WT | | TSHR-JMG37 | | TSHR-JMG45 | | TSHR-JMG52 | |
|---|---|---|---|---|---|---|---|---|
| (ng/mL) | OD450 | % inhibition | OD450 | % Inhibition | OD450 | % Inhibition | OD450 | % Inhibition |
| 1000 | 0.36 ± 0.02 | 86.0 ± 0.7 | 0.46 ± 0.00 | 82.3 ± 0.1 | 0.45 ± 0.01 | 81.5 ± 0.6 | 0.48 ± 0.00 | 81.4 ± 0.1 |
| 300 | 0.77 ± 0.01 | 70.3 ± 0.3 | 0.95 ± 0.00 | 63.3 ± 0.1 | 0.91 ± 0.03 | 62.3 ± 1.3 | 0.97 ± 0.02 | 62.5 ± 0.9 |
| 100 | 1.40 ± 0.09 | 45.9 ± 3.4 | 1.70 ± 0.01 | 34.4 ± 0.3 | 1.48 ± 0.01 | 38.6 ± 0.6 | 1.65 ± 0.01 | 36.2 ± 0.4 |
| 30 | 2.01 ± 0.00 | 21.9 ± 0.0 | 2.24 ± 0.01 | 13.6 ± 0.3 | 2.05 ± 0.01 | 15.2 ± 0.5 | 2.22 ± 0.03 | 14.1 ± 1.0 |
| 10 | 2.34 ± 0.01 | 9.3 ± 0.4 | 2.46 ± 0.04 | 5.2 ± 1.6 | 2.28 ± 0.01 | 5.3 ± 0.6 | 2.43 ± 0.06 | 5.8 ± 2.2 |
| 3 | 2.65 ± 0.11 | −2.9 ± 4.3 | 2.60 ± 0.03 | −0.3 ± 1.3 | 2.28 ± 0.09 | 5.4 ± 3.7 | 2.52 ± 0.01 | 2.3 ± 0.6 |
| 1 | 2.45 ± 0.04 | 4.9 ± 1.6 | 2.60 ± 0.04 | −0.3 ± 1.4 | 2.34 ± 0.01 | 3.1 ± 0.6 | 2.55 ± 0.05 | 1.4 ± 1.9 |
| 0.3 | 2.39 ± 0.12 | 7.4 ± 4.6 | 2.59 ± 0.04 | 0.1 ± 1.6 | 2.39 ± 0.04 | 0.9 ± 1.7 | 2.63 ± 0.04 | −1.6 ± 1.6 |
| 0.1 | 2.50 ± 0.04 | 3.2 ± 1.7 | 2.58 ± 0.03 | 0.6 ± 1.2 | 2.34 ± 0.09 | 3.0 ± 3.8 | 2.63 ± 0.04 | −1.8 ± 1.6 |

Results are presented as absorbance at 450 nm and as a percentage of inhibition of M22-POD binding ± SD for duplicate measurements in a single experiment.

TABLE 25

Inhibition by K1-70 IgG of M22-POD binding to full-length TSHR mutants.

| K1-70 IgG | TSHR-WT | | TSHR-JMG37 | | TSHR-JMG45 | | TSHR-JMG52 | |
|---|---|---|---|---|---|---|---|---|
| (ng/mL) | OD450 | % inhibition | OD450 | % Inhibition | OD450 | % Inhibition | OD450 | % Inhibition |
| 1000 | 0.13 ± 0.00 | 94.9 ± 0.1 | 0.20 ± 0.00 | 92.3 ± 0.1 | 0.14 ± 0.00 | 94.2 ± 0.1 | 0.15 ± 0.01 | 94.3 ± 0.2 |
| 300 | 0.28 ± 0.01 | 89.1 ± 0.5 | 0.58 ± 0.01 | 77.6 ± 0.6 | 0.50 ± 0.00 | 79.4 ± 0.2 | 0.56 ± 0.01 | 78.4 ± 0.4 |
| 100 | 0.76 ± 0.04 | 70.4 ± 1.6 | 1.36 ± 0.02 | 47.8 ± 0.7 | 1.21 ± 0.02 | 50.1 ± 0.7 | 1.34 ± 0.00 | 48.2 ± 0.1 |
| 30 | 1.61 ± 0.07 | 37.7 ± 2.8 | 2.08 ± 0.05 | 19.8 ± 1.7 | 1.80 ± 0.03 | 25.3 ± 1.2 | 2.10 ± 0.01 | 18.9 ± 0.5 |
| 10 | 2.07 ± 0.05 | 19.7 ± 1.8 | 2.36 ± 0.04 | 9.1 ± 1.7 | 2.12 ± 0.01 | 12.1 ± 0.5 | 2.48 ± 0.01 | 4.2 ± 0.4 |
| 3 | 2.32 ± 0.04 | 10.1 ± 1.5 | 2.52 ± 0.00 | 2.8 ± 0.2 | 2.31 ± 0.03 | 4.5 ± 1.1 | 2.55 ± 0.06 | 1.5 ± 2.4 |
| 1 | 2.44 ± 0.02 | 5.3 ± 0.7 | 2.60 ± 0.01 | −0.1 ± 0.3 | 2.41 ± 0.05 | 0.0 ± 2.2 | 2.65 ± 0.01 | −2.5 ± 0.5 |
| 0.3 | 2.45 ± 0.10 | 5.0 ± 3.9 | 2.54 ± 0.01 | 2.0 ± 0.3 | 2.32 ± 0.08 | 3.8 ± 3.5 | 2.58 ± 0.06 | 0.2 ± 2.4 |
| 0.1 | 2.48 ± 0.09 | 3.7 ± 3.3 | 2.61 ± 0.00 | −0.6 ± 0.0 | 2.39 ± 0.01 | 0.9 ± 0.4 | 2.65 ± 0.01 | −2.3 ± 0.5 |

Results are presented as absorbance at 450 nm and as a percentage of inhibition of M22-POD binding ± SD for duplicate measurements in a single experiment.

TABLE 26

Summary of effects of mutations (relative to TSHR60-WT or full-length TSHR-WT) on K1-18 IgG and K1-70 IgG inhibition of M22-POD binding to TSHR260 or full-length TSHR-WT.

| Mutant | M22-POD binding | K1-18 POD binding | K1-70 POD binding |
|---|---|---|---|
| TSHR260-JMG37 | Little change | Little change | Little change |
| TSHR260-JMG45 | Little change | Little change | Little change |
| TSHR260-JMG52 | Little change | Little change | Little change |
| TSHR260-JMG55 | Little change | Little change | Little change |
| TSHR-JMG37 | Little change | Little change | Little change |
| TSHR-JMG45 | Little change | Little change | Little change |
| TSHR-JMG52 | Little change | Little change | Little change |

TABLE 29

Summary of effects of mutations relative to TSHR60-WT or full-length TSHR-WT) on normal sera and TRAb positive patient sera inhibition of M22-POD binding to TSHR260 or full-length TSHR-WT.

| Mutant | Normal Sera | TRAb positive patient sera |
|---|---|---|
| TSHR260-JMG52 | Little change | Little change |
| TSHR260-JMG55 | Little change | Little change |
| TSHR-JMG45 | Little change | Little change |
| TSHR-JMG52 | Little change | Little change |

TABLE 27

Inhibition of M22-POD binding to TSHR260 mutants by patient sera

| | Test sample | TSHR260-WT | | TSHR260-JMG52 | | TSHR260-JMG55 | |
|---|---|---|---|---|---|---|---|
| | | OD450 | % Inhibition vs mean of normal sera | OD450 | % Inhibition vs mean of normal sera | OD450 | % Inhibition vs mean of normal sera |
| Normal sera | NT 9916 | 1.10 ± 0.03 | 0.7 | 1.01 ± 0.02 | −3.3 | 1.13 ± 0.04 | 3.7 |
| | NT 9918 | 1.01 ± 0.05 | 8.5 | 0.9 ± 0.03 | 7.5 | 1.13 ± 0.10 | 3.8 |
| | NT 11746 | 0.98 ± 0.11 | 10.7 | 0.86 ± 0.07 | 12.2 | 1.11 ± 0.11 | 5.9 |
| | NT 11748 | 1.12 ± 0.02 | −1.9 | 1.055 ± 0.011 | −8.1 | 1.20 ± 0.07 | −1.9 |
| | NT 9924 | 1.3 ± 0.03 | −17.9 | 1.06 ± 0.03 | −8.2 | 1.31 ± 0.03 | −11.6 |
| | Mean | 1.1 ± 0.12 | 0.0 | 0.98 ± 0.09 | 0.0 | 1.18 ± 0.08 | 0.0 |
| TRAb positive patient sera | F11/9573 | 0.000 ± 0.003 | 100.0 | 0.026 ± 0.006 | 97.3 | 0.025 ± 0.004 | 97.9 |
| | F078459 | 0.086 ± 0.003 | 92.2 | 0.302 ± 0.001 | 69.1 | 0.361 ± 0.006 | 69.3 |
| | 82 | 0.009 ± 0.000 | 99.2 | 0.026 ± 0.002 | 97.3 | 0.038 ± 0.005 | 96.8 |
| | 92 | 0.042 ± 0.008 | 96.2 | 0.159 ± 0.011 | 83.7 | 0.22 ± 0.013 | 81.3 |
| | 101 | 0.135 ± 0.010 | 87.8 | 0.229 ± 0.008 | 76.5 | 0.327 ± 0.015 | 72.2 |
| | 107 | 0.043 ± 0.004 | 96.1 | 0.088 ± 0.008 | 91.0 | 0.14 ± 0.004 | 88.1 |
| | 20 | 0.427 ± 0.012 | 61.3 | 0.423 ± 0.008 | 56.7 | 0.364 ± 0.001 | 69.0 |
| | 110 | 0.147 ± 0.012 | 86.7 | 0.312 ± 0.013 | 68.0 | 0.341 ± 0.006 | 71.0 |
| | 69 | 0.064 ± 0.001 | 94.2 | 0.096 ± 0.009 | 90.2 | 0.134 ± 0.004 | 88.6 |

Results are presented as absorbance at 450 nm ± SD and a percentage of inhibition of M22-POD binding for duplicate measurements in a single experiment.

TABLE 28

Inhibition of M22-POD binding to full-length TSHR mutants by patient sera.

| | Test sample | TSHR-WT | | TSHR-JMG45 | | TSHR-JMG52 | |
|---|---|---|---|---|---|---|---|
| | | OD450 | % Inhibition vs mean of normal sera | OD450 | % Inhibition vs mean of normal sera | OD450 | % Inhibition vs mean of normal sera |
| Normal sera | NT 9916 | 1.440 ± 0.003 | 6.1 | 1.66 ± 0.018 | 3.3 | 1.83 ± 0.04 | 2.4 |
| | NT 9918 | 1.375 ± 0.006 | 10.4 | 1.614 ± 0.016 | 6.0 | 1.78 ± 0.03 | 5.1 |
| | NT 11746 | 1.68 ± 0.07 | −9.4 | 1.795 ± 0.008 | −4.6 | 2.01 ± 0.04 | −7.0 |
| | NT 11748 | 1.69 ± 0.04 | −10.1 | 1.87 ± 0.04 | −9.1 | 1.93 ± 0.05 | −3.0 |
| | NT 9924 | 1.49 ± 0.06 | 2.9 | 1.64 ± 0.07 | 4.3 | 1.83 ± 0.05 | 2.5 |
| | Mean | 1.53 ± 0.14 | 0.0 | 1.716 ± 0.111 | 0.0 | 1.88 ± 0.09 | 0.0 |
| TRAb positive patient sera | 82 | 0.074 ± 0.003 | 95.2 | 0.124 ± 0.014 | 92.8 | 0.143 ± 0.004 | 92.4 |
| | 92 | 0.380 ± 0.006 | 75.2 | 0.835 ± 0.001 | 51.4 | 0.90 ± 0.03 | 52.1 |
| | 101 | 0.498 ± 0.001 | 67.5 | 0.58 ± 0.02 | 66.4 | 0.598 ± 0.007 | 68.1 |
| | 77 | 0.377 ± 0.011 | 75.4 | 0.69 ± 0.09 | 59.8 | 0.849 ± 0.002 | 54.8 |
| | 105 | 0.419 ± 0.013 | 72.7 | 0.80 ± 0.012 | 53.4 | 0.89 ± 0.03 | 52.6 |
| | 117 | 0.149 ± 0.001 | 90.3 | 0.234 ± 0.005 | 86.4 | 0.262 ± 0.000 | 86.0 |
| | 27 | 0.324 ± 0.011 | 78.9 | 0.81 ± 0.03 | 52.9 | 0.86 ± 0.03 | 54.4 |
| | 15 | 0.484 ± 0.006 | 68.5 | 0.89 ± 0.07 | 48.1 | 1.03 ± 0.03 | 45.3 |
| | 60 | 0.094 ± 0.007 | 93.9 | 0.253 ± 0.014 | 85.3 | 0.288 ± 0.008 | 84.7 |

Results are presented as absorbance at 450 nm ± SD and a percentage of inhibition of M22-POD binding for duplicate measurements in a single experiment.

TABLE 30

Effect of different concentrations of human monoclonal antibody to the TSHR (M22) and TSH on stimulation of cyclic AMP production in CHO cells expressing wild type TSHR and TSHR-JMG37 (I253R + D143P + D151E).

| Test sample | Cyclic AMP produced (pmol/mL; mean ± SD; n = 3) | | TSHR-JMG37/ Wild type (%) |
|---|---|---|---|
| | Wild type TSHR | TSHR-JMG37 | |
| Experiment 1 | | | |
| Cyclic AMP buffer | 8.3 ± 0.5 | 2.30 ± 0.08 | 28 |
| M22 | | | |
| 0.1 ng/mL | 15 ± 2 | 9 ± 3 | 60 |
| 0.3 ng/mL | 28 ± 4 | 22.9 ± 1.7 | 81 |
| 1 ng/mL | 74 ± 11 | 70.3 ± 1.7 | 95 |
| 3 ng/mL | 125 ± 17* | 82 ± 23 | 65 |
| 10 ng/mL | 150 ± 19* | 103 ± 15* | 68 |
| 30 ng/mL | 179 ± 23 | 105 ± 10 | 59 |
| TSH | | | |
| 0.01 ng/mL | 9 ± 5 | 2.68 ± 0.16 | 28 |
| 0.03 ng/mL | 16 ± 3* | 3.9 ± 1.0 | 24 |
| 0.1 ng/mL | 17 ± 3 | 17 ± 4 | 99 |
| 0.3 ng/mL | 47 ± 11 | 46.9 ± 1.6 | 99 |
| 1 ng/mL | 110 ± 19 | 102 ± 14 | 93 |
| 3 ng/mL | 116 ± 18 | 98 ± 18 | 84 |
| Experiment 2 | | | |
| Cyclic AMP buffer | 4.4 ± 0.3 | 2.9 ± 0.7 | 66 |
| M22 | | | |
| 0.1 ng/mL | 6.7 ± 1.6 | 6.3 ± 0.9 | 95 |
| 0.3 ng/mL | 14.1 ± 1.3 | 13.0 ± 1.1 | 92 |
| 1 ng/mL | 44 ± 10 | 35.4 ± 1.7 | 81 |
| 3 ng/mL | 79 ± 6 | 66 ± 3 | 84 |
| 10 ng/mL | 109 ± 3 | 102 ± 11 | 94 |
| 30 ng/mL | 113 ± 14 | 125 ± 2* | 110 |
| TSH | | | |
| 0.01 ng/mL | 3.68 ± 0.16 | 3.5 ± 0.3 | 96 |
| 0.03 ng/mL | 5.5 ± 0.7 | 5.9 ± 1.5 | 107 |
| 0.1 ng/mL | 13.2 ± 1.1 | 13.7 ± 1.6 | 104 |
| 0.3 ng/mL | 37 ± 5 | 42.6 ± 1.2 | 116 |
| 1 ng/mL | 78 ± 9 | 72 ± 12 | 93 |
| 3 ng/mL | 104 ± 5 | 101 ± 7 | 97 |

Results shown are mean ± SD of triplicate determinations.
*duplicate determinations.
Samples diluted in cyclic AMP buffer.
Experiment 1: For TSHR-WT: EC50(M22) = 1.62 ng/mL, EC50(TSH) = 1.02 ng/mL. For TSHR-JMG37: EC50(M22) = 0.94 ng/mL, EC50(TSH) = 0.39 ng/mL.
Experiment 2: For TSHR-WT: EC50(M22) = 2.13 ng/mL, EC50(TSH) = 0.77 ng/mL. For TSHR-JMG37: EC50(M22) = 3.10 ng/mL, EC50(TSH) = 0.86 ng/mL.

TABLE 31

Effect of different concentrations of human monoclonal antibody to the TSHR (M22) and TSH on stimulation of cyclic AMP production in CHO cells expressing wild type TSHR and TSHR-JMG45 (I253R + D143P + R112P + D151E).

| Test sample | Cyclic AMP produced (pmol/mL; mean ± SD; n = 3) | | TSHR-JMG45/ Wild type (%) |
|---|---|---|---|
| | Wild type TSHR | TSHR-JMG45 | |
| Experiment 1 | | | |
| Cyclic AMP buffer | 3.8 ± 0.3 | 1.2 ± 0.4 | 32 |
| M22 | | | |
| 0.1 ng/mL | 9 ± 3 | 2.90 ± 0.05 | 33 |
| 0.3 ng/mL | 15.5 ± 1.0 | 9 ± 4* | 59 |
| 1 ng/mL | 53 ± 7 | 18.3 ± 1.7 | 35 |
| 3 ng/mL | 100 ± 5 | 42.3 ± 1.6 | 42 |
| 10 ng/mL | 117 ± 15 | 90 ± 4 | 77 |
| 30 ng/mL | 121 ± 12 | 106 ± 5 | 88 |
| TSH | | | |
| 0.01 ng/mL | 4.3 ± 0.3 | 1.77 ± 0.18 | 41 |
| 0.03 ng/mL | 6.2 ± 0.6 | 3.4 ± 0.5 | 55 |
| 0.1 ng/mL | 14.2 ± 0.9 | 9.6 ± 0.6 | 67 |
| 0.3 ng/mL | 38 ± 2 | 30 ± 4 | 80 |
| 1 ng/mL | 77 ± 13 | 79 ± 6 | 103 |
| 3 ng/mL | 107.2 ± 1.4 | 94 ± 5 | 88 |
| Experiment 2 | | | |
| Cyclic AMP buffer | 7.5 ± 0.6 | 4.2 ± 0.5 | 88 |
| M22 | | | |
| 0.1 ng/mL | 9 ± 0.6 | 6.6 ± 0.7 | 73 |
| 0.3 ng/mL | 16 ± 3 | 11.7 ± 2.0 | 74 |
| 1 ng/mL | 42 ± 4 | 23.8 ± 1.5 | 57 |
| 3 ng/mL | 106 ± 9* | 58 ± 4 | 55 |
| 10 ng/mL | 127.4 ± 0.0* | 93 ± 4 | 73 |
| 30 ng/mL | 97 ± 17* | 106.7 ± 0.0* | 110 |
| TSH | | | |
| 0.01 ng/mL | 8.1 ± 1.0 | 5.3 ± 0.3 | 66 |
| 0.03 ng/mL | 8.5 ± 1.6 | 7.7 ± 1.0 | 91 |
| 0.1 ng/mL | 15.3 ± 1.1 | 14.2 ± 0.3 | 93 |
| 0.3 ng/mL | 38.3 ± 1.3 | 41 ± 4 | 107 |
| 1 ng/mL | 94 ± 5 | 86 ± 15 | 91 |
| 3 ng/mL | 122 ± 11 | 102 ± 11 | 83 |

Results shown are mean ± SD of triplicate determinations.
*duplicate determinations.
Samples diluted in cyclic AMP buffer.
Experiment 1: For TSHR-WT: EC50(M22) = 1.52 ng/mL, EC50(TSH) = 0.82 ng/mL. For TSHR-JMG45: EC50(M22) = 5.37 ng/mL, EC50(TSH) = 0.84 ng/mL.
Experiment 2: For TSHR-WT: EC50(M22) = 1.97 ng/mL, EC50(TSH) = 0.64 ng/mL. For TSHR-JMG45: EC50(M22) = 4.03 ng/mL, EC50(TSH) = 0.63 ng/mL.

TABLE 32

Effect of different concentrations of human monoclonal antibody to the TSHR (M22) and TSH on stimulation of cyclic AMP production in CHO cells expressing wild type TSHR and TSHR-JMG52 (I253R + D143P + R112P + D151E + V169R).

| Test sample | Cyclic AMP produced (pmol/mL; mean ± SD; n = 3) | | TSHR-JMG52/ Wild type (%) |
|---|---|---|---|
| | Wild type TSHR | TSHR-JMG52 | |
| Experiment 1 | | | |
| Cyclic AMP buffer | 2.8 ± 0.5 | 2.4 ± 0.2 | 84 |
| M22 | | | |
| 0.1 ng/mL | 9.2 ± 1.0 | 8.0 ± 0.9 | 87 |
| 0.3 ng/mL | 14.3 ± 0.6 | 9.69 ± 0.13 | 68 |
| 1 ng/mL | 39.8 ± 1.8 | 27 ± 5 | 69 |
| 3 ng/mL | 73 ± 3 | 60 ± 7 | 82 |
| 10 ng/mL | 99 ± 10 | 112 ± 19 | 113 |
| 30 ng/mL | 102 ± 7 | 118 ± 12 | 115 |
| TSH | | | |
| 0.01 ng/mL | 4.24 ± 0 | 3.81 ± 0.18 | 90 |
| 0.03 ng/mL | 7.0 ± 0.7 | 7.0 ± 0.5 | 100 |
| 0.1 ng/mL | 18.5 ± 0.7 | 25.4 ± 1.7 | 137 |
| 0.3 ng/mL | 49 ± 8 | 66 ± 4 | 136 |
| 1 ng/mL | 86 ± 5 | 91 ± 10 | 106 |
| 3 ng/mL | 99 ± 4* | 123 ± 11 | 124 |

TABLE 32-continued

Effect of different concentrations of human monoclonal antibody to the TSHR (M22) and TSH on stimulation of cyclic AMP production in CHO cells expressing wild type TSHR and TSHR-JMG52 (I253R + D143P + R112P + D151E + V169R).

| Test sample | Cyclic AMP produced (pmol/mL; mean ± SD; n = 3) | | TSHR-JMG52/ Wild type (%) |
|---|---|---|---|
| | Wild type TSHR | TSHR-JMG52 | |
| Experiment 2 | | | |
| Cyclic AMP buffer | 9.0 ± 0.4 | 5.6 ± 0.3 | 87 |
| M22 | | | |
| 0.1 ng/mL | 12.9 ± 0.4 | 7.81 ± 0.19 | 60 |
| 0.3 ng/mL | 23 ± 3 | 13.4 ± 1.3 | 59 |
| 1 ng/mL | 60 ± 3 | 35 ± 4 | 58 |
| 3 ng/mL | 101 ± 5 | 66 ± 2 | 66 |
| 10 ng/mL | 130 ± 7 | 95 ± 2 | 73 |
| 30 ng/mL | 110 ± 9 | 118 ± 11 | 107 |
| TSH | | | |
| 0.01 ng/mL | 8.8 ± 1.5 | 5.1 ± 0.3 | 58 |
| 0.03 ng/mL | 11.8 ± 0.2 | 7.45 ± 0.12 | 63 |
| 0.1 ng/mL | 16.94 ± 0.17 | 14.0 ± 0.6 | 83 |
| 0.3 ng/mL | 41 ± 2 | 37.2 ± 0.8 | 91 |
| 1 ng/mL | 90 ± 3 | 75.5 ± 0.7 | 84 |
| 3 ng/mL | 118 ± 10 | 99 ± 5 | 83 |

Results shown are mean ± SD of triplicate determinations.
*duplicate determinations.
Samples diluted in cyclic AMP buffer.
Experiment 1: For TSHR-WT: EC50(M22) = 1.92 ng/mL, EC50(TSH) = 0.42 ng/mL. For TSHR-JMG52: EC50(M22) = 3.72 ng/mL, EC50(TSH) = 0.43 ng/mL.
Experiment 2: For TSHR-WT: EC50(M22) = 1.40 ng/mL, EC50(TSH) = 0.67 ng/mL. For TSHR-JMG52: EC50(M22) = 3.27 ng/mL, EC50(TSH) = 0.99 ng/mL.

TABLE 33

Effect of different concentrations of human monoclonal antibody to the TSHR (M22) and TSH on stimulation of cyclic AMP production in CHO cells expressing wild type TSHR and TSHR-JMG55 (I253R + D143P + R112P + D151E + V169R + H63C).

| Test sample | Cyclic AMP produced (pmol/mL; mean ± SD; n = 3) | | TSHR-JMG55/ Wild type (%) |
|---|---|---|---|
| | Wild type TSHR | TSHR-JMG55 | |
| Experiment 1 | | | |
| Cyclic AMP buffer | 3.8 ± 1.4 | 2.48 ± 0.05 | 65 |
| M22 | | | |
| 0.1 ng/mL | 8.7 ± 0.2 | 6 ± 3 | 72 |
| 0.3 ng/mL | 16.5 ± 1.8 | 10.3 ± 1.5 | 63 |
| 1 ng/mL | 53 ± 8 | 30.1 ± 1.5 | 57 |
| 3 ng/mL | 102 ± 13 | 54 ± 5 | 53 |
| 10 ng/mL | 140 ± 38 | 80.7 ± 1.6* | 58 |
| 30 ng/mL | 113 ± 8 | 88 ± 7 | 78 |
| TSH | | | |
| 0.01 ng/mL | 3.3 ± 0.3 | 2.6 ± 0.9 | 79 |
| 0.03 ng/mL | 4.0 ± 0.7 | 3.6 ± 0.8 | 90 |
| 0.1 ng/mL | 7.1 ± 1.0 | 7.5 ± 1.7 | 106 |
| 0.3 ng/mL | 23.9 ± 0.3 | 25 ± 2 | 104 |
| 1 ng/mL | 73 ± 17 | 51 ± 5 | 70 |
| 3 ng/mL | 109 ± 16 | 92.1 ± 0.0* | 85 |
| Experiment 2 | | | |
| Cyclic AMP buffer | 2.6 ± 0.5 | 2.0 ± 0.0* | 76 |
| M22 | | | |
| 0.1 ng/mL | 7.3 ± 0.9 | 4.1 ± 0.4 | 55 |
| 0.3 ng/mL | 20.7 ± 2.0 | 10.0 ± 2.9 | 48 |
| 1 ng/mL | 51.9 ± 11.7 | 27.5 ± 2.2 | 53 |
| 3 ng/mL | 105.2 ± 3.1 | 66.2 ± 5.1 | 63 |

TABLE 33-continued

Effect of different concentrations of human monoclonal antibody to the TSHR (M22) and TSH on stimulation of cyclic AMP production in CHO cells expressing wild type TSHR and TSHR-JMG55 (I253R + D143P + R112P + D151E + V169R + H63C).

| Test sample | Cyclic AMP produced (pmol/mL; mean ± SD; n = 3) | | TSHR-JMG55/ Wild type (%) |
|---|---|---|---|
| | Wild type TSHR | TSHR-JMG55 | |
| 10 ng/mL | 117.8 ± 25.0 | 121.7 ± 8.3 | 103 |
| 30 ng/mL | 125.9 ± 10.2 | 121.5 ± 2.2 | 97 |
| TSH | | | |
| 0.01 ng/mL | 5.3 ± 1.0 | 3.5 ± 0.1 | 66 |
| 0.03 ng/mL | 5.3 ± 0.8 | 3.9 ± 0.3 | 73 |
| 0.1 ng/mL | 30.5 ± 1.7 | 20.3 ± 1.9 | 66 |
| 0.3 ng/mL | 44.7 ± 4.5 | 36.0 ± 2.0 | 81 |
| 1 ng/mL | 110.0 ± 2.4 | 108.5 ± 6.6 | 99 |
| 3 ng/mL | 102.4 ± 8.2 | 120.1 ± 16.9 | 117 |

Results shown are mean ± SD of triplicate determinations.
*duplicate determinations.
Samples diluted in cyclic AMP buffer.
Experiment 1: For TSHR-WT: EC50(M22) = 1.53 ng/mL, EC50(TSH) = 1.11 ng/mL. For TSHR-JMG52: EC50(M22) = 2.87 ng/mL, EC50(TSH) = 0.934 ng/mL
Experiment 2: For TSHR-WT: EC50(M22) = 1.30 ng/mL, EC50(TSH) = 0.445 ng/mL. For TSHR-JMG-52: EC50(M22) = 3.90 ng/mL, EC50(TSH) = 0.609 ng/mL.

TABLE 34

Effect of different concentrations of human monoclonal antibody to the TSHR (K1-18) and TSH on stimulation of cyclic AMP production in CHO cells expressing wild type TSHR and TSHR-JMG37 (I253R + D143P + D151E).

| Test sample | Cyclic AMP produced (pmol/mL; mean ± SD; n = 3) | | TSHR-JMG37/ Wild type (%) |
|---|---|---|---|
| | Wild type TSHR | TSHR-JMG37 | |
| Experiment 1 | | | |
| Cyclic AMP buffer | 6.6 ± 0.7 | 4.8 ± 0.3 | 102 |
| K1-18 | | | |
| 0.3 ng/mL | 7.8 ± 0.6 | 6.7 ± 0.2 | 86 |
| 1 ng/mL | 12.9 ± 0.7 | 12.7 ± 1.2 | 99 |
| 3 ng/mL | 29 ± 3 | 31.4 ± 1.0 | 107 |
| 10 ng/mL | 68.3 ± 2 | 71.8 ± 1.4 | 105 |
| 30 ng/mL | 113 ± 4 | 114 ± 11 | 100 |
| 100 ng/mL | 128 ± 10 | 128 ± 7 | 100 |
| TSH | | | |
| 0.01 ng/mL | 6.7 ± 0.4 | 4.94 ± 0.09 | 74 |
| 0.03 ng/mL | 9.3 ± 0.5 | 8.08 ± 0.07 | 87 |
| 0.1 ng/mL | 23 ± 2 | 22.7 ± 1.6 | 101 |
| 0.3 ng/mL | 48 ± 8 | 58 ± 3 | 121 |
| 1 ng/mL | 102 ± 5 | 100 ± 12 | 98 |
| 3 ng/mL | 123.6 ± 1.7 | 124 ± 13 | 101 |
| Experiment 2 | | | |
| Cyclic AMP buffer | 7.4 ± 0.5 | 4.5 ± 0.6 | 85 |
| K1-18 | | | |
| 0.3 ng/mL | 9.8 ± 0.4 | 6.4 ± 0.5 | 65 |
| 1 ng/mL | 16.6 ± 0.5 | 10.9 ± 0.6 | 66 |
| 3 ng/mL | 29.9 ± 0.9 | 23.2 ± 2.0 | 77 |
| 10 ng/mL | 71 ± 5 | 65.7 ± 1.3 | 92 |
| 30 ng/mL | 112 ± 3 | 80 ± 4 | 72 |
| 100 ng/mL | 121 ± 13 | 107 ± 13 | 88 |
| TSH | | | |
| 0.01 ng/mL | 8.0 ± 1.2 | 4.1 ± 0.3 | 51 |
| 0.03 ng/mL | 10.8 ± 1.4 | 5.8 ± 0.4 | 53 |
| 0.1 ng/mL | 18 ± 2 | 14.4 ± 1.1 | 79 |
| 0.3 ng/mL | 40.1 ± 0.8 | 39.6 ± 0.0 | 99 |

TABLE 34-continued

Effect of different concentrations of human monoclonal antibody to the TSHR (K1-18) and TSH on stimulation of cyclic AMP production in CHO cells expressing wild type TSHR and TSHR-JMG37 (I253R + D143P + D151E).

| Test sample | Cyclic AMP produced (pmol/mL; mean ± SD; n = 3) | | TSHR-JMG37/ Wild type (%) |
|---|---|---|---|
| | Wild type TSHR | TSHR-JMG37 | |
| 1 ng/mL | 97 ± 3 | 85 ± 5 | 88 |
| 3 ng/mL | 127 ± 10 | 93 ± 8 | 73 |

Results shown are mean ± SD of triplicate determinations.
Samples diluted in cyclic AMP buffer.
Experiment 1: For TSHR-WT: EC50(K1-18) = 13.3 ng/mL, EC50(TSH) = 0.64 ng/mL.
For TSHR-JMG37: EC50(K1-18) = 11.3 ng/mL, EC50(TSH) = 0.53 ng/mL.
Experiment 2: For TSHR-WT: EC50(K1-18) = 12.8 ng/mL, EC50(TSH) = 0.71 ng/mL.
For TSHR-JMG37: EC50(K1-18) = 11.1 ng/mL, EC50(TSH) = 0.58 ng/mL.

TABLE 35

Effect of different concentrations of human monoclonal antibody to the TSHR (K1-18) and TSH on stimulation of cyclic AMP production in CHO cells expressing wild type TSHR and TSHR-JMG45 (I253R + D143P + R112P + D151E).

| Test sample | Cyclic AMP produced (pmol/mL; mean ± SD; n = 3) | | TSHR-JMG45/ Wild type (%) |
|---|---|---|---|
| | Wild type TSHR | TSHR-JMG45 | |
| Experiment 1 | | | |
| Cyclic AMP buffer K1-18 | 6.5 ± 0.4 | 5 ± 0.3 | 84 |
| 0.3 ng/mL | 9.7 ± 0.9 | 5.5 ± 0.15 | 57 |
| 1 ng/mL | 15.2 ± 0.6 | 9.0 ± 0.7 | 59 |
| 3 ng/mL | 29 ± 3 | 27 ± 5 | 94 |
| 10 ng/mL | 79 ± 3 | 65 ± 4 | 82 |
| 30 ng/mL | 129 ± 18 | 108 ± 12 | 84 |
| 100 ng/mL | 142 ± 11 | 150 ± 11 | 106 |
| TSH | | | |
| 0.01 ng/mL | 8.3 ± 0.6 | 3.6 ± 1.0 | 43 |
| 0.03 ng/mL | 10.5 ± 0.7 | 5.8 ± 0.6 | 55 |
| 0.1 ng/mL | 24 ± 3 | 18 ± 2 | 75 |
| 0.3 ng/mL | 60 ± 4 | 58 ± 4 | 98 |
| 1 ng/mL | 117 ± 6 | 131 ± 18 | 112 |
| 3 ng/mL | 141 ± 13 | 151 ± 45 | 107 |
| Experiment 2 | | | |
| Cyclic AMP buffer K1-18 | 5.3 ± 0.5 | 4.3 ± 0.8 | 105 |
| 0.3 ng/mL | 9 ± 3 | 5.6 ± 0.4 | 64 |
| 1 ng/mL | 10.9 ± 1.0 | 10.3 ± 0.7 | 94 |
| 3 ng/mL | 25 ± 2* | 23.2 ± 1.1 | 93 |
| 10 ng/mL | 61 ± 5 | 59.9 ± 0.0 | 98 |
| 30 ng/mL | 99.9 ± 1.5 | 107 ± 11 | 107 |
| 100 ng/mL | 126 ± 10 | 125.6 ± 0.0 | 100 |
| TSH | | | |
| 0.01 ng/mL | 6.7 ± 1.7 | 4.3 ± 0.4 | 64 |
| 0.03 ng/mL | 8.1 ± 0.3 | 6.2 ± 0.4 | 77 |
| 0.1 ng/mL | 16 ± 3 | 15.4 ± 0.5 | 97 |
| 0.3 ng/mL | 38 ± 2 | 42.0 ± 0.5 | 110 |
| 1 ng/mL | 93 ± 3 | 94 ± 3 | 101 |
| 3 ng/mL | 124 ± 14 | 120 ± 5 | 97 |

Results shown are mean ± SD of triplicate determinations.
*duplicate determinations.
Samples diluted in cyclic AMP buffer.
Experiment 1: For TSHR-WT: EC50(K1-18) = 12.9 ng/mL, EC50(TSH) = 0.57 ng/mL.
For TSHR-JMG45: EC50(K1-18) = 22.5 ng/mL, EC50(TSH) = 0.63 ng/mL.
Experiment 2: For TSHR-WT: EC50(K1-18) = 17.8 ng/mL, EC50(TSH) = 0.82 ng/mL.
For TSHR-JMG45: EC50(K1-18) = 16.0 ng/mL, EC50(TSH) = 0.77 ng/mL.

TABLE 36

Effect of different concentrations of human monoclonal antibody to the TSHR (K1-18) and TSH on stimulation of cyclic AMP production in CHO cells expressing wild type TSHR and TSHR-JMG52 (I253R + D143P + R112P + D151E + V169R).

| Test sample | Cyclic AMP produced (pmol/mL; mean ± SD; n = 3) | | TSHR-JMG52/ Wild type (%) |
|---|---|---|---|
| | Wild type TSHR | TSHR-JMG52 | |
| Experiment 1 | | | |
| Cyclic AMP buffer K1-18 | 6.7 ± 1.2 | 5.05 ± 0.19 | 96 |
| 0.3 ng/mL | 9.5 ± 1.2 | 6.47 ± 0.07 | 68 |
| 1 ng/mL | 13.7 ± 0.7 | 10.1 ± 1.2 | 74 |
| 3 ng/mL | 27.6 ± 0.9 | 22.3 ± 0.7 | 81 |
| 10 ng/mL | 67 ± 5 | 53.3 ± 1.0 | 79 |
| 30 ng/mL | 115 ± 10 | 79 ± 3 | 69 |
| 100 ng/mL | 140 ± 17 | 106 ± 9 | 76 |
| TSH | | | |
| 0.01 ng/mL | 7.0 ± 0.6 | 5.3 ± 0.8 | 76 |
| 0.03 ng/mL | 9.8 ± 0.2 | 7.9 ± 0.4 | 81 |
| 0.1 ng/mL | 19 ± 2 | 17.7 ± 0.9* | 92 |
| 0.3 ng/mL | 53 ± 7 | 47.9 ± 1.4 | 91 |
| 1 ng/mL | 116 ± 9* | 85 ± 6 | 74 |
| 3 ng/mL | 142 ± 11 | 98 ± 9 | 69 |
| Experiment 2 | | | |
| Cyclic AMP buffer K1-18 | 6.0 ± 0.4 | 4.4 ± 0.4 | 81 |
| 0.3 ng/mL | 8.1 ± 0.7 | 4.9 ± 0.3 | 60 |
| 1 ng/mL | 13 ± 3 | 8.5 ± 0.6 | 64 |
| 3 ng/mL | 30 ± 7 | 16.4 ± 0.8 | 55 |
| 10 ng/mL | 52 ± 5 | 37 ± 2 | 70 |
| 30 ng/mL | 94 ± 7 | 64 ± 11 | 68 |
| 100 ng/mL | 109 ± 9 | 87 ± 6 | 80 |
| TSH | | | |
| 0.01 ng/mL | 6.8 ± 0.3 | 3.91 ± 0.07 | 58 |
| 0.03 ng/mL | 8.2 ± 0.6 | 4.1 ± 1.2 | 50 |
| 0.1 ng/mL | 14 ± 3 | 13 ± 3 | 87 |
| 0.3 ng/mL | 31 ± 6 | 25.5 ± 0.0 | 81 |
| 1 ng/mL | 70.3 ± 0.0* | 58 ± 5 | 83 |
| 3 ng/mL | 101 ± 17* | 74 ± 5 | 74 |

Results shown are mean ± SD of triplicate determinations.
*duplicate determinations.
Samples diluted in cyclic AMP buffer.
Experiment 1: For TSHR-WT: EC50(K1-18) = 17.9 ng/mL, EC50(TSH) = 0.69 ng/mL.
For TSHR-TMG52: EC50(K1-18) = 14.9 ng/mL, EC50(TSH) = 0.51 ng/mL.
Experiment 2: For TSHR-WT: EC50(K1-18) = 14.3 ng/mL, EC50(TSH) = 1.00 ng/mL.
For TSHR-JMG52: EC50(K1-18) = 19.7 ng/mL, EC50(TSH) = 0.99 ng/mL.

TABLE 37

Effect of different concentrations of human monoclonal antibody to the TSHR (K1-18) and TSH on stimulation of cyclic AMP production in CHO cells expressing wild type TSHR and TSHR-JMG55 (I253R + D143P + R112P + D151E + V169R + H63C).

| Test sample | Cyclic AMP produced (pmol/mL; mean ± SD; n = 3) | | TSHR-JMG55/ Wild type (%) |
|---|---|---|---|
| | Wild type TSHR | TSHR-JMG55 | |
| Experiment 1 | | | |
| Cyclic AMP buffer K1-18 | 3.7 ± 0.3 | 1.44 ± 0.11 | 104 |
| 0.3 ng/mL | 5.3 ± 0.9 | 3.9 ± 0.7 | 74 |
| 1 ng/mL | 9.90 ± 0.12 | 7.9 ± 0.5 | 80 |

TABLE 37-continued

Effect of different concentrations of human monoclonal antibody to the TSHR (K1-18) and TSH on stimulation of cyclic AMP production in CHO cells expressing wild type TSHR and TSHR-JMG55 (I253R + D143P + R112P + D151E + V169R + H63C).

| | Cyclic AMP produced (pmol/mL; mean ± SD; n = 3) | | TSHR-JMG55/ |
|---|---|---|---|
| Test sample | Wild type TSHR | TSHR-JMG55 | Wild type (%) |
| 3 ng/mL | 19 ± 2 | 15.1 ± 1.0 | 78 |
| 10 ng/mL | 67.8 ± 1.6 | 50 ± 3 | 74 |
| 30 ng/mL | 99 ± 15 | 73 ± 8 | 74 |
| 100 ng/mL | 111 ± 10 | 98 ± 10 | 88 |
| TSH | | | |
| 0.01 ng/mL | 4.9 ± 1.4 | 2.68 ± 0.07 | 55 |
| 0.03 ng/mL | 7.7 ± 0.9 | 5.7 ± 0.6 | 74 |
| 0.1 ng/mL | 19 ± 3 | 14.7 ± 0.6 | 77 |
| 0.3 ng/mL | 49 ± 5 | 45.0 ± 1.8 | 93 |
| 1 ng/mL | 93 ± 8 | 79 ± 11 | 84 |
| 3 ng/mL | 104 ± 19 | 91 ± 11 | 88 |
| Experiment 2 | | | |
| Cyclic AMP buffer | 3.4 ± 0.4 | 1.8 ± 0.1* | 53 |
| K1-18 | | | |
| 0.3 ng/mL | 4.9 ± 0.5 | 1.9 ± 0.2 | 40 |
| 1 ng/mL | 8.0 ± 1.4 | 3.7 ± 0.4 | 47 |
| 3 ng/mL | 18.9 ± 1.0 | 8.6 ± 0.7 | 45 |
| 10 ng/mL | 54.2 ± 13.8 | 26.8 ± 3.1 | 50 |
| 30 ng/mL | 82.6 ± 5.9 | 45.9 ± 3.3 | 55 |
| 100 ng/mL | 90.2 ± 13.1 | 66.1 ± 4.2 | 73 |
| TSH | | | |
| 0.01 ng/mL | 3.6 ± 1.3 | 2.6 ± 0.7 | 71 |
| 0.03 ng/mL | 4.9 ± 0.7 | 2.9 ± 0.8 | 60 |
| 0.1 ng/mL | 12.0 ± 0.7 | 6.6 ± 0.7 | 55 |
| 0.3 ng/mL | 33.3 ± 2.2 | 22.1 ± 4.0 | 66 |
| 1 ng/mL | 75.6 ± 8.7 | 53.2 ± 2.1 | 70 |
| 3 ng/mL | 89.8 ± 9.0 | 69.2 ± 2.5 | 77 |

Results shown are mean ± SD of triplicate determinations.
*duplicate determinations.
Samples diluted in cyclic AMP buffer.
Experiment 1: For TSHR-WT: EC50(K1-18) = 11.1 ng/mL, EC50(TSH) = 0.50 ng/mL. For TSHR-JMG55: EC50(K1-18) = 14.3 ng/mL, EC50(TSH) = 0.48 ng/mL.
Experiment 2: For TSHR-WT: EC50(K1-18) = 12.0 ng/mL, EC50(TSH) = 0.62 ng/mL. For TSHR-JMG55: EC50(K1-18) = 28.2 ng/mL, EC50(TSH) = 0.81 ng/mL.

TABLE 38

Summary of effects of mutations (relative to TSHR-WT) on stimulation of CHO cells expressing mutated full length TSHR by TSH, M22-Fab and K1-18 IgG.

| Mutant | TSH stimulation | M22-Fab stimulation | K1-18 IgG Stimulation |
|---|---|---|---|
| TSHR-JMG37 | Little change | Little change | Little change |
| TSHR-JMG45 | Little change | Small increase in EC50 (3-fold) | Little change |
| TSHR-JMG52 | Little change | Small increase in EC50 (2-fold) | Little change |
| TSHR-JMG55 | Little change | Small increase in EC50 (2-fold) | Little change |

TABLE 39a

Summary of the effects of mutations (relative to TSHR-WT) on the EC50 of M22-Fab and TSH stimulation of CHO cells expressing the mutated full length TSHR.

| | M22 Fab | | TSH | | |
|---|---|---|---|---|---|
| Sample | LogEC50 | EC50 (ng/mL) | LogEC50 | EC50 (ng/mL) | Number of assay repeats |
| WT | 0.21 ± 0.07 | 1.6 | −0.16 ± 0.14 | 0.69 | 10 |
| JMG37 | 0.23 ± 0.37 | 1.7 | −0.25 ± 0.26 | 0.56 | 2 |
| JMG45 | 0.67 ± 0.09 | 4.7 | −0.14 ± 0.09 | 0.73 | 2 |
| JMG52 | 0.54 ± 0.04 | 3.5 | −0.19 ± 0.26 | 0.65 | 2 |
| JMG55 | 0.52 ± 0.09 | 3.3 | −0.12 ± 0.13 | 0.75 | 2 |

EC50 is the concentration of ligand required to give half the maximum signalling response.
LogEC50 is shown as the mean ± SD from between 2 and 10 independent experiments.

TABLE 39b

Summary of the effects of mutations (relative to TSHR-WT) on the EC50 of K1-18 IgG and TSH stimulation of CHO cells expressing the mutated full length TSHR.

| | K1-18 IgG | | TSH | | |
|---|---|---|---|---|---|
| Sample | LogEC50 | EC50 (ng/mL) | LogEC50 | EC50 (ng/mL) | Number of assay repeats |
| WT | 1.13 ± 0.08 | 13.3 | −0.17 ± 0.09 | 0.68 | 10 |
| JMG37 | 1.045 ± 0.007 | 11.1 | −0.26 ± 0.03 | 0.55 | 2 |
| JMG45 | 1.28 ± 0.11 | 18.8 | −0.16 ± 0.06 | 0.70 | 2 |
| JMG52 | 1.23 ± 0.08 | 17.0 | −0.1 ± 0.2 | 0.71 | 2 |
| JMG55 | 1.31 ± 0.21 | 20.2 | −0.20 ± 0.16 | 0.62 | 2 |

EC50 is the concentration of ligand required to give half the maximum signalling response.
LogEC50 is shown as the mean ± SD from between 2 and 10 independent experiments.

TABLE 40

Cyclic AMP levels in CHO cells expressing wild type TSHR and TSHR-JMG45 (I253R + D143P + R112P + D151E). Effect of normal sera and patient sera on stimulation of cyclic AMP production.

| | | Stimulation (ratio to basal stimulation (NPS); mean ± SD; n = 3) | | TSHR-JMG45/ |
|---|---|---|---|---|
| | Sample | Wild type TSHR | TSHR-JMG45 | Wild type (%) |
| | cyclic AMP Buffer | 0.72 ± 0.15 | 0.56 ± 0.08 | 78 |
| | NPS | 1.00 ± 0.14 | 1.00 ± 0.12 | 100 |
| Normal Sera | NT 9916 | 0.95 ± 0.12 | 0.82 ± 0.06 | 86 |
| | NT 9918 | 1.00 ± 0.10 | 0.78 ± 0.07 | 78 |
| | NT 9924 | 0.87 ± 0.12 | 0.84 ± 0.07 | 97 |
| | NT 11746 | 1.02 ± 0.07 | 0.98 ± 0.07 | 96 |
| TRAb | F11/9573 | 12.9 ± 1.8 | 12.5 ± 0.8 | 97 |
| positive | F07/5459 | 4.2 ± 0.6 | 2.1 ± 0.06 | 50 |
| patient sera | 82 | 18 ± 3 | 29 ± 4 | 158 |
| | 92 | 11 ± 3 | 9.2 ± 0.9 | 83 |
| | 101 | 10.1 ± 1.0 | 8.8 ± 0.6 | 67 |
| | 107 | 15.7 ± 0.5 | 8.1 ± 0.4 | 52 |
| | 111 | 11.8 ± 0.9 | 10 ± 3 | 83 |

Results are expressed as a ratio to basal stimulation by NPS and are the mean ± SD of triplicate determinations.

TABLE 41

Cyclic AMP levels in CHO cells expressing wild type TSHR and TSHR-JMG52 (I253R + D143P + R112P + D151E + V169R). Effect of normal sera and patient sera on stimulation of cyclic AMP production.

| | Sample | Stimulation (ratio to basal stimulation (NPS); mean ± SD; n = 3) | | TSHR-JMG52/ Wild type (%) |
|---|---|---|---|---|
| | | Wild type TSHR | TSHR-JMG52 | |
| | cyclic AMP Buffer | 0.63 ± 0.07 | 0.63 ± 0.02 | 101 |
| | NPS | 1.00 ± 0.08 | 1.00 ± 0.05 | 100 |
| Normal Sera | NT 9916 | 0.83 ± 0.11 | 0.7 ± 0.2 | 86 |
| | NT 9918 | 0.96 ± 0.09 | 0.81 ± 0.009 | 85 |
| | NT 9924 | 0.84 ± 0.018 | 0.91 ± 0.11 | 109 |
| | NT 11746 | 0.96 ± 0.09 | 0.96 ± 0.05 | 100 |
| TRAb positive patient sera | F11/9573 | 14.5 ± 1.5 | 16.3 ± 0.4 | 112 |
| | F07/5459 | 5.1 ± 0.4 | 2.51 ± 0.08 | 49 |
| | 82 | 15.8 ± 1.3 | 30 ± 3 | 191 |
| | 92 | 11.9 ± 1.6 | 12.8 ± 0.9 | 108 |
| | 101 | 12.2 ± 1.5 | 10.3 ± 0.2 | 84 |
| | 107 | 15.3 ± 0.8 | 13 ± 0.3 | 85 |
| | 111 | 13.5 ± 1.1 | 11.5 ± 0.7 | 85 |

Results are expressed as a ratio to basal stimulation by NPS and are the mean ± SD of triplicate determinations.

TABLE 42

Analysis of the thermostabilising amino acid residues of the human TSHR compared to the equivalent TSHR amino acid residues in other mammalian TSHR sequences

| Position | hTSHR mutation | Human | Porcine | Bovine | Cat | Dog | Mouse | Rat | Sheep | Rhesus Monkey | Grivet monkey | Horse | Mutations in hTSHR-JMG55 |
|---|---|---|---|---|---|---|---|---|---|---|---|---|---|
| Cys-box-1 | P28E | P | P | P | P | P | P | P | P | P | P | P | |
| LRR2 | L59F | L | L | L | L | L | L | L | L | L | L | L | |
| LRR2 | T62V | T | T | T | T | T | T | T | T | T | T | T | |
| LRR2 | H63C | H | H | H | H | Q | H | H | H | R | R | H | * |
| LRR2 | L64Y | L | L | L | L | L | L | L | L | L | L | L | |
| LRR4 | R112P | R | R | R | R | R | R | R | R | R | R | R | * |
| LRR5 | P142I | P | P | P | P | P | P | P | P | P | P | P | |
| LRR5 | D143P | D | D | D | D | D | D | D | D | D | D | D | * |
| LRR5 | D151E | D | D | D | D | D | D | D | D | D | D | D | * |
| LRR6 | S166T | S | S | S | S | S | S | S | S | S | S | S | |
| LRR6 | I167F | I | I | I | I | I | V | V | V | I | I | I | |
| LRR6 | P168Y | P | P | P | P | P | P | P | P | P | P | P | |
| LRR6 | V169R | V | A | A | A | A | E | E | A | V | V | A | * |
| LRR6 | N170W | N | N | N | N | N | N | N | N | N | N | N | |
| LRR7 | T179C | T | T | T | T | T | T | T | T | T | T | T | |
| LRR10 | I253R | I | I | I | I | I | I | I | I | I | I | I | * |
| LRR10 | R255Y | R | R | R | R | R | K | K | R | R | R | R | |

Most of the thermostabilising mutated residues are well-conserved across TSHR from different species. The residues which differ from human TSHR are enclosed in boxes. Most of the sequence changes between homologues are to amino acids with similar properties e.g. basic, acidic, aliphatic or aromatic. Consequently, the thermostabilising mutations we have observed in human TSHR260 and human full-length TSHR are likely to be thermostabilising in the other mammalian species shown in Table 42 as well.
*The six most thermostabilising mutations that comprise the most thermostable TSHR260 mutant, JMG55, are indicated.

TABLE 43

Analysis of the thermostabilising amino acid residues of the human TSHR compared to the equivalent amino acid residues in human FSHR and human LHR

| Position | hTSHR mutation | hFSHR | hLHR | Mutations in TSHR-JMG55 |
|---|---|---|---|---|
| Cys-box-1 | P28E | H 20 | P 33 | |
| LRR2 | L59F | F 53 | L 56 | |
| LRR2 | L59F | T 56 | L 59 | |
| LRR2 | H63C | K 57 | P 60 | * |
| LRR2 | L64Y | L 58 | V 61 | |
| LRR4 | R112P | N 106 | K 109 | * |
| LRR5 | P142I | P 136 | P 139 | |
| LRR5 | D143P | D 137 | D 140 | * |
| LRR5 | D151E | Q 145 | E 148 | * |
| LRR6 | S166T | T 159 | T 163 | |
| LRR6 | I167F | I 160 | I 164 | |
| LRR6 | P168Y | E 161 | P 165 | |
| LRR6 | V169R | R 162 | G 166 | * |
| LRR6 | N170W | N 163 | N 167 | |
| LRR7 | T179C | S 172 | S 176 | |
| LRR10 | I253R | R 245 | I 249 | * |
| LRR10 | R255Y | R 247 | T 251 | |

The residues in hFSHR (SEQ ID No 57) and hLHR (SEQ ID No 58) that are identical in hTSHR (SEQ ID No 2) are in bold. In addition to these, many of the residue differences between the receptors are limited to amino acids with similar properties, e.g. basic, acidic, aliphatic or aromatic. These residues are enclosed in boxes to indicate residues where transferring the analogous thermostabilising mutations from hTSHR are likely to be thermostabilising in hFSHR and/or hLHR.
*The six most thermostabilising mutations that comprise the most thermostable TSHR260 mutant, JMG55, are indicated.

TABLE 44

Inhibition of M22-POD binding to TSHR260 mutants by patient sera

| | | TSHR260-WT | | TSHR260-JMG57 | | TSHR260-JMG58 | |
|---|---|---|---|---|---|---|---|
| Test sample | | OD450 | % Inhibition | OD450 | % Inhibition | OD450 | % Inhibition |
| Healthy blood donor sera | NT 9916 | 1.962 ± 0.156 | 12.7 | 1.523 ± 0.023 | 10.8 | 1.722 ± 0.117 | 8.0 |
| | NT 9918 | 2.359 ± 0.084 | −5.0 | 1.606 ± 0.093 | 5.9 | 1.890 ± 0.088 | −1.0 |
| | NT 11748 | 2.386 ± 0.302 | −6.2 | 1.868 ± 0.115 | −9.4 | 1.871 ± 0.090 | 0.0 |
| | NT 9924 | 2.280 ± 0.040 | −1.5 | 1.832 ± 0.077 | −7.3 | 2.003 ± 0.057 | −7.0 |
| | Mean | 2.247 ± 0.071 | 0.0 | 1.707 ± 0.037 | 0.0 | 1.872 ± 0.054 | 0.0 |
| TRAb positive patient sera | 77 | 0.165 ± 0.007 | 92.7 | 0.490 ± 0.013 | 71.3 | 0.638 ± 0.010 | 65.9 |
| | 105 | 0.225 ± 0.035 | 90.0 | 0.334 ± 0.019 | 80.4 | 0.437 ± 0.040 | 76.6 |
| | 117 | 0.069 ± 0.009 | 96.9 | 0.108 ± 0.001 | 93.7 | 0.110 ± 0.006 | 94.1 |
| | 27 | 0.085 ± 0.003 | 96.2 | 0.587 ± 0.004 | 65.6 | 0.650 ± 0.001 | 65.3 |
| | 15 | 0.621 ± 0.003 | 72.4 | 0.724 ± 0.023 | 57.6 | 0.851 ± 0.067 | 54.5 |
| | 60 | 0.092 ± 0.012 | 95.9 | 0.090 ± 0.010 | 94.7 | 0.088 ± 0.002 | 95.3 |
| | 70 | 0.078 ± 0.001 | 96.5 | 0.154 ± 0.006 | 91.0 | 0.163 ± 0.016 | 91.3 |
| | 80 | 0.166 ± 0.004 | 92.6 | 0.422 ± 0.002 | 75.3 | 0.503 ± 0.033 | 73.1 |
| | 100 | 0.382 ± 0.021 | 83.0 | 0.563 ± 0.021 | 67.0 | 0.603 ± 0.029 | 67.8 |

Results are shown as absorbance at 450 nm (mean ± SD; n = 2) and percent inhibition of M22-POD binding.

TABLE 45a

Binding of human monoclonal TSHR autoantibody M22 (diluted in a pool of healthy blood donor sera) to wild type and mutated TSHR260-AP in a bridge ELISA (FIG. 13a)

| M22 concentration | ABSORBANCE 405 nm | | | | |
|---|---|---|---|---|---|
| | WILD TYPE TSHR260-AP | TSHR260-AP-I253R | TSHR260-AP-JMG22 | TSHR260-AP-JMG37 | TSHR260-AP-JMG45 |
| 100 µg/ml | 0.913 ± 0.004 | 0.940 ± 0.042 | 1.006 ± 0.030 | 0.788

TABLE 45c-continued

Binding of human monoclonal TSHR autoantibody K1-18 (diluted in a pool of healthy blood donor sera) to wild type and mutated TSHR260-AP in a bridge ELISA (FIG. 13a)

| | | | | | |
|---|---|---|---|---|---|
| 0.1 µg/ml | 0.184 ± 0.008 | 0.230 ± 0.012 | 0.258 ± 0.007 | 0.221 ± 0.003 | 0.306 ± 0.023 |
| 0.01 µg/ml | 0.035 ± 0.008 | 0.042 ± 0.016 | 0.060 ± 0.025 | 0.037 ± 0.003 | 0.106 ± 0.031 |
| 0 µg/ml | 0.003 ± 0.003 | 0.003 ± 0.001 | 0.003 ± 0.000 | 0.007 ± 0.001 | 0.008 ± 0.000 |

| | ABSORBANCE 405 nm | | | |
|---|---|---|---|---|
| K1-18 concentration | TSHR260-AP-JMG52 | TSHR260-AP-JMG55 | TSHR260-AP-JMG57 | TSHR260-AP-JMG58 |
| 100 µg/ml | 0.962 ± 0.147 | 0.966 ± 0.002 | 0.747 ± 0.000 | 0.758 ± 0.003 |
| 10 µg/ml | 0.881 ± 0.086 | 0.860 ± 0.018 | 0.668 ± 0.006 | 0.689 ± 0.013 |
| 1 µg/ml | 0.645 ± 0.110 | 0.626 ± 0.045 | 0.551 ± 0.003 | 0.575 ± 0.006 |
| 0.1 µg/ml | 0.247 ± 0.003 | 0.260 ± 0.047 | 0.215 ± 0.001 | 0.229 ± 0.006 |
| 0.01 µg/ml | 0.046 ± 0.009 | 0.064 ± 0.003 | 0.039 ± 0.008 | 0.038 ± 0.001 |
| 0 µg/ml | 0.003 ± 0.001 | 0.017 ± 0.000 | 0.007 ± 0.002 | 0.004 ± 0.001 |

Results shown are mean absorbances at 405 nm ± SD of duplicate determinations

TABLE 45d

Binding of human monoclonal GAD autoantibody 5B3 (negative control) (diluted in a pool of healthy blood donor sera), to wild type and mutated TSHR260-AP in a bridge ELISA (FIG. 13a)

| | ABSORBANCE 405 nm | | | | |
|---|---|---|---|---|---|
| 5B3 concentration | WILD TYPE TSHR260-AP (?) | TSHR260-AP-I253R | TSHR260-AP-JMG22 | TSHR260-AP-JMG37 | TSHR260-AP-JMG45 |
| 100 µg/ml | 0.008 ± 0.008 | 0.016 ± 0.001 | 0.011 ± 0.004 | 0.005 ± 0.001 | 0.033 ± 0.01 |
| 10 µg/ml | 0.01 ± 0.01 | 0.017 ± 0.009 | 0.005 ± 0.001 | 0.003 ± 0.001 | 0.032 ± 0.006 |
| 0.01 µg/ml | 0.005 ± 0.005 | 0.006 | 0.005 | 0.004 | 0.013 |
| 0 µg/ml | 0.003 ± 0.003 | 0.003 ± 0.001 | 0.003 ± 0.000 | 0.007 ± 0.001 | 0.008 ± 0.000 |

| | ABSORBANCE 405 nm | | | |
|---|---|---|---|---|
| 5B3 concentration | TSHR260-AP-JMG52 | TSHR260-AP-JMG55 | TSHR260-AP-JMG56 | TSHR260-AP-JMG57 |
| 100 µg/ml | 0.009 ± 0.008 | 0.013 ± 0.006 | 0.012 ± 0.004 | 0.011 ± 0.002 |
| 10 µg/ml | 0.003 ± 0.0 | 0.014 ± 0.004 | 0.009 ± 0.001 | 0.005 ± 0.002 |
| 0.01 µg/ml | 0.005 | 0.0016 | 0.008 | 0.005 |
| 0 µg/ml | 0.003 ± 0.001 | 0.017 ± 0.000 | 0.007 ± 0.002 | 0.004 ± 0.001 |

Results shown are mean absorbances at 405 nm ± SD of duplicate determinations

TABLE 45e

Relative binding of M22 diluted in a pool of healthy blood donor sera) to wild type and mutated TSHR260-AP in a bridge ELISA (FIG. 13a).

| | Relative binding (%) | | | | | | | | |
|---|---|---|---|---|---|---|---|---|---|
| M22 concentration | WILD TYPE TSHR260-AP | TSHR260-AP-I253R | TSRH260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| 100 µg/ml | 100 ± 0.4 | 100 ± 4.5 | 100 ± 3.0 | 100 ± 7.2 | 100 ± 2.9 | 100 ± 0.4 | 100 ± 14 | 100 ± 0.5 | 100 ± 2.0 |
| 10 µg/ml | 90 ± 0.9 | 95 ± 1.4 | 88 ± 3.1 | 94 ± 2.0 | 93 ± 2.8 | 86 ± 5.4 | 95 ± 4.0 | 88 ± 1.2 | 90 ± 0.5 |
| 1 µg/ml | 79 ± 0.5 | 84 ± 1.7 | 79 ± 0.9 | 89 ± 2.3 | 85 ± 1.6 | 69 ± 0.7 | 78 ± 2.3 | 78 ± 2.0 | 79 ± 0.1 |
| 0.1 µg/ml | 39 ± 0.1 | 43 ± 1.7 | 41 ± 0.5 | 49 ± 0.5 | 43 ± 2.7 | 38 ± 0.6 | 41 ± 2.2 | 42 ± 0.7 | 41 ± 0.1 |
| 0.01 µg/ml | 6 ± 1.4 | 12 ± 2.2 | 13 ± 7.2 | 8 ± 1.9 | 11 ± 3.5 | 8 ± 3.3 | 19 ± 5.8 | 13 ± 0.9 | 9 ± 2.0 |
| 0 µg/ml | 0 ± 0.3 | 0 ± 0.1 | 0 ± 0.0 | 1 ± 0.1 | 1 ± 0.0 | 0 ± 0.1 | 2 ± 0.0 | 1 ± 0.3 | 1 ± 0.1 |

Results are shown as the absorbances observed with each particular TSHR260-AP construct with different concentration of M22 expressed as a percentage of the absorbances observed with 100 µg/mL M22 (Relative binding; mean ± SD, n = 2).

TABLE 45f

Relative binding of K1-70 (diluted in a pool of healthy blood donor sera) to wild type and mutated TSHR260-AP in a bridge ELISA (FIG. 13a)

| K1-70 concentration | Relative binding (%) | | | | | | | | |
|---|---|---|---|---|---|---|---|---|---|
| | WILD TYPE TSHR260-AP | TSHR260-AP-I253R | TSRH260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| 100 µg/ml | 100 ± 2.2 | 100 ± 2.9 | 100 ± 0.1 | 100 ± 0.9 | 100 ± 8.3 | 89 ± 0.7 | 100 ± 3.2 | 100 ± 4.1 | 100 ± 2.4 |
| 10 µg/ml | 100 ± 2.9 | 98 ± 2 | 90 ± 1.5 | 96 ± 0.9 | 87 ± 1.9 | 100 ± 0.6 | 89 ± 2.7 | 93 ± 0.8 | 93 ± 0.5 |
| 1 µg/ml | 86 ± 0.1 | 83 ± 2 | 77 ± 4.6 | 85 ± 2.7 | 77 ± 7.5 | 81 ± 7.7 | 82 ± 6.9 | 81 ± 0.8 | 79 ± 0.7 |
| 0.1 µg/ml | 35 ± 3.5 | 37 ± 4.8 | 32 ± 1.6 | 39 ± 0 | 33 ± 1.6 | 32 ± 5.7 | 34 ± 4.9 | 41 ± 0.7 | 39 ± 0.1 |
| 0.01 µg/ml | 6 ± 2.2 | 15 ± 3.1 | 11 ± 1.4 | 9 ± 4.9 | 15 ± 6.3 | 6 ± 1.4 | 15 ± 6.8 | 9 ± 0.8 | 7 ± 0.3 |
| 0 µg/ml | 0 ± 0.4 | 0 ± 0.1 | 0 ± 0.0 | 1 ± 0.1 | 1 ± 0.0 | 0 ± 0.1 | 2 ± 0.0 | 1 ± 0.3 | 1 ± 0.1 |

Results are shown as the absorbances observed with each particular TSHR260-AP construct with different concentration of K1-70 expressed as a percentage of the absorbances observed with 100 ug/mL K1-70 (Relative binding; mean ± SD, n = 2).

TABLE 45g

Relative binding of K1-18 (diluted in a pool of healthy blood donor sera) to wild type and mutated TSHR260-AP in a bridge ELISA (FIG.13a)

| K1-18 concentration | Relative binding (%) | | | | | | | | |
|---|---|---|---|---|---|---|---|---|---|
| | WILD TYPE TSHR260-AP | TSHR260-AP-I253R | TSRH260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| 100 µg/ml | 100 ± 3.3 | 100 ± 13 | 100 ± 0.6 | 100 ± 4.2 | 100 ± 2.7 | 100 ± 15 | 100 ± 0.2 | 100 ± 0 | 100 ± 0.4 |
| 10 µg/ml | 89 ± 2.4 | 105 ± 3.1 | 93 ± 2.8 | 87 ± 2 | 93 ± 2.8 | 92 ± 8.9 | 89 ± 1.9 | 89 ± 0.8 | 91 ± 1.7 |
| 1 µg/ml | 74 ± 0.2 | 83 ± 0.9 | 71 ± 2.6 | 74 ± 1.6 | 66 ± 0.4 | 67 ± 11 | 65 ± 4.7 | 74 ± 0.4 | 76 ± 0.8 |
| 0.1 µg/ml | 28 ± 1.2 | 36 ± 1.9 | 29 ± 0.8 | 32 ± 0.4 | 31 ± 2.3 | 26 ± 0.3 | 27 ± 4.9 | 29 ± 0.1 | 30 ± 0.8 |
| 0.01 µg/ml | 5 ± 1.2 | 7 ± 2.5 | 7 ± 2.8 | 5 ± 0.4 | 11 ± 3.1 | 5 ± 0.9 | 7 ± 0.3 | 5 ± 1.1 | 5 ± 0.1 |
| 0 µg/ml | 0 ± 0.5 | 0 ± 0.2 | 0 ± 0.0 | 1 ± 0.1 | 1 ± 0.1 | 0 ± 0.1 | 2 ± 0.0 | 1 ± 0.3 | 1 ± 0.1 |

Results are shown as the absorbances observed with each particular TSHR260-AP construct with different concentration of K1-18 expressed as a percentage of the absorbances observed with 100 µg/mL K1-18 (Relative binding; mean ± SD, n = 2).

TABLE 46a

Binding of human monoclonal TSHR autoantibody M22 (diluted in assay buffer), to wild type and mutated TSR260-AP in a bridge ELISA (FIG. 13a)

| M22 concentration | ABSORBANCE 405 nm | | | | | | | | |
|---|---|---|---|---|---|---|---|---|---|
| | WILD TYPE TSHR260-AP | TSHR260-AP-I253R | TSHR260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| 100 µg/ml | 0.915 ± 0.698 | 0.883 ± 0.028 | 0.977 ± 0.018 | 0.715 ± 0.025 | 1.205 ± 0.138 | 1.136 ± 0.016 | 0.977 ± 0.034 | 1.052 ± 0.011 | 1.086 ± 0.014 |
| 10 µg/ml | 0.779 ± 0.073 | 0.848 ± 0.005 | 0.862 ± 0.074 | 0.703 ± 0.004 | 1.043 ± 0.012 | 1.003 ± 0.056 | 0.872 ± 0.037 | 0.851 ± 0.004 | 0.897 ± 0.001 |
| 1 µg/ml | 0.660 ± 0.055 | 0.766 ± 0.052 | 0.792 ± 0.026 | 0.740 ± 0.022 | 0.928 ± 0.018 | 0.925 ± 0.01 | 0.786 ± 0.016 | 0.748 ± 0.012 | 0.777 ± 0.001 |
| 0.1 µg/ml | 0.436 ± 0.053 | 0.522 ± 0.019 | 0.536 ± 0.006 | 0.516 ± 0.002 | 0.603 ± 0.007 | 0.619 ± 0.001 | 0.510 ± 0.013 | 0.488 ± 0.002 | 0.509 ± 0.006 |
| 0.01 µg/ml | 0.105 ± 0.018 | 0.114 ± 0.08 | 0.135 ± 0.066 | 0.143 ± 0.004 | 0.098 ± 0.024 | 0.082 ± 0.001 | 0.133 ± 0.029 | 0.105 ± 0.059 | 0.110 ± 0.056 |
| 0 µg/ml | 0.003 ± 0.002 | 0.003 ± 0.001 | 0.005 ± 0.002 | 0.003 ± 0.001 | 0.012 ± 0.001 | 0.009 ± 0.004 | 0.021 ± 0.000 | 0.006 ± 0.001 | 0.005 ± 0.002 |

Results shown are mean absorbances at 405 nm ± SD of duplicate determinations

TABLE 46b

Binding of human monoclonal TSHR autoantibody K1-70 (diluted in assay buffer), to wild type and mutated TSHR260-AP in a bridge ELISA (FIG.13a)

| K1-70 concentration | ABSORBANCE 405nm | | | | | | | | |
|---|---|---|---|---|---|---|---|---|---|
| | WILD TYPE TSHR260-AP | TSHR260-AP-I253R | TSHR260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| 100 µg/ml | 0.843 ± 0.0435 | 0.908 ± 0.057 | 1.266 ± 0.017 | 0.672 ± 0.008 | 1.709 ± 0.037 | 1.703 ± 0.092 | 1.544 ± 0.011 | 1.146 ± 0.001 | 1.206 ± 0.020 |
| 10 µg/ml | 0.710 ± 0.0565 | 0.834 ± 0.021 | 0.980 ± 0.029 | 0.671 ± 0.052 | 1.159 ± 0.00 | 1.255 ± 0.059 | 1.123 ± 0.007 | 0.920 ± 0.001 | 0.953 ± 0.008 |
| 1 µg/ml | 0.613 ± 0.0266 | 0.732 ± 0.011 | 0.849 ± 0.006 | 0.651 ± 0.013 | 0.945 ± 0.002 | 1.084 ± 0.003 | 0.872 ± 0.072 | 0.756 ± 0.006 | 0.780 ± 0.018 |
| 0.1 µg/ml | 0.382 ± 0.0317 | 0.392 ± 0.002 | 0.468 ± 0.016 | 0.373 ± 0.003 | 0.561 ± 0.023 | 0.640 ± 0.053 | 0.598 ± 0.017 | 0.513 ± 0.007 | 0.542 ± 0.001 |

TABLE 46b-continued

Binding of human monoclonal TSHR autoantibody K1-70 (diluted in assay buffer), to wild type and mutated TSHR260-AP in a bridge ELISA (FIG.13a)

| K1-70 concentration | ABSORBANCE 405nm | | | | | | | | |
|---|---|---|---|---|---|---|---|---|---|
| | WILD TYPE TSHR260-AP | TSHR260-AP-I253R | TSHR260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| 0.01 µg/ml | 0.081 ± 0.0286 | 0.109 ± 0.021 | 0.168 ± 0.037 | 0.082 ± 0.042 | 0.079 ± 0.005 | 0.088 ± 0.021 | 0.156 ± 0.013 | 0.101 ± 0.004 | 0.097 ± 0.002 |
| 0 µg/ml | 0.003 ± 0.002 | 0.003 ± 0.001 | 0.005 ± 0.002 | 0.003 ± 0.001 | 0.012 ± 0.001 | 0.009 ± 0.004 | 0.021 ± 0.00 | 0.006 ± 0.001 | 0.005 ± 0.002 |

Results shown are mean absorbances at 405 nm ± SD of duplicate determinations

TABLE 46c

Binding of human monoclonal TSHR autoantibody K1-18 (diluted in assay buffer), to wild type and mutated TSHR260-AP in a bridge ELISA (FIG. 13a)

| K1-18 concentration | ABSORBANCE 405 nm | | | | | | | | |
|---|---|---|---|---|---|---|---|---|---|
| | WILD TYPE TSHR260-AP | TSHR260-AP-I253R | TSHR260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| 100 µg/ml | 0.748 ± 0.0675 | 0.757 ± 0.036 | 1.061 ± 0.004 | 0.739 ± 0.028 | 1.474 ± 0.021 | 1.422 ± 0.021 | 1.335 ± 0.103 | 1.040 ± 0.007 | 1.074 ± 0.011 |
| 10 µg/ml | 0.618 ± 0.0107 | 0.718 ± 0.02 | 0.856 ± 0.022 | 0.673 ± 0.023 | 1030 ± 0.007 | 1085 ± 0.025 | 0.970 ± 0.073 | 0.843 ± 0.002 | 0.862 ± 0.015 |
| 1 µg/ml | 0.494 ± 0.0122 | 0.581 ± 0.038 | 0.637 ± 0.024 | 0.552 ± 0.043 | 0.810 ± 0.011 | 0.820 ± 0.001 | 0.778 ± 0.067 | 0.709 ± 0.006 | 0.746 ± 0.005 |
| 0.1 µg/ml | 0.265 ± 0.004 | 0.305 ± 0.023 | 0.325 ± 0.00 | 0.346 ± 0.00 | 0.447 ± 0.015 | 0.445 ± 0.006 | 0.380 ± 0.035 | 0.378 ± 0.001 | 0.401 ± 0.001 |
| 0.01 µg/ml | 0.0428 ± 0.012 | 0.079 ± 0.028 | 0.058 ± 0.011 | 0.065 ± 0.012 | 0.108 ± 0.040 | 0.067 ± 0.006 | 0.072 ± 0.01 | 0.074 ± 0.007 | 0.094 ± 0.025 |
| 0 µg/ml | 0.003 ± 0.002 | 0.003 ± 0.001 | 0.005 ± 0.002 | 0.003 ± 0.001 | 0.012 ± 0.001 | 0.009 ± 0.004 | 0.021 ± 0.000 | 0.006 ± 0.001 | 0,005 ± 0.002 |

Results shown are mean absorbances at 405 nm ± SD of duplicate determinations

TABLE 46d

Binding of human monoclonal GAD autoantibody 5B3 IgG (negative control) (diluted in assay buffer), to wild type and mutated TSHR260-AP in a bridge ELISA (FIG. 13a)

| 5B3 concentration | ABSORBANCE 405 nm | | | | | | | | |
|---|---|---|---|---|---|---|---|---|---|
| | WILD TYPE TSHR260-AP | TSHR260-AP-I253R | TSHR260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| 100 µg/ml | 0.008 ± 0.005 | 0.023 ± 0.001 | 0.016 ± 0.001 | 0.005 ± 0.001 | 0.034 ± 0.001 | 0.013 ± 0.007 | 0.018 ± 0.001 | 0.014 ± 0.002 | 0.011 ± 0.001 |
| 10 µg/ml | 0.003 ± 0.005 | 0.014 ± 0.001 | 0.006 ± 0.001 | 0.001 ± 0.00 | 0.017 ± 0.001 | 0.007 ± 0.001 | 0.019 ± 0.001 | 0.013 ± 0.004 | 0.009 ± 0.003 |
| 0.01 µg/ml | 0.004 | 0.01 | 0.004 | 0.001 | 0.012 | 0.004 | 0.026 | 0.006 | 0.006 |
| 0 µg/ml | 0.003 ± 0.002 | 0.003 ± 0.001 | 0.005 ± 0.002 | 0.003 ± 0.001 | 0.012 ± 0.001 | 0.009 ± 0.004 | 0.021 ± 0.000 | 0.006 ± 0.001 | 0.005 ± 0.002 |

Results shown are mean absorbances at 405 nm ± SD of duplicate determinations

TABLE 46e

Relative binding of M22 (diluted in assay buffer), to wild type and mutated TSHR260-AP in a bridge ELISA (FIG. 13a)

| M22 concentration | Relative binding (%) | | | | | | | | |
|---|---|---|---|---|---|---|---|---|---|
| | WILD TYPE TSHR260-AP | TSHR260-AP-I253R | TSRH260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| 100 µg/ml | 100 ± 7.6 | 100 ± 3.2 | 100 ± 1.8 | 97 ± 3.5 | 100 ± 12 | 100 ± 1.4 | 100 ± 3.5 | 100 ± 1 | 100 ± 1.3 |
| 10 µg/ml | 85 ± 8.1 | 96 ± 0.6 | 88 ± 7.6 | 95 ± 0.6 | 87 ± 1 | 88 ± 4.9 | 89 ± 3.8 | 81 ± 0.4 | 83 ± 0.1 |
| 1 µg/ml | 72 ± 6.1 | 87 ± 5.9 | 81 ± 2.7 | 100 ± 3.1 | 77 ± 1.5 | 81 ± 0.9 | 80 ± 1.6 | 71 ± 1.1 | 72 ± 0.1 |
| 0.1 µg/ml | 48 ± 5.8 | 59 ± 2.2 | 55 ± 0.6 | 70 ± 0.3 | 50 ± 0.6 | 54 ± 0.1 | 52 ± 1.3 | 46 ± 0.2 | 47 ± 0.6 |
| 0.01 µg/ml | 11 ± 2 | 13 ± 9.1 | 14 ± 6.8 | 19 ± 0.6 | 8 ± 2 | 7 ± 0.1 | 14 ± 3 | 10 ± 5.6 | 10 ± 5.2 |
| 0 µg/ml | 0 ± 0.3 | 0 ± 0.1 | 1 ± 0.2 | 0 ± 0.1 | 1 ± 0.1 | 1 ± 0.4 | 2 ± 0.0 | 1 ± 0.1 | 0 ± 0.2 |

Results are shown as the absorbances observed with each particular TSHR260-AP construct with different concentration of M22 expressed as a percentage of the absorbances observed with 100 g/mL M22 (Relative binding; mean ± SD, n = 2).

TABLE 46f

Relative binding of K1-70 (diluted in assay buffer), to wild type and mutated TSHR260-AP in a bridge ELISA (FIG. 13a)

| K1-70 concentration | Relative binding (%) | | | | | | | | |
|---|---|---|---|---|---|---|---|---|---|
| | WILD TYPE TSHR260-AP | TSHR260-AP-I253R | TSRH260-AP-JMG22 | TSHR260-AP-JMG37 | TSHR260-AP-JMG45 | TSHR260-AP-JMG52 | TSHR260-AP-JMG55 | TSHR260-AP-JMG57 | TSH R260-AP-JMG58 |
| 100 µg/ml | 100 ± 5.2 | 100 ± 6.3 | 100 ± 1.3 | 100 ± 1.2 | 100 ± 2.2 | 100 ± 5.4 | 100 ± 0.7 | 100 ± 0.1 | 100 ± 1.7 |
| 10 µg/ml | 84 ± 6.7 | 92 ± 2.3 | 77 ± 2.3 | 100 ± 7.7 | 68 ± 0 | 74 ± 3.5 | 73 ± 0.5 | 80 ± 0.1 | 79 ± 0.7 |
| 1 µg/ml | 73 ± 3.2 | 81 ± 1.2 | 67 ± 0.5 | 97 ± 1.9 | 55 ± 0.1 | 64 ± 0.2 | 56 ± 4.7 | 66 ± 0.5 | 65 ± 1.5 |
| 0.1 µg/ml | 45 ± 3.8 | 43 ± 0.2 | 37 ± 1.3 | 56 ± 0.4 | 33 ± 13 | 38 ± 3.1 | 39 ± 11 | 45 ± 0.6 | 45 ± 0.1 |
| 0.01 µg/ml | 10 ± 3.4 | 12 ± 2.3 | 13 ± 2.9 | 12 ± 6.3 | 5 ± 03 | 5 ± 1.2 | 10 ± 0.8 | 9 ± 0.3 | 8 ± 0.2 |
| 0 µg/ml | 0 ± 0.3 | 0 ± 0.1 | 0 ± 0.2 | 0 ± 0.1 | 1 ± 0.1 | 1 ± 0.2 | 1 ± 0.0 | 1 ± 0.1 | 0 ± 0.2 |

Results are shown as the absorbances observed with each particular TSHR260-AP construct with different concentration of K1-70 expressed as a percentage of the absorbances observed with 100 µg/mL K1-70 (Relative binding; mean ± SD, n = 2).

TABLE 46g

Relative binding of K1-18 (diluted in assay buffer), to wild type and mutated TSHR260-AP in a bridge ELISA (FIG. 13a)

| K1-18 concentration | Relative binding (%) | | | | | | | | |
|---|---|---|---|---|---|---|---|---|---|
| | WILD TYPE TSHR260-AP | TSHR260-AP-I253R | TSRH260-AP-JMG22 | TSHR260-AP-JMG37 | TSHR260-AP-JMG45 | TSHR260-AP-JMG52 | TSHR260-AP-JMG55 | TSHR260-AP-JMG57 | TSH R260-AP-JMG58 |
| 100 µg/ml | 100 ± 9 | 100 ± 4.8 | 100 ± 0.4 | 100 ± 3.8 | 100 ± 1.4 | 100 ± 1.5 | 100 ± 7.7 | 100 ± 0.7 | 100 ± 1 |
| 10 µg/ml | 83 ± 1.4 | 95 ± 2.6 | 81 ± 2.1 | 91 ± 3.1 | 70 ± 0.5 | 76 ± 1.8 | 99 ± 7.5 | 81 ± 0.2 | 80 ± 1.3 |
| 1 µg/ml | 66 ± 1.6 | 77 ± 5 | 60 ± 2.3 | 75 ± 5.8 | 55 ± 0.7 | 58 ± 0.1 | 80 ± 6.9 | 68 ± 0.6 | 69 ± 0.5 |
| 0.1 µg/ml | 35 ± 0.5 | 40 ± 3 | 31 ± 0 | 47 ± 0 | 30 ± 1 | 32 ± 0.4 | 39 ± 3.6 | 36 ± 0.1 | 37 ± 0.1 |
| 0.01 µg/ml | 6 ± 15 | 10 ± 37 | 5 ± 1 | 9 ± 1.6 | 7 ± 2.7 | 5 ± 0.4 | 7 ± 1 | 7 ± 0.7 | 9 ± 2.3 |
| 0 µg/ml | 0 ± 0.3 | 0 ± 0.1 | 0 ± 0.2 | 0 ± 0.1 | 1 ± 01 | 1 ± 0.3 | 2 ± 0.0 | 1 ± 0.1 | 0 ± 0.2 |

Results are shown as the absorbances observed with each particular TSHR260-AP construct with different concentration of K1-18 expressed as a percentage of the absorbances observed with 100 µg/mL K1-18 (Relative binding; mean ± SD, n = 2).

TABLE 47a

Binding of TRAb positive patient sera (G1-G12) and healthy blood donor sera (N1-N11) to wild type and mutated TSHR260-AP in a bridge ELISA (FIG.13a)

| Test Sample | Absorbance 405 nm | | | | | | | | |
|---|---|---|---|---|---|---|---|---|---|
| | WILD TYPE TSHR260-AP | TSHR260-AP-I253R | TSHR260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| Healthy blood donor sera pool | 0.007 ± 0.001 | 0.007 ± 0.003 | 0.007 ± 0.001 | 0.002 ± 0.001 | 0.009 ± 0.002 | 0.005 ± 0.00 | 0.015 ± 0.001 | 0.002 ± 0.003 | 0.005 ± 0.001 |
| K1-70 IgG 0.003 µg/ml | 0.017 ± 0.002 | 0.016 ± 0.004 | 0.019 ± 0.003 | 0.019 ± 0.003 | 0.019 ± 0.001 | 0.014 ± 0.004 | 0.025 ± 0.003 | 0.019 ± 0.005 | 0.018 ± 0.001 |
| K1-70 IgG 0.01 µg/ml | 0.038 ± 0.007 | 0.041 ± 0.003 | 0.045 ± 0.001 | 0.051 ± 0.004 | 0.041 ± 0.00 | 0.036 ± 0.004 | 0.049 ± 0.009 | 0.050 ± 0.002 | 0.046 ± 0.001 |
| K1-70 IgG 0.03 µg/ml | 0.108 ± 0.021 | 0.097 ± 0.021 | 0.122 ± 0.01 | 0.147 ± 0.001 | 0.105 ± 0.014 | 0.110 ± 0.004 | 0.105 ± 0.012 | 0.123 ± 0.001 | 0.122 ± 0.003 |
| K1-70 IgG 0.01 µg/ml | 0.320 ± 0.077 | 0.354 ± 0.005 | 0.391 ± 0.018 | 0.464 ± 0.003 | 0.282 ± 0.006 | 0.316 ± 0.001 | 0.317 ± 0.004 | 0.319 ± 0.002 | 0.318 ± 0.004 |
| K1-70 IgG 0.3 ug/ml | 0.587 ± 0.063 | 0.641 ± 0.002 | 0.663 ± 0.018 | 0.792 ± 0.021 | 0.572 ± 0.003 | 0.662 ± 0.02 | 0.623 ± 0.011 | 0.496 ± 0.004 | 0.499 ± 0.004 |
| K1-70 IgG 1 µg/ml | 0.779 ± 0.011 | 0.768 ± 0.011 | 0.798 ± 0.024 | 0.943 ± 0.016 | 0.867 ± 0.005 | 0.940 ± 0.01 | 0.979 ± 0.009 | 0.576 ± 0.020 | 0.570 ± 0.011 |
| G1 | 0.291 ± 0.005 | 0.327 ± 0.016 | 0.356 ± 0.001 | 0.378 ± 0.013 | 0.322 ± 0.006 | 0.363 ± 0.023 | 0.288 ± 0.026 | 0.266 ± 0.005 | 0.274 ± 0.003 |
| G2 | 0.265 ± 0.003 | 0.265 ± 0.0 | 0.333 ± 0.013 | 0.373 ± 0.013 | 0.354 ± 0.014 | 0.363 ± 0.029 | 0.358 ± 0.001 | | |

TABLE 47a-continued

Binding of TRAb positive patient sera (G1-G12) and healthy blood donor sera (N1-N11) to wild type and mutated TSHR260-AP in a bridge ELISA (FIG.13a)

| | Absorbance 405 nm | | | | | | | | |
|---|---|---|---|---|---|---|---|---|---|
| Test Sample | WILD TYPE TSHR260-AP | TSHR260-AP-I253R | TSHR260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| G3 | 0.281 ± 0.014 | 0.249 ± 0.021 | 0.310 ± 0.012 | 0.363 ± 0.013 | 0.323 ± 0.021 | 0.351 ± 0.008 | 0.311 ± 0.006 | 0.247 ± 0.000 | 0.255 ± 0.003 |
| G4 | 0.095 ± 0.011 | 0.105 ± 0.009 | 0.127 ± 0.006 | 0.145 ± 0.002 | 0.123 ± 0.005 | 0.129 ± 0.006 | 0.117 ± 0.008 | — | — |
| G5 | 0.072 ± 0.006 | 0.075 ± 0.006 | 0.090 ± 0.008 | 0.096 ± 0.004 | 0.085 ± 0.001 | 0.088 ± 0.004 | 0.075 ± 0.001 | — | — |
| G6 | 0.179 ± 0.006 | 0.192 ± 0.004 | 0.209 ± 0.002 | 0.249 ± 0.001 | 0.213 ± 0.013 | 0.228 ± 0.009 | 0.184 ± 0.025 | — | — |
| G7 | 0.064 ± 0.007 | 0.054 ± 0.009 | 0.066 ± 0.012 | 0.070 ± 0.003 | 0.063 ± 0.00 | 0.070 ± 0.004 | 0.077 ± 0.011 | — | — |
| G8 | 0.149 ± 0.009 | 0.137 ± 0.005 | 0.153 ± 0.009 | 0.183 ± 0.004 | 0.150 ± 0.006 | 0.167 ± 0.008 | 0.161 ± 0.009 | 0.137 ± 0.000 | 0.137 ± 0.004 |
| G9 | 0.181 ± 0.006 | 0.203 ± 0.013 | 0.219 ± 0.007 | 0.220 ± 0.018 | 0.198 ± 0.011 | 0.207 ± 0.0 | 0.184 ± 0.016 | 0.151 ± 0.004 | 0.154 ± 0.003 |
| G10 | 0.372 ± 0.007 | 0.366 ± 0.034 | 0.408 ± 0.021 | 0.477 ± 0.019 | 0.439 ± 0.002 | 0.465 ± 0.035 | 0.418 ± 0.012 | 0.371 ± 0.000 | 0.326 ± 0.001 |
| G11 | 0.170 ± 0.001 | — | — | — | — | — | — | 0.160 ± 0.002 | 0.169 ± 0.005 |
| G12 | 0.339 ± 0.004 | — | — | — | — | — | — | 0.371 ± 0.000 | 0.378 ± 0.001 |
| N1 | 0.015 ± 0.003 | 0.01 ± 0.0 | 0.012 ± 0.005 | 0.005 ± 0.0 | 0.009 ± 0.001 | 0.014 ± 0.001 | 0.017 ± 0.004 | — | — |
| N2 | 0.009 ± 0.002 | 0.007 ± 0.001 | 0.01 ± 0.004 | 0.004 ± 0.007 | 0.008 ± 0.002 | 0.009 ± 0.004 | 0.015 ± 0.003 | — | — |
| N3 | 0.008 ± 0.002 | 0.007 ± 0.004 | 0.008 ± 0.001 | 0.003 ± 0.003 | 0.005 ± 0.00 | 0.009 ± 0.003 | 0.016 ± 0.003 | — | — |
| N4 | 0.006 ± 0.001 | 0.006 ± 0.001 | 0.007 ± 0.007 | 0.00 ± 0.00 | 0.007 ± 0.001 | 0.005 ± 0.001 | 0.013 ± 0.001 | — | — |
| N5 | 0.024 ± 0.005 | 0.006 ± 0.002 | 0.006 ± 0.001 | 0.01 ± 0.001 | 0.013 ± 0.001 | 0.008 ± 0.001 | 0.013 ± 0.001 | — | — |
| N6 | 0.007 ± 0.001 | 0.004 ± 0.001 | 0.005 ± 0.0 | 0.002 ± 0.004 | 0.006 ± 0.0 | 0.005 ± 0.001 | 0.014 ± 0.005 | 0.003 ± 0.002 | 0.006 ± 0.005 |
| N7 | 0.005 ± 0.000 | — | — | — | — | — | — | 0.003 ± 0.002 | 0.005 ± 0.0 |
| N8 | 0.007 ± 0.001 | — | — | — | — | — | — | 0.006 ± 0.004 | 0.007 ± 0.001 |
| N9 | 0.004 ± 0.001 | — | — | — | — | — | — | 0.003 ± 0.001 | 0.004 ± 0.001 |
| N10 | 0.011 ± 0.002 | — | — | — | — | — | — | 0.008 ± 0.004 | 0.011 ± 0.002 |
| N11 | 0.014 ± 0.001 | — | — | — | — | — | — | 0.005 ± 0.001 | 0.014 ± 0.001 |

Results shown are mean absorbances at 405 nm ± SD of duplicate determinations

TABLE 47b

TRAb concentration of sera shown in Table 47a (G1-G17 and N1-N11) calculated from the K1-70 calibration curve for wild type and mutated TSHR260-AP in the bridge ELISA (FIG. 13a)

| | TRAb concentration (µg/mL mean ± SD; n ± 2) calculated from the K1-70 standard curve | | | | | | | | |
|---|---|---|---|---|---|---|---|---|---|
| Test Sample | WILD TYPE TSHR260-AP | TSHR260-AP-I253R | TSHR260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| Healthy blood donor serum pool | <0.003 | <0.003 | <0.003 | <0.003 | <0.003 | <0.003 | <0.003 | <0.003 | <0.003 |
| G1 | 0.093 ± 0.029 | 0.091 ± 0.005 | 0.088 ± 0.0 | 0.076 ± 0.003 | 0.118 ± 0.009 | 0.118 ± 0.009 | 0.089 ± 0.01 | 0.075 ± 0.002 | 0.079 ± 0.001 |
| G2 | 0.083 ± 0.025 | 0.071 ± 0.0 | 0.081 ± 0.004 | 0.075 ± 0.003 | 0.135 ± 0.007 | 0.118 ± 0.012 | 0.118 ± 0.001 | — | — |
| G3 | 0.088 ± 0.023 | 0.067 ± 0.006 | 0.074 ± 0.003 | 0.073 ± 0.003 | 0.119 ± 0.006 | 0.113 ± 0.003 | 0.098 ± 0.003 | 0.068 ± 0.000 | 0.071 ± 0.001 |
| G4 | 0.027 ± 0.002 | 0.032 ± 0.002 | 0.031 ± 0.001 | 0.030 ± 0 | 0.036 ± 0.002 | 0.036 ± 0.002 | 0.033 ± 0.002 | — | — |
| G5 | 0.020 ± 0.002 | 0.024 ± 0.001 | 0023 ± 0.002 | 0.020 ± 0.001 | 0.024 ± 0.0 | 0.024 ± 0.001 | 0.021 ± 0.0 | — | — |
| G6 | 0.053 ± 0.014 | 0.052 ± 0.001 | 0.048 ± 0.0 | 0.048 ± 0.0 | 0.070 ± 0.005 | 0.068 ± 0.003 | 0.053 ± 0.008 | — | — |
| G7 | 0.018 ± 0.001 | 0.017 ± 0.004 | 0.017 ± 0.003 | 0.015 ± 0.001 | 0.017 ± 0.0 | 0.019 ± 0.001 | 0.021 ± 0.004 | — | — |
| G8 | 0.044 ± 0.008 | 0,039 ± 0.001 | 0.036 ± 0.002 | 0.036 ± 0.001 | 0.046 ± 0.002 | 0.048 ± 0.003 | 0.046 ± 0.003 | 0.034 ± 0.000 | 0.034 ± 0.001 |
| G9 | 0.054 ± 0.014 | 0.055 ± 0.003 | 0.051 ± 0.002 | 0.043 ± 0.003 | 0.064 ± 0.004 | 0.061 ± 0.0 | 0.053 ± 0.005 | 0.038 ± 0.001 | 0.038 ± 0.001 |
| G10 | 0.129 ± 0.041 | 0.105 ± 0.013 | 0.106 ± 0.008 | 0.104 ± 0.006 | 0.185 ± 0.001 | 0.163 ± 0.018 | 0.148 ± 0.006 | 0.110 ± 0.005 | 0.104 ± 0.001 |
| G11 | 0.036 ± 0.00 | — | — | — | — | — | — | 0.040 ± 0.001 | 0.043 ± 0.001 |
| G12 | 0.085 ± 0.001 | — | — | — | — | — | — | 0.133 ± 0.000 | 0.137 ± 0.001 |
| N1 | <0.003 | <0.003 | <0.003 | <0.003 | <0.003 | <0.003 | <0.003 | — | — |
| N2 | <0.003 | <0.003 | <0.003 | <0.003 | <0.003 | <0.003 | <0.003 | — | — |
| N3 | <0.003 | <0.003 | <0.003 | <0.003 | <0.003 | <0.003 | <0.003 | — | — |
| N4 | <0.003 | <0.003 | <0.003 | <0.003 | <0.003 | <0.003 | <0.003 | — | — |
| N5 | 0.006 ± 0.001 | <0.003 | <0.003 | <0.003 | <0.003 | <0.003 | <0.003 | — | — |
| N6 | <0.003 | <0.003 | <0.003 | <0.003 | <0.003 | <0.003 | <0.003 | <0.003 | <0.003 |
| N7 | <0.003 | — | — | — | — | — | — | <0.003 | <0.003 |
| N8 | <0.003 | — | — | — | — | — | — | <0.003 | <0.003 |
| N9 | <0.003 | — | — | — | — | — | — | <0.003 | <0.003 |
| N10 | <0.003 | — | — | — | — | — | — | <0.003 | <0.003 |
| N11 | <0.003 | — | — | — | — | — | — | <0.003 | <0.003 |

Results below the lowest K1-70 standard (0.003 µg/ml) are not attributed a value and are shown as <0.003 µg/ml.

TABLE 47c

Pearson correlation (r-value) of calculated TRAb IgG concentration for TRAb positive (G1-G11) and TRAb negative (N1-N11) sera tested in TSHR260-AP mutants compared to the average concentration of the sera determined using wild type TSHR260-AP

| | r-value of sera tested in TSHR260-AP mutant bridge ELISA compared to average wild type TSHR260-AP | | | | | | | |
|---|---|---|---|---|---|---|---|---|
| | TSHR260-AP-I253R | TSHR260-AP-JMG22 | TSHR260-AP-JMG37 | TSHR260-AP-JMG45 | TSHR260-AP-JMG52 | TSHR260-AP-JMG55 | TSHR260-AP-JMG57 | TSHR260-AP-JMG58 |
| ALL SERA | 0.988 | 0.993 | 0.996 | 0.992 | 0.996 | 0.985 | 0.970 | 0.990 |
| TRAb POSITIVE SERA ONLY | 0.980 | 0.989 | 0.994 | 0.987 | 0.994 | 0.971 | 0.952 | 0.986 |

TABLE 48

Thermostability of TSHR260-AP mutants at different temperatures and predicted stability ratio compared to wild type TSHR260-AP (FIG. 13b)

| | 50° C. | | 60° C. | | 65° C. | | |
|---|---|---|---|---|---|---|---|
| Mutant name | $t_{1/2}$ (min) | RATIO TO WILD TYPE | $t_{1/2}$ (min) | RATIO TO TSHR260-AP-JMG22 | $t_{1/2}$ (min) | RATIO TO TSHR260-AP-JMG45 | Predicted stability ratio to TSHR260-AP-WT |
| TSHR260-AP WILD TYPE | 4.13 | 1.0 | — | — | — | — | 1 |
| TSHR260-AP-JMG22 | 44.55 | 10.8 | 1.28 | 1.0 | — | — | ~11 |
| TSHR260-AP-JMG45 | — | — | 7.76 | 6.1 | 1.72 | 1.0 | ~66 |
| TSHR260-AP-JMG55 | — | — | 20.06 | 15.7 | 4.34 | 2.5 | ~165 |

Half lives ($t_{1/2}$) were calculated by fitting an exponential curve to the time course data (0 h-3 h) for each TSHR260-AP construct at each temperature, (duplicate measurements). Predicted stability ratios were determined by comparing $t_{1/2}$ to either TSHR260-AP-JMGH45 (65° C.), TSHR260-AP-JMG22 (60° C.) or TSHR260-AP-WT (50° C.). The half-life of TSHR260-AP-WT at 50° C. was 2.9x greater than for TSHR260 wild type (without alkaline phosphatase). Similarly, at 60° C. TSHR260-AP-JMG45 and TSHR260-AP-JMG55 gave half lives of 3.2x and 1.5x greater, respectively, than the equivalent TSHR260 constructs without alkaline phosphatase.

TABLE 49

Summary of the purification and specific activities of the two different forms of TSHR260-JMG55

| Sample | Volume | OD 280 nM | Total protein (mg) | TSHR260 activity (U/mL) | TSHR260 specific activity (U/mg) | Purification level |
|---|---|---|---|---|---|---|
| Streamline Loads (1-3) | 36 Litres | 13.9 | 500,400 | 422 | 30 | 1 |
| Streamline elution/14C4 affinity column load | 600 mL | 0.164 | 141 | 3,730 | 15,872 | 529 |
| Purification of high specific activity TSHR260-JMG55-4.5 | | | | | | |
| 14C4 pH 4.5 elution/Nickel column load | 50 mL | 0.061 | 4.36 | 99,787 | 1,144,346 | 38,145 |
| Nickel column elution | 5.6 mL | 0.083 | 0.665 | 761,333 | 6,414,000 | 213,708 |
| Purification of low specific activity TSHR260-JMG55-5.0 | | | | | | |
| 14C4 pH 5.0 elution/Nickel column load | 10 mL | 0.062 | 0.887 | 1,068 | 12,041 | 401 |
| Nickel column elution | 9.4 mL | 0.069 | 0.927 | 2,008 | 20,361 | 679 |

TSHR260 activity is the activity of the sample in the TSHR260-binding assay (FIG. 12a). Specific activity is the activity of the sample in the TSHR260-binding assay (U/mL), divided by the protein concentration of the sample (mg/mL) to give the activity of one milligram of protein. Purification level is the specific activity of the purified material at each step divided by the specific activity of the starting material (Streamline Loads).

TABLE 50a

Activity of purified TSHR260-JMG55-4.5 (high specific activity): Elution from nickel-affinity column at pH 4.5

| Sample | Total protein yield (mg) | Dilution | OD 450 nM | TSHR260 activity (U/mL) | Average TSHR260 activity (U/mL) | TSHR260 Specific activity (U/mg) |
|---|---|---|---|---|---|---|
| TSHR260-WT standard | | | 3.590 | 20 | | |
| | | | 3.414 | 10 | | |
| | | | 2.553 | 5 | | |
| | | | 1.418 | 2.5 | | |
| | | | 0.661 | 1.25 | | |
| | | | 0.272 | 0.625 | | |
| | | | 0.127 | 0.3125 | | |
| | | | 0.000 | 0 | | |
| TSHR260-JMG55-4.5 | 0.665 | 1/10000 | 3.689 | | | |
| | | 1/40000 | 3.633 | | | |
| | | 1/80000 | 3.380 | | | |
| | | 1/160000 | 2.448 | 738,400 | | |
| | | 1/320000 | 1.297 | 715,520 | 761,333 | 6,414,000 |
| | | 1/640000 | 0.654 | 830,080 | | |
| | | 1/12800000 | 0.282 | | | |
| | | 1/25600000 | 0.171 | | | |

TABLE 50b

Activity of purified TSHR260-JMG55-5.0 (low specific activity): Elution from nickel-affinity column at pH 5.0

| Sample | Total protein yield (mg) | Dilution | OD 450 nM | TSHR260 activity (U/mL) | Average TSHR260 activity (U/mL) | Specific activity (U/mg) |
|---|---|---|---|---|---|---|
| TSHR260-WT standard | | | 3.620 | 20 | | |
| | | | 3.442 | 10 | | |
| | | | 2.405 | 5 | | |
| | | | 1.330 | 2.5 | | |
| | | | 0.606 | 1.25 | | |
| | | | 0.267 | 0.625 | | |
| | | | 0.128 | 0.3125 | | |
| | | | 0.000 | 0 | | |
| TSHR260-JMG55-5.0 | 0.927 | 1/50 | 3.705 | | | |
| | | 1/100 | 3.604 | | | |
| | | 1/200 | 3.327 | | | |
| | | 1/400 | 2.444 | 1,972 | | |
| | | 1/800 | 1.292 | 1,923 | 2,008 | 20,361 |
| | | 1/1600 | 0.619 | 2,130 | | |
| | | 1/3200 | 0.316 | | | |
| | | 1/6400 | 0.163 | | | |

TABLE 51

Binding of TSHR monoclonal autoantibodies (K1-70, K1-18 and M22) to purified TSHR260-JMG55-4.5 coated ELISA plate wells

| Antibody-Peroxidase Concentration (µg/mL) | TSHR260-JMG55-4.5 coated plates (4 µg/mL). $OD_{450}$ | TSHR260-JMG55-4.5 coated plates (0.4 µg/mL). $OD_{450}$ |
|---|---|---|
| K1-70-POD | | |
| 7.5 | 3.542 | 1.421 |
| 5.0 | 3.129 | 1.067 |
| 2.5 | 2.035 | 0.679 |
| 1.0 | 0.904 | 0.302 |
| 0.75 | 0.750 | 0.238 |
| 0.50 | 0.488 | 0.159 |
| 0.25 | 0.263 | 0.070 |
| K1-18-POD | | |
| 7.5 | 3.301 | 1.535 |
| 5.0 | 2.945 | 1.203 |
| 2.5 | 1.946 | 0.782 |
| 1.0 | 0.871 | 0.369 |
| 0.75 | 0.659 | 0.266 |
| 0.50 | 0.458 | 0.178 |
| 0.25 | 0.188 | 0.070 |

TABLE 51-continued

Binding of TSHR monoclonal autoantibodies (K1-70, K1-18 and M22) to purified TSHR260-JMG55-4.5 coated ELISA plate wells

| Antibody-Peroxidase Concentration (µg/mL) | TSHR260-JMG55-4.5 coated plates (4 µg/mL). $OD_{450}$ | TSHR260-JMG55-4.5 coated plates (0.4 µg/mL). $OD_{450}$ |
|---|---|---|
| M22-POD | | |
| 7.5 | 2.645 | 0.941 |
| 5.0 | 2.319 | 0.770 |
| 2.5 | 1.809 | 0.528 |
| 1.0 | 1.160 | 0.309 |
| 0.75 | 0.951 | 0.258 |
| 0.50 | 0.748 | 1.192 |
| 0.25 | 0.479 | 0.120 |

TABLE 52

Analysis of TSHR260-JMG55-4.5 activity in the TSHR260 binding assay following deglycosylation with Endoglycosidase F3

| Endo F3 (mU of EndoF3 per mg of TSHR260-JMG55-4.5) | Incubation time (hours) | TSHR260 activity (U/mL) | TSHR260-JMGG55-4.5 activity (% of TSHR260-JMG55-4.5 control) |
|---|---|---|---|
| 0 (untreated control) | 0 | 362,880 | 100 |
| 0 | 120 | 401,280 | 111 |
| 40 | 120 | 361,200 | 100 |
| 60 | 120 | 377,840 | 104 |
| 80 | 120 | 378,960 | 104 |

TSHR260 activity is the activity of the sample in the TSHR260-binding assay compared to the TSHR260 standard as defined "TSHR260-binding assay" and "Transient transfections of TSHR260 mutants into CHO-K1 cells using Freestyle Max reagent" (FIG. 12a).

TABLE 53

Deglycosylation of TSHR260-JMG55-4.5 after nickel-affinity purification

| Endo F3 (mU of EndoF3 per mg of TSHR260-JMG55-4.5) | Incubation time (h) | Calculated Molecular Weight of Band (kDa) | Reduction in Molecular Weight By Deglycosylation (kDa) |
|---|---|---|---|
| 0 | 24 | 34.3 | 0.0 |
| | 72 | 34.5 | 0.0 |
| | 120 | 34.4 | 0.0 |
| 40 | 24 | 32.9 | 1.1 |
| | 72 | 32.3 | 1.7 |
| | 120 | 32.0 | 2.0 |
| 60 | 24 | 32.7 | 1.3 |
| | 72 | 31.9 | 2.1 |
| | 120 | 31.7 | 2.3 |
| 80 | 24 | 32.1 | 1.9 |
| | 72 | 31.8 | 2.2 |
| | 120 | 31.6 | 2.4 |

TABLE 54

Equivalent residues of hTSHR-JMG55 mutations in mouse and porcine TSHR

| Amino acid Position | hTSHR mutation | Mouse TSHR | Porcine TSHR |
|---|---|---|---|
| LRR2 | H63C | H63 | H63 |
| LRR4 | R112P | R112 | R112 |
| LRR5 | D143P | D143 | D143 |
| LRR5 | D151E | D151 | D151 |
| LRR6 | V169R | E169 | A169 |
| LRR10 | I253R | I253 | I253 |

Most of the thermostabilising mutated residues of hTSHR-JMG55 are well-conserved across TSHR from mouse and porcine. Only the residue at position 169 differs across species. Residue 169 is Valine in human, Glutamic acid in mouse and Alanine in porcine.

TABLE 55

Thermostability of full-length wild type and mutated mouse, porcine and human TSHR at 45° C.

| Species | TSHR | Half-life (min) | Half-life ratio (mutant/wild type) |
|---|---|---|---|
| Mouse | TSHR-Wild-type | 2.15 ± 0.07 | 6.3 ± 0.3 |
| | TSHR-mutant | 13.60 ± 0.14 | |
| Porcine | TSHR-Wild-type | 3.6 ± 0.3 | 3.34 ± 0.15 |
| | TSHR-mutant | 12.1 ± 1.5 | |
| Human | TSHR-Wild-type | 4.8 ± 1.0 | 39 ± 6 |
| | TSHR-mutant (JMG55) | 184 ± 12 | |

The half-life of each construct was measured in stability assay B by binding TSHR preparations to a 4E31-coated plate and then heating the plate for up to three hours at 45° C. in a water-bath. The amount of active TSHR protein was determined by the TSHR-binding assay (FIG. 14c). Results were plotted against time and fitted to a two-phase exponential decay curve. The half-life is the time at which the TSHR has lost half of its activity. Results shown are means ± SD, n = 2.

TABLE 56

Effect of different concentrations M22 IgG and TSH on stimulation of cAMP production in CHO cells expressing either wild type or mutated mouse TSHR

| | cyclic AMP produced (pmol/ml; mean ± SD; n = 3) | | |
|---|---|---|---|
| Test sample | Wild type mouse TSHR | Mutated mouse TSHR | Mutated mTSHR/wild type mTSHR (%) |
| cAMP assay buffer | 4.8 ± 0.2 | 2.9 ± 0.9 | 60 |
| M22 | | | |
| 100 ng/ml | 71.4 ± 5.1 | 80.6 ± 3.1 | 113 |
| 30 ng/ml | 55.4 ± 5.3 | 58.4 ± 6.4 | 105 |
| 10 ng/ml | 38.6 ± 3.1 | 29.4 ± 1.4 | 76 |
| 3 ng/ml | 18.6 ± 4.1 | 12.3 ± 0.9 | 66 |
| 1 ng/ml | 8.7 ± 0.3 | 6.3 ± 0.7 | 72 |
| 0.3 ng/ml | 5.9 ± 0.5 | 4.0 ± 0.4 | 67 |
| TSH | | | |
| 10 ng/ml | 78.3 ± 17.0 | 75.7 ± 12.5 | 97 |
| 3 ng/ml | 65.4 ± 11.2 | 60.5 ± 5.8 | 92 |
| 1 ng/ml | 49.1 ± 4.0 | 33.1 ± 3.6 | 67 |
| 0.3 ng/ml | 16.4 ± 0.6 | 12.7 ± 0.6 | 77 |

TABLE 56-continued

Effect of different concentrations M22 IgG and TSH on stimulation of cAMP production in CHO cells expressing either wild type or mutated mouse TSHR

| Test sample | cyclic AMP produced (pmol/ml; mean ± SD; n = 3) | | Mutated mTSHR/wild type mTSHR (%) |
|---|---|---|---|
| | Wild type mouse TSHR | Mutated mouse TSHR | |
| 0.1 ng/ml | 7.4 ± 0.6 | 5.1 ± 0.4 | 69 |
| 0.03 ng/ml | 4.6 ± 0.5 | 3.1 ± 0.3 | 67 |

Results shown are mean ± SD of triplicate determinations. Samples were diluted in cyclic AMP assay buffer. For mTSHR-WT: EC50 (M22) = 13.09 ng/ml; EC50 (TSH) = 0.81 ng/ml. For mTSHR-mutated; EC50 (M22) = 20.36 ng/ml; EC50 (TSH) = 1.41 ng/ml. Mutated mTSHR was based on the human TSHR mutant JMG55, Mutated amino acids in the mouse TSHR were analogous to amino acids mutated in the human TSHR-JMG55 construct and comprised H63C; R112P; D143P; D151E; E169R (analogous to hTSHR V169R) and I253R.

TABLE 57

Effect of different concentrations of M22 IgG and TSH on stimulation of cAMP production in CHO cells expressing either wild type or mutated porcine TSHR

| Test sample | cyclic AMP produced (pmol/ml; mean ± SD; n = 3) | | Mutated pTSHR/wild type pTSHR (%) |
|---|---|---|---|
| | Wild type porcine TSHR | Mutated porcine TSHR | |
| cAMP assay buffer | 2.9 ± 1.0 | 1.9 ± 0.2 | 66 |
| M22 | | | |
| 100 ng/ml | 84.9 ± 9.4 | 65.4 ± 0.8 | 77 |
| 30 ng/ml | 81.9 ± 4.9 | 68.3 ± 2.2 | 83 |
| 10 ng/ml | 60.8 ± 8.0 | 44.0 ± 2.4 | 72 |
| 3 ng/ml | 23.5 ± 2.3 | 21.2 ± 1.4 | 90 |
| 1 ng/ml | 10.7 ± 0.7 | 9.0 ± 1.4 | 84 |
| 0.3 ng/ml | 4.5 ± 0.8 | 3.7 ± 0.3 | 82 |
| TSH | | | |
| 10 ng/ml | 96.0 ± 6.8 | 91.2 ± 6.3 | 95 |
| 3 ng/ml | 86.7 ± 11.7 | 81.2 ± 3.0 | 94 |
| 1 ng/ml | 58.4 ± 4.1 | 46.0 ± 3.8 | 79 |
| 0.3 ng/ml | 19.8 ± 0.8 | 13.4 ± 2.3 | 67 |
| 0.1 ng/ml | 6.3 ± 0.5 | 5.4 ± 0.3 | 86 |
| 0.03 ng/ml | 2.5 ± 0.0 | 2.4 ± 0.1 | 96 |

Results shown are mean ± SD of triplicate determinations. Samples were diluted in cyclic AMP assay buffer. For pTSHR-WT: EC50 (M22) = 6.23 ng/ml; EC50 (TSH) = 0.79 ng/ml. For mTSHR-mutated; EC50 (M22) = 6.53 ng/ml; EC50 (TSH) = 1.04 ng/ml. Mutated pTSHR was based on the human TSHR mutant JMG55, Mutated amino acids in the porcine TSHR were analogous to amino acids mutated in the human TSHR-JMG55 construct and comprised H63C; R112P; D143P; D151E; A169R (analogous to hTSHR V169R) and I253R.

TABLE 58

Association constants for TSH binding to full-length wild type and mutated TSHR from different species (human, mouse and porcine)

| | $^{125}$I-TSH binding to full-length wild type and mutated TSHRs: association constant ($\times 10^9$ L/mol) | |
|---|---|---|
| TSHR species | Wild Type | Mutant (equivalent to JMG55) |
| Human | 1.80 | 0.98 |
| Mouse | 1.58 | 0.87 |
| Porcine | 1.99 | 1.25 |

Association constants calculated from single experiments with duplicate determinations.

TABLE 59

Single amino acid mutations made in the TMD of TSHR-JMG55

| Mutation | Mutation |
|---|---|
| E409K | T588L |
| D410K | I591A |
| D410N | V595I |
| H443N | V597A |
| N447T | C599S |
| L452Y | C600R |
| N455A | Y601F |
| D460A | Y601A |
| M463V | K603Q |
| Y466F | I604A |
| L467P | Y605A |
| T477I | I606A |
| Q489H | V608A |
| N495K | I622A |
| S505A | I622D |
| R519L | L629M |
| I523A | D633K |
| T524A | I635M |
| T524R | I648L |
| F525L | L649M |
| L529H | K660D |
| C539Y | Y667A |
| L557A | Y667V |
| K565A | S671A |
| K565L | C672S |
| V584I | N674A |
| V584L | Y678L |
| F585L | Y678A |

TABLE 60

Stability of TSHR-JMG55 mutants having a single mutation in the TMD

| | Stability Assay A and B[c] | | | | | | Stability Assay C[d] | | | |
|---|---|---|---|---|---|---|---|---|---|---|
| | 14C4[a] Activity | 4E31[b] Activity | Half-life at 55° C. (min) | | Half-life Ratio | | Survival at 33° C. (%) | | | Half-life at 33° C. (min) | Half-life Ratio |
| Mutant of TSHR-JMG55 | (U/ml) | (U/ml) | A | B | A | B | 10 min | 30 min | 120 min | | |
| TSHR-JMG55 | 100 | 100 | 12 | 13 | 1.0 | 1.0 | 55 | 39 | 21 | 14 ± 5 | 1.0 |
| E409K | 392 | 499 | 21 | 12 | 2.2 | 0.9 | 60 | 49 | 32 | 28 | 2.2 |
| D410K | 57 | 159 | 29 | 17 | 3.1 | 1.2 | 82 | 68 | 47 | 95 | 7.7 |
| D410N | 130 | 206 | 14 | 12 | 1.5 | 0.9 | 59 | 51 | 39 | 34 | 2.1 |
| H443N | 243 | 158 | 25 | 19 | 1.1 | 1.0 | 74 | 64 | 46 | 99 | 15.4 |
| N447T | 476 | 252 | 21 | 20 | 1.0 | 1.0 | 59 | 53 | 37 | 44 | 6.9 |
| L452Y | 71 | 155 | 32 | 20 | 1.4 | 1.0 | 65 | 61 | 46 | 93 | 4.7 |
| N455A | 42 | 102 | 35 | 15 | 2.1 | 1.2 | 68 | 63 | 46 | 96 | 15.1 |
| D460A | 20 | 76 | n.d. | n.d. | n.d. | n.d. | n.d. | n.d. | n.d. | n.d. | n.d. |

TABLE 60-continued

Stability of TSHR-JMG55 mutants having a single mutation in the TMD

| Mutant of TSHR-JMG55 | 14C4[a] Activity (U/ml) | 4E31[b] Activity (U/ml) | Stability Assay A and B[c] | | | | Stability Assay C[d] | | | | |
|---|---|---|---|---|---|---|---|---|---|---|---|
| | | | Half-life at 55° C. (min) | | Half-life Ratio | | Survival at 33° C. (%) | | | Half-life at 33° C. (min) | Half-life Ratio |
| | | | A | B | A | B | 10 min | 30 min | 120 min | | |
| TSHR-JMG55 | 100 | 100 | 12 | 13 | 1.0 | 1.0 | 55 | 39 | 21 | 14 ± 5 | 1.0 |
| M463V | 90 | 183 | 23 | 15 | 1.4 | 1.2 | 78 | 70 | 45 | 99 | 5.0 |
| Y466F | 47 | 90 | 26 | 12 | 1.6 | 0.9 | 61 | 58 | 48 | 78 | 12.2 |
| L467P | 113 | 428 | 28 | 15 | 3.4 | 1.3 | 66 | 53 | 41 | 49 | 3.9 |
| T477I | 48 | 187 | 35 | 16 | 4.2 | 1.3 | 80 | 72 | 50 | 120 | 6.4 |
| Q489H | 39 | 150 | 30 | 13 | 3.6 | 1.1 | 70 | 58 | 45 | 81 | 3.6 |
| N495K | 861 | 1749 | 10 | 10 | 0.9 | 1.1 | 63 | 44 | 26 | 20 | 0.9 |
| S505A | 26 | 0 | n.d. | n.d. | n.d. | n.d. | n.d. | n.d. | n.d. | n.d. | n.d. |
| R519L | 150 | 259 | 14 | 12 | 1.3 | 1.2 | 78 | 62 | 40 | 67 | 6.0 |
| I523A | 150 | 228 | 24 | 13 | 2.2 | 1.4 | 61 | 49 | 28 | 26 | 2.2 |
| T524A | 210 | 339 | 21 | 16 | 1.1 | 1.1 | 61 | 52 | 31 | 38 | 3.2 |
| T524R | 736 | 661 | 21 | 11 | 1.1 | 0.8 | 68 | 55 | 37 | 52 | 4.3 |
| F525L | 109 | 252 | 13 | 17 | 0.7 | 1.1 | 58 | 49 | 32 | 27 | 2.3 |
| L529H | 1266 | 1611 | 6 | 9 | 0.7 | 1.2 | 67 | 51 | 32 | 34 | 2.0 |
| C539Y | 376 | 518 | 16 | 10 | 2.0 | 1.3 | 66 | 56 | 38 | 54 | 3.1 |
| L557A | 345 | 906 | 11 | 9 | 1.3 | 1.2 | 67 | 53 | 36 | 41 | 2.4 |
| K565A | 215 | 219 | 16 | 17 | 0.8 | 1.2 | 56 | 50 | 34 | 30 | 5.7 |
| K565L | 70 | 150 | 19 | 15 | 1.0 | 1.1 | 68 | 56 | 44 | 46 | 8.6 |
| V584I | 326 | 172 | 15 | 16 | 0.7 | 1.1 | 63 | 55 | 36 | 49 | 9.3 |
| V584L | 399 | 1121 | 11 | 21 | 1.3 | 0.9 | 69 | 55 | 40 | 54 | 2.8 |
| F585L | 188 | 108 | 10 | 21 | 1.2 | 0.9 | 58 | 48 | 28 | 23 | 4.4 |
| T588L | 79 | 111 | 8 | 23 | 1.0 | 1.0 | 62 | 53 | 34 | 42 | 1.9 |
| I591A | 207 | 421 | 21 | 8 | 2.9 | 0.7 | 61 | 49 | 31 | 27 | 1.4 |
| V595I | 570 | 672 | 12 | 14 | 1.6 | 1.3 | 77 | 58 | 44 | 60 | 3.8 |
| V597A | 136 | 253 | 17 | 9 | 2.3 | 0.9 | 74 | 50 | 32 | 31 | 1.9 |
| C599S | 250 | 344 | 18 | 11 | 1.0 | 0.8 | 37 | 29 | 17 | 5 | 0.3 |
| C600R | 35 | 104 | n.d. | 10 | n.d. | 0.7 | 79 | 64 | 38 | 72 | 8.4 |
| Y601F | 194 | 108 | 20 | 13 | 1.1 | 0.9 | 63 | 54 | 32 | 44 | 3.7 |
| Y601A | 177 | 244 | 14 | 11 | 0.9 | 0.8 | 63 | 53 | 31 | 40 | 3.4 |
| K603Q | 1085 | 820 | 14 | 16 | 1.4 | 1.4 | 61 | 52 | 29 | 36 | 3.1 |
| I604A | 223 | 282 | 14 | 10 | 1.4 | 0.9 | 68 | 53 | 36 | 43 | 3.6 |
| Y605A | 164 | 284 | 13 | 9 | 1.3 | 0.8 | 63 | 45 | 27 | 21 | 1.6 |
| I606A | 214 | 469 | 5 | 9 | 0.8 | 0.8 | 53 | 43 | 27 | 14 | 1.0 |
| V608A | 243 | 210 | 7 | 13 | 1.0 | 1.2 | 50 | 40 | 20 | 11 | 0.8 |
| I622A | 319 | 497 | 5 | 8 | 0.8 | 0.8 | 57 | 38 | 16 | 13 | 1.0 |
| I622D | 440 | 479 | 16 | 8 | 1.2 | 1.4 | 50 | 36 | 13 | 10 | 1.0 |
| L629M | 217 | 447 | 18 | 7 | 1.4 | 1.2 | 68 | 59 | 39 | 65 | 3.5 |
| D633K | 145 | 445 | 12 | 14 | 0.9 | 2.3 | 67 | 48 | 35 | 36 | 3.9 |
| I635M | 205 | 568 | 8 | 11 | 0.7 | 1.2 | 60 | 45 | 30 | 31 | 3.4 |
| I648L | 611 | 767 | 18 | 15 | 1.6 | 1.6 | 64 | 51 | 50 | 118 | 12.8 |
| L649M | 231 | 276 | 15 | 8 | 1.3 | 0.8 | 74 | 58 | 38 | 58 | 3.3 |
| K660D | 179 | 573 | 24 | 9 | 2.5 | 1.0 | 68 | 59 | 48 | 101 | 5.5 |
| Y667A | 91 | 227 | 12 | 5 | 1.2 | 0.5 | 65 | 51 | 37 | 40 | 2.1 |
| Y667V | 119 | 477 | 28 | 10 | 3.0 | 1.1 | 82 | 68 | 48 | 109 | 5.9 |
| S671A | 178 | 267 | 5 | 13 | 0.6 | 0.9 | 74 | 57 | 43 | 114 | 13.2 |
| C672S | 55 | 130 | 8 | 21 | 1.0 | 1.4 | 68 | 54 | 42 | 51 | 4.3 |
| N674A | 86 | 121 | 5 | 15 | 0.6 | 1.0 | 62 | 52 | 37 | 41 | 3.5 |
| Y678L | 38 | 129 | 31 | 17 | 2.1 | 1.2 | 76 | 65 | 45 | 114 | 9.6 |
| Y678A | 58 | 130 | 27 | 22 | 1.9 | 1.5 | 71 | 61 | 44 | 83 | 7.1 |

All of these TSHR mutants also contain the six mutations of JMG55: I253R, D143P, R112P, D151E, H63C and V169R.

[a]14C4 activity is the activity of the unheated sample when bound to a 14C4-coated ELISA plate well, as detected in the TSHR binding assay. For use in stability assay A, the samples were diluted to 10 U/mL 14C4 activity. See section Transient transfections of full-length TSHR mutants into CHO-K1 cells using Freestyle Max reagent for definition of U/ml.

[b]4E31 activity is the activity of the unheated sample when bound to a 4E31-coated ELISA plate well as detected in the TSHR binding assay. For use in stability assay B, the samples were diluted to 10 U/mL 4E31 activity and for use in stability assay C, the samples were diluted to a final concentration of 12.5 U/ml. See Transient transfections of full-length TSHR mutants into CHO-K1 cells using Freestyle Max reagent for definition of U/ml.

[c]In stability assays A and B the half-life of each mutant is determined by coating a 14C4-plate (stability assay A, FIG. 14b) or 4E31-coated ELISA plate well (stability assay B, FIG. 14c) with the TSHR mutants. Strips of the plates with TSHR bound were heated at 55° C. for a period of up to two hours. The amount of active TSHR protein was determined by the TSHR-binding assay, plotted against time and fitted to an exponential decay curve. In each experiment, the thermostability (half-life, t½) of TSHR-JMG55 was measured and used to determine the half-life ratio compared to the half-life of TSHR-JMG55 mutants in the same experiment.

[d] In stability assay C (FIG. 14d), solubilised aliquots of each TSHR-JMG55 mutant were heated at 33° C. in solution for up to two hours. The amount of active TSHR protein was determined by the TSHR-binding assay, plotted against time and fitted to a two-phase exponential decay curve. The percentage of active TSHR-JMG55 mutant remaining after heating for 10, 30 and 120 min was calculated and compared to TSHR-JMG55. The apparent half-life is the time point at which the TSHR-JMG55 mutant has lost half of its activity. This is used to calculate the half-life ratio is by dividing it by the apparent half-life of TSHR-JMG55 measured in the same experiment.

In bold are the 20 most thermostabilising mutants, which were used to make double mutants. Experiments were performed once for each mutant in each assay, assayed in duplicate.

"n.d." = determined.

TABLE 61

Combination of single mutations in the TSHR-JMG55 TMD to produce double, triple and TSHR-JMG55 mutants.

| Mutant Name | Base mutant | Mutation 1 | Mutation 2 | Mutation 3 |
|---|---|---|---|---|
| JMG59 | JMG55 | T477I | H443N | |
| JMG60 | JMG55 | T477I | L452Y | |
| JMG61 | JMG55 | T477I | N455A | |
| JMG62 | JMG55 | T477I | M463V | |
| JMG63 | JMG55 | T477I | Y466F | |
| JMG64 | JMG55 | T477I | Q489H | |
| JMG65 | JMG55 | T477I | K565L | |
| JMG66 = 82 | JMG55 | T477I | V595I | |
| JMG67 | JMG55 | T477I | C600R | |
| JMG68 = 101 | JMG55 | T477I | I648L | |
| JMG69 | JMG55 | T477I | K660D | |
| JMG70 | JMG55 | T477I | Y667V | |
| JMG71 | JMG55 | T477I | S671A | |
| JMG72 | JMG55 | T477I | Y678L | |
| JMG73 | JMG55 | T477I | Y678A | |
| JMG74 | JMG55 | V595I | E409K | |
| JMG75 | JMG55 | V595I | D410K | |
| JMG76 | JMG55 | V595I | H443N | |
| JMG77 | JMG55 | V595I | L452Y | |
| JMG78 | JMG55 | V595I | N455A | |
| JMG79 | JMG55 | V595I | M463V | |
| JMG80 | JMG55 | V595I | Y466F | |
| JMG81 | JMG55 | V595I | L467P | |
| JMG82 = 66 | JMG55 | V595I | T477I | |
| JMG83 | JMG55 | V595I | Q489H | |
| JMG84 | JMG55 | V595I | K565L | |
| JMG85 | JMG55 | V595I | C600R | |
| JMG86 | JMG55 | V595I | Y601F | |
| JMG87 = 104 | JMG55 | V595I | I648L | |
| JMG88 | JMG55 | V595I | K660D | |
| JMG89 | JMG55 | V595I | Y667V | |
| JMG90 | JMG55 | V595I | S671A | |
| JMG91 | JMG55 | V595I | Y678L | |
| JMG92 | JMG55 | V595I | Y678A | |
| JMG93 | JMG55 | I648L | E409K | |
| JMG94 | JMG55 | I648L | D410K | |
| JMG95 | JMG55 | I648L | H443N | |
| JMG96 | JMG55 | I648L | L452Y | |
| JMG97 | JMG55 | I648L | N455A | |
| JMG98 | JMG55 | I648L | M463V | |
| JMG99 | JMG55 | I648L | Y466F | |
| JMG100 | JMG55 | I648L | L467P | |
| JMG101 = 68 | JMG55 | I648L | T477I | |
| JMG102 | JMG55 | I648L | Q489H | |
| JMG103 | JMG55 | I648L | K565L | |
| JMG104 = 87 | JMG55 | I648L | V595I | |
| JMG105 | JMG55 | I648L | C600R | |
| JMG106 | JMG55 | I648L | Y601F | |
| JMG107 | JMG55 | I648L | K660D | |
| JMG108 | JMG55 | I648L | Y667V | |
| JMG109 | JMG55 | I648L | S671A | |
| JMG110 | JMG55 | I648L | Y678L | |
| JMG111 | JMG55 | I648L | Y678A | |
| JMG112 | JMG55 | V595I | Y678L | E409K |
| JMG113 | JMG55 | V595I | Y678L | D410K |
| JMG114 | JMG55 | V595I | Y678L | H443N |
| JMG115 | JMG55 | V595I | Y678L | L452Y |
| JMG116 | JMG55 | V595I | Y678L | N455A |
| JMG117 | JMG55 | V595I | Y678L | Y466F |
| JMG118 | JMG55 | V595I | Y678L | L467P |
| JMG119 | JMG55 | V595I | Y678L | T477I |
| JMG120 | JMG55 | V595I | Y678L | Q498H |
| JMG121 | JMG55 | V595I | Y678L | K565L |
| JMG122 | JMG55 | V595I | Y678L | Y601F |
| JMG123 | JMG55 | V595I | Y678L | I648L |
| JMG124 | JMG55 | V595I | Y678L | K660D |
| JMG125 | JMG55 | V595I | Y678L | Y667V |
| JMG126 | JMG55 | V595I | Y678L | S671A |

All TSHR mutants listed contain the six mutations of JMG55: I253R, D143P, R112P, D151E, H63C and V169R.
JMG66 is identical to JMG82, JMG68 is identical to JMG101 and JMG87 is identical to JMG104. JMG85 construct was not made as the mutations V595I and C600R are too close together and are likely to interfere with each other.

TABLE 62

Thermostability of TSHR-JMG55 mutants having a double mutation in the TMD: Stability assay C

| | | | Stability Assay C[c] | | | | | | |
|---|---|---|---|---|---|---|---|---|---|
| | 14C4[a] Activity | 4E31[b] Activity | Survival at 33° C. (%) | | | Survival ratio at 33° C. | | | Half-life at | Half-life |
| Mutant name | (U/ml) | (U/ml) | 10 min | 30 min | 120 min | 10 min | 30 min | 120 min | 33° C. (min) | Ratio |
| JMG55-T477I | 48 | 187 | 78 | 63 | 44 | 1.0 | 1.0 | 1.0 | 84 ± 20 | 1.0 |
| JMG55-V595I | 570 | 672 | 66 | 55 | 37 | 1.0 | 1.0 | 1.0 | 58 ± 7 | 1.0 |
| JMG55-I1648L | 611 | 767 | 74 | 60 | 43 | 1.0 | 1.0 | 1.0 | 86 ± 52 | 1.0 |
| JMG59 | 51 | 367 | 79 | 66 | 42 | 1.0 | 1.0 | 0.8 | 84 | 0.8 |
| JMG60 | 31 | 246 | 79 | 66 | 50 | 1.0 | 1.0 | 1.0 | 123 | 1.1 |
| JMG61 | 24 | 194 | 74 | 65 | 50 | 0.9 | 1.0 | 1.1 | 122 | 1.3 |
| JMG62 | 32 | 282 | 75 | 68 | 48 | 0.9 | 1.0 | 0.9 | 114 | 1.0 |
| JMG63 | 10 | 70 | 85 | 63 | 31 | 1.1 | 1.0 | 0.7 | 48 | 0.5 |
| JMG64 | 29 | 248 | 71 | 64 | 45 | 1.0 | 1.1 | 1.1 | 94 | 1.0 |
| JMG65 | 25 | 199 | 70 | 60 | 42 | 0.9 | 1.0 | 1.0 | 75 | 0.8 |
| JMG66 | 29 | 184 | 71 | 58 | 44 | 0.9 | 0.9 | 1.0 | 63 | 0.8 |
| JMG67 | 84 | 352 | 85 | 69 | 46 | 1.0 | 1.0 | 1.0 | 97 | 1.1 |
| JMG68 | 42 | 52 | 75 | 68 | 52 | 1.0 | 1.1 | 1.2 | 75 | 0.9 |
| JMG69 | 57 | 311 | 77 | 62 | 43 | 0.9 | 0.9 | 0.9 | 80 | 0.9 |
| JMG70 | 54 | 305 | 74 | 60 | 42 | 0.9 | 0.8 | 0.9 | 74 | 0.9 |
| JMG71 | 118 | 599 | 75 | 65 | 47 | 1.0 | 1.1 | 1.2 | 104 | 1.6 |
| JMG72 | 52 | 278 | 74 | 60 | 36 | 1.1 | 1.1 | 0.9 | 62 | 1.1 |
| JMG73 | 41 | 249 | 85 | 64 | 41 | 1.2 | 1.1 | 1.1 | 59 | 1.0 |
| JMG74 | 230 | 432 | 68 | 56 | 37 | 1.2 | 1.1 | 1.2 | 55 | 0.9 |
| JMG75 | 121 | 289 | 77 | 60 | 44 | 1.1 | 1.1 | 1.1 | 77 | 1.6 |
| JMG76 | 389 | 705 | 70 | 55 | 38 | 1.2 | 1.1 | 1.2 | 48 | 0.8 |
| JMG77 | 78 | 248 | 77 | 64 | 46 | 1.3 | 1.2 | 1.4 | 94 | 1.5 |
| JMG78 | 42 | 257 | 73 | 62 | 38 | 1.0 | 1.0 | 0.9 | 69 | 1.1 |

TABLE 62-continued

Thermostability of TSHR-JMG55 mutants having a double mutation in the TMD: Stability assay C

| | | | | | | | | | | |
|---|---|---|---|---|---|---|---|---|---|---|
| | | | | Stability Assay C[c] | | | | | | |
| | 14C4[a] Activity | 4E31[b] Activity | Survival at 33° C. (%) | | | Survival ratio at 33° C. | | | Half-life at | Half-life |
| Mutant name | (U/ml) | (U/ml) | 10 min | 30 min | 120 min | 10 min | 30 min | 120 min | 33° C. (min) | Ratio |
| JMG55-T477I | 48 | 187 | 78 | 63 | 44 | 1.0 | 1.0 | 1.0 | 84 ± 20 | 1.0 |
| JMG55-V595I | 570 | 672 | 66 | 55 | 37 | 1.0 | 1.0 | 1.0 | 58 ± 7 | 1.0 |
| JMG55-I1648L | 611 | 767 | 74 | 60 | 43 | 1.0 | 1.0 | 1.0 | 86 ± 52 | 1.0 |
| JMG79 | 149 | 329 | 70 | 54 | 37 | 1.2 | 1.1 | 1.2 | 47 | 0.8 |
| JMG80 | 54 | 257 | 64 | 55 | 36 | 0.9 | 1.0 | 11 | 51 | 0.8 |
| JMG81 | 32 | 81 | 59 | 46 | 29 | 0.9 | 0.9 | 0.7 | 20 | 0.4 |
| JMG82 = 66 | 30 | 151 | 76 | 62 | 47 | 1.1 | 1.1 | 1.4 | 98 | 1.6 |
| JMG83 | 61 | 300 | 68 | 63 | 46 | 1.0 | 1.1 | 1.4 | 93 | 1.5 |
| JMG84 | 232 | 718 | 72 | 60 | 48 | 1.1 | 1.1 | 1.4 | 102 | 1.6 |
| JMG85 | n.d. | n.d. | n.d. | n.d. | n.d. | n.d. | n.d. | n.d. | n.d. | n.d. |
| JMG86 | 197 | 448 | 70 | 56 | 41 | 1.0 | 1.0 | 1.1 | 62 | 1.3 |
| JMG87 = 104 | 333 | 742 | 79 | 64 | 54 | 1.2 | 1.2 | 1.5 | 164 | 3.2 |
| JMG88 | 85 | 198 | 72 | 62 | 41 | 1.1 | 1.1 | 1.1 | 76 | 1.6 |
| JMG89 | 159 | 299 | 77 | 53 | 31 | 1.0 | 0.9 | 0.7 | 34 | 0.5 |
| JMG90 | 366 | 851 | 79 | 64 | 54 | 1.3 | 1.1 | 1.5 | 134 | 2.6 |
| JMG91 | 102 | 245 | 80 | 64 | 49 | 1.3 | 1.1 | 1.3 | 108 | 2.1 |
| JMG92 | 136 | 558 | 84 | 66 | 47 | 1.1 | 1.1 | 1.0 | 95 | 1.5 |
| JMG93 | 144 | 336 | 69 | 61 | 44 | 0.9 | 0.9 | 0.9 | 85 | 0.6 |
| JMG94 | 123 | 476 | 79 | 67 | 50 | 1.1 | 1.3 | 1.5 | 117 | 2.9 |
| JMG95 | 161 | 276 | 64 | 51 | 27 | 0.9 | 1.0 | 0.8 | 33 | 0.8 |
| JMG96 | 41 | 224 | 83 | 67 | 47 | 1.2 | 1.3 | 1.4 | 85 | 2.1 |
| JMG97 | 81 | 189 | 73 | 60 | 45 | 0.9 | 0.9 | 0.9 | 85 | 0.6 |
| JMG98 | 58 | 507 | 73 | 66 | 48 | 1.1 | 1.3 | 1.4 | 108 | 3.0 |
| JMG99 | 29 | 134 | 71 | 56 | 43 | 1.0 | 1.1 | 1.3 | 64 | 1.6 |
| JMG100 | 44 | 105 | 70 | 56 | 34 | 0.9 | 0.8 | 0.7 | 45 | 0.3 |
| JMG101 = 68 | 52 | 628 | 75 | 68 | 52 | 1.1 | 1.3 | 1.5 | 132 | 3.7 |
| JMG102 | 36 | 216 | 72 | 58 | 45 | 1.1 | 1.1 | 1.3 | 82 | 2.3 |
| JMG103 | 24 | 66 | 76 | 64 | 50 | 1.2 | 1.2 | 1.5 | 122 | 3.4 |
| JMG104 = 87 | 333 | 742 | 79 | 64 | 54 | 1.0 | 0.9 | 1.0 | 164 | 1.2 |
| JMG105 | 35 | 206 | 74 | 60 | 44 | 1.2 | 1.1 | 1.3 | 81 | 2.1 |
| JMG106 | 36 | 443 | 76 | 62 | 49 | 1.2 | 1.2 | 1.5 | 113 | 2.9 |
| JMG107 | 49 | 124 | 76 | 59 | 39 | 1.0 | 0.9 | 0.8 | 62 | 0.5 |
| JMG108 | 66 | 339 | 76 | 60 | 45 | 1.2 | 1.1 | 1.4 | 82 | 2.1 |
| JMG109 | 161 | 757 | 81 | 64 | 47 | 1.3 | 1.2 | 1.4 | 94 | 2.4 |
| JMG110 | 77 | 182 | 76 | 61 | 42 | 1.0 | 0.9 | 0.8 | 72 | 0.6 |
| JMG111 | 47 | 4 | n.d. | n.d. | n.d. | n.d. | n.d. | n.d. | n.d. | n.d. |

TSHR mutants as defined in Table 61.
[a]14C4 activity is the activity of the unheated sample when bound to a 14C4-coated ELISA plate well, as detected in the TSHR binding assay. See Transient transfections of full-length TSHR mutants into CHO-K1 cells using Freestyle Max reagent for definition of U/ml.
[b]4E31 activity is the activity of the unheated sample when bound to a 4E31-coated ELISA plate well as detected in the TSHR binding assay. For use in stability assay C, the samples were diluted to a final concentration of 12.5 U/ml. See Transient transfections of full-length TSHR mutants into CHO-K1 cells using Freestyle Max reagent for definition of U/ml.
[c]In stability assay C, solubilised aliquots of each TSHR mutant were heated at 33° C. in solution for up to two hours. The amount of active TSHR protein remaining was determined by TSHR-binding assay and plotted against time (FIG. 14d). The percentage of active TSHR mutant remaining after heating for 10, 30 and 120 min was calculated and compared to TSHR-JMG55-T477I for JMG59 to JMG73, TSHR-JMG55-V595I in the case of JMG74 to JMG92 or TSHR-JMG55-I648L for JMG93 to JMG111. Additionally, the apparent half-life is the time point at which the TSHR-JMG55 mutant has lost half of its activity. This is used to calculate the half-life ratio is by dividing it by the apparent half-life of TSHR-JMG55-T477I, TSHR-JMG55-V595I or TSHR-JMG55-I648L measured in the same experiment.
Experiments were performed once for each mutant in each assay (assayed in duplicate).
"n.d." = not determined.

TABLE 63

Thermostability of mutants having a double mutation in the TMD of TSHR-JMG55 (JMG74 to JMG92): Stability assays A, B and C

| | Stability Assay A and B[a] | | | | Stability Assay C[b] | | | | | | | |
|---|---|---|---|---|---|---|---|---|---|---|---|---|
| | Half-life at 55° C. (min) | | Half-life ratio at 55° C. | | Survival at 33° C. (%) | | | Survival ratio at 33° C. | | | Half-life at | Half-life |
| Mutant name | A | B | A | B | 10 min | 30 min | 120 min | 10 min | 30 min | 120 min | 33° C. (min) | Ratio |
| JMG55-V595I | 27 | 18 | 1.0 | 1.0 | 66 | 55 | 37 | 1.0 | 1.0 | 1.0 | 58 ± 7 | 1.0 |
| JMG74 | 38 | 37 | 1.4 | 1.7 | 68 | 56 | 37 | 1.2 | 1.1 | 1.2 | 55 | 0.9 |

TABLE 63-continued

Thermostability of mutants having a double mutation in the TMD of
TSHR-JMG55 (JMG74 to JMG92): Stability assays A, B and C

| | Stability Assay A and B[a] | | | | Stability Assay C[b] | | | | | | | |
|---|---|---|---|---|---|---|---|---|---|---|---|---|
| | Half-life at 55° C. (min) | | Half-life ratio at 55° C. | | Survival at 33° C. (%) | | | Survival ratio at 33° C. | | | Half-life at 33° C. (min) | Half-life Ratio |
| Mutant name | A | B | A | B | 10 min | 30 min | 120 min | 10 min | 30 min | 120 min | | |
| JMG75 | 45 | 25 | 1.6 | 1.2 | 77 | 60 | 44 | 1.1 | 1.1 | 1.1 | 77 | 1.6 |
| JMG76 | 38 | 32 | 1.4 | 1.5 | 70 | 55 | 38 | 1.2 | 1.1 | 1.2 | 48 | 0.8 |
| JMG77 | 38 | 21 | 1.3 | 1.3 | 77 | 64 | 46 | 1.3 | 1.2 | 1.4 | 94 | 1.5 |
| JMG78 | 44 | 19 | 1.6 | 0.9 | 73 | 62 | 38 | 1.0 | 1.0 | 0.9 | 69 | 1.1 |
| JMG79 | 26 | 15 | 1.1 | 0.9 | 70 | 54 | 37 | 1.2 | 1.1 | 1.2 | 47 | 0.8 |
| JMG80 | 48 | 19 | 1.8 | 1.0 | 64 | 55 | 36 | 0.9 | 1.0 | 1.1 | 51 | 0.8 |
| JMG81 | 53 | 20 | 2.0 | 1.1 | 59 | 46 | 29 | 0.9 | 0.9 | 0.7 | 20 | 0.4 |
| JMG82 = 66 | 59 | 19 | 2.4 | 1.2 | 76 | 62 | 47 | 1.1 | 1.1 | 1.4 | 98 | 1.6 |
| JMG83 | 39 | 24 | 1.4 | 1.5 | 68 | 63 | 46 | 1.0 | 1.1 | 1.4 | 93 | 1.5 |
| JMG84 | 44 | 38 | 1.6 | 2.4 | 72 | 60 | 48 | 1.1 | 1.1 | 1.4 | 102 | 1.6 |
| JMG85 | n.d. | n.d. | n.d. | n.d. | n.d. | n.d. | n.d. | n.d. | n.d. | n.d. | n.d. | n.d. |
| JMG86 | 35 | 33 | 1.2 | 1.7 | 70 | 56 | 41 | 1.0 | 1.0 | 1.1 | 62 | 1.3 |
| JMG87 = 104 | 33 | 33 | 1.2 | 1.7 | 79 | 64 | 54 | 1.2 | 1.2 | 1.5 | 164 | 3.2 |
| JMG88 | 47 | 29 | 1.6 | 1.5 | 72 | 62 | 41 | 1.1 | 1.1 | 1.1 | 76 | 1.6 |
| JMG89 | 45 | 31 | 2.0 | 2.1 | 77 | 53 | 31 | 1.0 | 0.9 | 0.7 | 34 | 0.5 |
| JMG90 | 27 | 25 | 1.0 | 1.4 | 79 | 64 | 54 | 1.3 | 1.0 | 1.5 | 134 | 2.6 |
| JMG91 | 48 | 30 | 1.8 | 1.7 | 80 | 64 | 49 | 1.3 | 1.1 | 1.3 | 108 | 2.1 |
| JMG92 | 40 | 36 | 1.4 | 1.7 | 84 | 66 | 47 | 1.1 | 1.1 | 1.0 | 95 | 1.5 |

TSHR mutants as defined in Table 61.

[a] In stability assays A and B the half-life of each mutant was determined by first binding the mutant to a 14C4-coated ELISA plate well (stability assay A, FIG. 14b) or 4E31-coated ELISA plate well (stability assay B, FIG. 14c). Strips of the plate wells with mutant TSHR bound were heated at 55° C. for periods of up to two hours. The amount of active mutant TSHR protein remaining was determined by the TSHR-binding assay and plotted against time. In each experiment, the thetmostability (half-life, t½) of TSHR-JMG55-V595I was measured and used to determine the half-life ratio for each mutant compared to the half-life of TSHR-JMG55-V595I in the same experiment.

[b] In stability assay C (FIG. 14d), solubilised aliquots of TSHR mutant were heated at 33° C. in solution for up to two hours. The amount of active TSHR protein was determined by TSHR-binding assay and plotted against time. The percentage of active TSHR mutant remaining after heating for 10, 30 and 120 min was calculated and compared to TSHR-JMG55-V595I. The apparent half-life is the time point at which the TSHR-JMG55 mutant has lost half of its activity. This is used to calculate the half-life ratio is by dividing it by the apparent half-life of TSHR-JMG55-V595I measured in the same experiment.

The most thermostabilising mutants overall, JMG91 and JMG84, are shown in bold and these were used as a basis for making triple mutants. Experiments were performed once for each mutant in each assay (assayed in duplicate).

"n.d." = determined.

TABLE 64

Thermostability of mutants having a triple mutation in the TMD of
TSHR-JMG55 (JMG112 to JMG142): Stability assays A, B and C.

| | Stability Assay A and B[a] | | | | Stability Assay C[b] | | | | | | | |
|---|---|---|---|---|---|---|---|---|---|---|---|---|
| | Half-life at 55° C. (min) | | Half-life ratio at 55° C. | | Survival at 40° C. (%) | | | Survival ratio at 40° C. | | | Half-life at 40° C. (min) | Half-life ratio at 40° C. |
| TSHR mutant | A | B | A | B | 10 min | 30 min | 120 min | 10 min | 30 min | 120 min | | |
| JMG91 | 34 ± 8 | 23 ± 2 | 1.0 | 1.0 | 57 | 48 | 29 | 1.0 | 1.0 | 1.0 | 24 ± 9 | 1.0 |
| JMG84 | 38 ± 4 | 23 ± 7 | 1.0 | 1.0 | 57 | 42 | 24 | 1.0 | 1.0 | 1.0 | 14 ± 3 | 1.0 |
| JMG112 | n.d. | n.d. | n.d. | n.d. | n.d. | n.d. | n.d. | n.d. | n.d. | n.d. | n.d. | n.d. |
| JMG113 | 46 | 23 | 1.1 | 1.2 | 46 | 34 | 19 | 0.8 | 0.7 | 0.6 | 8 | 0.4 |
| JMG114 | 36 | 16 | 1.1 | 0.7 | 49 | 41 | 24 | 0.9 | 0.9 | 0.8 | 9 | 0.4 |
| JMG115 | 44 | 22 | 1.1 | 1.1 | 36 | 25 | 8 | 0.6 | 0.5 | 0.3 | 5 | 0.2 |
| JMG116 | 57 | 21 | 1.7 | 1.0 | 51 | 43 | 25 | 0.9 | 0.9 | 0.8 | 11 | 0.5 |
| JMG117 | 41 | 21 | 1.0 | 1.1 | 37 | 29 | 12 | 0.7 | 0.6 | 0.4 | 5 | 0.3 |
| JMG118 | n.d. | 32 | n.d. | 1.4 | 45 | 31 | 9 | 0.8 | 0.6 | 0.3 | 8 | 0.2 |
| JMG119 | n.d. | 34 | n.d. | 1.5 | 57 | 32 | 14 | 1.0 | 0.6 | 0.5 | 13 | 0.4 |
| JMG120 | 38 | 25 | 1.3 | 1.1 | 71 | 48 | 27 | 1.2 | 0.9 | 0.9 | 27 | 0.8 |
| JMG121 | 45 | 24 | 1.5 | 1.0 | 44 | 35 | 16 | 0.7 | 0.7 | 0.6 | 6 | 0.2 |
| JMG122 | 44 | 19 | 1.5 | 0.8 | 40 | 30 | 12 | 0.7 | 0.7 | 0.4 | 5 | 0.4 |
| JMG123 | 40 | 20 | 1.2 | 0.9 | 49 | 41 | 21 | 0.9 | 0.9 | 0.7 | 9 | 0.7 |
| JMG124 | 66 | 22 | 1.8 | 0.9 | 47 | 38 | 19 | 0.9 | 0.9 | 0.7 | 8 | 0.6 |
| JMG125 | 32 | 19 | 0.9 | 0.8 | 48 | 38 | 17 | 0.8 | 0.8 | 0.6 | 8 | 0.3 |
| JMG126 | 29 | 33 | 1.3 | 1.4 | 52 | 39 | 23 | 0.9 | 0.8 | 0.9 | 11 | 0.4 |
| JMG127 | 61 | 31 | 1.6 | 1.4 | 55 | 43 | 26 | 1.0 | 1.0 | 1.1 | 19 | 1.3 |
| JMG128 | 73 | 26 | 2.0 | 1.7 | 55 | 43 | 28 | 0.9 | 1.0 | 1.1 | 14 | 0.9 |
| JMG129 | 39 | 19 | 1.1 | 1.2 | 47 | 41 | 23 | 0.8 | 0.9 | 0.9 | 8 | 0.4 |
| JMG130 | 56 | 28 | 1.6 | 0.9 | 47 | 39 | 24 | 0.8 | 0.9 | 0.9 | 10 | 0.6 |

TABLE 64-continued

Thermostability of mutants having a triple mutation in the TMD of
TSHR-JMG55 (JMG112 to JMG142): Stability assays A, B and C.

|  | Stability Assay A and B[a] | | | | Stability Assay C[b] | | | | | | | |
|---|---|---|---|---|---|---|---|---|---|---|---|---|
|  | Half-life at | | Half-life ratio at | | | Survival at | | | Survival ratio at | | Half-life | Half-life |
|  | 55° C. | | | | | | | | | | | |
| JMG131 | 60 | 32 | 1.5 | 1.1 | 63 | 50 | 32 | 1.2 | 1.2 | 1.4 | 47 | 3.5 |
| JMG132 | 54 | 28 | 1.5 | 0.9 | 47 | 39 | 25 | 0.8 | 1.0 | 1.0 | 8 | 0.6 |
| JMG133 | 49 | 28 | 1.4 | 0.9 | 41 | 34 | 22 | 0.7 | 0.8 | 0.9 | 7 | 0.5 |
| JMG134 | 64 | 30 | 1.8 | 1.6 | 50 | 42 | 24 | 0.9 | 1.0 | 1.0 | 11 | 0.8 |
| JMG135 | 63 | 23 | 1.8 | 1.3 | 52 | 43 | 24 | 0.9 | 1.0 | 1.0 | 19 | 1.3 |
| JMG136 | 59 | 24 | 1.7 | 1.3 | 52 | 40 | 24 | 0.9 | 1.0 | 1.0 | 11 | 0.8 |
| JMG137 | 52 | 22 | 1.5 | 1.2 | 56 | 49 | 31 | 1.0 | 1.2 | 1.3 | 35 | 2.4 |
| JMG138 | 55 | 35 | 1.3 | 1.2 | 60 | 48 | 26 | 1.1 | 1.2 | 1.1 | 30 | 2.2 |
| JMG139 | 65 | 29 | 1.5 | 1.4 | 56 | 43 | 23 | 1.0 | 1.0 | 1.0 | 15 | 1.1 |
| JMG140 | 57 | 24 | 1.3 | 1.1 | 48 | 41 | 21 | 0.9 | 1.0 | 0.9 | 17 | 1.3 |
| JMG141 | 46 | 23 | 1.3 | 1.2 | 47 | 38 | 19 | 0.8 | 0.9 | 0.8 | 8 | 0.6 |
| JMG142 | 73 | 29 | 1.6 | 1.3 | 43 | 35 | 20 | 0.8 | 0.9 | 0.9 | 7 | 0.5 |

TSHR mutants as defined in Table 61.
[a]In stability assay A (FIG. 14b) and stability assay B (FIG. 14c) the half-life of each mutant was determined by first binding the mutant to a 14C4-coated ELISA plate well (stability assay A) or 4E31-coated ELISA plate well (stability assay B). Strips of the plate wells with mutant TSHR bound were heated at 55° C. for periods of up to two hours. The amount of active mutant TSHR protein remaining was determined by the TSHR-binding assay and plotted against time. In each experiment, the thermostability (half-life, t½) of TSHR-JMG91 or TSHR-JMG84 was measured and used to determine the half-life ratio for each mutant compared to the half-life of TSHR-JMG91 or TSHR-JMG84 in the same experiment.
[b]In stability assay C (FIG. 14d), solubilised aliquots of TSHR mutant were heated at 40° C. in solution for up to two hours. The amount of active TSHR protein remaining was determined by TSHR-binding assay, plotted against time and fitted to a two-phase exponential decay curve. The percentage of active TSHR mutant remaining after heating for 10, 30 and 120 min was calculated and compared to TSHR-JMG91 or TSHR-JMG84 (JMG112 to JMG126 compared to TSHR-JMG91 and JMG127 to JMG142 compared to TSHR-JMG84). The apparent half-life was also determined as the time point at which the TSHR-JMG55 mutant has lost half of its activity. This is used to calculate the half-life ratio is by dividing it by the apparent half-life of TSHR-JMG91 or TSHR-JMG84 measured in the same experiment.
Experiments were performed once for each mutant in each assay (assayed in duplicate).
"n.d." = not determined.

TABLE 65

M22-POD binding to TSHR-JMG55 with mutants in the TMD (FIG. 14a)

| M22-POD (ng/ml) | TSHR-JMG55 | | TSHR-JMG55-V595I | | TSHR-JMG84 | | TSHR-JMG91 | |
|---|---|---|---|---|---|---|---|---|
|  | OD450 | % Max | OD450 | % Max | OD450 | % Max | OD450 | % Max |
| 500 | 3.21 ± 0.07 | 100.0 ± 2.5 | 3.20 ± 0.07 | 100.0 ± 2.4 | 3.16 ± 0.03 | 100.0 ± 0.1 | 3.15 ± 0.05 | 100.0 ± 1.1 |
| 200 | 2.51 ± 0.04 | 77.0 ± 1.0 | 2.62 ± 0.03 | 80.6 ± 0.7 | 2.56 ± 0.09 | 88.7 ± 0.2 | 2.23 ± 0.02 | 69.9 ± 0.8 |
| 100 | 1.65 ± 0.05 | 50.5 ± 1.7 | 1.77 ± 0.04 | 54.2 ± 1.4 | 1.65 ± 0.02 | 59.7 ± 1.6 | 1.38 ± 0.01 | 43.2 ± 0.4 |
| 75 | 1.29 ± 0.02 | 39.4 ± 0.5 | 1.41 ± 0.03 | 43.3 ± 0.9 | 1.30 ± 0.13 | 48.5 ± 0.3 | 1.13 ± 0.00 | 35.3 ± 0.1 |
| 50 | 0.89 ± 0.02 | 27.1 ± 0.7 | 0.98 ± 0.02 | 30.0 ± 0.7 | 0.91 ± 0.03 | 33.9 ± 0.1 | 0.64 ± 0.02 | 19.9 ± 0.6 |
| 25 | 0.47 ± 0.00 | 14.4 ± 0.0 | 0.51 ± 0.01 | 15.8 ± 0.4 | 0.41 ± 0.01 | 17.5 ± 0.2 | 0.35 ± 0.00 | 11.0 ± 0.1 |
| 10 | 0.19 ± 0.00 | 5.9 ± 0.1 | 0.18 ± 0.02 | 5.6 ± 0.4 | 0.11 ± 0.09 | 7.1 ± 0.2 | 0.14 ± 0.00 | 4.5 ± 0.0 |
| 5 | 0.10 ± 0.01 | 3.2 ± 0.2 | 0.10 ± 0.01 | 3.2 ± 0.0 | 0.06 ± 0.04 | 3.8 ± 0.1 | 0.07 ± 0.00 | 2.3 ± 0.1 |
| 1 | 0.01 ± 0.01 | 0.4 ± 0.2 | 0.02 ± 0.00 | 0.7 ± 0.0 | −0.02 ± 0.03 | 0.8 ± 0.1 | 0.02 ± 0.00 | 0.5 ± 0.0 |
| 0 | 0.00 ± 0.00 | 0.0 ± 0.0 | 0.00 ± 0.00 | 0.0 ± 0.0 | −0.05 ± 0.04 | 0.1 ± 0.1 | 0.00 ± 0.00 | 0.0 ± 0.0 |
| $K_d$ (ng/mL) | 176.9 | | 149.4 | | 121.5 | | 255.9 | |
| $K_d$ (% JMG55) | 100 | | 84 | | 69 | | 145 | |

Results are expressed as absorbance at 450 nm, with non-specific binding (i.e. absorbance of well with no TSHR bound, at the M22-POD concentrations listed) subtracted. Also the percentage of the OD450 reading obtained with 500 ng/mL M22-POD (% Max) is shown, Kd was determined by fitting a saturation binding curve to the data with GraphPad Prism. Values shown are means ± SD; n = 2, for single experiments.

TABLE 66

K1-70-POD binding to TSHR-JMG55 with mutants in the TMD (FIG. 14a)

| K1-70-POD (µg/ml) | TSHR-JMG55 | | TSHR-JMG55-V595I | | TSHR-JMG84 | | TSHR-JMG91 | |
|---|---|---|---|---|---|---|---|---|
|  | OD450 | % Max | OD450 | % Max | OD450 | % Max | OD450 | % Max |
| 10 | 2.83 ± 0.07 | 100.0 ± 2.4 | 2.86 ± 0.05 | 100.0 ± 0.7 | 2.34 ± 0.31 | 100.0 ± 0.1 | 2.82 ± 0.04 | 100.0 ± 0.5 |
| 7.5 | 2.95 ± 0.08 | 98.3 ± 3.2 | 2.97 ± 0.04 | 97.9 ± 0.3 | 2.59 ± 0.22 | 98.3 ± 1.1 | 2.85 ± 0.06 | 96.1 ± 0.8 |
| 5 | 2.59 ± 0.21 | 83.2 ± 7.0 | 2.76 ± 0.02 | 87.3 ± 0.6 | 2.50 ± 0.01 | 89.0 ± 7.7 | 2.57 ± 0.07 | 83.0 ± 0.8 |
| 2.5 | 1.66 ± 0.01 | 52.4 ± 1.6 | 1.86 ± 0.03 | 57.5 ± 0.5 | 1.88 ± 0.23 | 71.1 ± 1.8 | 1.70 ± 0.03 | 53.8 ± 0.6 |
| 1 | 0.67 ± 0.05 | 21.8 ± 0.2 | 0.80 ± 0.05 | 25.2 ± 0.2 | 0.88 ± 0.04 | 35.8 ± 1.7 | 0.62 ± 0.00 | 20.6 ± 1.4 |
| 0.75 | 0.52 ± 0.02 | 17.2 ± 1.0 | 0.62 ± 0.06 | 19.7 ± 0.2 | 0.66 ± 0.04 | 19.5 ± 0.4 | 0.59 ± 0.14 | 19.3 ± 2.4 |
| 0.5 | 0.35 ± 0.05 | 12.0 ± 0.2 | 0.40 ± 0.11 | 13.2 ± 1.5 | 0.43 ± 0.01 | 30.7 ± 2.1 | 0.40 ± 0.09 | 13.4 ± 1.0 |
| 0.25 | 0.16 ± 0.04 | 6.1 ± 0.4 | 0.21 ± 0.07 | 7.4 ± 0.5 | 0.21 ± 0.00 | 9.4 ± 1.3 | 0.20 ± 0.04 | 7.4 ± 0.5 |

TABLE 66-continued

K1-70-POD binding to TSHR-JMG55 with mutants in the TMD (FIG. 14a)

| K1-70-POD | TSHR-JMG55 | | TSHR-JMG55-V595I | | TSHR-JMG84 | | TSHR-JMG91 | |
|---|---|---|---|---|---|---|---|---|
| (µg/ml) | OD450 | % Max | OD450 | % Max | OD450 | % Max | OD450 | % Max |
| 10 | 2.83 ± 0.07 | 100.0 ± 2.4 | 2.86 ± 0.05 | 100.0 ± 0.7 | 2.34 ± 0.31 | 100.0 ± 0.1 | 2.82 ± 0.04 | 100.0 ± 0.5 |
| 7.5 | 2.95 ± 0.08 | 98.3 ± 3.2 | 2.97 ± 0.04 | 97.9 ± 0.3 | 2.59 ± 0.22 | 98.3 ± 1.1 | 2.85 ± 0.06 | 96.1 ± 0.8 |
| 0.1 | 0.04 ± 0.07 | 2.5 ± 0.3 | 0.07 ± 0.06 | 3.4 ± 0.1 | 0.08 ± 0.00 | 4.8 ± 0.3 | 0.02 ± 0.02 | 3.4 ± 0.2 |
| 0 | −0.05 ± 0.06 | −0.2 ± 0.0 | −0.04 ± 0.06 | 0.2 ± 0.1 | −0.02 ± 0.00 | 0.0 ± 0.0 | −0.04 ± 0.06 | 0.0 ± 0.0 |
| $K_d$ (µg/mL) | 4.5 | | 3.5 | | 2.3 | | 4.1 | |
| $K_d$ (% JMG55) | 100 | | 79 | | 52 | | 92 | |

Results are expressed as absorbance at 450 nm, with non-specific binding (i.e. absorbance of well with no TSHR bound, at the K1-70-POD concentrations listed) subtracted. Also the percentage of the OD450 reading obtained with 10 µg/mL K1-70-POD (% Max) is shown, Kd was determined by fitting a saturation binding curve to the data with GraphPad Prism. Values shown are means ± SD; n = 2, for single experiments.

TABLE 67

K1-18-POD binding to TSHR-JMG55 with mutants in the TMD (FIG. 14a)

| K1-18-POD | TSHR-JMG55 | | TSHR-JMG55-V595I | | TSHR-JMG84 | | TSHR-JMG91 | |
|---|---|---|---|---|---|---|---|---|
| (µg/ml) | OD450 | % Max | OD450 | % Max | OD450 | % Max | OD450 | % Max |
| 10 | 2.76 ± 0.11 | 100.0 ± 0.4 | 2.69 ± 0.07 | 100.0 ± 0.8 | 2.34 ± 0.27 | 100.0 ± 1.4 | 2.77 ± 0.13 | 100.0 ± 0.9 |
| 7.5 | 2.88 ± 0.14 | 97.4 ± 2.0 | 2.72 ± 0.05 | 94.8 ± 0.5 | 2.45 ± 0.21 | 99.1 ± 0.2 | 2.86 ± 0.03 | 96.7 ± 1.0 |
| 5 | 2.76 ± 0.06 | 88.1 ± 0.6 | 2.34 ± 0.08 | 78.2 ± 1.3 | 2.40 ± 0.11 | 97.2 ± 1.0 | 2.68 ± 0.03 | 85.7 ± 1.8 |
| 2.5 | 1.84 ± 0.11 | 56.8 ± 2.9 | 1.61 ± 0.13 | 51.5 ± 3.5 | 1.66 ± 0.03 | 82.5 ± 0.5 | 1.76 ± 0.18 | 54.6 ± 5.0 |
| 1 | 0.79 ± 0.03 | 24.3 ± 1.3 | 0.70 ± 0.02 | 22.2 ± 0.2 | 0.80 ± 0.04 | 43.1 ± 3.3 | 0.80 ± 0.11 | 24.6 ± 3.5 |
| 0.75 | 0.55 ± 0.03 | 17.1 ± 0.4 | 0.47 ± 0.06 | 15.1 ± 1.2 | 0.60 ± 0.06 | 32.7 ± 0.8 | 0.59 ± 0.02 | 18.1 ± 1.2 |
| 0.5 | 0.37 ± 0.01 | 11.6 ± 0.3 | 0.34 ± 0.03 | 10.8 ± 0.1 | 0.43 ± 0.01 | 26.7 ± 0.5 | 0.34 ± 0.02 | 10.6 ± 0.1 |
| 0.25 | 0.16 ± 0.01 | 5.3 ± 0.5 | 0.12 ± 0.02 | 4.3 ± 0.2 | 0.22 ± 0.04 | 13.5 ± 0.5 | 0.15 ± 0.04 | 4.8 ± 0.3 |
| 0.1 | 0.06 ± 0.02 | 2.0 ± 0.1 | 0.06 ± 0.03 | 2.1 ± 0.0 | 0.06 ± 0.01 | 5.5 ± 0.4 | 0.07 ± 0.03 | 2.3 ± 0.1 |
| 0 | −0.02 ± 0.03 | −0.4 ± 0.1 | −0.01 ± 0.02 | −0.2 ± 0.2 | −0.02 ± 0.01 | 0.2 ± 0.2 | 0.00 ± 0.06 | 0.1 ± 0.7 |
| $K_d$ (µg/mL) | 3.5 | | 4.3 | | 1.7 | | 3.6 | |
| $K_d$ (% JMG55) | 100 | | 124 | | 49 | | 104 | |

Results are expressed as absorbance at 450 nm, with non-specific binding (i.e. absorbance of well with no TSHR bound, at the K1-18-POD concentrations listed) subtracted. Also the percentage of the OD450 reading obtained with 10 µg/mL K1-18-POD (% Max) is shown, Kd was determined by fitting a saturation binding curve to the data with GraphPad Prism. Values shown are means ± SD; n = 2, for single experiments.

TABLE 68

Inhibition by M22 IgG of M22-POD binding to TSHR mutants (FIG. 14e).

| M22 IgG | TSHR-JMG55 | | TSHR-JMG55 + V595I | | TSHR-JMG84 | | TSHR-JMG91 | |
|---|---|---|---|---|---|---|---|---|
| (ng/mL) | OD450 | Inhibition (%) | OD450 | Inhibition (%) | OD450 | Inhibition (%) | OD450 | Inhibition (%) |
| 1000 | 0.80 ± 0.02 | 75.7 ± 0.5 | 0.61 ± 0.01 | 78.7 ± 0.3 | 0.55 ± 0.02 | 80.9 ± 0.8 | 0.52 ± 0.00 | 82.3 ± 0.1 |
| 300 | 1.08 ± 0.01 | 67.3 ± 0.3 | 0.81 ± 0.00 | 71.5 ± 0.1 | 0.82 ± 0.00 | 71.8 ± 0.1 | 0.83 ± 0.04 | 72.2 ± 1.4 |
| 100 | 1.78 ± 0.01 | 45.8 ± 0.4 | 1.36 ± 0.01 | 52.1 ± 0.2 | 1.54 ± 0.03 | 46.9 ± 0.9 | 1.59 ± 0.03 | 46.4 ± 1.1 |
| 30 | 2.65 ± 0.07 | 19.4 ± 2.2 | 2.08 ± 0.01 | 26.7 ± 0.2 | 2.44 ± 0.02 | 16.0 ± 0.8 | 2.50 ± 0.02 | 15.6 ± 0.6 |
| 10 | 2.94 ± 0.02 | 10.7 ± 0.6 | 2.43 ± 0.03 | 14.3 ± 1.1 | 2.68 ± 0.04 | 7.6 ± 1.4 | 2.64 ± 0.07 | 11.1 ± 2.5 |
| 3 | 3.24 ± 0.01 | 1.6 ± 0.4 | 2.69 ± 0.04 | 5.3 ± 1.5 | 2.99 ± 0.00 | −3.1 ± 0.1 | 2.91 ± 0.00 | 1.9 ± 0.0 |
| 1 | 3.27 ± 0.01 | 0.8 ± 0.4 | 2.77 ± 0.01 | 2.3 ± 1.5 | 2.96 ± 0.03 | −1.8 ± 1.0 | 2.98 ± 0.05 | −0.6 ± 1.8 |
| 0 | 3.29 ± 0.02 | 0.0 ± 0.5 | 2.84 ± 0.03 | 0.0 ± 0.9 | 2.90 ± 0.10 | 0.0 ± 3.3 | 2.97 ± 0.09 | 0.0 ± 3.1 |

Results are presented as absorbance at 450 nm and a percentage of inhibition of M22-POD binding ± SD for duplicate measurements in a single experiment.

TABLE 69

Inhibition by K1-18 IgG of M22-POD binding to TSHR mutants (FIG. 14e).

| K1-18 IgG | TSHR-JMG55 | | TSHR-JMG55 + V595I | | TSHR-JMG84 | | TSHR-JMG91 | |
|---|---|---|---|---|---|---|---|---|
| (ng/mL) | OD450 | Inhibition (%) | OD450 | Inhibition (%) | OD450 | Inhibition (%) | OD450 | Inhibition (%) |
| 1000 | 0.43 ± 0.01 | 86.9 ± 0.4 | 0.36 ± 0.01 | 87.4 ± 0.2 | 0.29 ± 0.02 | 89.9 ± 0.8 | 0.30 ± 0.01 | 90.0 ± 0.3 |
| 300 | 1.05 ± 0.05 | 68.1 ± 1.6 | 0.89 ± 0.03 | 68.7 ± 1.1 | 0.88 ± 0.05 | 69.6 ± 1.8 | 0.98 ± 0.04 | 67.1 ± 1.5 |
| 100 | 2.11 ± 0.02 | 35.8 ± 0.6 | 1.72 ± 0.02 | 39.5 ± 0.5 | 1.91 ± 0.03 | 34.1 ± 1.0 | 1.83 ± 0.00 | 38.2 ± 0.1 |

TABLE 69-continued

Inhibition by K1-18 IgG of M22-POD binding to TSHR mutants (FIG. 14e).

| K1-18 IgG | TSHR-JMG55 | | TSHR-JMG55 + V595I | | TSHR-JMG84 | | TSHR-JMG91 | |
|---|---|---|---|---|---|---|---|---|
| (ng/mL) | OD450 | Inhibition (%) | OD450 | Inhibition (%) | OD450 | Inhibition (%) | OD450 | Inhibition (%) |
| 30 | 2.95 ± 0.03 | 10.4 ± 0.8 | 2.47 ± 0.01 | 13.0 ± 0.3 | 2.52 ± 0.04 | 13.3 ± 1.2 | 2.54 ± 0.04 | 14.5 ± 1.4 |
| 10 | 3.16 ± 0.05 | 4.1 ± 1.6 | 2.65 ± 0.05 | 6.5 ± 1.9 | 2.84 ± 0.04 | 2.2 ± 1.5 | 2.83 ± 0.01 | 4.8 ± 0.3 |
| 3 | 3.29 ± 0.03 | 0.2 ± 0.9 | 2.80 ± 0.00 | 1.3 ± 0.1 | 3.03 ± 0.07 | −4.3 ± 2.4 | 2.90 ± 0.00 | 2.1 ± 0.1 |
| 1 | 3.26 ± 0.03 | 1.1 ± 0.9 | 2.84 ± 0.01 | −0.3 ± 0.4 | 3.00 ± 0.01 | −3.3 ± 0.2 | 2.89 ± 0.03 | 2.5 ± 0.9 |
| 0 | 3.29 ± 0.02 | 0.0 ± 0.5 | 2.84 ± 0.03 | 0.0 ± 0.9 | 2.90 ± 0.10 | 0.0 ± 3.3 | 2.97 ± 0.09 | 0.0 ± 3.1 |

Results are presented as absorbance at 450 nm and a percentage of inhibition of M22-POD binding ± SD for duplicate measurements in a single experiment.

TABLE 70

Inhibition by K1-70 IgG of M22-POD binding to TSHR mutants (FIG. 14e).

| K1-70 IgG | TSHR-JMG55 | | TSHR-JMG55 + V595I | | TSHR-JMG84 | | TSHR-JMG91 | |
|---|---|---|---|---|---|---|---|---|
| (ng/mL) | OD450 | Inhibition (%) | OD450 | Inhibition (%) | OD450 | Inhibition (%) | OD450 | Inhibition (%) |
| 1000 | 0.23 ± 0.00 | 93.0 ± 0.1 | 0.20 ± 0.01 | 93.1 ± 0.4 | 0.19 ± 0.00 | 93.5 ± 0.0 | 0.19 ± 0.00 | 93.8 ± 0.1 |
| 300 | 0.88 ± 0.02 | 73.4 ± 0.7 | 0.70 ± 0.01 | 75.5 ± 0.2 | 0.79 ± 0.02 | 72.8 ± 0.8 | 0.83 ± 0.04 | 72.1 ± 1.4 |
| 100 | 2.11 ± 0.07 | 35.8 ± 2.0 | 1.64 ± 0.10 | 42.1 ± 3.5 | 1.81 ± 0.01 | 37.6 ± 0.3 | 2.02 ± 0.00 | 32.0 ± 0.1 |
| 30 | 2.86 ± 0.00 | 13.0 ± 0.0 | 2.29 ± 0.05 | 19.3 ± 1.6 | 2.55 ± 0.01 | 12.3 ± 0.3 | 2.54 ± 0.10 | 14.3 ± 3.3 |
| 10 | 3.16 ± 0.06 | 3.9 ± 1.8 | 2.61 ± 0.04 | 8.1 ± 1.2 | 2.85 ± 0.00 | 1.8 ± 0.0 | 2.82 ± 0.09 | 4.9 ± 3.1 |
| 3 | 3.20 ± 0.02 | 2.8 ± 0.5 | 2.74 ± 0.04 | 3.5 ± 1.2 | 2.94 ± 0.09 | −1.2 ± 3.0 | 2.96 ± 0.12 | 0.2 ± 3.9 |
| 1 | 3.28 ± 0.08 | 0.3 ± 2.5 | 2.80 ± 0.06 | 1.4 ± 2.0 | 2.97 ± 0.01 | −2.2 ± 0.5 | 3.04 ± 0.03 | −2.6 ± 1.1 |
| 0 | 3.29 ± 0.02 | 0.0 ± 0.5 | 2.84 ± 0.03 | 0.0 ± 0.9 | 2.90 ± 0.10 | 0.0 ± 3.3 | 2.97 ± 0.09 | 0.0 ± 3.1 |

Results are presented as absorbance at 450 nm and a percentage of inhibition of M22-POD binding ± SD for duplicate measurements in a single experiment.

TABLE 71

Inhibition of M22-POD binding to TSHR mutants by patient sera (FIG. 14e).

| | | TSHR-JMG55 | | TSHR-JMG55 + V595I | | TSHR-JMG84 | | TSHR-JMG91 | |
|---|---|---|---|---|---|---|---|---|---|
| Test sample | | OD450 | % Inhibition | OD450 | % Inhibition | OD450 | % Inhibition | OD450 | % Inhibition |
| Normal sera | 9924 | 1.43 ± 0.00 | 13.2 | 2.108 ± 0.05 | 7.1 | 2.585 ± 0.04 | 4.9 | 1.231 ± 0.01 | 8.3 |
| | 18284 | 1.67 ± 0.00 | −1.2 | 2.223 ± 0.00 | 2.1 | 2.635 ± 0.04 | 3.1 | 1.275 ± 0.04 | 5.0 |
| | 18288 | 1.70 ± 0.10 | −3.3 | 2.319 ± 0.06 | −2.2 | 2.783 ± 0.01 | −2.4 | 1.354 ± 0.07 | −0.9 |
| | 18289 | 1.72 ± 0.05 | −4.4 | 2.292 ± 0.02 | −1.0 | 2.787 ± 0.03 | −2.5 | 1.419 ± 0.06 | −5.7 |
| | 18290 | 1.70 ± 0.01 | −3.0 | 2.436 ± — | −7.3 | 2.796 ± 0.03 | −2.8 | 1.405 ± 0.05 | −4.7 |
| | 18296 | 1.67 ± 0.01 | −1.3 | 2.24 ± 0.07 | 1.3 | 2.726 ± 0.01 | −0.3 | 1.37 ± 0.05 | −2.1 |
| | Mean | 1.647 ± 0.05 | 0.0 | 2.270 ± 0.05 | 0.0 | 2.719 ± 0.03 | 0.0 | 1.342 ± 0.05 | 0.0 |
| TRAb positive patient sera | 52 | 0.80 ± 0.01 | 51.7 | 1.107 ± 0.01 | 51.2 | 1.504 ± 0.03 | 44.7 | 0.699 ± 0.05 | 47.9 |
| | 57 | 0.33 ± 0.00 | 80.1 | 0.448 ± 0.00 | 80.3 | 0.704 ± 0.02 | 74.1 | 0.353 ± 0.03 | 73.7 |
| | 69 | 0.51 ± 0.05 | 69.3 | 0.715 ± 0.01 | 68.5 | 1.05 ± 0.03 | 61.4 | 0.516 ± 0.01 | 61.5 |
| | 73 | 0.16 ± 0.00 | 90.5 | 0.164 ± 0.00 | 92.8 | 0.192 ± 0.01 | 92.9 | 0.141 ± 0.00 | 89.5 |
| | 98 | 0.15 ± 0.00 | 90.9 | 0.174 ± 0.01 | 92.3 | 0.231 ± 0.00 | 91.5 | 0.122 ± 0.01 | 90.9 |
| | 102 | 0.65 ± 0.02 | 60.8 | 0.923 ± 0.06 | 59.3 | 1.297 ± 0.01 | 52.3 | 0.544 ± 0.06 | 59.5 |
| | 104 | 0.62 ± 0.05 | 62.7 | 0.876 ± 0.01 | 61.4 | 1.244 ± 0.00 | 54.2 | 0.549 ± 0.01 | 59.1 |
| | 112 | 0.66 ± 0.01 | 59.9 | 1.014 ± 0.06 | 55.3 | 1.283 ± 0.01 | 52.8 | 0.602 ± 0.04 | 55.1 |
| | 113 | 0.51 ± 0.02 | 69.2 | 0.714 ± 0.03 | 68.5 | 1.048 ± 0.02 | 61.5 | 0.471 ± 0.00 | 64.9 |

Results are shown as absorbance at 450 nm (mean ± SD; n = 2) and percent inhibition of M22-POD binding.

TABLE 72

Equivalent residues of hTSHR-JMG55 mutations in mouse and porcine TSHR

| hTSHR mutation | Equivalent mouse TSHR residue | Equivalent porcine TSHR residue |
|---|---|---|
| E409K | E409 | E409 |
| D410K | D410 | D410 |
| H443N | H443 | H443 |
| L452Y | L452 | L452 |

TABLE 72-continued

Equivalent residues of hTSHR-JMG55 mutations in mouse and porcine TSHR

| hTSHR mutation | Equivalent mouse TSHR residue | Equivalent porcine TSHR residue |
|---|---|---|
| N455A | N455 | N455 |
| M463V | M463 | M463 |
| Y466F | Y466 | Y466 |
| L467P | L467 | L467 |
| T477I | T477 | T477 |
| Q489H | Q489 | Q489 |
| K565L | K565 | K565 |
| V595I | V595 | T595 |
| C600R | C600 | C600 |
| Y601F | Y601 | Y601 |
| I648L | L648 | L648 |
| K660D | K660 | K660 |
| Y667V | Y667 | Y667 |
| S671A | S671 | S671 |
| Y678L | Y678 | Y678 |
| Y678A | Y678 | Y678 |

Most of the thermostabilising mutated residues of hTSHR-JMG55 are well-conserved across TSHR from mouse and porcine. Only the residues at positions 595 and 648 differ across species. Residue 595 is Valine in human and mouse, but Threonine in porcine. Residue 648 is Isoleucine in human but Leucine in mouse and porcine.

TABLE 73

Analysis of the thermostabilising amino acid residues in the TMD of the human TSHR compared to the equivalent amino acid residues in human FSHR and human LHR

| hTSHR mutation | Equivalent hFSHR residue | Equivalent hLHR residue |
|---|---|---|
| E409K | E357 | E354 |
| D410K | D358 | D355 |
| H443N | Q391 | R388 |
| L452Y | L400 | L397 |
| N455A | N403 | N400 |
| M463V | I411 | M408 |
| Y466F | Y414 | Y411 |
| L467P | L415 | L412 |
| T477I | T425 | T422 |
| Q489H | Q437 | Q434 |
| K565L | K513 | K510 |
| V595I | V543 | V540 |
| C600R | C548 | C545 |
| Y601F | Y549 | Y546 |
| I648L | S596 | A593 |
| K660D | K608 | K605 |
| Y667V | H615 | Y612 |
| S671A | S619 | S616 |
| Y678L | Y626 | Y623 |
| Y678A | Y626 | Y623 |

The residues in hFSHR (SEQ ID No 57) and hLHR (SEQ ID No 58) that are identical in hTSHR (SEQ ID No 2) are in bold. In addition to these, many of the residue differences between the receptors are limited to amino acids with similar properties, e.g. basic, acidic, aliphatic or aromatic. Transferring the analogous thermostabilising mutations from hTSHR to hFSHR and hLHR is likely to improve the thermostability of these receptors.

The invention claimed is:

1. A mutant thyroid stimulating hormone receptor (TSHR) which is a mutated form of human wild type TSHR shown in SEQ ID NO: 2 or fragment thereof, which mutant TSHR or fragment thereof is able to bind TSHR autoantibodies and comprises residues 22-260 of the TSHR as shown in SEQ ID NO: 4 or a sequence having 9011% sequence identity therewith, wherein the mutant TSHR or fragment thereof, has increased thermostability with respect to the equivalent non-mutated wild type TSHR or fragment thereof, wherein thermostability refers to the half-life of the mutant TSHR or fragment thereof, as compared to the half-life of the equivalent wild-type TSHR or fragment thereof, as measured under identical conditions in a binding assay which determines the amount of mutant TSHR or fragment thereof that retains ability to bind, at the test temperature, an autoantibody selected from the group consisting of: M22, KI-70; K1-18, and patient serum autoantibodies, wherein the half-life of the mutant TSHR or fragment thereof at 42° C. is 1.5 times greater or more than the half-life of the equivalent wild type TSHR or fragment thereof, and wherein the mutant TSHR or fragment thereof comprises one or more mutations are within residues 22 to 260 of the mutant TSHR as shown in SEQ ID NO: 2 or fragment thereof, wherein the one or more mutations are selected from the group consisting of:
1) I253R;
2) D143P and I253R;
3) R112P and D143P and I253R;
4) R112P and D143P and D151E and I253R;
5) R112P and D143P and D151E and V169R and I253R;
6) H63C and R112P and D143P and D151E and V169R and I253R;
7) H63C and R112P and D143P and V169R and I253R; and
8) H63C and R112P and D143P and S166T and I253R.

2. A mutant TSHR or fragment thereof according to claim 1, wherein the mutant TSHR or fragment thereof is from, or is derived from, a mammalian species selected from the group consisting of: human TSHR shown in SEQ ID NO: 2 or a fragment thereof, and a species having 86 to 97.5% sequence identity with said human TSHR or fragment thereof.

3. A mutant TSHR or fragment thereof according to claim 1, further comprising one or more mutations within the transmembrane domain selected from the group consisting of: E409K, D410K, H443N, L452Y, N455A, M463V, Y466F, L467P, T477I, Q489H, K565L, V595I, C600R, Y601F, I648L, K660D, Y667V, S671A, Y678L, and Y678A.

4. A mutant TSHR or fragment thereof according to claim 1, further comprising two point mutations within the transmembrane domain (TMD), one of which is T477I or V595I or I648L and the second of which is a different mutation selected from the group consisting of: E409K, D410K, H443N, L452Y, N455A, M463V, Y466F, L467P, Q489H, K565L, C600R, Y601F, K660D, Y667V, S671A, Y678L, and Y678A.

5. A mutant TSHR or fragment thereof according to claim 1, further comprising three point mutation(s) within the transmembrane domain (TMD), one of which is V595L, the second of which is Y678L or K565L, and the third of which is selected from the group consisting of: E409K, D410K, H443N, L452Y, N455A, M463V, Y466F, L467P, Q489H, K565L, C600R, Y601F, K660D, Y667V, S671A, Y678L, and Y678A.

6. A mutant TSHR or fragment thereof according to claim 1, wherein the mutant further comprises a detectable label selected from the group consisting of: enzymatic labels, isotopic labels, chemiluminescent labels, fluorescent labels, dyes, alkaline phosphatase (AP) labels and biotin labels.

7. A mutant TSHR or fragment thereof according to claim 1, wherein the mutant further comprises an alkaline phosphatase (AP) label.

8. A mutant TSHR or fragment thereof according to claim 7, selected from the group consisting of:

TSHR260-AP-I253R comprising TSHR260-AP and I253R;

TSHR260-AP-JMG22 comprising TSHR260-AP and D143P and I253R;

TSHR260-AP-JMG37 comprising TSHR260-AP and R112P and D143P and I253R;

TSHR260-AP-JMG45 comprising TSHR260-AP and R112P and D143P and D151E and I253R;

TSHR260-AP-JMG52 comprising TSHR260-AP and R112P and D143P and D151E and V169R and I253R;

TSHR260-AP-JMG55 comprising TSHR260-AP and H63C and R112P and D143P and D151E and V169R and I253R;

TSHR260-AP-JMG57 comprising TSHR260-AP and H63C and R112P and D143P and V169R and I253R; and TSHR260-AP-JMG58 comprising TSHR260-AP and H63C and R112P and D143P and S166T and I253R.

* * * * *

SEQUENCE LISTING

```
<160> NUMBER OF SEQ ID NOS: 108

<210> SEQ ID NO 1
<211> LENGTH: 2295
<212> TYPE: DNA
<213> ORGANISM: Homo sapiens

<400> SEQUENCE: 1
atgaggccgg cggacttgct gcagctggtg ctgctgctcg acctgcccag ggacctgggc      60
ggaatggggt gttcgtctcc accctgcgag tgccatcagg aggaggactt cagagtcacc     120
tgcaaggata ttcaacgcat ccccagctta ccgcccagta cgcagactct gaagcttatt     180
gagactcacc tgagaactat tccaagtcat gcattttcta atctgcccaa tatttccaga     240
atctacgtat ctatagatgt gactctgcag cagctggaat cacactcctt ctacaatttg     300
agtaaagtga ctcacataga aattcggaat accaggaact taacttacat agaccctgat     360
gccctcaaag agctccccct cctaaagttc cttggcattt tcaacactgg acttaaaatg     420
ttccctgacc tgaccaaagt ttattccact gatatattct ttatacttga aattacagac     480 aaccttaca tgacgtcaat ccctgtgaat gcttttcagg actatgcaa tgaaaccttg     540 acactgaagc tgtacaacaa cggctttact tcagtccaag atatgctttt caatgggaca     600
aagctggatg ctgtttacct aaacaagaat aaatacctga cagttattga caaagatgca     660
tttggaggag tatacagtgg accaagcttg ctggacgtgt ctcaaaccag tgtcactgcc     720
cttccatcca aaggcctgga gcacctgaag gaactgatag caagaaacac ctggactctt     780
aagaaacttc cactttcctt gagtttcctt cacctcacac gggctgacct tcttacccca     840
agccactgct gtgcctttaa gaatcagaag aaaatcagag aatccttga gtccttgatg     900 tgtaatgaga gcagtatgca gagcttgcgc cagagaaaat ctgtgaatgc cttgaatagc     960
```

```
cccctccacc aggaatatga agagaatctg ggtgacagca ttgttgggta caaggaaaag    1020
tccaagttcc aggatactca taacaacgct cattattacg tcttctttga agaacaagag    1080
gatgagatca ttggttttgg ccaggagctc aaaaaccccc aggaagagac tctacaagct    1140
tttgacagcc attatgacta caccatatgt ggggacagtg aagacatggt gtgtaccccc    1200
aagtccgatg agttcaaccc gtgtgaagac ataatgggct acaagttcct gagaattgtg    1260
gtgtggttcg ttagtctgct ggctctcctg gcaatgtct ttgtcctgct tattctcctc      1320
accagccact acaaactgaa cgtccccgc tttctcatgt gcaacctggc ctttgcggat      1380
ttctgcatgg ggatgtacct gctcctcatc gcctctgtag acctctacac tcactctgag    1440
tactacaacc atgccatcga ctggcagaca ggccctgggt gcaacgggc tggtttcttc      1500 actgtctttg caagcgagtt atcggtgtat acgctgacgg tcatcaccct ggagcgctgg    1560
tatgccatca ccttcgccat gcgcctggac cggaagatcc gcctcaggca cgcatgtgcc    1620
atcatggttg ggggctgggt ttgctgcttc cttctcgccc tgcttccttt ggtgggaata    1680
agtagctatg ccaaagtcag tatctgcctg cccatggaca ccgagacccc tcttgctctg    1740
gcatatattg tttttgttct gacgctcaac atagttgcct tcgtcatcgt ctgctgctgt    1800
tatgtgaaga tctacatcac agtccgaaat ccgcagtaca acccagggga caaagatacc    1860
aaaattgcca agaggatggc tgtgttgatc ttcaccgact tcatatgcat ggccccaatc    1920
tcattctatg ctctgtcagc aattctgaac aagcctctca tcactgttag caactccaaa    1980
atcttgctgg tactcttcta tccacttaac tcctgtgcca atccattcct ctatgctatt    2040
ttcaccaagg ccttccagag ggatgtgttc atcctactca gcaagtttgg catctgtaaa    2100
cgccaggctc aggcataccg ggggcagagg gttcctccaa agaacagcac tgatattcag    2160
gttcaaaagg ttacccacga gatgaggcag ggtctccaca acatggaaga tgtctatgaa    2220
ctgattgaaa agtcccatct aaccccaaag aagcaaggcc aaatctcaga agagtatatg    2280
caaacggttt tgtaa                                                     2295
```

<210> SEQ ID NO 2
<211> LENGTH: 764
<212> TYPE: PRT
<213> ORGANISM: Homo sapiens

<400> SEQUENCE: 2

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Leu Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu

-continued

```
            130                 135                 140
Thr Lys Val Tyr Ser Thr Asp Ile Phe Phe Ile Leu Glu Ile Thr Asp
145                 150                 155                 160
Asn Pro Tyr Met Thr Ser Ile Pro Val Asn Ala Phe Gln Gly Leu Cys
                165                 170                 175
Asn Glu Thr Leu Thr Leu Lys Leu Tyr Asn Asn Gly Phe Thr Ser Val
            180                 185                 190
Gln Gly Tyr Ala Phe Asn Gly Thr Lys Leu Asp Ala Val Tyr Leu Asn
        195                 200                 205
Lys Asn Lys Tyr Leu Thr Val Ile Asp Lys Asp Ala Phe Gly Gly Val
    210                 215                 220
Tyr Ser Gly Pro Ser Leu Leu Asp Val Ser Gln Thr Ser Val Thr Ala
225                 230                 235                 240
Leu Pro Ser Lys Gly Leu Glu His Leu Lys Glu Leu Ile Ala Arg Asn
                245                 250                 255
Thr Trp Thr Leu Lys Lys Leu Pro Leu Ser Leu Ser Phe Leu His Leu
            260                 265                 270
Thr Arg Ala Asp Leu Ser Tyr Pro Ser His Cys Cys Ala Phe Lys Asn
        275                 280                 285
Gln Lys Lys Ile Arg Gly Ile Leu Glu Ser Leu Met Cys Asn Glu Ser
    290                 295                 300
Ser Met Gln Ser Leu Arg Gln Arg Lys Ser Val Asn Ala Leu Asn Ser
305                 310                 315                 320
Pro Leu His Gln Glu Tyr Glu Glu Asn Leu Gly Asp Ser Ile Val Gly
                325                 330                 335
Tyr Lys Glu Lys Ser Lys Phe Gln Asp Thr His Asn Asn Ala His Tyr
            340                 345                 350
Tyr Val Phe Phe Glu Glu Gln Glu Asp Glu Ile Ile Gly Phe Gly Gln
        355                 360                 365
Glu Leu Lys Asn Pro Gln Glu Glu Thr Leu Gln Ala Phe Asp Ser His
    370                 375                 380
Tyr Asp Tyr Thr Ile Cys Gly Asp Ser Glu Asp Met Val Cys Thr Pro
385                 390                 395                 400
Lys Ser Asp Glu Phe Asn Pro Cys Glu Asp Ile Met Gly Tyr Lys Phe
                405                 410                 415
Leu Arg Ile Val Val Trp Phe Val Ser Leu Leu Ala Leu Leu Gly Asn
            420                 425                 430
Val Phe Val Leu Leu Ile Leu Leu Thr Ser His Tyr Lys Leu Asn Val
        435                 440                 445
Pro Arg Phe Leu Met Cys Asn Leu Ala Phe Ala Asp Phe Cys Met Gly
    450                 455                 460
Met Tyr Leu Leu Leu Ile Ala Ser Val Asp Leu Tyr Thr His Ser Glu
465                 470                 475                 480
Tyr Tyr Asn His Ala Ile Asp Trp Gln Thr Gly Pro Gly Cys Asn Thr
                485                 490                 495
Ala Gly Phe Phe Thr Val Phe Ala Ser Glu Leu Ser Val Tyr Thr Leu
            500                 505                 510
Thr Val Ile Thr Leu Glu Arg Trp Tyr Ala Ile Thr Phe Ala Met Arg
        515                 520                 525
Leu Asp Arg Lys Ile Arg Leu Arg His Ala Cys Ala Ile Met Val Gly
    530                 535                 540
Gly Trp Val Cys Cys Phe Leu Leu Ala Leu Leu Pro Leu Val Gly Ile
545                 550                 555                 560
```

```
Ser Ser Tyr Ala Lys Val Ser Ile Cys Leu Pro Met Asp Thr Glu Thr
            565                 570                 575
Pro Leu Ala Leu Ala Tyr Ile Val Phe Val Leu Thr Leu Asn Ile Val
            580                 585                 590
Ala Phe Val Ile Val Cys Cys Cys Tyr Val Lys Ile Tyr Ile Thr Val
            595                 600                 605
Arg Asn Pro Gln Tyr Asn Pro Gly Asp Lys Asp Thr Lys Ile Ala Lys
            610                 615                 620
Arg Met Ala Val Leu Ile Phe Thr Asp Phe Ile Cys Met Ala Pro Ile
625                 630                 635                 640
Ser Phe Tyr Ala Leu Ser Ala Ile Leu Asn Lys Pro Leu Ile Thr Val
            645                 650                 655
Ser Asn Ser Lys Ile Leu Leu Val Leu Phe Tyr Pro Leu Asn Ser Cys
            660                 665                 670
Ala Asn Pro Phe Leu Tyr Ala Ile Phe Thr Lys Ala Phe Gln Arg Asp
            675                 680                 685
Val Phe Ile Leu Leu Ser Lys Phe Gly Ile Cys Lys Arg Gln Ala Gln
            690                 695                 700
Ala Tyr Arg Gly Gln Arg Val Pro Pro Lys Asn Ser Thr Asp Ile Gln
705                 710                 715                 720
Val Gln Lys Val Thr His Asp Met Arg Gln Gly Leu His Asn Met Glu
            725                 730                 735
Asp Val Tyr Glu Leu Ile Glu Asn Ser His Leu Thr Pro Lys Lys Gln
            740                 745                 750
Gly Gln Ile Ser Glu Glu Tyr Met Gln Thr Val Leu
            755                 760
```

<210> SEQ ID NO 3
<211> LENGTH: 780
<212> TYPE: DNA
<213> ORGANISM: Homo sapiens

<400> SEQUENCE: 3

```
atgaggccgg cggacttgct gcagctggtg ctgctgctcg acctgcccag ggacctgggc    60
ggaatggggt gttcgtctcc accctgcgag tgccatcagg aggaggactt cagagtcacc   120
tgcaaggata ttcaacgcat ccccagctta ccgcccagta cgcagactct gaagcttatt   180
gagactcacc tgagaactat tccaagtcat gcattttcta atctgcccaa tatttccaga   240
atctacgtat ctatagatgt gactctgcag cagctggaat cacactcctt ctacaatttg   300
agtaaagtga ctcacataga aattcggaat accaggaact taacttacat agaccctgat   360
gccctcaaag agctccccct cctaaagttc cttggcattt tcaacactgg acttaaaatg   420
ttccctgacc tgaccaaagt ttattccact gatatattct ttatacttga aattacagac   480
aacccttaca tgcgtcaat ccctgtgaat gcttttcagg gactatgcaa tgaaaccttg   540
acactgaagc tgtacaacaa cggcttact tcagtccaag gatatgcttt caatgggaca   600
aagctggatg ctgtttacct aaacaagaat aaatacctga cagttattga caaagatgca   660
tttggaggag atacagtgg accaagcttg ctggacgtgt ctcaaaccag tgtcactgcc   720
cttccatcca aaggcctgga gcacctgaag gaactgatag caagaaacac ctggactctt   780
```

<210> SEQ ID NO 4
<211> LENGTH: 260
<212> TYPE: PRT
<213> ORGANISM: Homo sapiens -continued

<400> SEQUENCE: 4

Met Arg Pro Ala Asp Leu Leu Gln Leu Val Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Leu Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu
            260

<210> SEQ ID NO 5
<211> LENGTH: 33
<212> TYPE: DNA
<213> ORGANISM: Homo sapiens

<400> SEQUENCE: 5
cactgcagga tccaaatgag gccggcggac ttg         33

<210> SEQ ID NO 6
<211> LENGTH: 62
<212> TYPE: DNA
<213> ORGANISM: Homo sapiens

<400> SEQUENCE: 6
cagtcctcta gattatcagt gatggtggtg gtgatggtta agagtccagg tgttcttgct    60
at                                                                  62

<210> SEQ ID NO 7
<211> LENGTH: 36

```
<212> TYPE: DNA
<213> ORGANISM: Homo sapiens

<400> SEQUENCE: 7
cactgcgaat tcaaaatgag gccggcggac ttgctg                                36

<210> SEQ ID NO 8
<211> LENGTH: 48
<212> TYPE: DNA
<213> ORGANISM: Homo sapiens

<400> SEQUENCE: 8
gttctcctcc tcaactggga tgatgttaag agtccaggtg tttcttgc                  48

<210> SEQ ID NO 9
<211> LENGTH: 48
<212> TYPE: DNA
<213> ORGANISM: Homo sapiens

<400> SEQUENCE: 9
gcaagaaaca cctggactct aacatcatc ccagttgagg aggagaac                   48

<210> SEQ ID NO 10
<211> LENGTH: 20
<212> TYPE: DNA
<213> ORGANISM: Homo sapiens

<400> SEQUENCE: 10
taatacgact cactataggg                                                 20

<210> SEQ ID NO 11
<211> LENGTH: 45
<212> TYPE: DNA
<213> ORGANISM: Homo sapiens

<400> SEQUENCE: 11
ggaatggggt gttcgtctcc agagtgcgag tgccatcagg aggag                     45

<210> SEQ ID NO 12
<211> LENGTH: 45
<212> TYPE: DNA
<213> ORGANISM: Homo sapiens

<400> SEQUENCE: 12
cccagtacgc agactctgaa gttcattgag actcacctga gaact                     45

<210> SEQ ID NO 13
<211> LENGTH: 45
<212> TYPE: DNA
<213> ORGANISM: Homo sapiens

<400> SEQUENCE: 13
cagactctga agcttattga ggtgcacctg agaactattc caagt                     45

<210> SEQ ID NO 14
<211> LENGTH: 45
<212> TYPE: DNA
<213> ORGANISM: Homo sapiens

<400> SEQUENCE: 14
actctgaagc ttattgagac ttgcctgaga actattccaa gtcat                     45

<210> SEQ ID NO 15
```

```
<211> LENGTH: 45
<212> TYPE: DNA
<213> ORGANISM: Homo sapiens

<400> SEQUENCE: 15
ctgaagctta ttgagactca ctacagaact attccaagtc atgca            45

<210> SEQ ID NO 16
<211> LENGTH: 45
<212> TYPE: DNA
<213> ORGANISM: Homo sapiens

<400> SEQUENCE: 16
cacatagaaa ttcggaatac ccccaactta acttacatag accct            45

<210> SEQ ID NO 17
<211> LENGTH: 45
<212> TYPE: DNA
<213> ORGANISM: Homo sapiens

<400> SEQUENCE: 17
aacactggac ttaaaatgtt catcgacctg accaaagttt attcc            45

<210> SEQ ID NO 18
<211> LENGTH: 45
<212> TYPE: DNA
<213> ORGANISM: Homo sapiens

<400> SEQUENCE: 18
actggactta aaatgttccc tccctgacc aaagtttatt ccact             45

<210> SEQ ID NO 19
<211> LENGTH: 45
<212> TYPE: DNA
<213> ORGANISM: Homo sapiens

<400> SEQUENCE: 19
ctgaccaaag tttattccac tgagatattc tttatacttg aaatt            45

<210> SEQ ID NO 20
<211> LENGTH: 45
<212> TYPE: DNA
<213> ORGANISM: Homo sapiens

<400> SEQUENCE: 20
acagacaacc cttacatgac gaccatccct gtgaatgctt ttcag            45

<210> SEQ ID NO 21
<211> LENGTH: 45
<212> TYPE: DNA
<213> ORGANISM: Homo sapiens

<400> SEQUENCE: 21
gacaaccctt acatgacgtc attccctgtg aatgcttttc aggga            45

<210> SEQ ID NO 22
<211> LENGTH: 45
<212> TYPE: DNA
<213> ORGANISM: Homo sapiens

<400> SEQUENCE: 22
aacccttaca tgacgtcaat ctacgtgaat gcttttcagg gacta            45
```

```
<210> SEQ ID NO 23
<211> LENGTH: 45
<212> TYPE: DNA
<213> ORGANISM: Homo sapiens

<400> SEQUENCE: 23
ccttacatga cgtcaatccc taggaatgct tttcagggac tatgc            45

<210> SEQ ID NO 24
<211> LENGTH: 45
<212> TYPE: DNA
<213> ORGANISM: Homo sapiens

<400> SEQUENCE: 24
tacatgacgt caatccctgt gtgggctttt cagggactat gcaat            45

<210> SEQ ID NO 25
<211> LENGTH: 45
<212> TYPE: DNA
<213> ORGANISM: Homo sapiens

<400> SEQUENCE: 25
tttcagggac tatgcaatga atgcttgaca ctgaagctgt acaac            45

<210> SEQ ID NO 26
<211> LENGTH: 45
<212> TYPE: DNA
<213> ORGANISM: Homo sapiens

<400> SEQUENCE: 26
ctgtacaaca acggctttac tgaggtccaa ggatatgctt tcaat            45

<210> SEQ ID NO 27
<211> LENGTH: 45
<212> TYPE: DNA
<213> ORGANISM: Homo sapiens

<400> SEQUENCE: 27
ctggagcacc tgaaggaact gagagcaaga aacacctgga ctctt            45

<210> SEQ ID NO 28
<211> LENGTH: 39
<212> TYPE: DNA
<213> ORGANISM: Homo sapiens

<400> SEQUENCE: 28
cacctgaagg aactgatagc atacaacacc tggactctt                   39

<210> SEQ ID NO 29
<211> LENGTH: 15
<212> TYPE: PRT
<213> ORGANISM: Homo sapiens

<400> SEQUENCE: 29

Gly Met Gly Cys Ser Ser Pro Glu Cys Glu Cys His Gln Glu Glu
1               5                   10                  15

<210> SEQ ID NO 30
<211> LENGTH: 15
<212> TYPE: PRT
<213> ORGANISM: Homo sapiens

<400> SEQUENCE: 30

Pro Ser Thr Gln Thr Leu Lys Phe Ile Glu Thr His Leu Arg Thr
```

```
                1               5                   10                  15
```

<210> SEQ ID NO 31
<211> LENGTH: 15
<212> TYPE: PRT
<213> ORGANISM: Homo sapiens

<400> SEQUENCE: 31

```
Gln Thr Leu Lys Leu Ile Glu Val His Leu Arg Thr Ile Pro Ser
1               5                   10                  15
```

<210> SEQ ID NO 32
<211> LENGTH: 15
<212> TYPE: PRT
<213> ORGANISM: Homo sapiens

<400> SEQUENCE: 32

```
Thr Leu Lys Leu Ile Glu Thr Cys Leu Arg Thr Ile Pro Ser His
1               5                   10                  15
```

<210> SEQ ID NO 33
<211> LENGTH: 15
<212> TYPE: PRT
<213> ORGANISM: Homo sapiens

<400> SEQUENCE: 33

```
Leu Lys Leu Ile Glu Thr His Tyr Arg Thr Ile Pro Ser His Ala
1               5                   10                  15
```

<210> SEQ ID NO 34
<211> LENGTH: 15
<212> TYPE: PRT
<213> ORGANISM: Homo sapiens

<400> SEQUENCE: 34

```
His Ile Glu Ile Arg Asn Thr Pro Asn Leu Thr Tyr Ile Asp Pro
1               5                   10                  15
```

<210> SEQ ID NO 35
<211> LENGTH: 15
<212> TYPE: PRT
<213> ORGANISM: Homo sapiens

<400> SEQUENCE: 35

```
Asn Thr Gly Leu Lys Met Phe Ile Asp Leu Thr Lys Val Tyr Ser
1               5                   10                  15
```

<210> SEQ ID NO 36
<211> LENGTH: 15
<212> TYPE: PRT
<213> ORGANISM: Homo sapiens

<400> SEQUENCE: 36

```
Thr Gly Leu Lys Met Phe Pro Pro Leu Thr Lys Val Tyr Ser Thr
1               5                   10                  15
```

<210> SEQ ID NO 37
<211> LENGTH: 15
<212> TYPE: PRT
<213> ORGANISM: Homo sapiens

<400> SEQUENCE: 37

```
Leu Thr Lys Val Tyr Ser Thr Glu Ile Phe Phe Ile Leu Glu Ile
1               5                   10                  15
```

```
<210> SEQ ID NO 38
<211> LENGTH: 15
<212> TYPE: PRT
<213> ORGANISM: Homo sapiens

<400> SEQUENCE: 38

Thr Asp Asn Pro Tyr Met Thr Thr Ile Pro Val Asn Ala Phe Gln
1               5                   10                  15

<210> SEQ ID NO 39
<211> LENGTH: 15
<212> TYPE: PRT
<213> ORGANISM: Homo sapiens

<400> SEQUENCE: 39

Asp Asn Pro Tyr Met Thr Ser Phe Pro Val Asn Ala Phe Gln Gly
1               5                   10                  15

<210> SEQ ID NO 40
<211> LENGTH: 15
<212> TYPE: PRT
<213> ORGANISM: Homo sapiens

<400> SEQUENCE: 40

Asn Pro Tyr Met Thr Ser Ile Tyr Val Asn Ala Phe Gln Gly Leu
1               5                   10                  15

<210> SEQ ID NO 41
<211> LENGTH: 15
<212> TYPE: PRT
<213> ORGANISM: Homo sapiens

<400> SEQUENCE: 41

Pro Tyr Met Thr Ser Ile Pro Arg Asn Ala Phe Gln Gly Leu Cys
1               5                   10                  15

<210> SEQ ID NO 42
<211> LENGTH: 15
<212> TYPE: PRT
<213> ORGANISM: Homo sapiens

<400> SEQUENCE: 42

Tyr Met Thr Ser Ile Pro Val Trp Ala Phe Gln Gly Leu Cys Asn
1               5                   10                  15

<210> SEQ ID NO 43
<211> LENGTH: 15
<212> TYPE: PRT
<213> ORGANISM: Homo sapiens

<400> SEQUENCE: 43

Phe Gln Gly Leu Cys Asn Glu Cys Leu Thr Leu Lys Leu Tyr Asn
1               5                   10                  15

<210> SEQ ID NO 44
<211> LENGTH: 15
<212> TYPE: PRT
<213> ORGANISM: Homo sapiens

<400> SEQUENCE: 44

Leu Tyr Asn Asn Gly Phe Thr Glu Val Gln Gly Tyr Ala Phe Asn
1               5                   10                  15

<210> SEQ ID NO 45
```

```
<211> LENGTH: 15
<212> TYPE: PRT
<213> ORGANISM: Homo sapiens

<400> SEQUENCE: 45

Leu Glu His Leu Lys Glu Leu Arg Ala Arg Asn Thr Trp Thr Leu
1               5                   10                  15

<210> SEQ ID NO 46
<211> LENGTH: 13
<212> TYPE: PRT
<213> ORGANISM: Homo sapiens

<400> SEQUENCE: 46

His Leu Lys Glu Leu Ile Ala Tyr Asn Thr Trp Thr Leu
1               5                   10

<210> SEQ ID NO 47
<211> LENGTH: 764
<212> TYPE: PRT
<213> ORGANISM: Cercopithecus aethiops

<400> SEQUENCE: 47

Met Arg Pro Ala Asp Leu Leu Gln Leu Val Leu Leu Val Leu Pro
1               5                   10                  15

Arg Asp Leu Gly Gly Lys Gly Cys Ser Ser Pro Cys Glu Cys Gln
                20                  25                  30

Gln Glu Glu Asp Phe Arg Val Thr Cys Lys Asp Ile Gln Arg Ile Pro
            35                  40                  45

Ser Leu Pro Pro Ser Thr Gln Thr Leu Lys Leu Ile Glu Thr Arg Leu
50                  55                  60

Arg Thr Ile Pro Ser His Ala Phe Ser Ser Leu Pro Asn Ile Ser Arg
65                  70                  75                  80

Ile Tyr Leu Ser Ile Asp Ala Thr Leu Gln Gln Leu Glu Ser His Ser
                85                  90                  95

Phe Tyr Asn Leu Asn Lys Val Thr His Ile Glu Ile Arg Asn Thr Arg
                100                 105                 110

Ser Leu Thr Tyr Ile Asp Pro Asp Ala Leu Lys Glu Leu Pro Leu Leu
                115                 120                 125

Lys Phe Leu Gly Ile Phe Asn Thr Gly Leu Lys Met Phe Pro Asp Leu
130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Ile
                180                 185                 190

Gln Gly Tyr Ala Phe Asn Gly Thr Lys Leu Asp Ala Val Tyr Leu Asn
                195                 200                 205

Lys Asn Lys Tyr Leu Thr Val Ile Asp Lys Asp Ala Phe Gly Gly Val
                210                 215                 220

Tyr Ser Gly Pro Ser Leu Leu Asp Val Ser His Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
                260                 265                 270
```

```
Thr Arg Ala Asp Leu Ser Tyr Pro Ser His Cys Cys Ala Phe Lys Asn
            275                 280                 285

Gln Lys Lys Ile Arg Gly Ile Leu Glu Ser Leu Met Cys Asn Glu Ser
        290                 295                 300

Ser Met Gln Ser Leu Arg Gln Arg Lys Ser Val Asn Ala Leu Asn Ser
305                 310                 315                 320

Pro Leu His Gln Glu Tyr Glu Asn Leu Asp Asp Gly Ile Val Gly
                325                 330                 335

Tyr Lys Glu Lys Ser Lys Phe Gln Asp Ala His Asn Asn Ala His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
        370                 375                 380

Tyr Asp Tyr Thr Val Cys Gly Asp Asn Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Leu Ile Leu Leu Thr Ser His Tyr Lys Leu Asn Val
        435                 440                 445

Pro Arg Phe Leu Met Cys Asn Leu Ala Phe Ala Asp Phe Cys Met Gly
        450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
            485                 490                 495

Ala Gly Phe Phe Thr Val Phe Ala Ser Glu Leu Ser Val Tyr Thr Leu
        500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Cys Ala Ile Met Val Gly
        530                 535                 540

Gly Trp Val Cys Cys Phe Leu Ala Leu Leu Pro Leu Val Gly Ile
545                 550                 555                 560

Ser Ser Tyr Ala Lys Val Ser Ile Cys Leu Pro Met Asp Thr Glu Thr
            565                 570                 575

Pro Leu Ala Leu Ala Tyr Ile Val Phe Val Leu Thr Leu Asn Ile Val
        580                 585                 590

Ala Phe Val Ile Val Cys Cys Cys Tyr Val Lys Ile Tyr Ile Thr Val
        595                 600                 605

Arg Asn Pro Gln Tyr Asn Pro Gly Asp Lys Asp Thr Lys Ile Ala Lys
        610                 615                 620

Arg Met Ala Val Leu Ile Phe Thr Asp Phe Met Cys Met Ala Pro Ile
625                 630                 635                 640

Ser Phe Tyr Ala Leu Ser Ala Ile Leu Asn Lys Pro Leu Ile Thr Val
            645                 650                 655

Ser Asn Ser Lys Ile Leu Leu Val Leu Phe Tyr Pro Leu Asn Ser Cys
        660                 665                 670

Ala Asn Pro Phe Leu Tyr Ala Ile Phe Thr Lys Ala Phe Gln Arg Asp
        675                 680                 685

Val Phe Ile Leu Leu Ser Lys Phe Gly Ile Cys Lys Arg Gln Ala Gln
```

```
            690             695             700
Ala Tyr Arg Gly Gln Arg Val Pro Pro Lys Asn Ser Thr Asp Ile Gln
705             710             715             720

Val Gln Lys Val Thr His Glu Met Arg Gln Gly Leu His Asn Met Glu
            725             730             735

Asp Val Tyr Glu Leu Ile Glu Asn Ser His Leu Thr Pro Lys Lys Gln
            740             745             750

Gly Gln Ile Ser Glu Glu Tyr Thr Gln Thr Val Leu
        755             760
```

<210> SEQ ID NO 48
<211> LENGTH: 764
<212> TYPE: PRT
<213> ORGANISM: Macaca mulatta

<400> SEQUENCE: 48

```
Met Arg Pro Ala Asp Leu Leu Gln Leu Val Leu Leu Val Leu Pro
1               5               10              15

Arg Asp Leu Gly Gly Lys Gly Cys Ser Ser Pro Cys Glu Cys Gln
            20              25              30

Gln Glu Glu Asp Phe Arg Val Thr Cys Lys Asp Ile Gln Arg Ile Pro
        35              40              45

Ser Leu Pro Pro Ser Thr Gln Thr Leu Lys Leu Ile Glu Thr Arg Leu
50              55              60

Arg Thr Ile Pro Ser His Ala Phe Ser Ser Leu Pro Asn Ile Ser Arg
65              70              75              80

Ile Tyr Leu Ser Ile Asp Ala Thr Leu Gln Gln Leu Glu Thr His Ser
            85              90              95

Phe Tyr Asn Leu Asn Lys Val Thr His Ile Glu Ile Arg Asn Thr Arg
        100             105             110

Ser Leu Thr Tyr Ile Asp Pro Asp Ala Leu Lys Glu Leu Pro Leu Leu
    115             120             125

Lys Phe Leu Gly Ile Phe Asn Thr Gly Leu Lys Met Phe Pro Asp Leu
130             135             140

Thr Lys Val Tyr Ser Thr Asp Ile Phe Phe Ile Leu Glu Ile Thr Asp
145             150             155             160

Asn Pro Tyr Met Thr Ser Ile Pro Val Asn Ala Phe Gln Gly Leu Cys
            165             170             175

Asn Glu Thr Leu Thr Leu Lys Leu Tyr Asn Asn Gly Phe Thr Ser Ile
        180             185             190

Gln Gly Tyr Ala Phe Asn Gly Thr Lys Leu Asp Ala Val Tyr Leu Asn
    195             200             205

Lys Asn Lys Tyr Leu Thr Val Ile Asp Lys Asp Ala Phe Gly Gly Val
210             215             220

Tyr Ser Gly Pro Ser Leu Leu Asp Val Ser His Thr Ser Val Thr Ala
225             230             235             240

Leu Pro Ser Lys Gly Leu Glu His Leu Lys Glu Leu Ile Ala Arg Asn
            245             250             255

Thr Trp Thr Leu Lys Lys Leu Pro Leu Ser Leu Ser Phe Leu His Leu
        260             265             270

Thr Arg Ala Asp Leu Ser Tyr Pro Ser His Cys Cys Ala Phe Lys Asn
    275             280             285

Gln Lys Lys Ile Arg Gly Ile Pro Glu Ser Leu Met Cys Asn Glu Ser
290             295             300
```

```
Ser Met Gln Ser Leu Arg Gln Arg Lys Ser Val Asn Ala Leu Asn Ser
305                 310                 315                 320

Pro Leu His Gln Glu Tyr Glu Asn Leu Asp Asp Gly Ile Val Gly
            325                 330                 335

Tyr Lys Glu Lys Ser Lys Phe Gln Asp Ala His Asn Asn Ala His Tyr
            340                 345                 350

Tyr Val Phe Phe Glu Glu Gln Glu Asp Glu Ile Ile Gly Phe Gly Gln
            355                 360                 365

Glu Leu Lys Asn Pro Gln Glu Glu Thr Leu Gln Ala Phe Asp Ser His
    370                 375                 380

Tyr Asp Tyr Thr Val Cys Gly Asp Asn Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Leu Ile Leu Leu Thr Ser His Tyr Lys Leu Asn Val
            435                 440                 445

Pro Arg Phe Leu Met Cys Asn Leu Ala Phe Ala Asp Phe Cys Met Gly
    450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
    515                 520                 525

Leu Asp Arg Lys Ile Arg Leu Arg His Ala Cys Ala Ile Met Val Gly
    530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Val Phe Val Leu Thr Leu Asn Ile Val
            580                 585                 590

Ala Phe Val Ile Val Cys Cys Cys Tyr Val Lys Ile Tyr Ile Thr Val
            595                 600                 605

Arg Asn Pro Gln Tyr Asn Pro Gly Asp Lys Asp Thr Lys Ile Ala Lys
    610                 615                 620

Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
                645                 650                 655

Ser Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
            690                 695                 700

Ala Tyr Arg Gly Gln Arg Val Pro Pro Lys Asn Ser Thr Asp Ile Gln
705                 710                 715                 720

Val Gln Lys Val Thr His Glu Met Arg Gln Asp Leu His Asn Met Gln
```

Asp Val Tyr Glu Leu Leu Glu Asn Ser His Leu Thr Pro Lys Lys Gln
                725                 730                 735

Gly Gln Ile Ser Glu Glu Tyr Thr Gln Thr Val Leu
        740                 745                 750

<210> SEQ ID NO 49
<211> LENGTH: 764
<212> TYPE: PRT
<213> ORGANISM: Sus scrofa

<400> SEQUENCE: 49

Met Ser Leu Thr Pro Leu Leu Gln Leu Ala Leu Val Leu Ala Leu Pro
1               5                   10                  15

Arg Ser Leu Arg Gly Lys Gly Cys Pro Ser Pro Cys Glu Cys His
            20                  25                  30

Gln Glu Asp Asp Phe Arg Val Thr Cys Lys Asp Ile His Ser Ile Pro
            35                  40                  45

Pro Leu Pro Pro Asn Thr Gln Thr Leu Lys Phe Ile Glu Thr His Leu
        50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Gln Leu Glu Ser Gln Ser
                85                  90                  95

Phe Tyr Asn Leu Ser Lys Met Thr His Ile Glu Ile Arg Asn Thr Arg
            100                 105                 110

Ser Leu Thr Tyr Ile Asn Pro Gly Ala Leu Lys Asp Leu Pro Leu Leu
        115                 120                 125

Lys Phe Leu Gly Ile Phe Asn Thr Gly Leu Arg Ile Phe Pro Asp Leu
130                 135                 140

Thr Lys Val Tyr Ser Thr Asp Val Phe Phe Ile Leu Glu Ile Thr Asp
145                 150                 155                 160

Asn Pro Tyr Met Thr Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly His Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
210                 215                 220

Phe Ser Gly Pro Thr Leu Leu Asp Val Ser Tyr Thr Ser Val Thr Ala
225                 230                 235                 240

Leu Pro Pro Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
290                 295                 300

Ser Ile Arg Ser Leu Arg Gln Arg Lys Ser Val Asn Ala Val Asn Gly
305                 310                 315                 320

Pro Phe Tyr Gln Glu Tyr Glu Glu Asp Leu Gly Asp Thr Ser Val Gly
                325                 330                 335

```
Asn Lys Glu Asn Ser Lys Phe Gln Asp Thr His Ser Asn Ser His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
    370                 375                 380

Tyr Asp Tyr Thr Val Cys Gly Gly Ser Glu Asp Met Val Cys Thr Pro
385                 390                 395                 400

Lys Ser Asp Glu Phe Asn Pro Cys Glu Asp Ile Met Gly Tyr Arg Phe
                405                 410                 415

Leu Arg Ile Val Val Trp Phe Val Ser Leu Leu Ala Leu Leu Gly Asn
        420                 425                 430

Val Phe Val Leu Val Ile Leu Leu Thr Ser His Tyr Lys Leu Thr Val
        435                 440                 445

Pro Arg Phe Leu Met Cys Asn Leu Ala Phe Ala Asp Phe Cys Met Gly
        450                 455                 460

Met Tyr Leu Leu Leu Ile Ala Ser Val Asp Leu Tyr Thr Gln Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Tyr Ala Ile Met Ala Gly
    530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Ile Leu Val Leu Leu Leu Asn Ile Val
            580                 585                 590

Ala Phe Thr Ile Val Cys Ser Cys Tyr Val Lys Ile Tyr Ile Thr Val
        595                 600                 605

Arg Asn Pro Gln Tyr Asn Pro Gly Asp Lys Asp Thr Lys Ile Ala Lys
    610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
        675                 680                 685

Val Phe Ile Leu Leu Ser Lys Phe Gly Phe Cys Lys Arg Gln Ala Gln
    690                 695                 700

Ala Tyr Arg Gly Gln Arg Val Ser Pro Lys Asn Ser Thr Gly Ile Gln
705                 710                 715                 720

Val Gln Lys Val Thr Gln Asn Met Arg Gln Ser Leu Pro Asn Met Gln
                725                 730                 735

Asp Asp Tyr Glu Leu Leu Glu Asn Ser His Leu Thr His Lys Lys His
            740                 745                 750

Asp Gln Ile Ser Lys Glu Tyr Lys Gln Thr Val Leu
```

<210> SEQ ID NO 50
<211> LENGTH: 764
<212> TYPE: PRT
<213> ORGANISM: Bos taurus
<220> FEATURE:
<221> NAME/KEY: misc_feature
<222> LOCATION: (329)..(329)
<223> OTHER INFORMATION: Xaa can be any naturally occurring amino acid

<400> SEQUENCE: 50

```
Met Arg Pro Thr Pro Leu Leu Arg Leu Ala Leu Phe Leu Val Leu Pro
1               5                   10                  15

Ser Ser Leu Gly Gly Glu Arg Cys Pro Ser Pro Cys Glu Cys Arg
            20                  25                  30

Gln Glu Asp Asp Phe Arg Val Thr Cys Lys Asp Ile Gln Ser Ile Pro
            35                  40                  45

Ser Leu Pro Pro Ser Thr Gln Thr Leu Lys Phe Ile Glu Thr His Leu
50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Ser Leu Thr Tyr Ile Asp Ser Gly Ala Leu Lys Glu Leu Pro Leu Leu
        115                 120                 125

Lys Phe Leu Gly Ile Phe Asn Thr Gly Leu Arg Val Phe Pro Asp Leu
130                 135                 140

Thr Lys Ile Tyr Ser Thr Asp Val Phe Phe Ile Leu Glu Ile Thr Asp
145                 150                 155                 160

Asn Pro Tyr Met Thr Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Ile
            180                 185                 190

Gln Gly His Ala Phe Asn Gly Thr Lys Leu Asp Ala Val Tyr Leu Asn
        195                 200                 205

Lys Asn Lys Tyr Leu Thr Val Ile Gly Gln Asp Ala Phe Ala Gly Val
210                 215                 220

Tyr Ser Gly Pro Thr Leu Leu Asp Ile Ser Tyr Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Arg Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Gln Ser Leu Met Cys Asn Glu Ser
290                 295                 300

Ser Ile Arg Gly Leu Arg Gln Arg Lys Ser Ala Ser Ala Leu Asn Gly
305                 310                 315                 320

Pro Phe Tyr Gln Glu Tyr Glu Asp Xaa Leu Gly Asp Gly Ser Ala Gly
                325                 330                 335

Tyr Lys Glu Asn Ser Lys Phe Gln Asp Thr Gln Ser Asn Ser His Tyr
            340                 345                 350
```

```
Tyr Val Phe Glu Glu Gln Glu Asp Glu Ile Ile Gly Phe Gly Gln
        355                 360                 365

Gln Leu Lys Asn Pro Gln Glu Thr Leu Gln Ala Phe Asp Ser His
        370                 375                 380

Tyr Asp Tyr Thr Val Cys Gly Ser Glu Asp Met Val Cys Thr Pro
385                 390                 395                 400

Lys Ser Asp Glu Phe Asn Pro Cys Glu Asp Ile Met Gly Tyr Lys Phe
                    405                 410                 415

Leu Arg Ile Val Val Trp Phe Val Ser Leu Leu Ala Leu Leu Gly Asn
                420                 425                 430

Val Phe Val Leu Val Ile Leu Leu Thr Ser His Tyr Lys Leu Thr Val
                435                 440                 445

Pro Arg Phe Leu Met Cys Asn Leu Ala Phe Ala Asp Phe Cys Met Gly
        450                 455                 460

Leu Tyr Leu Leu Leu Ile Ala Ser Val Asp Leu Tyr Thr Gln Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp His Ala Ile Thr Phe Ala Met Arg
            515                 520                 525

Leu Asp Arg Lys Ile Arg Leu Trp His Ala Tyr Val Ile Met Leu Gly
        530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Ile Leu Val Leu Leu Leu Asn Ile Ile
            580                 585                 590

Ala Phe Ile Ile Val Cys Ala Cys Tyr Val Lys Ile Tyr Ile Thr Val
        595                 600                 605

Arg Asn Pro His Tyr Asn Pro Gly Asp Lys Asp Thr Arg Ile Ala Lys
        610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
            675                 680                 685

Val Phe Met Leu Leu Ser Lys Phe Gly Ile Cys Lys Arg Gln Ala Gln
        690                 695                 700

Ala Tyr Arg Gly Gln Arg Val Ser Pro Lys Asn Ser Thr Gly Ile Arg
705                 710                 715                 720

Val Gln Lys Val Pro Pro Asp Val Arg Gln Ser Leu Pro Asn Val Gln
                725                 730                 735

Asp Asp Tyr Glu Leu Leu Glu Asn Ser His Leu Thr Pro Lys Gln Gln
            740                 745                 750

Asp Gln Thr Ser Lys Glu Tyr Lys Arg Thr Val Leu
            755                 760
```

```
<210> SEQ ID NO 51
<211> LENGTH: 764
<212> TYPE: PRT
<213> ORGANISM: Felis catus
<220> FEATURE:
<221> NAME/KEY: misc_feature
<222> LOCATION: (360)..(360)
<223> OTHER INFORMATION: Xaa can be any naturally occurring amino acid

<400> SEQUENCE: 51
```

| | | | | | | | | | | | | | | |
|---|---|---|---|---|---|---|---|---|---|---|---|---|---|---|
| Met | Arg | Gln | Thr | Pro | Leu | Leu | Gln | Leu | Ala | Leu | Leu | Leu | Ser | Leu | Pro |
| 1 | | | | 5 | | | | | 10 | | | | | 15 | |
| Arg | Ser | Leu | Gly | Gly | Lys | Gly | Cys | Pro | Ser | Pro | Cys | Glu | Cys | His | |
| | | | 20 | | | | | 25 | | | | | 30 | | |
| Gln | Glu | Asp | Asp | Phe | Arg | Val | Thr | Cys | Lys | Asp | Ile | His | Arg | Ile | Pro |
| | | | 35 | | | | | 40 | | | | | 45 | | |
| Ser | Leu | Pro | Pro | Ser | Thr | Gln | Thr | Leu | Lys | Phe | Ile | Glu | Thr | His | Leu |
| | 50 | | | | | 55 | | | | | 60 | | | | |
| Lys | Thr | Ile | Pro | Ser | Arg | Ala | Phe | Ser | Asn | Leu | Pro | Asn | Ile | Ser | Arg |
| 65 | | | | | 70 | | | | | 75 | | | | | 80 |
| Ile | Tyr | Leu | Ser | Ile | Asp | Ala | Thr | Leu | Gln | Arg | Leu | Glu | Ser | His | Ser |
| | | | | 85 | | | | | 90 | | | | | 95 | |
| Phe | Tyr | Asn | Leu | Ser | Lys | Met | Thr | His | Ile | Glu | Ile | Arg | Asn | Thr | Arg |
| | | | 100 | | | | | 105 | | | | | 110 | | |
| Ser | Leu | Thr | Tyr | Ile | Asp | Pro | Gly | Ala | Leu | Lys | Glu | Leu | Pro | Leu | Leu |
| | | 115 | | | | | 120 | | | | | 125 | | | |
| Lys | Phe | Leu | Gly | Ile | Phe | Asn | Thr | Gly | Leu | Gly | Val | Phe | Pro | Asp | Leu |
| 130 | | | | | 135 | | | | | 140 | | | | | |
| Thr | Lys | Val | Tyr | Ser | Thr | Asp | Val | Phe | Phe | Ile | Leu | Glu | Ile | Thr | Asp |
| 145 | | | | | 150 | | | | | 155 | | | | | 160 |
| Asn | Pro | Tyr | Met | Thr | Ser | Ile | Pro | Ala | Asn | Ala | Phe | Gln | Gly | Leu | Cys |
| | | | | 165 | | | | | 170 | | | | | 175 | |
| Asn | Glu | Thr | Leu | Thr | Leu | Lys | Leu | Tyr | Asn | Asn | Gly | Phe | Thr | Ser | Ile |
| | | | 180 | | | | | 185 | | | | | 190 | | |
| Gln | Gly | His | Ala | Phe | Asn | Gly | Thr | Lys | Leu | Asp | Ala | Val | Tyr | Leu | Asn |
| | | 195 | | | | | 200 | | | | | 205 | | | |
| Lys | Asn | Lys | Tyr | Leu | Thr | Ala | Ile | Asp | Gln | Asp | Ala | Phe | Gly | Gly | Val |
| 210 | | | | | 215 | | | | | 220 | | | | | |
| Tyr | Ser | Gly | Pro | Thr | Leu | Leu | Asp | Val | Ser | Tyr | Thr | Ser | Val | Thr | Ala |
| 225 | | | | | 230 | | | | | 235 | | | | | 240 |
| Leu | Pro | Ser | Lys | Gly | Leu | Glu | His | Leu | Lys | Glu | Leu | Ile | Ala | Arg | Asn |
| | | | | 245 | | | | | 250 | | | | | 255 | |
| Thr | Trp | Thr | Leu | Lys | Lys | Leu | Pro | Leu | Thr | Leu | Ser | Phe | Leu | His | Leu |
| | | | 260 | | | | | 265 | | | | | 270 | | |
| Thr | Arg | Ala | Asp | Leu | Ser | Tyr | Pro | Ser | His | Cys | Cys | Ala | Phe | Lys | Asn |
| | | 275 | | | | | 280 | | | | | 285 | | | |
| Gln | Lys | Lys | Ile | Arg | Gly | Ile | Leu | Glu | Ser | Phe | Met | Cys | Asn | Asp | Ser |
| 290 | | | | | 295 | | | | | 300 | | | | | |
| Ser | Ile | Arg | Ser | Leu | Arg | Gln | Arg | Lys | Ser | Val | Asn | Ala | Leu | Asn | Gly |
| 305 | | | | | 310 | | | | | 315 | | | | | 320 |
| Pro | Phe | Asp | Gln | Glu | Tyr | Glu | Glu | Tyr | Leu | Gly | Asp | Ser | His | Ala | Gly |
| | | | | 325 | | | | | 330 | | | | | 335 | |
| Tyr | Lys | Asp | Asn | Ser | Lys | Phe | Gln | Asp | Thr | Arg | Ser | Asn | Ser | His | Tyr |
| | | | 340 | | | | | 345 | | | | | 350 | | |
| Tyr | Val | Phe | Phe | Glu | Glu | Gln | Xaa | Asp | Glu | Ile | Leu | Gly | Phe | Gly | Gln |

```
                    355                 360                 365
Glu Leu Lys Asn Pro Gln Glu Glu Thr Leu Gln Ala Phe Asp Ser His
        370                 375                 380

Tyr Asp Tyr Thr Val Cys Gly Gly Asn Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Ala Leu Leu Gly Asn
            420                 425                 430

Val Phe Val Leu Ile Ile Leu Leu Thr Ser His Tyr Lys Leu Thr Val
        435                 440                 445

Pro Arg Phe Leu Met Cys Asn Leu Ala Phe Ala Asp Phe Cys Met Gly
        450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Ala
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Met Arg Leu Arg His Ala Tyr Ala Ile Met Val Gly
        530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Ile Leu Val Leu Leu Asn Ile Val
            580                 585                 590

Ala Phe Ile Ile Val Cys Ser Cys Tyr Val Lys Ile Tyr Ile Thr Val
        595                 600                 605

Arg Asn Pro Gln Tyr Asn Thr Gly Asp Lys Asp Thr Lys Ile Ala Lys
        610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Thr Phe Gln Arg Asp
        675                 680                 685

Val Phe Ile Leu Leu Ser Lys Phe Gly Ile Cys Lys Arg Gln Ala Gln
        690                 695                 700

Ala Tyr Arg Gly Gln Arg Val Ser Pro Lys Asn Ser Thr Gly Ile Gln
705                 710                 715                 720

Val Gln Lys Val Thr Arg Asn Met Arg Gln Ser Leu Pro Asn Met Gln
                725                 730                 735

Asp Asp Tyr Glu Leu Leu Glu Asn Ser His Leu Thr Pro Asn Lys Gln
            740                 745                 750

Ser His Ile Ser Lys Glu Tyr Asn Gln Thr Val Leu
        755                 760

<210> SEQ ID NO 52
```

```
<211> LENGTH: 764
<212> TYPE: PRT
<213> ORGANISM: Canis lupus

<400> SEQUENCE: 52

Met Arg Pro Pro Leu Leu His Leu Ala Leu Leu Ala Leu Pro
1               5                   10                  15

Arg Ser Leu Gly Gly Lys Gly Cys Pro Ser Pro Cys Glu Cys His
            20                  25                  30

Gln Glu Asp Asp Phe Arg Val Thr Cys Lys Asp Ile His Arg Ile Pro
        35                  40                  45

Thr Leu Pro Pro Ser Thr Gln Thr Leu Lys Phe Ile Glu Thr Gln Leu
    50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Arg Leu Glu Ser His Ser
                85                  90                  95

Phe Tyr Asn Leu Ser Lys Met Thr His Ile Glu Ile Arg Asn Thr Arg
            100                 105                 110

Ser Leu Thr Ser Ile Asp Pro Asp Ala Leu Lys Glu Leu Pro Leu Leu
        115                 120                 125

Lys Phe Leu Gly Ile Phe Asn Thr Gly Leu Gly Val Phe Pro Asp Val
    130                 135                 140

Thr Lys Val Tyr Ser Thr Asp Val Phe Phe Ile Leu Glu Ile Thr Asp
145                 150                 155                 160

Asn Pro Tyr Met Ala Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Ile
            180                 185                 190

Gln Gly His Ala Phe Asn Gly Thr Lys Leu Asp Ala Val Tyr Leu Asn
        195                 200                 205

Lys Asn Lys Tyr Leu Ser Ala Ile Asp Lys Asp Ala Phe Gly Gly Val
    210                 215                 220

Tyr Ser Gly Pro Thr Leu Leu Asp Val Ser Tyr Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
    290                 295                 300

Ser Ile Arg Ser Leu Arg Gln Arg Lys Ser Val Asn Thr Leu Asn Gly
305                 310                 315                 320

Pro Phe Asp Gln Glu Tyr Glu Glu Tyr Leu Gly Asp Ser His Ala Gly
                325                 330                 335

Tyr Lys Asp Asn Ser Gln Phe Gln Asp Thr Asp Ser Asn Ser His Tyr
            340                 345                 350

Tyr Val Phe Phe Glu Glu Gln Glu Asp Glu Ile Leu Gly Phe Gly Gln
        355                 360                 365

Glu Leu Lys Asn Pro Gln Glu Glu Thr Leu Gln Ala Phe Asp Ser His
    370                 375                 380

Tyr Asp Tyr Thr Val Cys Gly Gly Asn Glu Asp Met Val Cys Thr Pro
```

```
                385                 390                 395                 400
Lys Ser Asp Glu Phe Asn Pro Cys Glu Asp Ile Met Gly Tyr Lys Phe
                    405                 410                 415

Leu Arg Ile Val Val Trp Phe Val Ser Leu Ala Leu Leu Gly Asn
                    420                 425                 430

Val Phe Val Leu Ile Val Leu Thr Ser His Tyr Lys Leu Thr Val
            435                 440                 445

Pro Arg Phe Leu Met Cys Asn Leu Ala Phe Ala Asp Phe Cys Met Gly
    450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
                500                 505                 510

Thr Val Ile Thr Leu Glu Arg Trp Tyr Ala Ile Thr Phe Ala Met Arg
            515                 520                 525

Leu Asp Arg Lys Ile Arg Leu Arg His Ala Tyr Ala Ile Met Val Gly
    530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Ile Leu Val Leu Leu Leu Asn Ile Val
                580                 585                 590

Ala Phe Ile Ile Val Cys Ser Cys Tyr Val Lys Ile Tyr Ile Thr Val
            595                 600                 605

Arg Asn Pro Gln Tyr Asn Pro Gly Asp Lys Asp Thr Lys Ile Ala Lys
    610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
                660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
    690                 695                 700

Ala Tyr Arg Gly Gln Arg Val Ser Pro Lys Asn Ser Ala Gly Ile Gln
705                 710                 715                 720

Ile Gln Lys Val Thr Arg Asp Met Arg Gln Ser Leu Pro Asn Met Gln
                725                 730                 735

Asp Glu Tyr Glu Leu Leu Glu Asn Ser His Leu Thr Pro Asn Lys Gln
                740                 745                 750

Gly Gln Ile Ser Lys Glu Tyr Asn Gln Thr Val Leu
            755                 760

<210> SEQ ID NO 53
<211> LENGTH: 764
<212> TYPE: PRT
<213> ORGANISM: Mus musculus

<400> SEQUENCE: 53
```

```
Met Arg Pro Gly Ser Leu Leu Leu Val Leu Leu Ala Leu Ser
1               5                   10                  15

Arg Ser Leu Arg Gly Lys Glu Cys Ala Ser Pro Cys Glu Cys His
            20                  25              30

Gln Glu Asp Asp Phe Arg Val Thr Cys Lys Glu Leu His Arg Ile Pro
            35                  40                  45

Ser Leu Pro Pro Ser Thr Gln Thr Leu Lys Leu Ile Glu Thr His Leu
50                  55                  60

Lys Thr Ile Pro Ser Leu Ala Phe Ser Ser Leu Pro Asn Ile Ser Arg
65                  70                  75                  80

Ile Tyr Leu Ser Ile Asp Ala Thr Leu Gln Arg Leu Glu Pro His Ser
                85                  90                  95

Phe Tyr Asn Leu Ser Lys Met Thr His Ile Glu Ile Arg Asn Thr Arg
            100                 105                 110

Ser Leu Thr Tyr Ile Asp Pro Asp Ala Leu Thr Glu Leu Pro Leu Leu
            115                 120                 125

Lys Phe Leu Gly Ile Phe Asn Thr Gly Leu Arg Ile Phe Pro Asp Leu
130                 135                 140

Thr Lys Ile Tyr Ser Thr Asp Ile Phe Phe Ile Leu Glu Ile Thr Asp
145                 150                 155                 160

Asn Pro Tyr Met Thr Ser Val Pro Glu Asn Ala Phe Gln Gly Leu Cys
            165                 170                 175

Asn Glu Thr Leu Thr Leu Lys Leu Tyr Asn Asn Gly Phe Thr Ser Val
            180                 185                 190

Gln Gly His Ala Phe Asn Gly Thr Lys Leu Asp Ala Val Tyr Leu Asn
            195                 200                 205

Lys Asn Lys Tyr Leu Thr Ala Ile Asp Asn Asp Ala Phe Gly Gly Val
            210                 215                 220

Tyr Ser Gly Pro Thr Leu Leu Asp Val Ser Ser Thr Ser Val Thr Ala
225                 230                 235                 240

Leu Pro Ser Lys Gly Leu Glu His Leu Lys Glu Leu Ile Ala Lys Asp
            245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
            275                 280                 285

Gln Lys Lys Ile Arg Gly Ile Leu Glu Ser Leu Met Cys Asn Glu Ser
            290                 295                 300

Ser Ile Arg Asn Leu Arg Gln Arg Lys Ser Val Asn Ile Leu Arg Gly
305                 310                 315                 320

Pro Ile Tyr Gln Glu Tyr Glu Glu Asp Pro Gly Asp Asn Ser Val Gly
            325                 330                 335

Tyr Lys Gln Asn Ser Lys Phe Gln Glu Ser Pro Ser Asn Ser His Tyr
            340                 345                 350

Tyr Val Phe Phe Glu Glu Gln Glu Asp Glu Val Val Gly Phe Gly Gln
            355                 360                 365

Glu Leu Lys Asn Pro Gln Glu Glu Thr Leu Gln Ala Phe Glu Ser His
            370                 375                 380

Tyr Asp Tyr Thr Val Cys Gly Asp Asn Glu Asp Met Val Cys Thr Pro
385                 390                 395                 400

Lys Ser Asp Glu Phe Asn Pro Cys Glu Asp Ile Met Gly Tyr Arg Phe
            405                 410                 415

Leu Arg Ile Val Val Trp Phe Val Ser Leu Leu Ala Leu Leu Gly Asn
```

```
                420                 425                 430
Ile Phe Val Leu Leu Ile Leu Leu Thr Ser His Tyr Lys Leu Thr Val
            435                 440                 445

Pro Arg Phe Leu Met Cys Asn Leu Ala Phe Ala Asp Phe Cys Met Gly
        450                 455                 460

Val Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Tyr Thr Ile Met Ala Gly
        530                 535                 540

Gly Trp Val Ser Cys Phe Leu Ala Leu Leu Pro Met Val Gly Ile
545                 550                 555                 560

Ser Ser Tyr Ala Lys Val Ser Ile Cys Leu Pro Met Asp Thr Asp Thr
                565                 570                 575

Pro Leu Ala Leu Ala Tyr Ile Val Leu Val Leu Leu Leu Asn Val Val
            580                 585                 590

Ala Phe Val Val Cys Ser Cys Tyr Val Lys Ile Tyr Ile Thr Val
        595                 600                 605

Arg Asn Pro Gln Tyr Asn Pro Arg Asp Lys Asp Thr Lys Ile Ala Lys
        610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
        675                 680                 685

Val Phe Ile Leu Leu Ser Lys Phe Gly Ile Cys Lys Arg Gln Ala Gln
        690                 695                 700

Ala Tyr Gln Gly Gln Arg Val Cys Pro Asn Asn Ser Thr Gly Ile Gln
705                 710                 715                 720

Ile Gln Lys Ile Pro Gln Asp Thr Arg Gln Ser Leu Pro Asn Met Gln
                725                 730                 735

Asp Thr Tyr Glu Leu Leu Gly Asn Ser Gln Leu Ala Pro Lys Leu Gln
            740                 745                 750

Gly Gln Ile Ser Glu Glu Tyr Lys Gln Thr Ala Leu
        755                 760

<210> SEQ ID NO 54
<211> LENGTH: 764
<212> TYPE: PRT
<213> ORGANISM: Rattus rattus

<400> SEQUENCE: 54

Met Arg Pro Gly Ser Leu Leu Gln Leu Thr Leu Leu Ala Leu Pro
1               5                   10                  15

Arg Ser Leu Trp Gly Arg Gly Cys Thr Ser Pro Pro Cys Glu Cys His
            20                  25                  30
```

```
Gln Glu Asp Asp Phe Arg Val Thr Cys Lys Glu Leu His Gln Ile Pro
             35                  40                  45

Ser Leu Pro Pro Ser Thr Gln Thr Leu Lys Leu Ile Glu Thr His Leu
 50                  55                  60

Lys Thr Ile Pro Ser Leu Ala Phe Ser Ser Leu Pro Asn Ile Ser Arg
 65                  70                  75                  80

Ile Tyr Leu Ser Ile Asp Ala Thr Leu Gln Arg Leu Glu Pro His Ser
                 85                  90                  95

Phe Tyr Asn Leu Ser Lys Met Thr His Ile Glu Ile Arg Asn Thr Arg
            100                 105                 110

Ser Leu Thr Tyr Ile Asp Pro Asp Ala Leu Thr Glu Leu Pro Leu Leu
        115                 120                 125

Lys Phe Leu Gly Ile Phe Asn Thr Gly Leu Arg Ile Phe Pro Asp Leu
130                 135                 140

Thr Lys Ile Tyr Ser Thr Asp Val Phe Phe Ile Leu Glu Ile Thr Asp
145                 150                 155                 160

Asn Pro Tyr Met Thr Ser Val Pro Glu Asn Ala Phe Gln Gly Leu Cys
                165                 170                 175

Asn Glu Thr Leu Thr Leu Lys Leu Tyr Asn Asn Gly Phe Thr Ser Ile
            180                 185                 190

Gln Gly His Ala Phe Asn Gly Thr Lys Leu Asp Ala Val Tyr Leu Asn
        195                 200                 205

Lys Asn Lys Tyr Leu Thr Ala Ile Asp Lys Asp Ala Phe Gly Gly Val
210                 215                 220

Tyr Ser Gly Pro Thr Leu Leu Asp Val Ser Ser Thr Ser Val Thr Ala
225                 230                 235                 240

Leu Pro Ser Lys Gly Leu Glu His Leu Lys Glu Leu Ile Ala Lys Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
290                 295                 300

Ser Ile Arg Asn Leu Arg Gln Arg Lys Ser Val Asn Val Met Arg Gly
305                 310                 315                 320

Pro Val Tyr Gln Glu Tyr Glu Glu Gly Leu Gly Asp Asn His Val Gly
                325                 330                 335

Tyr Lys Gln Asn Ser Lys Phe Gln Glu Gly Pro Ser Asn Ser His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Thr Leu Gln Ala Phe Asp Ser His
370                 375                 380

Tyr Asp Tyr Thr Val Cys Gly Asp Asn Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Pro Met Ala Leu Leu Gly Asn
            420                 425                 430

Val Phe Val Leu Phe Val Leu Leu Thr Ser His Tyr Lys Leu Thr Val
        435                 440                 445

Pro Arg Phe Leu Met Cys Asn Leu Ala Phe Ala Asp Phe Cys Met Gly
```

```
                   450                 455                 460
Val Tyr Leu Leu Leu Ile Ala Ser Val Asp Leu Tyr Thr His Thr Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Tyr Thr Ile Met Ala Gly
    530                 535                 540

Gly Trp Val Ser Cys Phe Leu Ala Leu Leu Pro Met Val Gly Ile
545                 550                 555                 560

Ser Ser Tyr Ala Lys Val Ser Ile Cys Leu Pro Met Asp Thr Asp Thr
                565                 570                 575

Pro Leu Ala Leu Ala Tyr Ile Ala Leu Val Leu Leu Asn Val Val
            580                 585                 590

Ala Phe Val Ile Val Cys Ser Cys Tyr Val Lys Ile Tyr Ile Thr Val
        595                 600                 605

Arg Asn Pro Gln Tyr Asn Pro Arg Asp Lys Asp Thr Lys Ile Ala Lys
    610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Gly Val Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
        675                 680                 685

Val Phe Ile Leu Leu Ser Lys Phe Gly Leu Cys Lys His Gln Ala Gln
    690                 695                 700

Ala Tyr Gln Ala Gln Arg Val Cys Pro Asn Asn Thr Gly Ile Gln
705                 710                 715                 720

Ile Gln Lys Ile Pro Gln Asp Thr Arg Gln Ser Leu Pro Asn Val Gln
                725                 730                 735

Asp Thr Tyr Glu Pro Leu Gly Ser Ser His Leu Thr Pro Lys Leu Gln
            740                 745                 750

Gly Arg Ile Ser Glu Glu Tyr Thr Gln Thr Ala Leu
        755                 760

<210> SEQ ID NO 55
<211> LENGTH: 764
<212> TYPE: PRT
<213> ORGANISM: Ovis aries

<400> SEQUENCE: 55

Met Arg Pro Thr Pro Leu Leu Arg Leu Ala Leu Leu Leu Val Leu Pro
1               5                   10                  15

Ser Ser Leu Trp Gly Glu Arg Cys Pro Ser Pro Cys Glu Cys Arg
            20                  25                  30

Gln Glu Asp Asp Phe Arg Val Thr Cys Lys Asp Ile Gln Arg Ile Pro
        35                  40                  45

Ser Leu Pro Pro Ser Thr Gln Thr Leu Lys Phe Ile Glu Thr His Leu
    50                  55                  60
```

```
Lys Thr Ile Pro Ser Arg Ala Phe Ser Asn Leu Pro Asn Ile Ser Arg
 65                  70                  75                  80

Ile Tyr Leu Ser Ile Asp Ala Thr Leu Gln Gln Leu Glu Ser His Ser
                 85                  90                  95

Phe Tyr Asn Leu Ser Lys Val Thr His Ile Glu Ile Arg Asn Thr Arg
            100                 105                 110

Ser Leu Thr Tyr Ile Asp Ser Gly Ala Leu Lys Glu Leu Pro Leu Leu
        115                 120                 125

Lys Phe Leu Gly Ile Phe Asn Thr Gly Leu Arg Val Phe Pro Asp Leu
    130                 135                 140

Thr Lys Ile Tyr Ser Thr Asp Val Phe Phe Ile Leu Glu Ile Thr Asp
145                 150                 155                 160

Asn Pro Tyr Met Thr Ser Val Pro Ala Asn Ala Phe Gln Gly Leu Ser
                165                 170                 175

Asn Glu Thr Leu Thr Leu Lys Leu Tyr Asn Asn Gly Phe Thr Ser Ile
            180                 185                 190

Gln Gly His Ala Phe Asn Gly Thr Lys Leu Asp Ala Val Tyr Leu Asn
        195                 200                 205

Lys Asn Lys Tyr Leu Thr Val Ile Asp Gln Asp Ala Phe Ala Gly Val
    210                 215                 220

Tyr Ser Gly Pro Thr Leu Leu Asp Ile Ser Tyr Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Asn Ile Arg Gly Ile Leu Gln Ser Leu Met Cys Asn Glu Ser
    290                 295                 300

Ser Ile Trp Gly Leu Arg Gln Arg Lys Ser Ala Ser Ala Leu Asn Gly
305                 310                 315                 320

Pro Phe Tyr Gln Glu Tyr Glu Glu Asp Leu Gly Asp Gly Ser Ala Gly
                325                 330                 335

Tyr Lys Glu Asn Ser Lys Phe Gln Asp Thr His Ser Asn Ser His Tyr
            340                 345                 350

Tyr Val Phe Phe Glu Asp Gln Glu Asp Glu Ile Ile Gly Phe Gly Gln
        355                 360                 365

Glu Leu Lys Asn Pro Gln Glu Glu Thr Leu Gln Ala Phe Asp Asn His
    370                 375                 380

Tyr Asp Tyr Thr Val Cys Gly Gly Ser Glu Glu Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Val Ile Leu Leu Thr Ser His Tyr Lys Leu Thr Val
        435                 440                 445

Pro Arg Phe Leu Met Cys Asn Leu Ala Phe Ala Asp Phe Cys Met Gly
    450                 455                 460

Leu Tyr Leu Leu Leu Ile Ala Ser Val Asp Leu Tyr Thr Gln Ser Glu
465                 470                 475                 480

Tyr Tyr Asn His Ala Ile Asp Trp Gln Thr Gly Pro Gly Cys Asn Thr
```

```
            485                 490                 495
Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met His
            515                 520                 525

Leu Asp Arg Lys Ile Arg Leu Trp His Ala Tyr Val Ile Met Leu Gly
            530                 535                 540

Gly Trp Val Cys Cys Phe Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Ile Leu Val Leu Leu Leu Asn Ile Ile
            580                 585                 590

Ala Phe Ile Ile Val Cys Ala Cys Tyr Val Lys Ile Tyr Ile Thr Val
            595                 600                 605

Arg Asn Pro His Tyr Asn Pro Gly Asp Lys Asp Thr Arg Ile Ala Lys
610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
            675                 680                 685

Val Phe Met Leu Leu Ser Lys Phe Gly Ile Cys Lys Arg Gln Ala Gln
            690                 695                 700

Ala Tyr Arg Gly Gln Arg Val Ser Ser Lys Asn Ser Thr Gly Ile Arg
705                 710                 715                 720

Val Gln Lys Val Pro Pro Asp Val Arg Gln Ser Leu Pro Asn Val Gln
                725                 730                 735

Asp Asp Tyr Glu Leu Leu Gly Asn Ser His Leu Thr Pro Lys Gln Gln
            740                 745                 750

Asp Gln Thr Ser Lys Glu Tyr Lys Gln Thr Val Leu
            755                 760

<210> SEQ ID NO 56
<211> LENGTH: 764
<212> TYPE: PRT
<213> ORGANISM: Equus caballus

<400> SEQUENCE: 56

Met Arg Pro Thr Pro Leu Leu Gln Leu Val Leu Leu Ala Leu Pro
1               5                   10                  15

Arg Ser Leu Gly Gly Lys Gly Cys Pro Ser Pro Cys Glu Cys His
            20                  25                  30

Gln Glu Asp Asp Phe Arg Val Thr Cys Lys Asp Ile His His Ile Pro
            35                  40                  45

Ser Leu Pro Pro Ser Thr Gln Thr Leu Lys Phe Thr Glu Thr His Leu
            50                  55                  60

Lys Thr Ile Pro Ser Arg Ala Phe Ser Asn Leu Pro Asn Ile Ser Arg
65                  70                  75                  80

Ile Tyr Leu Ser Ile Asp Thr Ser Leu Gln Arg Leu Glu Ser His Ser
                85                  90                  95
```

-continued

```
Phe Tyr Asn Leu Ser Lys Met Thr His Ile Glu Ile Arg Asn Thr Arg
            100                 105                 110

Ser Leu Thr Tyr Ile Glu Pro Gly Ala Leu Lys Glu Leu Pro Leu Leu
        115                 120                 125

Lys Phe Leu Gly Ile Phe Asn Thr Gly Leu Arg Val Phe Pro Asp Leu
    130                 135                 140

Thr Lys Val Tyr Ser Thr Asp Val Phe Phe Ile Leu Glu Ile Thr Asp
145                 150                 155                 160

Asn Pro Tyr Met Thr Ser Ile Pro Ala Asn Ala Phe Gln Gly Leu Cys
                165                 170                 175

Asn Glu Thr Leu Thr Val Lys Leu Tyr Asn Asn Gly Phe Thr Ser Ile
            180                 185                 190

Gln Gly His Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Thr Leu Leu Asp Val Ser Tyr Thr Thr Leu Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
    290                 295                 300

Ser Ile Arg Asn Leu Arg Gln Lys Lys Ser Val Asn Ala Leu Asn Gly
305                 310                 315                 320

Pro Phe Tyr Gln Glu Tyr Glu Gly Leu Gly Asp Ser Ser Ala Gly
                325                 330                 335

Tyr Lys Glu Asn Ser Lys Phe Gln Asp Ile His Ser Asn Ser His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser Ser
    370                 375                 380

Tyr Asp Tyr Thr Val Cys Gly Gly Asn Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Val Ile Leu Leu Thr Ser His Tyr Lys Leu Thr Val
        435                 440                 445

Pro Arg Phe Leu Met Cys Asn Leu Ala Phe Ala Asp Phe Cys Met Gly
    450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
```

```
            515                 520                 525
Leu Asp Arg Lys Ile Arg Leu Arg His Ala Tyr Ile Ile Met Val Gly
    530                 535                 540

Gly Trp Val Cys Cys Phe Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Ile Leu Val Leu Leu Asn Ile Val
            580                 585                 590

Ala Phe Ile Ile Val Cys Ser Cys Tyr Val Lys Ile Tyr Ile Thr Val
            595                 600                 605

Arg Asn Pro Gln Tyr Asn Pro Gly Asp Lys Asp Thr Lys Ile Ala Lys
    610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
    690                 695                 700

Ala Tyr Arg Gly Gln Arg Val Ser Gln Lys Asn Ser Thr Gly Leu Gln
705                 710                 715                 720

Val Gln Lys Val Thr Gln Asp Met Arg Gln Asn Leu Pro Asn Ile Gln
                725                 730                 735

Asp Ala Tyr Glu Leu Leu Glu Asn Ser His Leu Thr Pro Asn Lys Arg
            740                 745                 750

Ser Gln Ile Ser Lys Val Tyr Lys Gln Thr Val Leu
            755                 760

<210> SEQ ID NO 57
<211> LENGTH: 695
<212> TYPE: PRT
<213> ORGANISM: Homo sapiens

<400> SEQUENCE: 57

Met Ala Leu Leu Leu Val Ser Leu Leu Ala Phe Leu Ser Leu Gly Ser
1               5                   10                  15

Gly Cys His His Arg Ile Cys His Cys Ser Asn Arg Val Phe Leu Cys
                20                  25                  30

Gln Glu Ser Lys Val Thr Glu Ile Pro Ser Asp Leu Pro Arg Asn Ala
            35                  40                  45

Ile Glu Leu Arg Phe Val Leu Thr Lys Leu Arg Val Ile Gln Lys Gly
    50                  55                  60

Ala Phe Ser Gly Phe Gly Asp Leu Glu Lys Ile Glu Ile Ser Gln Asn
65                  70                  75                  80

Asp Val Leu Glu Val Ile Glu Ala Asp Val Phe Ser Asn Leu Pro Lys
                85                  90                  95

Leu His Glu Ile Arg Ile Glu Lys Ala Asn Asn Leu Leu Tyr Ile Asn
            100                 105                 110

Pro Glu Ala Phe Gln Asn Leu Pro Asn Leu Gln Tyr Leu Leu Ile Ser
            115                 120                 125
```

```
Asn Thr Gly Ile Lys His Leu Pro Asp Val His Lys Ile His Ser Leu
    130                 135                 140

Gln Lys Val Leu Leu Asp Ile Gln Asp Asn Ile Asn Ile His Thr Ile
145                 150                 155                 160

Glu Arg Asn Ser Phe Val Gly Leu Ser Phe Glu Ser Val Ile Leu Trp
                165                 170                 175

Leu Asn Lys Asn Gly Ile Gln Glu Ile His Asn Cys Ala Phe Asn Gly
            180                 185                 190

Thr Gln Leu Asp Glu Leu Asn Leu Ser Asp Asn Asn Leu Glu Glu
        195                 200                 205

Leu Pro Asn Asp Val Phe His Gly Ala Ser Gly Pro Val Ile Leu Asp
    210                 215                 220

Ile Ser Arg Thr Arg Ile His Ser Leu Pro Ser Tyr Gly Leu Glu Asn
225                 230                 235                 240

Leu Lys Lys Leu Arg Ala Arg Ser Thr Tyr Asn Leu Lys Lys Leu Pro
                245                 250                 255

Thr Leu Glu Lys Leu Val Ala Leu Met Glu Ala Ser Leu Thr Tyr Pro
            260                 265                 270

Ser His Cys Cys Ala Phe Ala Asn Trp Arg Arg Gln Ile Ser Glu Leu
        275                 280                 285

His Pro Ile Cys Asn Lys Ser Ile Leu Arg Gln Glu Val Asp Tyr Met
    290                 295                 300

Thr Gln Ala Arg Gly Gln Arg Ser Ser Leu Ala Glu Asp Asn Glu Ser
305                 310                 315                 320

Ser Tyr Ser Arg Gly Phe Asp Met Thr Tyr Thr Glu Phe Asp Tyr Asp
                325                 330                 335

Leu Cys Asn Glu Val Val Asp Val Thr Cys Ser Pro Lys Pro Asp Ala
            340                 345                 350

Phe Asn Pro Cys Glu Asp Ile Met Gly Tyr Asn Ile Leu Arg Val Leu
        355                 360                 365

Ile Trp Phe Ile Ser Ile Leu Ala Ile Thr Gly Asn Ile Ile Val Leu
    370                 375                 380

Val Ile Leu Thr Thr Ser Gln Tyr Lys Leu Thr Val Pro Arg Phe Leu
385                 390                 395                 400

Met Cys Asn Leu Ala Phe Ala Asp Leu Cys Ile Gly Ile Tyr Leu Leu
                405                 410                 415

Leu Ile Ala Ser Val Asp Ile His Thr Lys Ser Gln Tyr His Asn Tyr
            420                 425                 430

Ala Ile Asp Trp Gln Thr Gly Ala Gly Cys Asp Ala Ala Gly Phe Phe
        435                 440                 445

Thr Val Phe Ala Ser Glu Leu Ser Val Tyr Thr Leu Thr Ala Ile Thr
    450                 455                 460

Leu Glu Arg Trp His Thr Ile Thr His Ala Met Gln Leu Asp Cys Lys
465                 470                 475                 480

Val Gln Leu Arg His Ala Ala Ser Val Met Val Met Gly Trp Ile Phe
                485                 490                 495

Ala Phe Ala Ala Ala Leu Phe Pro Ile Phe Gly Ile Ser Ser Tyr Met
            500                 505                 510

Lys Val Ser Ile Cys Leu Pro Met Asp Ile Asp Ser Pro Leu Ser Gln
        515                 520                 525

Leu Tyr Val Met Ser Leu Leu Val Leu Asn Val Leu Ala Phe Val Val
    530                 535                 540

Ile Cys Gly Cys Tyr Ile His Ile Tyr Leu Thr Val Arg Asn Pro Asn
```

```
                545                 550                 555                 560
Ile Val Ser Ser Ser Asp Thr Arg Ile Ala Lys Arg Met Ala Met
                565                 570                 575

Leu Ile Phe Thr Asp Phe Leu Cys Met Ala Pro Ile Ser Phe Phe Ala
                580                 585                 590

Ile Ser Ala Ser Leu Lys Val Pro Leu Ile Thr Val Ser Lys Ala Lys
                595                 600                 605

Ile Leu Leu Val Leu Phe His Pro Ile Asn Ser Cys Ala Asn Pro Phe
    610                 615                 620

Leu Tyr Ala Ile Phe Thr Lys Asn Phe Arg Arg Asp Phe Phe Ile Leu
625                 630                 635                 640

Leu Ser Lys Cys Gly Cys Tyr Glu Met Gln Ala Gln Ile Tyr Arg Thr
                645                 650                 655

Glu Thr Ser Ser Thr Val His Asn Thr His Pro Arg Asn Gly His Cys
                660                 665                 670

Ser Ser Ala Pro Arg Val Thr Asn Gly Ser Thr Tyr Ile Leu Val Pro
                675                 680                 685

Leu Ser His Leu Ala Gln Asn
                690                 695

<210> SEQ ID NO 58
<211> LENGTH: 699
<212> TYPE: PRT
<213> ORGANISM: Homo sapiens

<400> SEQUENCE: 58

Met Lys Gln Arg Phe Ser Ala Leu Gln Leu Leu Lys Leu Leu Leu Leu
1               5                   10                  15

Leu Gln Pro Pro Leu Pro Arg Ala Leu Arg Glu Ala Leu Cys Pro Glu
                20                  25                  30

Pro Cys Asn Cys Val Pro Asp Gly Ala Leu Arg Cys Pro Gly Pro Thr
                35                  40                  45

Ala Gly Leu Thr Arg Leu Ser Leu Ala Tyr Leu Pro Val Lys Val Ile
    50                  55                  60

Pro Ser Gln Ala Phe Arg Gly Leu Asn Glu Val Ile Lys Ile Glu Ile
65                  70                  75                  80

Ser Gln Ile Asp Ser Leu Glu Arg Ile Glu Ala Asn Ala Phe Asp Asn
                85                  90                  95

Leu Leu Asn Leu Ser Glu Ile Leu Ile Gln Asn Thr Lys Asn Leu Arg
                100                 105                 110

Tyr Ile Glu Pro Gly Ala Phe Ile Asn Leu Pro Arg Leu Lys Tyr Leu
            115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220
```

-continued

```
Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
            245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
            275                 280                 285

Glu Gln Asn Phe Ser His Ser Ile Ser Glu Asn Phe Ser Lys Gln Cys
            290                 295                 300

Glu Ser Thr Val Arg Lys Val Asn Asn Lys Thr Leu Tyr Ser Ser Met
305                 310                 315                 320

Leu Ala Glu Ser Glu Leu Ser Gly Trp Asp Tyr Glu Tyr Gly Phe Cys
            325                 330                 335

Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
            355                 360                 365

Ile Asn Ile Leu Ala Ile Met Gly Asn Met Thr Val Leu Phe Val Leu
370                 375                 380

Leu Thr Ser Arg Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
            405                 410                 415

Ser Val Asp Ser Gln Thr Lys Gly Gln Tyr Tyr Asn His Ala Ile Asp
            420                 425                 430

Trp Gln Thr Gly Ser Gly Cys Ser Thr Ala Gly Phe Phe Thr Val Phe
            435                 440                 445

Ala Ser Glu Leu Ser Val Tyr Thr Leu Thr Val Ile Thr Leu Glu Arg
450                 455                 460

Trp His Thr Ile Thr Tyr Ala Ile His Leu Asp Gln Lys Leu Arg Leu
465                 470                 475                 480

Arg His Ala Ile Leu Ile Met Leu Gly Gly Trp Leu Phe Ser Ser Leu
            485                 490                 495

Ile Ala Met Leu Pro Leu Val Gly Val Ser Asn Tyr Met Lys Val Ser
            500                 505                 510

Ile Cys Phe Pro Met Asp Val Glu Thr Thr Leu Ser Gln Val Tyr Ile
            515                 520                 525

Leu Thr Ile Leu Ile Leu Asn Val Val Ala Phe Phe Ile Ile Cys Ala
530                 535                 540

Cys Tyr Ile Lys Ile Tyr Phe Ala Val Arg Asn Pro Glu Leu Met Ala
545                 550                 555                 560

Thr Asn Lys Asp Thr Lys Ile Ala Lys Lys Met Ala Ile Leu Ile Phe
            565                 570                 575

Thr Asp Phe Thr Cys Met Ala Pro Ile Ser Phe Phe Ala Ile Ser Ala
            580                 585                 590

Ala Phe Lys Val Pro Leu Ile Thr Val Thr Asn Ser Lys Val Leu Leu
            595                 600                 605

Val Leu Phe Tyr Pro Ile Asn Ser Cys Ala Asn Pro Phe Leu Tyr Ala
            610                 615                 620

Ile Phe Thr Lys Thr Phe Gln Arg Asp Phe Leu Leu Leu Ser Lys
625                 630                 635                 640

Phe Gly Cys Cys Lys Arg Arg Ala Glu Leu Tyr Arg Arg Lys Asp Phe
```

645                 650                 655
Ser Ala Tyr Thr Ser Asn Cys Lys Asn Gly Phe Thr Gly Ser Asn Lys
            660                 665                 670

Pro Ser Gln Ser Thr Leu Lys Leu Ser Thr Leu His Cys Gln Gly Thr
        675                 680                 685

Ala Leu Leu Asp Lys Thr Arg Tyr Thr Glu Cys
        690                 695

<210> SEQ ID NO 59
<211> LENGTH: 2292
<212> TYPE: DNA
<213> ORGANISM: Homo sapiens

<400> SEQUENCE: 59

| | | | | | |
|---|---|---|---|---|---|
| atgaggccgg | cggacttgct | gcagctggtg | ctgctgctcg | acctgcccag | ggacctgggc | 60 |
| ggaatggggt | gttcgtctcc | accctgcgag | tgccatcagg | aggaggactt | cagagtcacc | 120 |
| tgcaaggata | ttcaacgcat | ccccagctta | ccgcccagta | cgcagactct | gaagcttatt | 180 |
| gagactcacc | tgagaactat | tccaagtcat | gcattttcta | atctgcccaa | tatttccaga | 240 |
| atctacgtat | ctatagatgt | gactctgcag | cagctggaat | cacactcctt | ctacaatttg | 300 |
| agtaaagtga | ctcacataga | aattcggaat | accaggaact | taacttacat | agaccctgat | 360 |
| gccctcaaag | agctcccccct | cctaaagttc | cttggcattt | tcaacactgg | acttaaaatg | 420 |
| ttccctgacc | tgaccaaagt | ttattccact | gatatattct | ttatacttga | aattacagac | 480 |
| aaccccttaca | tgacgtcaat | ccctgtgaat | gcttttcagg | gactatgcaa | tgaaaccttg | 540 |
| acactgaagc | tgtacaacaa | cggctttact | tcagtccaag | gatatgcttt | caatgggaca | 600 |
| aagctggatg | ctgtttacct | aaacaagaat | aaatacctga | cagttattga | caaagatgca | 660 |
| tttggaggag | tatacagtgg | accaagcttg | ctggacgtgt | ctcaaaccag | tgtcactgcc | 720 |
| cttccatcca | aaggcctgga | gcacctgaag | gaactgatag | caagaaacac | ctggactctt | 780 |
| aacatcatcc | cagttgagga | ggagaacccg | gacttctgga | accgcgaggc | agccgaggcc | 840 |
| ctgggtgccg | ccaagaagct | gcagcctgca | cagacagccg | ccaagaacct | catcatcttc | 900 |
| ctgggcgatg | ggatgggggt | gtctacggtg | acagctgcca | ggatcctaaa | agggcagaag | 960 |
| aaggacaaac | tggggcctga | gatacccctg | gccatggacc | gcttcccata | tgtggctctg | 1020 |
| tccaagacat | acaatgtaga | caaacatgtg | ccagacagtg | agccacagc | acggcctac | 1080 |
| ctgtgcgggg | tcaagggcaa | cttccagacc | attggcttga | gtgcagccgc | ccgctttaac | 1140 |
| cagtgcaaca | cgacacgcgg | caacgaggtc | atctccgtga | tgaatcgggc | caagaaagca | 1200 |
| gggaagtcag | tgggagtggt | aaccaccaca | cgagtgcagc | acgcctcgcc | agccggcacc | 1260 |
| tacgcccaca | cggtgaaccg | caactggtac | tcggacgccg | acgtgcctgc | ctcggcccgc | 1320 |
| caggagggggt | gccaggacat | cgctacgcag | ctcatctcca | acatggacat | tgacgtgatc | 1380 |
| ctaggtggag | gccgaaagta | catgtttcgc | atgggaaccc | cagaccctga | gtacccagat | 1440 |
| gactacagcc | aaggtgggac | caggctggac | gggaagaatc | tggtgcagga | atggctggcg | 1500 |
| aagcgccagg | gtgcccggta | tgtgtggaac | cgcactgagc | tcatgcaggc | ttccctggac | 1560 |
| ccgtctgtga | cccatctcat | gggtctcttt | gagcctggag | acatgaaata | cgagatccac | 1620 |
| cgagactcca | cactggaccc | ctccctgatg | gagatgacag | aggctgccct | gcgcctgctg | 1680 |
| agcaggaacc | cccgcggctt | cttcctcttc | gtggagggtg | gtcgcatcga | ccatggtcat | 1740 |
| catgaaagca | gggcttaccg | ggcactgact | gagacgatca | tgttcgacga | cgccattgag | 1800 |

```
agggcgggcc agctcaccag cgaggaggac acgctgagcc tcgtcactgc cgaccactcc    1860
cacgtcttct ccttcggagg ctaccccctg cgagggagct ccatcttcgg gctggcccct    1920
ggcaaggccc gggacaggaa ggcctacacg gtcctcctat acggaaacgg tccaggctat    1980
gtgctcaagg acggcgcccg gccggatgtt accgagagcg agagcgggag ccccgagtat    2040
cggcagcagt cagcagtgcc cctggacgaa gagacccacg caggcgagga cgtggcggtg    2100
ttcgcgcgcg gcccgcaggc gcacctggtt cacggcgtgc aggagcagac cttcatagcg    2160
cacgtcatgg ccttcgccgc ctgcctggag ccctacaccg cctgcgacct ggcgccccc    2220 gccggcacca ccgacgccgc gcacccgggt tactctagag tcggggcggc cggccgcttc    2280
gagcagacat ga                                                        2292
```

<210> SEQ ID NO 60
<211> LENGTH: 763
<212> TYPE: PRT
<213> ORGANISM: Homo sapiens

<400> SEQUENCE: 60

```
Met Arg Pro Ala Asp Leu Leu Gln Leu Val Leu Leu Asp Leu Pro
1               5                   10                  15

Arg Asp Leu Gly Gly Met Gly Cys Ser Ser Pro Cys Glu Cys His
                20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Asn Ile Ile Pro Val Glu Glu Glu Asn Pro Asp Phe
            260                 265                 270

Trp Asn Arg Glu Ala Ala Glu Ala Leu Gly Ala Ala Lys Lys Leu Gln
        275                 280                 285
```

```
Pro Ala Gln Thr Ala Ala Lys Asn Leu Ile Ile Phe Leu Gly Asp Gly
    290                 295                 300

Met Gly Val Ser Thr Val Thr Ala Ala Arg Ile Leu Lys Gly Gln Lys
305                 310                 315                 320

Lys Asp Lys Leu Gly Pro Glu Ile Pro Leu Ala Met Asp Arg Phe Pro
                325                 330                 335

Tyr Val Ala Leu Ser Lys Thr Tyr Asn Val Asp Lys His Val Pro Asp
                340                 345                 350

Ser Gly Ala Thr Ala Thr Ala Tyr Leu Cys Gly Val Lys Gly Asn Phe
            355                 360                 365

Gln Thr Ile Gly Leu Ser Ala Ala Arg Phe Asn Gln Cys Asn Thr
    370                 375                 380

Thr Arg Gly Asn Glu Val Ile Ser Val Met Asn Arg Ala Lys Lys Ala
385                 390                 395                 400

Gly Lys Ser Val Gly Val Val Thr Thr Thr Arg Val Gln His Ala Ser
                405                 410                 415

Pro Ala Gly Thr Tyr Ala His Thr Val Asn Arg Asn Trp Tyr Ser Asp
                420                 425                 430

Ala Asp Val Pro Ala Ser Ala Arg Gln Glu Gly Cys Gln Asp Ile Ala
            435                 440                 445

Thr Gln Leu Ile Ser Asn Met Asp Ile Asp Val Ile Leu Gly Gly Gly
    450                 455                 460

Arg Lys Tyr Met Phe Arg Met Gly Thr Pro Asp Pro Glu Tyr Pro Asp
465                 470                 475                 480

Asp Tyr Ser Gln Gly Gly Thr Arg Leu Asp Gly Lys Asn Leu Val Gln
                485                 490                 495

Glu Trp Leu Ala Lys Arg Gln Gly Ala Arg Tyr Val Trp Asn Arg Thr
            500                 505                 510

Glu Leu Met Gln Ala Ser Leu Asp Pro Ser Val Thr His Leu Met Gly
    515                 520                 525

Leu Phe Glu Pro Gly Asp Met Lys Tyr Glu Ile His Arg Asp Ser Thr
530                 535                 540

Leu Asp Pro Ser Leu Met Glu Met Thr Glu Ala Ala Leu Arg Leu Leu
545                 550                 555                 560

Ser Arg Asn Pro Arg Gly Phe Phe Leu Phe Val Glu Gly Gly Arg Ile
                565                 570                 575

Asp His Gly His His Glu Ser Arg Ala Tyr Arg Ala Leu Thr Glu Thr
            580                 585                 590

Ile Met Phe Asp Asp Ala Ile Glu Arg Ala Gly Gln Leu Thr Ser Glu
    595                 600                 605

Glu Asp Thr Leu Ser Leu Val Thr Ala Asp His Ser His Val Phe Ser
610                 615                 620

Phe Gly Gly Tyr Pro Leu Arg Gly Ser Ser Ile Phe Gly Leu Ala Pro
625                 630                 635                 640

Gly Lys Ala Arg Asp Arg Lys Ala Tyr Thr Val Leu Leu Tyr Gly Asn
                645                 650                 655

Gly Pro Gly Tyr Val Leu Lys Asp Gly Ala Arg Pro Asp Val Thr Glu
                660                 665                 670

Ser Glu Ser Gly Ser Pro Glu Tyr Arg Gln Gln Ser Ala Val Pro Leu
            675                 680                 685

Asp Glu Glu Thr His Ala Gly Glu Asp Val Ala Val Phe Ala Arg Gly
    690                 695                 700
```

```
Pro Gln Ala His Leu Val His Gly Val Gln Glu Gln Thr Phe Ile Ala
705                 710                 715                 720

His Val Met Ala Phe Ala Ala Cys Leu Glu Pro Tyr Thr Ala Cys Asp
                725                 730                 735

Leu Ala Pro Pro Ala Gly Thr Thr Asp Ala Ala His Pro Gly Tyr Ser
            740                 745                 750

Arg Val Gly Ala Ala Gly Arg Phe Glu Gln Thr
        755                 760

<210> SEQ ID NO 61
<211> LENGTH: 2295
<212> TYPE: DNA
<213> ORGANISM: Sus scrofa

<400> SEQUENCE: 61
atgagtctga cgcccctgtt gcagctggcg ctgcttctcg ccctgcccag gagcctcagg    60 gggaagggt gtccgtctcc gccctgcgaa tgccaccagg aggacgactt cagagtcacc    120
tgcaaggata tccacagcat ccccccctta ccacccaata ctcagacact aaagtttata    180
gagactcatc tgaaaaccat ccccagtcgt gcattttcaa atctgcccaa tatttccagg    240
atctacctgt caatagatgc aactctacag cagctggaat cacagtcctt ctacaatttg    300
agcaaaatga ctcacataga gattcggaat accagaagct taacgtacat aaaccctggt    360
gccctaaaag atctccccct tctaaagttc cttggcattt caacactgg acttagaata     420 ttcccagacc tgaccaaagt gtattccact gatgtattct tcatacttga aattacagac    480
aacccttaca tgcatcaat ccctgcgaat gcttttcagg gctgtgcaa cgaaaccttg      540 acactgaaac tatacaacaa tggctttact tcagtccaag acatgctttt caatgggaca    600
aagctggatg ctgtttacct gaacaagaat aaatacctga cagttattga caaagatgca    660
tttggaggag ttttcagtgg accaaccttg ctggatgtct cttataccag tgttactgcc    720
ctgccaccca aggcctgga acacctgaag gaactgatag caagaaatac ttggactcta    780
aagaaacttc cactgtcctt gagtttcctt cacctcacac gagctgacct ttcttatcca    840
agccactgct gtgcttttaa gaatcagaag aagatcagag gaatccttga gtctttaatg    900
tgtaatgaga gcagtattcg gagcctgcgt cagagaaaat ctgtgaatgc tgtaaatggt    960 ccctttacc aagaatatga agaggatctg ggcgacagca gtgttgggaa taaggaaaac    1020
tccaagttcc aggatacca tagcaactcc cattactacg tcttctttga agaacaagag    1080
gatgagatca ttggttttgg ccaagagctc aaaaacccccc aggaagagac cctccaggcc    1140
tttgacagcc attacgacta caccgtgtgt ggggcagtg aagacatggt gtgcacccccc    1200 aagtcagatg agttcaaccc ctgtgaagac ataatgggct acaggttcct gagaatcgtg    1260
gtgtggttcg ttagcctgct ggctctcctg ggcaatgtct ttgtcctggt catcctcctc    1320
acgagccact acaaactgac ggtcccacgc tttctcatgt gcaacttggc ctttgcagat    1380
ttctgcatgg ggatgtatct gctcctcatt gcctcggtgg acctctacac tcagtctgag    1440
tactacaacc atgccatcga ctggcagaca ggtcccgggt gcaacacggc tggttttcttc    1500 accgtctttg ccagcgagct gtcagtgtac acactaacag tcatcactct ggagcgctgg    1560
tatgccatca ccttcgccat gcgcctggat cgcaagatcc gcctcaggca cgcctacgcc    1620
atcatggctg gcggctgggt tgctgcttc ctgctcgccc tgctgccttt ggtggggata    1680
agcagctatg ctaaggtcag catctgcctg cccatggaca ctgagactcc tcttgccctg    1740
gcgtatatta tccttgttct gctgctcaac atagttgcct ttaccatcgt ctgctcctgt    1800
```

```
tacgtgaaga tctacatcac agtccgaaat ccccagtata acccgggaga caaagacact   1860
aaaattgcca aaaggatggc tgtgttgatc ttcactgact tcatgtgcat ggccccgatc   1920
tccttttacg ccctctcagc acttatgaac aagcctctca tcactgtcac caactccaaa   1980
atcttgctcg ttctcttcta cccacttaac tcctgtgcca acccgttcct ctatgccatt   2040
ttcaccaaag ccttccagag ggatgtgttt atcctgctca gcaagttcgg cttctgtaaa   2100
cgccaggctc aggcataccg gggtcagaga gtgtctccaa gaacagcac tggtattcag    2160 gtccaaaagg ttacccaaaa catgaggcaa agtctcccca acatgcagga tgactatgaa   2220
ctgcttgaaa actcgcatct aacccacaaa aagcatgacc aaatttcaaa ggagtataag   2280
caaccagttt tgtaa                                                    2295
```

```
<210> SEQ ID NO 62
<211> LENGTH: 764
<212> TYPE: PRT
<213> ORGANISM: Sus scrofa

<400> SEQUENCE: 62

Met Ser Leu Thr Pro Leu Leu Gln Leu Ala Leu Leu Leu Ala Leu Pro
1               5                   10                  15

Arg Ser Leu Arg Gly Lys Gly Cys Ser Pro Pro Cys Glu Cys His
            20                  25                  30

Gln Glu Asp Asp Phe Arg Val Thr Cys Lys Asp Ile His Ser Ile Pro
        35                  40                  45

Pro Leu Pro Pro Asn Thr Gln Thr Leu Lys Phe Ile Glu Thr His Leu
    50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Gln Leu Glu Ser Gln Ser
                85                  90                  95

Phe Tyr Asn Leu Ser Lys Met Thr His Ile Glu Ile Arg Asn Thr Arg
            100                 105                 110

Ser Leu Thr Tyr Ile Asn Pro Gly Ala Leu Lys Asp Leu Pro Leu Leu
        115                 120                 125

Lys Phe Leu Gly Ile Phe Asn Thr Gly Leu Arg Ile Phe Pro Asp Leu
    130                 135                 140

Thr Lys Val Tyr Ser Thr Asp Val Phe Phe Ile Leu Glu Ile Thr Asp
145                 150                 155                 160

Asn Pro Tyr Met Thr Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly His Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Phe Ser Gly Pro Thr Leu Leu Asp Val Ser Tyr Thr Ser Val Thr Ala
225                 230                 235                 240

Leu Pro Pro Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
```

-continued

```
            275                 280                 285
Gln Lys Lys Ile Arg Gly Ile Leu Glu Ser Leu Met Cys Asn Glu Ser
            290                 295                 300
Ser Ile Arg Ser Leu Arg Gln Arg Lys Ser Val Asn Ala Val Asn Gly
305                 310                 315                 320
Pro Phe Tyr Gln Glu Tyr Glu Asp Leu Gly Asp Ser Ser Val Gly
            325                 330                 335
Asn Lys Glu Asn Ser Lys Phe Gln Asp Thr His Ser Asn Ser His Tyr
            340                 345                 350
Tyr Val Phe Phe Glu Glu Gln Glu Asp Glu Ile Ile Gly Phe Gly Gln
            355                 360                 365
Glu Leu Lys Asn Pro Gln Glu Glu Thr Leu Gln Ala Phe Asp Ser His
            370                 375                 380
Tyr Asp Tyr Thr Val Cys Gly Ser Glu Asp Met Val Cys Thr Pro
385                 390                 395                 400
Lys Ser Asp Glu Phe Asn Pro Cys Glu Asp Ile Met Gly Tyr Arg Phe
            405                 410                 415
Leu Arg Ile Val Val Trp Phe Val Ser Leu Leu Ala Leu Leu Gly Asn
            420                 425                 430
Val Phe Val Leu Val Ile Leu Leu Thr Ser His Tyr Lys Leu Thr Val
            435                 440                 445
Pro Arg Phe Leu Met Cys Asn Leu Ala Phe Ala Asp Phe Cys Met Gly
            450                 455                 460
Met Tyr Leu Leu Leu Ile Ala Ser Val Asp Leu Tyr Thr Gln Ser Glu
465                 470                 475                 480
Tyr Tyr Asn His Ala Ile Asp Trp Gln Thr Gly Pro Gly Cys Asn Thr
            485                 490                 495
Ala Gly Phe Phe Thr Val Phe Ala Ser Glu Leu Ser Val Tyr Thr Leu
            500                 505                 510
Thr Val Ile Thr Leu Glu Arg Trp Tyr Ala Ile Thr Phe Ala Met Arg
            515                 520                 525
Leu Asp Arg Lys Ile Arg Leu Arg His Ala Tyr Ala Ile Met Ala Gly
            530                 535                 540
Gly Trp Val Cys Cys Phe Leu Leu Ala Leu Leu Pro Leu Val Gly Ile
545                 550                 555                 560
Ser Ser Tyr Ala Lys Val Ser Ile Cys Leu Pro Met Asp Thr Glu Thr
            565                 570                 575
Pro Leu Ala Leu Ala Tyr Ile Ile Leu Val Leu Leu Leu Asn Ile Val
            580                 585                 590
Ala Phe Thr Ile Val Cys Ser Cys Tyr Val Lys Ile Tyr Ile Thr Val
            595                 600                 605
Arg Asn Pro Gln Tyr Asn Pro Gly Asp Lys Asp Thr Lys Ile Ala Lys
            610                 615                 620
Arg Met Ala Val Leu Ile Phe Thr Asp Phe Met Cys Met Ala Pro Ile
625                 630                 635                 640
Ser Phe Tyr Ala Leu Ser Ala Leu Met Asn Lys Pro Leu Ile Thr Val
            645                 650                 655
Thr Asn Ser Lys Ile Leu Leu Val Leu Phe Tyr Pro Leu Asn Ser Cys
            660                 665                 670
Ala Asn Pro Phe Leu Tyr Ala Ile Phe Thr Lys Ala Phe Gln Arg Asp
            675                 680                 685
Val Phe Ile Leu Leu Ser Lys Phe Gly Phe Cys Lys Arg Gln Ala Gln
            690                 695                 700
```

```
Ala Tyr Arg Gly Gln Arg Val Ser Pro Lys Asn Ser Thr Gly Ile Gln
705                 710                 715                 720

Val Gln Lys Val Thr Gln Asn Met Arg Gln Ser Leu Pro Asn Met Gln
            725                 730                 735

Asp Asp Tyr Glu Leu Leu Glu Asn Ser His Leu Thr His Lys Lys His
        740                 745                 750

Asp Gln Ile Ser Lys Glu Tyr Lys Gln Pro Val Leu
        755                 760
```

<210> SEQ ID NO 63
<211> LENGTH: 2295
<212> TYPE: DNA
<213> ORGANISM: Mus musculus

<400> SEQUENCE: 63

| | | |
|---|---|---|
| atgaggccag ggtccctgct gctgcttgtt ctgctgctcg ccctgtccag gagcctgcgg | 60 |
| ggcaaagagt gtgcgtctcc accctgtgag tgtcaccagg aggacgactt cagagtcacc | 120 |
| tgcaaggagc tccaccgaat ccccagcctg ccgcccagca cccagactct gaagctcatc | 180 |
| gagactcatc tgaagaccat accagtcttg catttcgag gtctgcccaa tatttccagg | 240 |
| atctatttat ctatagatgc aactctgcag cggctggaac acattctttt ctacaatttg | 300 |
| agtaaaatga ctcacataga atccggaac accagaagct taacctatat agaccctgat | 360 |
| gccttgacag agctccccctt gctcaagttt cttggcattt tcaatactgg acttagaata | 420 |
| ttccctgact tgaccaaaat ttattccacg gacatattct ttatacttga atcacagac | 480 |
| aaccccttaca tgacttcggt ccctgaaaac gcattccagg cctatgcaa tgaaaccttg | 540 |
| accctgaaac tgtacaacaa tggatttact tcagtccaag acatgctttt caatggaaca | 600 |
| aagctggatg ctgtttacct aaacaagaat aaatacctga cagctataga caacgatgcc | 660 |
| tttggaggag tatacagtgg accaactttg ctagatgtgt cttccaccag cgtcactgcc | 720 |
| cttccttcca aaggcctgga gcacctcaaa gaactgatca caaagacac ctggactctc | 780 |
| aaaaagctcc cgctgtcgtt gagtttcctc cacctcactc gggctgacct ctcttacccg | 840 |
| agccactgct gcgcttttaa gaaccagaag aaaatcaggg gaatcctgga gtctttgatg | 900 |
| tgtaatgaga gcagtatccg gaaccttcgt caaaggaaat cagtgaacat cttgaggggt | 960 |
| cccatctacc aggaatatga agaagatccg ggtgacaaca gtgttgggta caaacaaaac | 1020 |
| tccaagttcc aggagagccc aagcaactct cactattacg tcttctttga agaacaagag | 1080 |
| gatgaggtcg ttggtttcgg ccaagagctc aaaaatcctc aggaagagac tctccaagcc | 1140 |
| ttcgagagcc actatgacta cacggtgtgt ggggacaacg aggacatggt gtgtacccc | 1200 |
| aagtcggacg agtttaaccc ctgtgaagat atcatgggct acaggttcct gagaatcgtg | 1260 |
| gtgtggtttg tcagtctgct ggctctcctg gcaatatct tcgtcctgct cattctgcta | 1320 |
| accagccact acaaattgac cgtgccgcgg ttcctcatgt gcaacttggc ctttgcagat | 1380 |
| ttctgcatgg gggtatacct gcttctcatt gcctctgtag acctgtacac acactctgag | 1440 |
| tactacaacc acgccatcga ctggcagacg ggccctgggt gcaacacggc tggcttcttc | 1500 |
| actgttttcg ccagtgagtt atcagtgtac acactgacgg tcatcaccct ggagcgatgg | 1560 |
| tacgccatca ccttcgccat gcgcctggat aggaagatcc gcctcaggca cgcgtacacc | 1620 |
| atcatggctg ggggctgggt ttcctgcttc cttctcgccc tgctcccgat ggtgggaatc | 1680 |
| agcagctatg ccaaggtcag catctgcctg ccaatggaca ccgacacccc tcttgcactc | 1740 |

```
gcatacattg tcctcgttct gctgctcaat gttgttgcct tgttgtcgt ctgttcctgc    1800 tatgtgaaga tctacatcac ggtccgaaat ccccagtaca accctcgaga taaagacacc    1860
aagattgcca agaggatggc tgtgttgatc ttcactgact tcatgtgcat ggcgcccatc    1920
tccttctatg cgctgtcggc acttatgaac aagcctctaa tcactgttac taactccaaa    1980
atcttgttgg ttctcttcta ccccctcaac tcctgtgcca atccgtttct ctatgctatt    2040
ttcaccaagg ccttccagag ggacgtgttc atcctgctca gcaagtttgg catctgcaaa    2100
cgccaggccc aggcctatca gggtcagaga gtctgtccca acaatagcac tggtattcag    2160
atccaaaaga ttccccagga cacgaggcag agtctcccca acatgcaaga tacctatgaa    2220
ctgcttggaa actcccagct agctccaaaa ctgcagggac aaatctcaga agagtataag    2280
caaacagcct tgtaa                                                     2295
```

```
<210> SEQ ID NO 64
<211> LENGTH: 764
<212> TYPE: PRT
<213> ORGANISM: Mus musculus

<400> SEQUENCE: 64

Met Arg Pro Gly Ser Leu Leu Leu Val Leu Leu Ala Leu Ser
1               5                   10                  15

Arg Ser Leu Arg Gly Lys Glu Cys Ala Ser Pro Cys Glu Cys His
            20                  25                  30

Gln Glu Asp Asp Phe Arg Val Thr Cys Lys Glu Leu His Arg Ile Pro
        35                  40                  45

Ser Leu Pro Pro Ser Thr Gln Thr Leu Lys Leu Ile Glu Thr His Leu
    50                  55                  60

Lys Thr Ile Pro Ser Leu Ala Phe Ser Ser Leu Pro Asn Ile Ser Arg
65                  70                  75                  80

Ile Tyr Leu Ser Ile Asp Ala Thr Leu Gln Arg Leu Glu Pro His Ser
                85                  90                  95

Phe Tyr Asn Leu Ser Lys Met Thr His Ile Glu Ile Arg Asn Thr Arg
            100                 105                 110

Ser Leu Thr Tyr Ile Asp Pro Asp Ala Leu Thr Glu Leu Pro Leu Leu
        115                 120                 125

Lys Phe Leu Gly Ile Phe Asn Thr Gly Leu Arg Ile Phe Pro Asp Leu
    130                 135                 140

Thr Lys Ile Tyr Ser Thr Asp Ile Phe Phe Ile Leu Glu Ile Thr Asp
145                 150                 155                 160

Asn Pro Tyr Met Thr Ser Val Pro Glu Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly His Ala Phe Asn Gly Thr Lys Leu Asp Ala Val Tyr Leu Asn
        195                 200                 205

Lys Asn Lys Tyr Leu Thr Ala Ile Asp Asn Asp Ala Phe Gly Gly Val
    210                 215                 220

Tyr Ser Gly Pro Thr Leu Leu Asp Val Ser Ser Thr Ser Val Thr Ala
225                 230                 235                 240

Leu Pro Ser Lys Gly Leu Glu His Leu Lys Glu Leu Ile Ala Lys Asp
                245                 250                 255

Thr Trp Thr Leu Lys Lys Leu Pro Leu Ser Leu Ser Phe Leu His Leu
            260                 265                 270
```

```
Thr Arg Ala Asp Leu Ser Tyr Pro Ser His Cys Cys Ala Phe Lys Asn
            275                 280                 285

Gln Lys Lys Ile Arg Gly Ile Leu Glu Ser Leu Met Cys Asn Glu Ser
        290                 295                 300

Ser Ile Arg Asn Leu Arg Gln Arg Lys Ser Val Asn Ile Leu Arg Gly
305                 310                 315                 320

Pro Ile Tyr Gln Glu Tyr Glu Asp Pro Gly Asp Asn Ser Val Gly
                325                 330                 335

Tyr Lys Gln Asn Ser Lys Phe Gln Glu Ser Pro Ser Asn Ser His Tyr
            340                 345                 350

Tyr Val Phe Phe Glu Glu Gln Glu Asp Glu Val Val Gly Phe Gly Gln
        355                 360                 365

Glu Leu Lys Asn Pro Gln Glu Glu Thr Leu Gln Ala Phe Glu Ser His
        370                 375                 380

Tyr Asp Tyr Thr Val Cys Gly Asp Asn Glu Asp Met Val Cys Thr Pro
385                 390                 395                 400

Lys Ser Asp Glu Phe Asn Pro Cys Glu Asp Ile Met Gly Tyr Arg Phe
                405                 410                 415

Leu Arg Ile Val Val Trp Phe Val Ser Leu Leu Ala Leu Leu Gly Asn
            420                 425                 430

Ile Phe Val Leu Leu Ile Leu Leu Thr Ser His Tyr Lys Leu Thr Val
        435                 440                 445

Pro Arg Phe Leu Met Cys Asn Leu Ala Phe Ala Asp Phe Cys Met Gly
        450                 455                 460

Val Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Tyr Thr Ile Met Ala Gly
        530                 535                 540

Gly Trp Val Ser Cys Phe Leu Ala Leu Leu Pro Met Val Gly Ile
545                 550                 555                 560

Ser Ser Tyr Ala Lys Val Ser Ile Cys Leu Pro Met Asp Thr Asp Thr
                565                 570                 575

Pro Leu Ala Leu Ala Tyr Ile Val Leu Val Leu Leu Leu Asn Val Val
            580                 585                 590

Ala Phe Val Val Val Cys Ser Cys Tyr Val Lys Ile Tyr Ile Thr Val
        595                 600                 605

Arg Asn Pro Gln Tyr Asn Pro Arg Asp Lys Asp Thr Lys Ile Ala Lys
        610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
        675                 680                 685

Val Phe Ile Leu Leu Ser Lys Phe Gly Ile Cys Lys Arg Gln Ala Gln
```

Ala Tyr Gln Gly Gln Arg Val Cys Pro Asn Asn Ser Thr Gly Ile Gln
705                710                715                720

Ile Gln Lys Ile Pro Gln Asp Thr Arg Gln Ser Leu Pro Asn Met Gln
            725                730                735

Asp Thr Tyr Glu Leu Leu Gly Asn Ser Gln Leu Ala Pro Lys Leu Gln
        740                745                750

Gly Gln Ile Ser Glu Glu Tyr Lys Gln Thr Ala Leu
        755                760

<210> SEQ ID NO 65
<211> LENGTH: 2295
<212> TYPE: DNA
<213> ORGANISM: Sus scrofa

<400> SEQUENCE: 65

| | | |
|---|---|---|
| atgagtctga cgcccctgtt gcagctggcg ctgcttctcg ccctgcccag gagcctcagg | 60 |
| gggaaagggt gtccgtctcc gccctgcgaa tgccaccagg aggacgactt cagagtcacc | 120 |
| tgcaaggata tccacagcat ccccccctta ccacccaata ctcagacact aaagtttata | 180 |
| gagacttgtc tgaaaaccat ccccagtcgt gcattttcaa atctgcccaa tatttccagg | 240 |
| atctacctgt caatagatgc aactctacag cagctggaat cacagtcctt ctacaatttg | 300 |
| agcaaaatga ctcacataga gattcggaat accccaagct aacgtacat aaaccctggt | 360 |
| gccctaaaag atctccccct tctaaagttc cttggcattt tcaacactgg acttagaata | 420 |
| ttcccacccc tgaccaaagt gtattccact gaggtattct tcatacttga aattacagac | 480 |
| aaccctttaca tgacatcaat ccctcggaat gcttttcagg gcctgtgcaa cgaaaccttg | 540 |
| acactgaaac tatacaacaa tggctttact tcagtccaag acatgctttt caatgggaca | 600 |
| aagctggatg ctgtttacct gaacaagaat aaatacctga cagttattga caaagatgca | 660 |
| tttggaggag ttttcagtgg accaaccttg ctggatgtct cttataccag tgttactgcc | 720 |
| ctgccaccca aaggcctgga cacctgaag gaactgagag caagaaatac ttggactcta | 780 |
| aagaaacttc cactgtcctt gagtttcctt cacctcacac gagctgacct ttcttatcca | 840 |
| agccactgct gtgcttttaa gaatcagaag aagatcagag gaatccttga gtctttaatg | 900 |
| tgtaatgaga gcagtattcg gagcctgcgt cagagaaaat ctgtgaatgc tgtaaatggt | 960 |
| cccttttacc aagaatatga gaggatctg gcgacagca gtgttgggaa taaggaaaac | 1020 |
| tccaagttcc aggatacccca tagcaactcc cattactacg tcttctttga agaacaagag | 1080 |
| gatgagatca ttggtttttgg ccaagagctc aaaaaccccc aggaagagac cctccaggcc | 1140 |
| tttgacagcc attacgacta caccgtgtgt ggggggcagtg aagacatggt gtgcaccccc | 1200 |
| aagtcagatg agttcaaccc ctgtgaagac ataatgggct acaggttcct gagaatcgtg | 1260 |
| gtgtggttcg ttagcctgct ggctctcctg ggcaatgtct ttgtcctggt catcctcctc | 1320 |
| acgagccact acaaactgac ggtcccacgc tttctcatgt gcaacttggc cttggcagat | 1380 |
| ttctgcatgg ggatgtatct gctcctcatt ggctcggtgg acctctacac tcagtctgag | 1440 |
| tactacaacc atgccatcga ctggcagaca ggtcccgggt gcaacacggc tggtttcttc | 1500 |
| accgtctttg ccagcgagct gtcagtgtac acactaacag tcatcactct ggagcgctgg | 1560 |
| tatgccatca ccttcgccat gcgcctggat cgcaagatcc gcctcaggca cgcctacgcc | 1620 |
| atcatggctg gcggctgggt ttgctgcttc ctgctcgccc tgctgccttt ggtggggata | 1680 |
| agcagctatg ctaaggtcag catctgcctg cccatggaca ctgagactcc tcttgccctg | 1740 |

-continued

```
gcgtatatta tccttgttct gctgctcaac atagttgcct ttaccatcgt ctgctcctgt    1800
tacgtgaaga tctacatcac agtccgaaat ccccagtata acccgggaga caaagacact    1860
aaaattgcca aaaggatggc tgtgttgatc ttcactgact tcatgtgcat ggccccgatc    1920 tcctttacg ccctctcagc acttatgaac aagcctctca tcactgtcac caactccaaa     1980
atcttgctcg ttctcttcta cccacttaac tcctgtgcca accgttcct ctatgccatt     2040 ttcaccaaag ccttccagag ggatgtgttt atcctgctca gcaagttcgg cttctgtaaa    2100
cgccaggctc aggcataccg gggtcagaga gtgtctccaa agaacagcac tggtattcag    2160
gtccaaaagg ttacccaaaa catgaggcaa agtctcccca acatgcagga tgactatgaa    2220
ctgcttgaaa actcgcatct aacccacaaa aagcatgacc aaatttcaaa ggagtataag    2280
caaccagttt tgtaa                                                     2295
```

<210> SEQ ID NO 66
<211> LENGTH: 764
<212> TYPE: PRT
<213> ORGANISM: Sus scrofa

<400> SEQUENCE: 66

```
Met Ser Leu Thr Pro Leu Leu Gln Leu Ala Leu Leu Leu Ala Leu Pro
1               5                   10                  15

Arg Ser Leu Arg Gly Lys Gly Cys Pro Ser Pro Cys Glu Cys His
            20                  25                  30

Gln Glu Asp Asp Phe Arg Val Thr Cys Lys Asp Ile His Ser Ile Pro
        35                  40                  45

Pro Leu Pro Pro Asn Thr Gln Thr Leu Lys Phe Ile Glu Thr Cys Leu
    50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Gln Leu Glu Ser Gln Ser
                85                  90                  95

Phe Tyr Asn Leu Ser Lys Met Thr His Ile Glu Ile Arg Asn Thr Pro
            100                 105                 110

Ser Leu Thr Tyr Ile Asn Pro Gly Ala Leu Lys Asp Leu Pro Leu Leu
        115                 120                 125

Lys Phe Leu Gly Ile Phe Asn Thr Gly Leu Arg Ile Phe Pro Pro Leu
    130                 135                 140

Thr Lys Val Tyr Ser Thr Glu Val Phe Phe Ile Leu Glu Ile Thr Asp
145                 150                 155                 160

Asn Pro Tyr Met Thr Ser Ile Pro Arg Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly His Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Phe Ser Gly Pro Thr Leu Leu Asp Val Ser Tyr Thr Ser Val Thr Ala
225                 230                 235                 240

Leu Pro Pro Lys Gly Leu Glu His Leu Lys Glu Leu Arg Ala Arg Asn
                245                 250                 255

Thr Trp Thr Leu Lys Lys Leu Pro Leu Ser Leu Ser Phe Leu His Leu
            260                 265                 270
```

```
Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
        290                 295                 300

Ser Ile Arg Ser Leu Arg Gln Arg Lys Ser Val Asn Ala Val Asn Gly
305                 310                 315                 320

Pro Phe Tyr Gln Glu Tyr Glu Glu Asp Leu Gly Asp Ser Ser Val Gly
                325                 330                 335

Asn Lys Glu Asn Ser Lys Phe Gln Asp Thr His Ser Asn Ser His Tyr
                340                 345                 350

Tyr Val Phe Phe Glu Glu Gln Asp Glu Ile Ile Gly Phe Gly Gln
                355                 360                 365

Glu Leu Lys Asn Pro Gln Glu Glu Thr Leu Gln Ala Phe Asp Ser His
        370                 375                 380

Tyr Asp Tyr Thr Val Cys Gly Gly Ser Glu Asp Met Val Cys Thr Pro
385                 390                 395                 400

Lys Ser Asp Glu Phe Asn Pro Cys Glu Asp Ile Met Gly Tyr Arg Phe
                405                 410                 415

Leu Arg Ile Val Val Trp Phe Val Ser Leu Leu Ala Leu Leu Gly Asn
        420                 425                 430

Val Phe Val Leu Val Ile Leu Leu Thr Ser His Tyr Lys Leu Thr Val
        435                 440                 445

Pro Arg Phe Leu Met Cys Asn Leu Ala Phe Ala Asp Phe Cys Met Gly
        450                 455                 460

Met Tyr Leu Leu Leu Ile Ala Ser Val Asp Leu Tyr Thr Gln Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
                500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Tyr Ala Ile Met Ala Gly
        530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Ile Leu Val Leu Leu Leu Asn Ile Val
                580                 585                 590

Ala Phe Thr Ile Val Cys Ser Cys Tyr Val Lys Ile Tyr Ile Thr Val
        595                 600                 605

Arg Asn Pro Gln Tyr Asn Pro Gly Asp Lys Asp Thr Lys Ile Ala Lys
        610                 615                 620

Arg Met Ala Val Leu Ile Phe Thr Asp Phe Met Cys Met Ala Pro Ile
625                 630                 635                 640

Ser Phe Tyr Ala Leu Ser Ala Leu Met Asn Lys Pro Leu Ile Thr Val
                645                 650                 655

Thr Asn Ser Lys Ile Leu Leu Val Leu Phe Tyr Pro Leu Asn Ser Cys
                660                 665                 670

Ala Asn Pro Phe Leu Tyr Ala Ile Phe Thr Lys Ala Phe Gln Arg Asp
                675                 680                 685
```

```
Val Phe Ile Leu Leu Ser Lys Phe Gly Phe Cys Lys Arg Gln Ala Gln
    690                 695                 700
Ala Tyr Arg Gly Gln Arg Val Ser Pro Lys Asn Ser Thr Gly Ile Gln
705                 710                 715                 720
Val Gln Lys Val Thr Gln Asn Met Arg Gln Ser Leu Pro Asn Met Gln
                725                 730                 735
Asp Asp Tyr Glu Leu Leu Glu Asn Ser His Leu Thr His Lys Lys His
            740                 745                 750
Asp Gln Ile Ser Lys Glu Tyr Lys Gln Pro Val Leu
        755                 760

<210> SEQ ID NO 67
<211> LENGTH: 2295
<212> TYPE: DNA
<213> ORGANISM: Mus musculus

<400> SEQUENCE: 67
```

| | | | | | |
|---|---|---|---|---|---|
| atgaggccag | ggtccctgct | gctgcttgtt | ctgctgctcg | ccctgtccag | gagcctgcgg | 60 |
| ggcaaagagt | gtgcgtctcc | accctgtgag | tgtcaccagg | aggacgactt | cagagtcacc | 120 |
| tgcaaggagc | tccaccgaat | ccccagcctg | ccgcccagca | cccagactct | gaagctcatc | 180 |
| gagacttgtc | tgaagaccat | acccagtctt | gcattttcga | gtctgcccaa | tatttccagg | 240 |
| atctatttat | ctatagatgc | aactctgcag | cggctggaac | acattccttt | ctacaatttg | 300 |
| agtaaaatga | ctcacataga | aatccggaac | accccaagct | taacctatat | agaccctgat | 360 |
| gccttgacag | agctcccctt | gctcaagttt | cttggcattt | caatactgga | acttagaata | 420 |
| ttccctccct | tgaccaaaat | ttattccacg | gagatattct | ttatacttga | aatcacagac | 480 |
| aaccttaca | tgacttcggt | ccctcgaaac | gcattccagg | gcctatgcaa | tgaaaccttg | 540 |
| accctgaaac | tgtacaacaa | tggatttact | tcagtccaag | gacatgcttt | caatggaaca | 600 |
| aagctggatg | ctgtttacct | aaacaagaat | aaatacctga | cagctataga | caacgatgcc | 660 |
| tttgaggag | tatacagtgg | accaactttg | ctagatgtgt | cttccaccag | cgtcactgcc | 720 |
| cttccttcca | aaggcctgga | gcacctcaaa | gaactgcgcg | caaaagacac | ctggactctc | 780 |
| aaaaagctcc | cgctgtcgtt | gagtttcctc | cacctcactc | gggctgacct | ctcttacccg | 840 |
| agccactgct | gcgcttttaa | gaaccagaag | aaaatcaggg | gaatcctgga | gtctttgatg | 900 |
| tgtaatgaga | gcagtatccg | gaaccttcgt | caaaggaaat | cagtgaacat | cttgagggt | 960 |
| cccatctacc | aggaatatga | gaagatccg | ggtgacaaca | gtgttgggta | caaacaaaac | 1020 |
| tccaagttcc | aggagagccc | aagcaactct | cactattacg | tcttctttga | agaacaagag | 1080 |
| gatgaggtcg | ttggtttcgg | ccaagagctc | aaaaatcctc | aggaagagac | tctccaagcc | 1140 |
| ttcgagagcc | actatgacta | cacggtgtgt | ggggacaacg | aggacatggt | gtgtacccc | 1200 |
| aagtcggacg | agtttaaccc | ctgtgaagat | atcatgggct | acaggttcct | gagaatcgtg | 1260 |
| gtgtggtttg | tcagtctgct | ggctctcctg | gcaatatct | tcgtcctgct | cattctgcta | 1320 |
| accagccact | acaaattgac | cgtgccgcgg | ttcctcatgt | gcaacttggc | ctttgcagat | 1380 |
| ttctgcatgg | gggtatacct | gcttctcatt | gcctctgtag | acctgtacac | acactctgag | 1440 |
| tactacaacc | acgccatcga | ctggcagacg | ggccctgggt | gcaacacggc | tggcttcttc | 1500 |
| actgttttcg | ccagtgagtt | atcagtgtac | acactgacgg | tcatcaccct | ggagcgatgg | 1560 |
| tacgccatca | ccttcgccat | gcgcctggat | aggaagatcc | gcctcaggca | cgcgtacacc | 1620 |
| atcatggctg | ggggctgggt | tcctgcttc | cttctcgccc | tgctcccgat | ggtgggaatc | 1680 |

-continued

```
agcagctatg ccaaggtcag catctgcctg ccaatggaca ccgacacccc tcttgcactc    1740
gcatacattg tcctcgttct gctgctcaat gttgttgcct tgttgtcgt ctgttcctgc     1800 tatgtgaaga tctacatcac ggtccgaaat ccccagtaca accctcgaga taaagacacc    1860
aagattgcca agaggatggc tgtgttgatc ttcactgact tcatgtgcat ggcgcccatc    1920
tccttctatg cgctgtcggc acttatgaac aagcctctaa tcactgttac taactccaaa   1980
atcttgttgg ttctcttcta ccccctcaac tcctgtgcca atccgtttct ctatgctatt    2040
ttcaccaagg ccttccagag ggacgtgttc atcctgctca gcaagtttgg catctgcaaa    2100
cgccaggccc aggcctatca gggtcagaga gtctgtccca acaatagcac tggtattcag    2160
atccaaaaga ttccccagga cacgaggcag agtctcccca acatgcaaga tacctatgaa    2220
ctgcttggaa actcccagct agctccaaaa ctgcagggac aaatctcaga agagtataag    2280
caaacagcct tgtaa                                                    2295
```

<210> SEQ ID NO 68
<211> LENGTH: 764
<212> TYPE: PRT
<213> ORGANISM: Mus musculus

<400> SEQUENCE: 68

```
Met Arg Pro Gly Ser Leu Leu Leu Val Leu Leu Leu Ala Leu Ser
1               5                   10                  15

Arg Ser Leu Arg Gly Lys Glu Cys Ala Ser Pro Cys Glu Cys His
            20                  25                  30

Gln Glu Asp Asp Phe Arg Val Thr Cys Lys Glu Leu His Arg Ile Pro
        35                  40                  45

Ser Leu Pro Pro Ser Thr Gln Thr Leu Lys Leu Ile Glu Thr Cys Leu
    50                  55                  60

Lys Thr Ile Pro Ser Leu Ala Phe Ser Ser Leu Pro Asn Ile Ser Arg
65                  70                  75                  80

Ile Tyr Leu Ser Ile Asp Ala Thr Leu Gln Arg Leu Glu Pro His Ser
                85                  90                  95

Phe Tyr Asn Leu Ser Lys Met Thr His Ile Glu Ile Arg Asn Thr Pro
            100                 105                 110

Ser Leu Thr Tyr Ile Asp Pro Asp Ala Leu Thr Glu Leu Pro Leu Leu
        115                 120                 125

Lys Phe Leu Gly Ile Phe Asn Thr Gly Leu Arg Ile Phe Pro Pro Leu
    130                 135                 140

Thr Lys Ile Tyr Ser Thr Glu Ile Phe Phe Ile Leu Glu Ile Thr Asp
145                 150                 155                 160

Asn Pro Tyr Met Thr Ser Val Pro Arg Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly His Ala Phe Asn Gly Thr Lys Leu Asp Ala Val Tyr Leu Asn
        195                 200                 205

Lys Asn Lys Tyr Leu Thr Ala Ile Asp Asn Asp Ala Phe Gly Gly Val
    210                 215                 220

Tyr Ser Gly Pro Thr Leu Leu Asp Val Ser Ser Thr Ser Val Thr Ala
225                 230                 235                 240

Leu Pro Ser Lys Gly Leu Glu His Leu Lys Glu Leu Arg Ala Lys Asp
                245                 250                 255

Thr Trp Thr Leu Lys Lys Leu Pro Leu Ser Leu Ser Phe Leu His Leu
```

```
                260                 265                 270
Thr Arg Ala Asp Leu Ser Tyr Pro Ser His Cys Cys Ala Phe Lys Asn
            275                 280                 285
Gln Lys Lys Ile Arg Gly Ile Leu Glu Ser Leu Met Cys Asn Glu Ser
            290                 295                 300
Ser Ile Arg Asn Leu Arg Gln Arg Lys Ser Val Asn Ile Leu Arg Gly
305                 310                 315                 320
Pro Ile Tyr Gln Glu Tyr Glu Glu Asp Pro Gly Asp Asn Ser Val Gly
                325                 330                 335
Tyr Lys Gln Asn Ser Lys Phe Gln Glu Ser Pro Ser Asn Ser His Tyr
            340                 345                 350
Tyr Val Phe Phe Glu Glu Gln Glu Asp Glu Val Val Gly Phe Gly Gln
            355                 360                 365
Glu Leu Lys Asn Pro Gln Glu Glu Thr Leu Gln Ala Phe Glu Ser His
            370                 375                 380
Tyr Asp Tyr Thr Val Cys Gly Asp Asn Glu Asp Met Val Cys Thr Pro
385                 390                 395                 400
Lys Ser Asp Glu Phe Asn Pro Cys Glu Asp Ile Met Gly Tyr Arg Phe
                405                 410                 415
Leu Arg Ile Val Val Trp Phe Val Ser Leu Leu Ala Leu Leu Gly Asn
            420                 425                 430
Ile Phe Val Leu Leu Ile Leu Leu Thr Ser His Tyr Lys Leu Thr Val
            435                 440                 445
Pro Arg Phe Leu Met Cys Asn Leu Ala Phe Ala Asp Phe Cys Met Gly
            450                 455                 460
Val Tyr Leu Leu Leu Ile Ala Ser Val Asp Leu Tyr Thr His Ser Glu
465                 470                 475                 480
Tyr Tyr Asn His Ala Ile Asp Trp Gln Thr Gly Pro Gly Cys Asn Thr
                485                 490                 495
Ala Gly Phe Phe Thr Val Phe Ala Ser Glu Leu Ser Val Tyr Thr Leu
            500                 505                 510
Thr Val Ile Thr Leu Glu Arg Trp Tyr Ala Ile Thr Phe Ala Met Arg
            515                 520                 525
Leu Asp Arg Lys Ile Arg Leu Arg His Ala Tyr Thr Ile Met Ala Gly
            530                 535                 540
Gly Trp Val Ser Cys Phe Leu Ala Leu Leu Pro Met Val Gly Ile
545                 550                 555                 560
Ser Ser Tyr Ala Lys Val Ser Ile Cys Leu Pro Met Asp Thr Asp Thr
                565                 570                 575
Pro Leu Ala Leu Ala Tyr Ile Val Leu Val Leu Leu Asn Val Val
            580                 585                 590
Ala Phe Val Val Cys Ser Cys Tyr Val Lys Ile Tyr Ile Thr Val
            595                 600                 605
Arg Asn Pro Gln Tyr Asn Pro Arg Asp Lys Asp Thr Lys Ile Ala Lys
            610                 615                 620
Arg Met Ala Val Leu Ile Phe Thr Asp Phe Met Cys Met Ala Pro Ile
625                 630                 635                 640
Ser Phe Tyr Ala Leu Ser Ala Leu Met Asn Lys Pro Leu Ile Thr Val
                645                 650                 655
Thr Asn Ser Lys Ile Leu Leu Val Leu Phe Tyr Pro Leu Asn Ser Cys
            660                 665                 670
Ala Asn Pro Phe Leu Tyr Ala Ile Phe Thr Lys Ala Phe Gln Arg Asp
            675                 680                 685
```

```
Val Phe Ile Leu Leu Ser Lys Phe Gly Ile Cys Lys Arg Gln Ala Gln
    690                 695                 700

Ala Tyr Gln Gly Gln Arg Val Cys Pro Asn Asn Ser Thr Gly Ile Gln
705                 710                 715                 720

Ile Gln Lys Ile Pro Gln Asp Thr Arg Gln Ser Leu Pro Asn Met Gln
                725                 730                 735

Asp Thr Tyr Glu Leu Leu Gly Asn Ser Gln Leu Ala Pro Lys Leu Gln
            740                 745                 750

Gly Gln Ile Ser Glu Glu Tyr Lys Gln Thr Ala Leu
        755                 760
```

<210> SEQ ID NO 69
<211> LENGTH: 45
<212> TYPE: DNA
<213> ORGANISM: Homo sapiens

<400> SEQUENCE: 69
tccgatgagt tcaacccgtg taaggacata atgggctaca agttc             45

<210> SEQ ID NO 70
<211> LENGTH: 45
<212> TYPE: DNA
<213> ORGANISM: Homo sapiens

<400> SEQUENCE: 70
gatgagttca acccgtgtga aagataatg gctacaagt tcctg               45

<210> SEQ ID NO 71
<211> LENGTH: 45
<212> TYPE: DNA
<213> ORGANISM: Homo sapiens

<400> SEQUENCE: 71
ctgcttattc tcctcaccag caactacaaa ctgaacgtcc ccgc              45

<210> SEQ ID NO 72
<211> LENGTH: 45
<212> TYPE: DNA
<213> ORGANISM: Homo sapiens

<400> SEQUENCE: 72
aaactgaacg tcccccgctt ttacatgtgc aacctggcct ttgcg             45

<210> SEQ ID NO 73
<211> LENGTH: 45
<212> TYPE: DNA
<213> ORGANISM: Homo sapiens

<400> SEQUENCE: 73
gtcccccgct ttctcatgtg cgccctggcc tttgcggatt tctgc             45

<210> SEQ ID NO 74
<211> LENGTH: 45
<212> TYPE: DNA
<213> ORGANISM: Homo sapiens

<400> SEQUENCE: 74
ctggcctttg cggatttctg cgtggggatg tacctgctcc tcatc             45

<210> SEQ ID NO 75
<211> LENGTH: 45

<212> TYPE: DNA
<213> ORGANISM: Homo sapiens

<400> SEQUENCE: 75
gcggatttct gcatggggat gttcctgctc ctcatcgcct ctgta        45

<210> SEQ ID NO 76
<211> LENGTH: 45
<212> TYPE: DNA
<213> ORGANISM: Homo sapiens

<400> SEQUENCE: 76
gatttctgca tgggatgta ccccctcctc atcgcctctg tagac         45

<210> SEQ ID NO 77
<211> LENGTH: 45
<212> TYPE: DNA
<213> ORGANISM: Homo sapiens

<400> SEQUENCE: 77
atcgcctctg tagacctcta catccactct gagtactaca accat        45

<210> SEQ ID NO 78
<211> LENGTH: 45
<212> TYPE: DNA
<213> ORGANISM: Homo sapiens

<400> SEQUENCE: 78
tacaaccatg ccatcgactg gcacacaggc cctgggtgca acacg        45

<210> SEQ ID NO 79
<211> LENGTH: 45
<212> TYPE: DNA
<213> ORGANISM: Homo sapiens

<400> SEQUENCE: 79
gtgggaataa gtagctatgc cctggtcagt atctgcctgc ccatg        45

<210> SEQ ID NO 80
<211> LENGTH: 45
<212> TYPE: DNA
<213> ORGANISM: Homo sapiens

<400> SEQUENCE: 80
acgctcaaca tagttgcctt catcatcgtc tgctgctgtt atgtg        45

<210> SEQ ID NO 81
<211> LENGTH: 45
<212> TYPE: DNA
<213> ORGANISM: Homo sapiens

<400> SEQUENCE: 81
gccttcgtca tcgtctgctg caggtatgtg aagatctaca tcaca        45

<210> SEQ ID NO 82
<211> LENGTH: 45
<212> TYPE: DNA
<213> ORGANISM: Homo sapiens

<400> SEQUENCE: 82
ttcgtcatcg tctgctgctg tttcgtgaag atctacatca cagtc        45

<210> SEQ ID NO 83

```
<211> LENGTH: 45
<212> TYPE: DNA
<213> ORGANISM: Homo sapiens

<400> SEQUENCE: 83
tcattctatg ctctgtcagc actgctgaac aagcctctca tcact          45

<210> SEQ ID NO 84
<211> LENGTH: 45
<212> TYPE: DNA
<213> ORGANISM: Homo sapiens

<400> SEQUENCE: 84
ctcatcactg ttagcaactc cgacatcttg ctggtactct tctat          45

<210> SEQ ID NO 85
<211> LENGTH: 45
<212> TYPE: DNA
<213> ORGANISM: Homo sapiens

<400> SEQUENCE: 85
aaaatcttgc tggtactctt cgtgccactt aactcctgtg ccaat          45

<210> SEQ ID NO 86
<211> LENGTH: 45
<212> TYPE: DNA
<213> ORGANISM: Homo sapiens

<400> SEQUENCE: 86
gtactcttct atccacttaa cgcctgtgcc aatccattcc tctat          45

<210> SEQ ID NO 87
<211> LENGTH: 45
<212> TYPE: DNA
<213> ORGANISM: Homo sapiens

<400> SEQUENCE: 87
tcctgtgcca atccattcct cctggctatt ttcaccaagg ccttc          45

<210> SEQ ID NO 88
<211> LENGTH: 45
<212> TYPE: DNA
<213> ORGANISM: Homo sapiens

<400> SEQUENCE: 88
tcctgtgcca atccattcct cgccgctatt ttcaccaagg ccttc          45

<210> SEQ ID NO 89
<211> LENGTH: 15
<212> TYPE: PRT
<213> ORGANISM: Homo sapiens

<400> SEQUENCE: 89

Ser Asp Glu Phe Asn Pro Cys Lys Asp Ile Met Gly Tyr Lys Phe
1               5                   10                  15

<210> SEQ ID NO 90
<211> LENGTH: 15
<212> TYPE: PRT
<213> ORGANISM: Homo sapiens

<400> SEQUENCE: 90

Asp Glu Phe Asn Pro Cys Glu Glu Ile Met Gly Tyr Lys Phe Leu
1               5                   10                  15
```

<210> SEQ ID NO 91
<211> LENGTH: 15
<212> TYPE: PRT
<213> ORGANISM: Homo sapiens

<400> SEQUENCE: 91

Leu Leu Ile Leu Leu Thr Ser Asn Tyr Lys Leu Asn Val Pro Arg
1               5                   10                  15

<210> SEQ ID NO 92
<211> LENGTH: 15
<212> TYPE: PRT
<213> ORGANISM: Homo sapiens

<400> SEQUENCE: 92

Lys Leu Asn Val Pro Arg Phe Tyr Met Cys Asn Leu Ala Phe Ala
1               5                   10                  15

<210> SEQ ID NO 93
<211> LENGTH: 15
<212> TYPE: PRT
<213> ORGANISM: Homo sapiens

<400> SEQUENCE: 93

Val Pro Arg Phe Leu Met Cys Ala Leu Ala Phe Ala Asp Phe Cys
1               5                   10                  15

<210> SEQ ID NO 94
<211> LENGTH: 15
<212> TYPE: PRT
<213> ORGANISM: Homo sapiens

<400> SEQUENCE: 94

Leu Ala Phe Ala Asp Phe Cys Val Gly Met Tyr Leu Leu Leu Ile
1               5                   10                  15

<210> SEQ ID NO 95
<211> LENGTH: 15
<212> TYPE: PRT
<213> ORGANISM: Homo sapiens

<400> SEQUENCE: 95

Ala Asp Phe Cys Met Gly Met Phe Leu Leu Leu Ile Ala Ser Val
1               5                   10                  15

<210> SEQ ID NO 96
<211> LENGTH: 15
<212> TYPE: PRT
<213> ORGANISM: Homo sapiens

<400> SEQUENCE: 96

Asp Phe Cys Met Gly Met Tyr Pro Leu Leu Ile Ala Ser Val Asp
1               5                   10                  15

<210> SEQ ID NO 97
<211> LENGTH: 15
<212> TYPE: PRT
<213> ORGANISM: Homo sapiens

<400> SEQUENCE: 97

Ile Ala Ser Val Asp Leu Tyr Ile His Ser Glu Tyr Tyr Asn His
1               5                   10                  15

```
<210> SEQ ID NO 98
<211> LENGTH: 15
<212> TYPE: PRT
<213> ORGANISM: Homo sapiens

<400> SEQUENCE: 98

Tyr Asn His Ala Ile Asp Trp His Thr Gly Pro Gly Cys Asn Thr
1               5                   10                  15

<210> SEQ ID NO 99
<211> LENGTH: 15
<212> TYPE: PRT
<213> ORGANISM: Homo sapiens

<400> SEQUENCE: 99

Val Gly Ile Ser Ser Tyr Ala Leu Val Ser Ile Cys Leu Pro Met
1               5                   10                  15

<210> SEQ ID NO 100
<211> LENGTH: 15
<212> TYPE: PRT
<213> ORGANISM: Homo sapiens

<400> SEQUENCE: 100

Thr Leu Asn Ile Val Ala Phe Ile Ile Val Cys Cys Cys Tyr Val
1               5                   10                  15

<210> SEQ ID NO 101
<211> LENGTH: 15
<212> TYPE: PRT
<213> ORGANISM: Homo sapiens

<400> SEQUENCE: 101

Ala Phe Val Ile Val Cys Cys Arg Tyr Val Lys Ile Tyr Ile Thr
1               5                   10                  15

<210> SEQ ID NO 102
<211> LENGTH: 15
<212> TYPE: PRT
<213> ORGANISM: Homo sapiens

<400> SEQUENCE: 102

Phe Val Ile Val Cys Cys Cys Phe Val Lys Ile Tyr Ile Thr Val
1               5                   10                  15

<210> SEQ ID NO 103
<211> LENGTH: 15
<212> TYPE: PRT
<213> ORGANISM: Homo sapiens

<400> SEQUENCE: 103

Ser Phe Tyr Ala Leu Ser Ala Leu Leu Asn Lys Pro Leu Ile Thr
1               5                   10                  15

<210> SEQ ID NO 104
<211> LENGTH: 15
<212> TYPE: PRT
<213> ORGANISM: Homo sapiens

<400> SEQUENCE: 104

Leu Ile Thr Val Ser Asn Ser Asp Ile Leu Leu Val Leu Phe Tyr
1               5                   10                  15

<210> SEQ ID NO 105
<211> LENGTH: 15
```

```
<212> TYPE: PRT
<213> ORGANISM: Homo sapiens

<400> SEQUENCE: 105

Lys Ile Leu Leu Val Leu Phe Val Pro Leu Asn Ser Cys Ala Asn
1               5                   10                  15

<210> SEQ ID NO 106
<211> LENGTH: 15
<212> TYPE: PRT
<213> ORGANISM: Homo sapiens

<400> SEQUENCE: 106

Val Leu Phe Tyr Pro Leu Asn Ala Cys Ala Asn Pro Phe Leu Tyr
1               5                   10                  15

<210> SEQ ID NO 107
<211> LENGTH: 15
<212> TYPE: PRT
<213> ORGANISM: Homo sapiens

<400> SEQUENCE: 107

Ser Cys Ala Asn Pro Phe Leu Leu Ala Ile Phe Thr Lys Ala Phe
1               5                   10                  15

<210> SEQ ID NO 108
<211> LENGTH: 15
<212> TYPE: PRT
<213> ORGANISM: Homo sapiens

<400> SEQUENCE: 108

Ser Cys Ala Asn Pro Phe Leu Ala Ala Ile Phe Thr Lys Ala Phe
1               5                   10                  15
```

UNITED STATES PATENT AND TRADEMARK OFFICE
CERTIFICATE OF CORRECTION

PATENT NO. : 11,732,026 B2  
APPLICATION NO. : 15/317687  
DATED : August 22, 2023  
INVENTOR(S) : Bernard Rees Smith et al.

Page 1 of 1

It is certified that error appears in the above-identified patent and that said Letters Patent is hereby corrected as shown below:

In the Specification

Column 21 Line 14 replace "(0" with -- (f) --

In the Claims

Column 245 Line 44 Claim 1, replace "9011 %" with -- 95% --

Signed and Sealed this  
Fifth Day of December, 2023

Katherine Kelly Vidal  
*Director of the United States Patent and Trademark Office*